(12) United States Patent
Singh et al.

(10) Patent No.: US 9,308,244 B2
(45) Date of Patent: Apr. 12, 2016

(54) COMBINATION THERAPY USING ACTIVE IMMUNOTHERAPY

(71) Applicant: immatics Biotechnologies GmbH, Tubingen (DE)

(72) Inventors: Harpreet Singh, Tubingen (DE); Niels Emmerich, Tubingen (DE); Nobert Hilf, Kirchentellinsfurt (DE); Steffen Walter, Dusslingen (DE); Toni Weinschenk, Aichwald (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 14/453,410

(22) Filed: Aug. 6, 2014

(65) Prior Publication Data

US 2015/0023993 A1    Jan. 22, 2015

Related U.S. Application Data

(63) Continuation of application No. 12/055,151, filed on Mar. 25, 2008, now abandoned.

(60) Provisional application No. 60/908,012, filed on Mar. 26, 2007.

(51) Int. Cl.
*A61K 39/00* (2006.01)
*A61K 31/404* (2006.01)

(52) U.S. Cl.
CPC ........... *A61K 39/0011* (2013.01); *A61K 31/404* (2013.01); *A61K 2039/54* (2013.01); *A61K 2039/545* (2013.01); *A61K 2039/55505* (2013.01); *A61K 2039/55561* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,188,837 A | 2/1993 | Domb |
| 5,254,342 A | 10/1993 | Shen et al. |
| 5,268,164 A | 12/1993 | Kozarich et al. |
| 5,271,961 A | 12/1993 | Mathiowitz et al. |
| 5,413,797 A | 5/1995 | Khan et al. |
| 5,484,596 A | 1/1996 | Hanna, Jr. et al. |
| 5,487,556 A | 1/1996 | Jenkins et al. |
| 5,506,206 A | 4/1996 | Kozarich et al. |
| 5,514,670 A | 5/1996 | Friedman et al. |
| 5,534,496 A | 7/1996 | Lee et al. |
| 5,550,214 A | 8/1996 | Eberlein et al. |
| 5,849,589 A | 12/1998 | Tedder et al. |
| 6,333,028 B1 | 12/2001 | Berd |
| 6,406,705 B1 | 6/2002 | Davis et al. |
| 6,573,293 B2 | 6/2003 | Tang et al. |
| 7,087,712 B1 * | 8/2006 | Brossart ............ C07K 14/4727 530/300 |
| 7,528,224 B1 | 5/2009 | Brossart et al. |
| 2002/0085997 A1 | 7/2002 | Schmidt et al. |
| 2003/0069298 A1 | 4/2003 | Hawley et al. |
| 2003/0125359 A1 | 7/2003 | Lyons et al. |
| 2003/0170756 A1 | 9/2003 | Berd |
| 2003/0216410 A1 | 11/2003 | Masferrer et al. |
| 2003/0229229 A1 | 12/2003 | Jin et al. |
| 2004/0152759 A1 | 8/2004 | Abrams et al. |
| 2005/0038080 A1 | 2/2005 | Boyer et al. |
| 2005/0059824 A1 | 3/2005 | Vaidyanathan et al. |
| 2005/0075218 A1 | 4/2005 | Anderson et al. |
| 2005/0182122 A1 | 8/2005 | Bello et al. |
| 2005/0222390 A1 | 10/2005 | Weinschenk et al. |
| 2006/0002932 A1 | 1/2006 | Vieweg |
| 2006/0051354 A1 | 3/2006 | Simard et al. |
| 2006/0165668 A1 | 7/2006 | Liu et al. |
| 2006/0275777 A1 | 12/2006 | Waelti |
| 2007/0014775 A1 | 1/2007 | Link, Jr. et al. |
| 2008/0057701 A1 | 3/2008 | Weinschenk et al. |
| 2008/0152665 A1 | 6/2008 | Leclerc et al. |
| 2008/0206216 A1 * | 8/2008 | Dengjel ............ C07K 14/4748 424/93.71 |
| 2009/0041794 A1 | 2/2009 | Zeis |
| 2009/0123489 A1 | 5/2009 | Weinschenk et al. |

(Continued)

FOREIGN PATENT DOCUMENTS

| | | |
|---|---|---|
| EP | 0686030 | 12/1995 |
| EP | 1484397 | 12/2004 |

(Continued)

OTHER PUBLICATIONS

Hodge et al., The Tipping Point for Combination Therapy: Cancer Vaccines with Radiation, Chemotherapy, or Targeted Small Molecule Inhibitors, Semin Oncol. vol. 39, Issue 3 (Jun. 2012).

Finke et al., Sunitinib reverses type-1 immune suppression and decreases T-regulatory cells in renal cell carcinoma patients. Clin. Cancer Res. vol. 14, Issue 20 (Oct. 15, 2008) at pp. 6674-6682.

Ko et al., Sunitinib mediates reversal of myeloid-derived suppressor cell accumulation in renal cell carcinoma patients. Clin. Cancer Res. vol. 15, Issue 6 (Mar. 15, 2009) at pp. 2148-2157.

(Continued)

*Primary Examiner* — Laura B Goddard
(74) *Attorney, Agent, or Firm* — MMWV IP, LLC

(57) ABSTRACT

The present invention relates to methods of treating cancer in a mammal comprising administering to the mammal a combination therapy comprising a vaccine and a multi-kinase inhibitor, wherein the vaccine comprises an isolated tumor associated peptide having the ability to bind to a molecule of the human major histocompatibility complex (MHC) class-I or class-II. Preferably the multi-kinase inhibitor is sunitinib malate and/or sorafenib tosylate or a pharmaceutically acceptable salt thereof.

16 Claims, 78 Drawing Sheets

(56) References Cited

U.S. PATENT DOCUMENTS

| | | | |
|---|---|---|---|
| 2009/0136528 | A1 | 5/2009 | Singh et al. |
| 2009/0148400 | A1 | 6/2009 | Singh et al. |
| 2009/0221509 | A1 | 9/2009 | Rammensee et al. |
| 2009/0317428 | A1 | 12/2009 | Rammensee et al. |
| 2010/0029573 | A1 | 2/2010 | Weinschenk et al. |
| 2010/0040590 | A1 | 2/2010 | Dengjel |

FOREIGN PATENT DOCUMENTS

| | | |
|---|---|---|
| EP | 1760088 | 3/2007 |
| EP | 1760089 | 3/2007 |
| WO | 9511008 | 4/1995 |
| WO | 95/17167 | 6/1995 |
| WO | 9640173 | 12/1996 |
| WO | 0009140 | 2/2000 |
| WO | 03047523 | 6/2003 |
| WO | 03100432 | 12/2003 |
| WO | 03102023 | 12/2003 |
| WO | WO03100432 | * 12/2003 |
| WO | WO03102023 | * 12/2003 |
| WO | 2004024127 | 3/2004 |
| WO | 2004085461 | 10/2004 |
| WO | 2005009961 | 2/2005 |
| WO | 2005076009 | 8/2005 |
| WO | 2005116051 | 12/2005 |
| WO | WO2005116051 | * 12/2005 |
| WO | 2006037421 | 4/2006 |
| WO | 2006114307 | 11/2006 |
| WO | 2006120473 | 11/2006 |

OTHER PUBLICATIONS

Walter et al., Multipeptide immune response to cancer vaccine IMA901 after single-dose cyclophosphamide associates with longer patient survival. Nature Medicine vol. 18 at pp. 1254-1261 (published online Jul. 29, 2012).

Hilf et al., AACR Annual Meeting Abstract No. 3971 (2013).

Beyer et al., "Regulatory T cells in cancer," Blood, Aug. 1, 2006, vol. 108, No. 3, pp. 804-811, The American Society of Hematology.

Dannull et al., "Enhancement of vaccine-medicated antitumor immunity in cancer patients after depletion of regulatory T cells," The Journal of Clinical Investigation, Dec. 2005, vol. 115, No. 12, pp. 3623-3633.

Saeki et al., "CD4+CD25+ regulatory T cells in the peripheral blood of patients with breast cancer and non-small cell lung cancer," Oncol Rep., Nov. 2005; 114(5), pp. 1269-1273.

Herber et al., "Mechanism and Therapeutic Reversal of Immune Suppression in Cancer", www.aacrjournals.org, Cancer Research 2007; 67: (11), Jun. 1, 2007; p. 5067-5069, American Association for Cancer Research; Tampa, Florida.

Suppiah et al., "T regulatory cells (Treg) in patients with metastatic renal cell carcinoma (mRCC) decrease during sunitinib treatment: Correlations with clinical responses and T helper 1/T helper 2 (Th1/Th2) bias", Journal of Clinical Oncology, 2006 ASCO Annual Meetings Proceedings Part I., vol. 24, No. 18S, Jun. 20, 2006.

Timothy M. Kuzel et al. clinicaltrials.gov, Genistein and Interleukin-2 in Treating Patients With Metastatic Melanoma or Kidney Cancer. NCT00276835, Jan. 12, 2006 Updated Feb. 6, 2009. Updated With a Title Change.

F.J. Koppenhagen et al. "Sustained Cytokine Delivery for Anticancer Vaccination: Liposomes as Alternative for Gene-Transfected Tumor Cells", Clinical Cancer Research vol. 4, 1881-1886, Aug. 1998.

JP. H. Machiels et al. "Cyclophosphamide, Doxorubicin, and Paclitaxel Enhance the Antitumor Immune Response of Granulocyte/Macrophage-Colony Stimulating Factor-Secreting Whole-Cell Vaccines in HER-2/NEU Tolerized Mice", Cancer Research 61, 3689-3697, May 1, 2001.

C.J. Wheeler et al. "Clinical Responsiveness of Glioblastoma Multiforme to Chemotherapy After Vaccination", Clinical Cancer Research vol. 10, 5316-5326, Aug. 15, 2004.

Suppiah et al. Journal of Clinical oncology, 2006, ASCO Annual Meeting Proceedings, vol. 24, No. 18S, (Jun. 20 Supp), Abstract 2526.

Danull et al. (Journal of Clinical Investigation, 2005, 115:3623-3633).

Zhou et al. (Blood, 2006, 107:628-636).

Ramanathan et al. (Cancer Immunol, Immunother. 2005, 54:254-264).

Motzer et al. (JAMA, Jun. 2006, 21:2516-2524).

Brossart et al. (Blood, 1999, 93:4309-4317).

Brossart et al. (Blood, 2000, 96:3102-3108).

Cabebe et al. (Drugs of Today, 2006, 42:387-398).

Capizzi (Investigational New Drugs, 1996, 14:249-256).

* cited by examiner

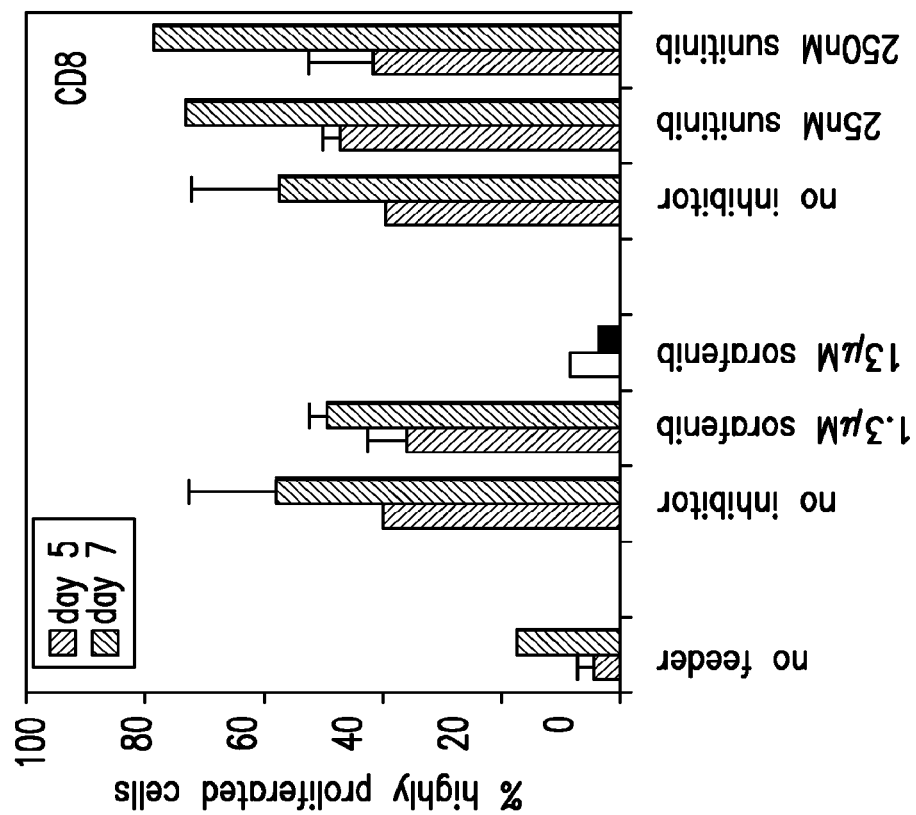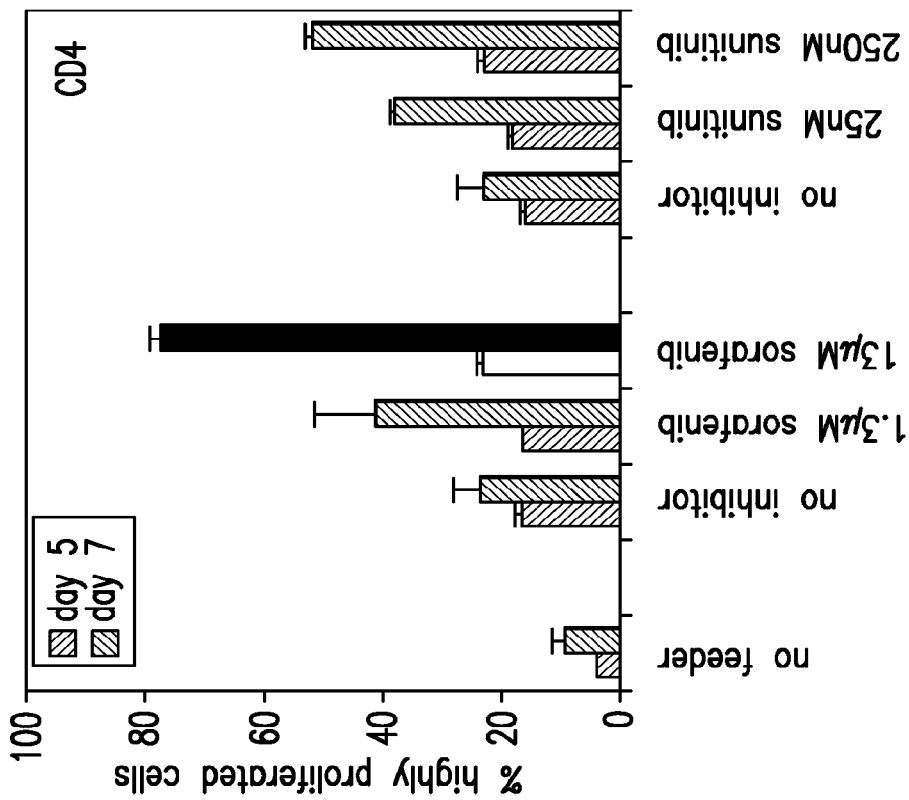
FIG. 1

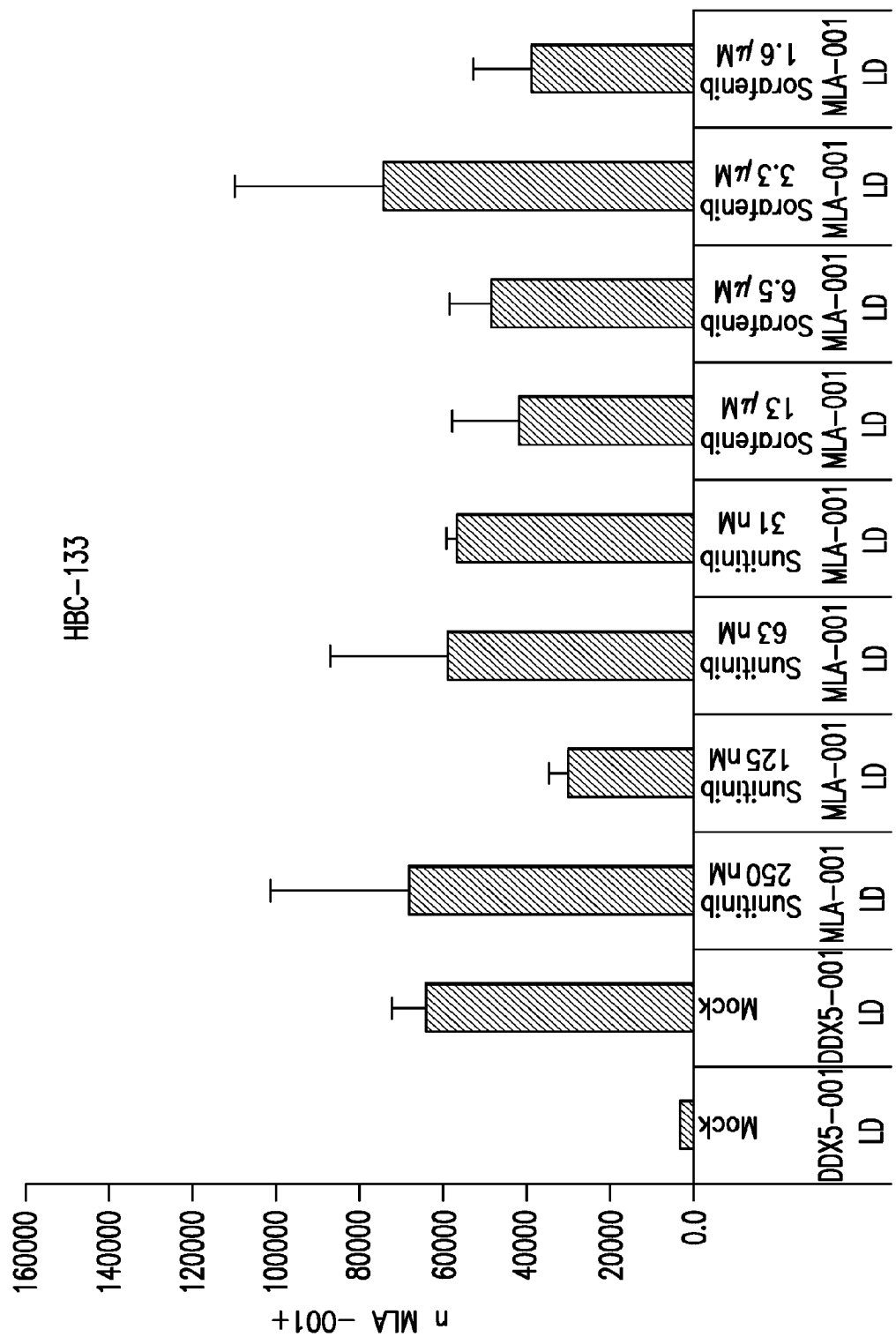

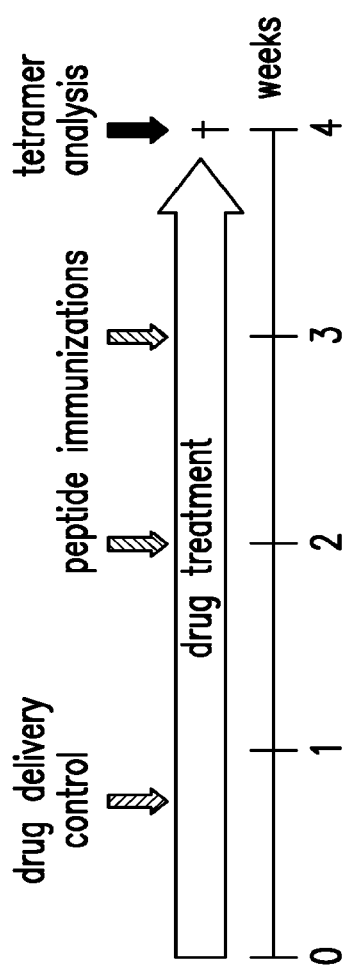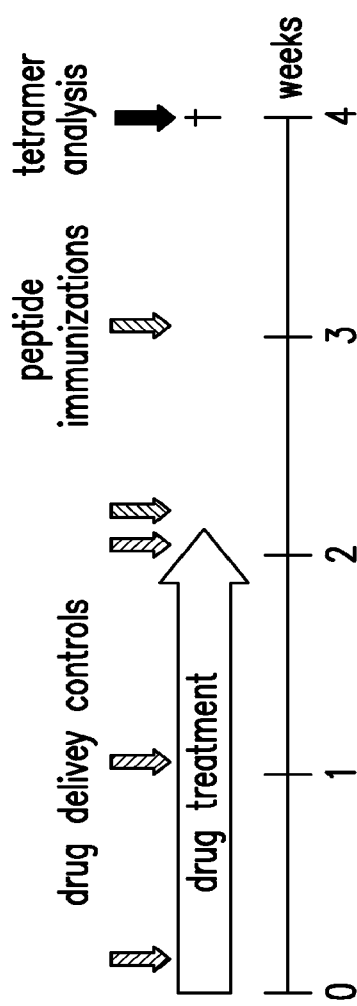

| SEQ. ID No: | PEPTIDE | SEQUENCE | GENE SYMBOL |
|---|---|---|---|
| 24 | C20-001 | ALSNLEVTL | C20orf42 |
| 25 | NOX-001 | ILAPVILYI | NOX1 |
| 26 | PCN-001 | KLMDLDVEQL | PCNA |
| 27 | PCN-002 | SMSADVPLV | PCNA |
| 28 | TOP-001 | KIFDEILVNA | TOP2A, TOP2B |
| 29 | TOP-002 | AAFVEELDKV | TOP2B |
| 30 | CEA-009 | VLLLVHNLPQHLFG | CEACAM5 |
| 31 | TGFBI-001 | ALFVRLLALA | TGFBI |
| 32 | TGFBI-006 | GDKLEVSLKNNVVS | TGFBI |
| 33 | TGFBI-007 | GKKLRVFVYRNSLCIENS | TGFBI |
| 34 | TGFBI-008 | LKNNVVSVNKEPVAEPD | TGFBI |
| 35 | | KNNVVSVNKEPVAEPD | TGFBI |
| 36 | | KNNVVSVNKEPVA | TGFBI |
| 37 | | LKNNVVSVNKEPVA | TGFBI |
| 38 | TGFBI-009 | NGVIHYIDELLIPDS | TGFBI |
| 39 | | GVIHYIDELLIPDSA | TGFBI |
| 40 | TGFBI-010 | LNRILGDPEALRDL | TGFBI |
| 41 | TGFBI-004 | TPPIDAHTRNLLRNH | TGFBI |
| 42 | PTP-001 | ALTTLMHQL | PTPRZ1 |
| 43 | GAL-001 | SLDPSSPQV | GAL3ST1 |
| 44 | CHI-001 | SLWAGVVL | CHI3L2 |
| 45 | JAK-001 | KLTDIQIEL | JAKMIP2 |
| 46 | AKR-001 | YLIHFPVSV | AKR1C1, AKR1C2 |
| 47 | FN1-001 | IVDDITYNV | FN1 |
| 48 | EGFR-002 | GAVRFSNNPALCNVES | EGFR |
| 49 | | AVRFSNNPALCNVES | EGFR |
| 50 | | AVRFSNNPALCNVE | EGFR |
| 51 | EGFR-005 | NPTTYQMDVNPEGKYS | EGFR |
| 52 | EGFR-006 | FKKIKVLGSGAFG | EGFR |
| 53 | CHI3L1-001 | TTLIKEMKAEFIKEAQPG | CHI3L1 |
| 54 | | TLIKEMKAEFIKEAQPG | CHI3L1 |
| 55 | | TTLIKEMKAEFIKEA | CHI3L1 |
| 56 | | TLIKEMKAEFIKEA | CHI3L1 |
| 57 | | IKEMKAEFIKEAQPG | CHI3L1 |
| 58 | | TTLIKEMKAEFIKE | CHI3L1 |
| 59 | CHI3L1-007 | VKSKVQYLKDRQLAG | CHI3L1 |
| 60 | CHI3L1-008 | SRRTFIKSVPPFLRT | CHI3L1 |
| 61 | DCA-001 | KLGDFGLATV | DCAMKL2 |
| 62 | KCN-001 | SLFDQWKV | KCNJ10 |
| 63 | GPM-001 | ALLSEVIQL | GPM6B |

FIG. 11

| SEQ. ID NO: | Peptide ID | Sequence | Gene Symbol | Function | binds to MHC |
|---|---|---|---|---|---|
| 24 | C20-001 | ALSNLEVTL | C20orf42 | implicated in linking actin cytoskeleton to ECM | HLA-A*02 |
| 25 | NOX-001 | ILAPVILYI | NOX1 | NADPH oxidase | HLA-A*02 |
| 64 | ODC-001 | ILDQKINEV | ODC1 | Ornithine decarboxylase | HLA-A*02 |
| 26 | PCN-001 | KLMDLDVEQL | PCNA | DNA polymerase delta auxiliary protein | HLA-A*02 |
| 31 | TGFBI-001 | ALFVRLLALA | TGFBI | transforming growth factor, beta-induced | HLA-A*02 |
| 28 | TOP-001 | KIFDEILVNA | TOP2A/TOP2B | Topoisomerase | HLA-A*02 |
| 41 | TGFBI-004 | TPPIDAHTRNLLRNH | TGFBI | transforming growth factor, beta-induced | HLA-DR |

| SEQ. ID NO: | Peptide ID | Sequence | Gene Symbol | Function | binds to MHC |
|---|---|---|---|---|---|
| 65 | CEA-006 | SPQYSWRINGIPQQHT | CEACAM5 | Carcinoembryonic antigen | HLA-DR |
| 4 | CCN-001 | LLGATCMFV | CCND1 | Cyclin D1 | HLA-A*02 |
| 9 | MUC-001 | STAPPVHNV | MUC1 | Mucin 1 | HLA-A*02 |
| 8 | MMP-001 | SQQDIKGIQKLYGKRS | MMP7 | Metalloproteinase 7 | HLA-DR |
| 1136 | CEA-005 | YLSGADLNL | *CEACAM5* | variant of CEA peptide | HLA-A*02 |
| 7 | MET-001 | YVDPVITSI | MET | met proto-oncogene | HLA-A*02 |
| 1135 | (HBV-001) | FLPSDFFPSV | | control peptide | |
| 1137 | CEA-005 | YLSGANLNL | CEACAM5 | CEA petide | HLA-A*02 |

FIG.12

| SEQ. ID NO: | Sequence | Position/Gene symbol | Acc. No. |
|---|---|---|---|
| Sequenences of NCH359 | | | |
| 1138 | VPDSSGPERIL | 78-88<br>HNRPK | NP_002131.2 |
| 1139 | GLAPSIRTK | 1510-1518<br>TNC | NP_002151.1 |
| 1140 | RLFEHPLYR | 149-157<br>FAM20C | NP_064608.1 |
| 1141 | TPSEPHPVL | 381-389<br>HGRG8 | NP_057342.1 |
| 1142 | QIFVKTLTGK | 2-11<br>RPS27A | AAH01392.1 |
| 1143 | SLMHSFILK | 44-52<br>DNCL2A | NP_054902.1 |
| 1144 | YPHLHNAEL | 127-135<br>SOX9 | NP_000337.1 |
| 1145 | RLFVGSIPK | 244-252<br>SYNCRIP | NP_006363 |
| 1146 | RVFPDKYGYSF | 233-242<br>TIA1 | NP_071320.1 |
| 1147 | SLYKKLEIK | 554-562<br>SLC9A2 | NP_003039.2 |
| 1148 | HPVSDHEATL | 216-225<br>HLA-C | NP_002108 |
| 1149 | LPTRVDFSL | 46-54<br>Symbol does not exist;<br>Gene type: unnamed protein product | BAC87610 |
| 1150 | KSFGSAQEFAW | 386-396<br>COPB2 | NP_004757 |
| 1151 | SPSTSRTPLL | 1026-1035<br>EGFR | NP_005219.2 |
| 1152 | STFDSPAHW | 1149-1157<br>EGFR | NP_005219.2 |
| 1153 | APEEHPVLL | 97-105<br>ACTB | NP_001092.1 |
| 1154 | RQITQVYGF | 117-125<br>PPP6C | NP_002712.1 |
| 1155 | KVSDYILQH | 1046-1054<br>ASTN2 | NP_054729.3 |
| 1156 | KLLPSWLK | 2-10<br>DTR | NP_001936.1 |
| 1157 | GVLKKVIRH | 23-31<br>TNC | NP_002151.1 |

FIG.13A

| SEQ. ID NO: | Sequence | Position/Gene symbol | Acc. No. |
|---|---|---|---|
| 1158 | KLFDHAVSKF | 40-49<br>ACSL4 | NP_004449.1 |
| 1159 | ITVLTKPLPV | 112-121<br>PTPRO | NP_002839.1 |
| 1160 | HPVHPDIKL | 130-138<br>PIAS1 | NP_057250.1 |
| 1161 | IPRAALLPLL | 3-12<br>PRSS11 | NP_002766.1 |
| 1162 | ATNRITVTW | 254-262<br>PIASY | NP_056981.2 |
| 1163 | KIADRFLLY | 29-37<br>LMO4 | NP_006760.1 |
| Sequences of NCH359 | | | |
| 1164 | DHDPVDKIVL | 150-159<br>HNRPA2B1 | NP_002128.1 |
| 1165 | DHHQEVIGF | 165-173<br>C9ORF10 | NP_055427.2 |
| 1166 | IHDLDNISF | 188-196<br>PSMB2 | NP_002785.1 |
| 1167 | DHINDIIKI | 834-842<br>IQGAP1 | NP_003861.1 |
| 1168 | DHMRFISEL | 355-363<br>CYFIP1 | NP_055423.1 |
| 1169 | THSLPVVI | 456-464<br>STAT3 | NP_003141.2 |
| 1170 | MPVGPDAILRY | 929-939<br>BAT3 | NP_004630.2 |
| 1171 | RLDDAIHVL | 406-414<br>TCF12 | NP_003196.1 |
| 1172 | QHEGTVNIF | 1953-1961<br>PTPRZ1 | NP_002842.1 |
| 1173 | ETVNIWTHF | 48-56<br>PAQR6 | NP_940798 |
| 1174 | VHILDTETF | 195-203<br>KLHDC2 | NP_055130.1 |
| 1175 | QTPDFTPTKY | 607-616<br>ZHX3 | NP_055850.1 |
| 1176 | RHVEVFELL | 133-141<br>MPDZ | NP_003820.1 |
| 66 | TTIDIGVKY | 136-144<br>CNN3 | NP_001830.1 |
| 1177 | DLIEHFSQF | 113-121<br>HNRPA0 | NP_006796.1 |
| 1178 | ETVWRLEEF | 65-73<br>HLA-DRA | NP_061984 |

FIG. 13B

| SEQ. ID NO: | Sequence | Position/Gene symbol | Acc. No. |
|---|---|---|---|
| 1179 | DVLESVNLL | 176-184<br>AP2M1 | NP_004059.2 |
| 1180 | IHDDFVTTF | 466-474<br>AEBP1 | NP_001120.2 |
| 67 | IHIPINNII | 57-65<br>Sec61G | NP_055117.1 |
| 1181 | IHLIDPNTL | 281-289<br>CGI-07 | NP_057022.2 |
| 1182 | IHVIGGNDV | 1016-1024<br>KIAA1268 | XP_291055.1 |
| 1183 | KAFQKIWL | 291-299<br>BZW1 | NP_055485.2 |
| 68 | YQDLLNVKL | 349-357<br>GFAP | NP_002046.1 |
| 1184 | GHYEVAELL | 728-736<br>TNKS | NP_003738.1 |
| 69 | LVVYPWTQRF | 33-42<br>HBB | NP_000509.1 |
| 70 | MHLRQYELL | 386-393<br>GNAS | NP_000507.1 |
| 71 | EAIEQILKY | 149-157<br>FLJ10539 | NP_060600.1 |
| 72 | DVAEGDLIEHF | 108-118<br>HNRPA0 | NP_006796.1 |
| 73 | DVLQKIKY | 191-198<br>EPS8L1 | NP_060199.2 |
| 74 | DSFPMEIRQY | 24-33<br>STAT1 | NP_009330.1 |
| 75 | DVISNIETF | 281-289<br>SOX9 | NP_0003??.1 |
| 76 | DVIRLIMQY | 9-17<br>SMU-1 | NP_060695.1 |
| 77 | DVIERVIQY | 792-800<br>IDN3 | NP_056199.1 |
| 78 | DVIAQGIGKL | 53-62<br>RPLP2 | NP_000995.1 |
| 79 | DVFNEKGWNY | 94-103<br>PBEF1 | NP_005737.1 |
| 80 | THLDSVTKI | 254-262<br>C6.1A | NP_077308.1 |
| 81 | DVAGIIADY | 294-302<br>KIAA1238 | XP_048675.4 |
| 82 | TAAPFPFHL | 536-544<br>TBX2 | NP_005985.2 |

FIG.13C

| SEQ. ID NO: | Sequence | Position/Gene symbol | Acc. No. |
|---|---|---|---|
| 83 | DTLDKVFTY | 86-94 ACSL3 | NP_004448.2 |
| 84 | DTISPTLGF | 42-50 ARL2 | NP_001658.1 |
| 85 | DTGILDSIGRF | 35-45 MBP | NP_002376.1 |
| 86 | VYPWTQRF | 34-42 HBB | NP_000509.1 |
| 87 | EVVAGIKEYF | 128-137 MORF4 | NP_006783.2 |
| 88 | SSVPGVRLL | 72-80 VIM | NP_003371.1 |
| 89 | SVVDAIGISRF | 364-374 FLJ45273 | BAC86883.1 |
| 90 | EVIPPMKEF | 115-123 NDUFB6 | NP_002484.1 |
| 91 | EVIPPYYSY | 152-160 TTRAP | NP_057698.2 |
| 92 | EVNGLISMY | 284-292 U5-116KD | NP_004238.2 |
| 93 | EVIDLMIKEY | 57-66 PHF10 | NP_060758.1 |
| 94 | EVVAGIKEY | 128-136 MORF4 | NP_006783.2 |
| 95 | EVFPLAMNY | 76-84 CCND1 | NP_444284.1 |
| 96 | EVVERVLTF | 28-36 FBXO22 | NP_036302.1 |
| 97 | SHSPFGLDSF | 1251-1260 JMJD1B | NP_057688.2 |
| 98 | FGVDRAILY | 457-465 ITGAV | NP_002201.1 |
| 99 | SHSDYLLTI | 76-84 SOCS2 | NP_003868.1 |
| 100 | SHLDYDITL | 511-519 KIAA0794 | XP_087353.5 |
| 101 | SHFVSDWI | 63-71 GNB2L1 | NP_006089.1 |
| 102 | EVTELLARY | 155-163 POLR2E | NP_002686.2 |
| 103 | ETADTLMGLRY | 425-435 GFPT1 | NP_002047.1 |
| 104 | EHAHLIWL | 662-670 ABCB9 | NP_062570.1 |

FIG. 13D

| SEQ. ID NO: | Sequence | Position/Gene symbol | Acc. No. |
|---|---|---|---|
| 105 | EHSLVIDTL | 53-61 PFDN2 | NP_036526.2 |
| 106 | EIAEAYLGY | 129-137 HSPA1A | NP_005336.2 |
| 107 | EIYGGSDSRF | 42-51 SF3B1 | NP_036565.1 |
| 108 | ELIAKIPNF | 73-81 SET | NP_003002.1 |
| 109 | EVIKNFIQY | 50-58 EIF3S6IP | NP_057175.1 |
| 110 | ETADTLLALRY | 426-436 GFPT2 | NP_005101.1 |
| 111 | EWSEPFRSF | 581-590 PSMD2 | NP_002799.3 |
| 112 | ETFDAGLQAF | 2019-2028 SPTAN1 | NP_003118.1 |
| 113 | SHSQLMQLI | 164-172 ADRM1 | NP_008933.2 |
| 114 | ETVRELTEF | 255-263 PPARD | NP_006229.1 |
| 115 | EVAATEIKM | 10-18 HNRPM | NP_005959.2 |
| 116 | EVAAVLLHF | 214-222 SEC10L1 | NP_006535.1 |
| 117 | EVFDKTYQF | 132-140 C6orf153 | NP_149103.1 |
| 118 | ELVKRILNF | 174-182 DEK | NP_003463.1 |
| 119 | AHDDGRWSL | 95-103 FSCN1 | NP_003079.1 |
| 120 | SWSVISRF | 4-12 DAD1 | NP_001335.1 |
| 121 | SWELINHY | 132-140 PIK3R3 | NP_003620.2 |
| 122 | SWDLINHY | 397-405 PIK3R2 | NP_005018.1 |
| 123 | AHVDLIEKL | 51-59 POLR2L | NP_066951.1 |
| 124 | FHNELLTQL | 97-105 BAIAP2 | NP_006331.1 |
| 125 | SVIEAVAHF | 812-820 C6orf133 | NP_056070.1 |
| 126 | GHFEKPLFL | 149-157 NTE | NP_006693.2 |

FIG. 13E

| SEQ. ID NO: | Sequence | Position/Gene symbol | Acc. No. |
|---|---|---|---|
| 127 | GHDASQITL | 273-281 TH1L | NP_057481.2 |
| 128 | SAVDFIRTL | 293-301 STK17A | NP_004751.1 |
| 129 | ISTPVIRTF | 989-997 C9orf10 | NP_055427.2 |
| 130 | GVIEKLLTSY | 28-37 D1S155E | AAH32446 |
| 131 | SHDLTLVNL | 395-403 KIAA1706 | NP_085139.1 |

Sequence of JY

| | | | |
|---|---|---|---|
| 11 | FPSLREAAL | 294-302 MAGEA1 | NP_004979.2 |

Sequence of RCC075

| | | | |
|---|---|---|---|
| 132 | SIFKQPVTK | 250-258 MBD2 | NP_0039??.1 |
| 133 | KPNANRIAL | 139-147 LGALS3 | NP_002297.1 |
| 134 | KLYEMILKR | 174-182 ARL7 | NP_005728.2 |
| 135 | SLFSRLFGK | 7-15 ARF4 | NP_001651.1 |
| 136 | KLFDKLLEY | 309-317 API5 | NP_006586.1 |
| 137 | SLFPNSPKWTSK | 96-107 MMP7 | NP_002414.1 |
| 138 | LESLDQLEL | 29-37 BAG2 | NP_004273.1 |
| 139 | WNKVPLTGK | 101-110 MGC17943 | NP_689474.1 |
| 140 | SVYDSVLQK | 4470-4478 SYNE1 | NP_149062.1 |
| 141 | SVYVLVRQK | 39-47 MLSTD2 | NP_115604.1 |
| 142 | ILENIQRNK | 557-565 ERCC2 | NP_000391.1 |
| 143 | GSYNKVFLAK | 146-155 PSMD8 | NP_002803.1 |
| 144 | TESGLNVTL | 6-14 PCBP1 | NP_006187.1 |
| 145 | TEHGVEVVL | 612-620 SH2D3C | NP_005480.1 |
| 146 | TEARFGAQL | 327-335 KRT19 | NP_002267.2 |

FIG.13F

| SEQ. ID NO: | Sequence | Position/Gene symbol | Acc. No. |
|---|---|---|---|
| 147 | TLADILLYY | 114-122 | NP_004271.1 |
| 148 | LVFPSEIVGK | EEF1E1 133-142 | NP_001002.1 |
| 149 | VLFGKALNPK | RPS7 709-718 | NP_003777.2 |
| 150 | RPELVRPAL | ABCC3 91-99 | NP_003730.4 |
| 151 | VPNQKRLTLL | AKR1C3 576-585 | NP_004449.1 |
| 152 | QLYWSHPRK | ACSL4 5-13 | NP_001023.1 |
| 153 | SVYVYKVLK | RPS29 39-47 | NP_059141.1 |
| 154 | REKLQEEML | H2BFS 186-194 | NP_003371.1 |
| 155 | RVFSGLVSTGLK | VIM 415-426 | NP_001952.1 |
| 156 | KPRDVSSVEL | EEF2 1939-1948 | NP_003119.1 |
| 157 | NEFPEPIKL | SPTBN1 184-192 | NP_004628.4 |
| 158 | KTYGEIFEK | RAB7 106-114 | NP_004540.1 |
| 159 | RILFFNTPK | NDUFC2 196-204 | NP_002803.1 |
| 160 | RVFPWFSVK | PSMD8 1764-1772 | NP_005924.1 |
| 161 | SEVQDRVML | MLL 54-62 | NP_057145.1 |
| 162 | SLWDRLIFH | CGI-127 410-418 | NP_0019?6.2 |
| 163 | KVYNIQIRY | ACSL1 468-476 | NP_005556.1 |
| 164 | RLLEMILNK | LCP2 171-179 | NP_001345.1 |
| 165 | SEDKKNIIL | AKR1C2 41-49 | NP_005498.1 |
| 166 | YEELVRMVL | CFL1 106-114 | NP_524147.1 |
| 167 | GEITGEVHM | MYL6 1758-1766 | NP_001448.1 |
| 168 | IVAGSLITK | FLNB 183-191 | AAH11788 |
|  |  | FNBP3 |  |

FIG.13G

| SEQ. ID NO: | Sequence | Position/Gene symbol | Acc. No. |
|---|---|---|---|
| 169 | APRIITGPAPVL | 225-236 QKI | NP_006766.1 |
| 12 | GLASFKSFLK | 74-83 RGS5 | NP_003608.1 |
| 170 | FPNSPKWTSK | 98-107 MMP7 | NP_002414.1 |
| 171 | FVIETARQL | 49-57 C14orf4 | NP_078772.1 |
| 172 | IEVDGKQVEL | 46-55 RHOA | NP_001655.1 |
| 173 | GELTGEVRM | 1776-1786 FLNC | NP_001449.1 |
| 174 | GESDDSILRL | 63-72 RPS21 | NP_001015.1 |
| 175 | GEGDFLAEGGGV | 23-34 FGA | NP_000499.1 |
| 176 | DNFPQSL | 690-696 CACNA1C | NP_000710.3 |
| 177 | GLTDVILYH | 269-277 SYNCRIP | NP_006363.3 |
| 178 | AALVASGVALY | 247-257 P2RY11 | NP_002557.2 |
| 179 | AEIRHVLVTL | 107-116 MYL6 | NP_066299.2 |
| 180 | AEPEEVEVL | 10-18 PGR1 | NP_150638.1 |
| 181 | AIIDHIFASK | 256-265 KIS | NP_787062 |
| 182 | ALLDGSNVVFK | 48-58 HKE2 | NP_055075.1 |
| 183 | AMLDTWFK | 302-310 PSMD14 | NP_005796.1 |
| 1185 | APARLFALL | 2-10 SDC4 | NP_002990.2 |
| 184 | AVNAHSNILK | 248-257 IMMT | NP_006830 |
| 185 | APRPGVLLL | 8-16 ELN | NP_000492 |
| 186 | EAFPLRVID | 749-757 MAN2A2 | NP_006113.1 |
| 187 | GVADKILKK | 211-219 NMI | NP_004679.1 |
| 188 | AVFPKPFVEK | 189-198 KIAA0377 | NP_055474.2 |

FIG.13H

| SEQ. ID NO: | Sequence | Position/Gene symbol | Acc. No. |
|---|---|---|---|
| 189 | VYVGGILTK | 258-267 UGT8 | NP_003351.2 |
| 190 | HLEDIVRQK | 1751-1759 TRIP12 | XP_3761??.1 |
| 191 | VTLTLVILSY | 207-216 LOC390323 | XP_372460.1 |
| 192 | SLLSLVTGLK | reading frame +3 Symbol does not exist; Gene type: expressed sequence tag | CD105815 |
| 193 | QTYVGITEK | 687-695 U5-200KD | NP_054733.2 |
| 194 | HEDKIRWL | 210-218 EHD2 | NP_055416.2 |
| 195 | QISIPFLLK | 208-216 C9orf88 | AAH1979 |
| 196 | GLMGFIVYK | 29-37 C14orf2 | NP_004885.1 |
| 197 | FADQEVRSL | 950-958 PIK3C2A | NP_002636.1 |
| 198 | IVALILSTK | 147-155 ATP6V0C | NP_001685.1 |
| 199 | GTYAPAEVPK | 22-31 AKR1C1 | NP_001344.2 |
| 200 | GTMTGMLYK | 161-169 TIMM23 | NP_006318.1 |
| 201 | SLAEILLKK | 439-447 IPO8 | NP_006381.1 |
| 202 | KLTYIYIQK | Reading frame +1 Symbol does not exist; Gene type: expressed sequence tag | AA295205 |
| 203 | KLLNYAPLEK | 58-67 POLR2L | NP_055427 |
| 204 | GTLPHPLQR | 182-190 SCNN1A | NP_001029.1 |
| 205 | GLYEFFRAK | 680-688 CHERP | NP_006378.2 |
| 206 | KEPEINTTL | 226-234 FLJ34588 | NP_689939.1 |
| 207 | HASDRIIAL | 330-338 TKT | NP_001055.1 |

FIG.13I

| SEQ. ID NO: | Sequence | Position/Gene symbol | Acc. No. |
|---|---|---|---|
| Sequences of RCC098 | | | |
| 208 | RPTLWAAAL | 5-13<br>IGFBP3 | NP_000589.1 |
| 209 | APSPRPLSL | 11-19<br>C19orf28 | NP_778148.1 |
| 210 | ASDFITKMDY | 362-371<br>GSN | NP_000168.1 |
| 211 | EERVINEEY | 13-21<br>RBBP4 | NP_005601.1 |
| 212 | ATGSWDSFLK | 328-337<br>GNB1 | NP_002065.1 |
| 213 | RMFDMGFEY | 411-419<br>DDX42 | NP_031398.2 |
| 214 | APLLRWVL | 265-272<br>HMOX1 | NP_002124.1 |
| 215 | ALRPSTSRSLY | 43-53<br>VIM | NP_003371.1 |
| 216 | RQIPYTMMK | 225-233<br>SLC25A3 | NP_0026??.1 |
| 217 | AETHIVLLF | 267-275<br>DKFZp564K142 | NP_115497.3 |
| 218 | RVHAYIISY | 305-313<br>EHD2 | NP_055416.2 |
| 219 | AVIVLVENFYK | 11-21<br>S100A16 | NP_525127.1 |
| 220 | SEELLREHY | 61-69<br>NME3 | NP_002504.2 |
| 221 | RADGNFLLY | 368-376<br>KIAA0930 | XP_047214.6 |
| 1186 | SEFTGVWKY | 83-91<br>PDCD6 | NP_037364.1 |
| 222 | SIDRTVMYY | 389-397<br>SLC3A1 | NP_000332.1 |
| 223 | ETDLLDIRSEY | 463-473<br>ANXA11 | NP_001148.1 |
| 224 | ESYEALPQH | 397-405<br>DNMT1 | NP_001370.1 |
| 225 | SEEEIREAF | 82-90<br>CALM2 | NP_001734.1 |
| 226 | KVMQQNLVY | 329-337<br>CRTAP | NP_006362.1 |
| 227 | DEKSIITY | 262-269<br>SPTBN1 | NP_003119.1 |
| 228 | EEIEGFRY | 421-428<br>DDX56 | NP_061955.1 |

FIG.13J

| SEQ. ID NO: | Sequence | Position/Gene symbol | Acc. No. |
|---|---|---|---|
| 229 | MENLFINRF | 186-194<br>ALOX5 | NP_000689.1 |
| 230 | MEKIWHHTF | 82-90<br>ACTB | NP_001092.1 |
| 231 | MEHAMETMMF | 5-14<br>S100A10 | NP_002957.1 |
| 232 | EEIFNLKF | 353-542<br>GTF2I | NP_001509.2 |
| 233 | LVLMVLYLI | 153-161<br>PIGM | NP_660150.1 |
| 234 | EELQQKVSY | 285-293<br>STAT3 | NP_003141.2 |
| 235 | LRVAPEEHPVL | 94-104<br>ACTB | NP_001092.1 |
| 236 | DGHLFQVEY | 13-21<br>PSMA7 | NP_002783.1 |
| 237 | LAELAHREY | 14-22<br>OGT | NP_003596.2 |
| 238 | NEADVHGIYF | 651-660<br>CP | NP_000087.1 |
| 239 | KVFQEPLFY | 114-122<br>CTSL | NP_001903.1 |
| 240 | GVLAWVKEK | 171-179<br>NK4 | NP_004212.3 |
| 241 | HEALLYYVL | 738-746<br>KIAA0746 | NP_056002.1 |
| 242 | HEMIILKL | 3489-3496<br>KIAA1554 | XP_290768.3 |
| 243 | IVPANFPSL | 443-451<br>C9orf3 | NP_116212.3 |
| 244 | HLDLGILYY | 162-170<br>DPAGT1 | NP_001373.2 |
| 245 | ITDSAGHILY | 76-85<br>TMP21 | NP_00681?.2 |
| 246 | HTDDPLTWDY | 267-276<br>HCA66 | NP_060898.1 |
| 14 | IARNLTQQL | 313-321<br>ADFP | NP_001113.2 |
| 247 | IDQTALAVY | 1087-1095<br>TPP2 | NP_003282.1 |
| 248 | LEDWIERY | 41-49<br>FKBP10 | NP_068758.2 |
| 249 | QIASFILLR | 316-324<br>HIMAP4 | NP_060796.1 |
| 250 | DEHYILTF | 550-557<br>OSBPL9 | NP_078862.2 |

FIG.13K

| SEQ. ID NO: | Sequence | Position/Gene symbol | Acc. No. |
|---|---|---|---|
| 251 | DEIGLPKIFY | 124-133<br>IQGAP1 | NP_003861.1 |
| 252 | DEIVRINGY | 132-140<br>USH1C | NP_005700.1 |
| 253 | DEKLLYDTF | 112-120<br>SF3B4 | NP_005841.1 |
| 254 | RIIEETLALK | 9-18<br>ARPC2 | NP_005722.1 |
| 255 | GTDELRLLY | 107-115<br>FLJ12525 | NP_112483.1 |
| 256 | DELEIIEGMKF | 209-219<br>HSPD1 | NP_002147.2 |
| 257 | QVDPLSALKY | 649-658<br>MKLN1 | NP_037387.2 |
| 258 | DELHYLEVY | 72-80<br>VPS35 | NP_060676.2 |
| 259 | EEFELLGKAY | 81-90<br>EIF3S8 | NP_003743.1 |
| 260 | QLEDGRTLSDY | 49-59<br>UBB | NP_061828.1 |
| 261 | DEFLWREQF | 42-50<br>FBXW5 | NP_061871.1 |
| 262 | DEMLSRGF | 185-192<br>EIF4A1 | NP_001407.1 |
| 263 | DEPLLKHWEF | 196-205<br>HLA-DRA | NP_061984.1 |
| 264 | PSRDSLPLPV | 418-427<br>GPSM1 | NP_056412.2 |
| 265 | NLRETNLDSLP | 422-432<br>VIM | NP_003371.1 |
| 266 | DEVKFLTVL | 191-199<br>ANXA4 | NP_001144.1 |
| 267 | NEVEKTMEY | 440-4848<br>RSHL2 | NP_114130.3 |
| 268 | DEVQWRGHY | 53-62<br>RPL26 | NP_000978.1 |
| 269 | DEWLKPELF | 296-304<br>CGI-26 | NP_057038.1 |
| 270 | DEYSLVREL | 125-133<br>TLN1 | NP_006280.2 |
| 271 | NEFEATQKL | 343-351<br>NFIL3 | NP_005375.1 |
| 272 | DELQQPLEL | 704-712<br>STAT2 | NP_005410.1 |

FIG.13L

| SEQ. ID NO: | Sequence | Position/Gene symbol | Acc. No. |
|---|---|---|---|
| 273 | DVVMTQSPLSL | 20-30<br>IGKV@ | S40322 |
| 274 | SEREAIEVF | 358-366<br>GBP2 | NP_004111 |
| 275 | RYFYHQEEY | 21-29<br>HLA-DRB1 | CAA09468 |
| 276 | TSALPIIQK | 63-71<br>ADFP | NP_001113.2 |
| 277 | RVQEAVESMVK | 8-18<br>FLJ14668 | AAH14975 |
| 278 | TVMELVKIIYK | 237-247<br>LACTB2 | NP_057111.1 |
| 279 | RLLQKVLAY | 103-111<br>FLJ10211 | BAA91493 |
| 280 | RIHFPLATY | 264-272<br>K-ALPHA-1 | NP_006073 |
| 281 | VGGLKNTLVHRL | 279-290<br>FLJ31579 | NP_695000.1 |
| 282 | QAQADSLTVY | 679-688<br>PCDH8 | AAP97251.1 |
| 283 | VLDPYLLKY | 34-42<br>MRPS17 | NP_057053.1 |
| 284 | IFSPPFPLFY | 83-92<br>FKSG63 | AAK08108.1 |
| 285 | TELLLKEGF | 260-268<br>SND1 | NP_055205.1 |
| 286 | GLFEVGAGWIGK | 235-246<br>HSD17B4 | NP_000405.1 |
| 287 | YEYKFGFEL | 97-105<br>TXNIP | NP_0006463.2 |
| 288 | WPLWRLVSL | 2-10<br>BGN | NP_001702.1 |
| 289 | YIDEQFERY | 121-129<br>NEDD5 | NP_004395.1 |
| 290 | YLDEKLALLNA | 897-907<br>BAIAP3 | NP_003924.2 |
| 291 | DEHLITFF | 1248-1255<br>U5-200KD | NP_054733.2 |
| 292 | DDFHIYVY | 234-241<br>SPIN | NP_006708 |
| 293 | APRTVLLLL | 5-13<br>HLA-A, -B or -C | AAL30417.1 |
| 294 | APRTVALTALL | 9-19<br>HLA-DPB1 | NP_002112 |
| 295 | FTDVNSILRY | 58-67<br>EPRS | AAH58921 |

FIG.13M

| SEQ. ID NO: | Sequence | Position/Gene symbol | Acc. No. |
|---|---|---|---|
| 296 | YSEEECRQY | 61-69 GNAI2 | NP_002061.1 |
| 297 | YSEKIVDMY | 134-142 MYH11 | NP_002465.1 |
| 298 | YTDLLRLFEY | 68-77 PPP1CB | NP_002700.1 |
| 299 | YVDPQFLTY | 341-349 PJA1 | NP_071763.2 |
| 300 | HERTFLLEY | 96-104 SNX6 | NP_067072.2 |
| 1205 | SSVPGVRLLQDSVDFSL | 72-88 VIM | NP_003371.1 |
| 301 | SLLTSSKGQLQK | 369-380 ADFP | NP_001113.2 |
| 302 | SPRENILVSL | 281-290 SCD | NP_005054.2 |
| 303 | DEVDIKSRAAY | 18-28 FTO | XP_051200.4 |
| 304 | TSPSQSLFY | 154-162 SLC11A1 | AAH41787.1 |
| 305 | YTETEPYHNY | 392-401 LOC124245 | NP_653205.2 |
| 306 | SSVPGVRLLQDSVDF | 72-86 VIM | NP_003371.1 |
| 307 | VALISPKDI | Reading frame -1 Symbol does not exist; Gene type: expressed sequence tag | AC079587.4 |
| 308 | STDKAEYTFY | 332-341 RBPSUH | NP_005340.2 |
| 309 | VTEIFRQAF | 250-258 GARNL1 | BAA74907.1 |
| 310 | SVLSPLLNK | 380-388 EPS8 | NP_004438.2 |
| Sequences of RCC100 | | | |
| 311 | RAFSSLGLLK | 615-624 UMOD | NP_003352.1 |
| 312 | FSKLRPLISK | 243-252 PGBD3 | NP_736609.1 |
| 313 | RTFTWLVGK | 353-361 MYO1C | NP_203693.2 |
| 314 | KVANIILSY | 1273-1281 FLJ21439 | NP_079413.2 |

FIG. 13N

| SEQ. ID NO: | Sequence | Position/Gene symbol | Acc. No. |
|---|---|---|---|
| 315 | TMLARLASA | 21-29<br>CSPG4 | NP_001888.1 |
| 316 | HELPLPHSV | 39-47<br>EPAS1 | NP_001421.2 |

Sequence of RCC103

| SEQ. ID NO: | Sequence | Position/Gene symbol | Acc. No. |
|---|---|---|---|
| 317 | AVQRTLLEK | 177-185<br>CD99 | NP_002405.1 |
| 318 | ETRPAGDGTFQKW | 256-268<br>HLA-A | NP_002107 |
| 319 | AVLSILPAIFQK | 392-403<br>KIAA0033 | XP_084530.5 |
| 320 | EIAGHIMEF | 848-856<br>PUM1 | NP_055491.1 |
| 321 | ELIRTIMGW | 131-139<br>BAX | NP_004315.1 |
| 322 | EVFPLKVFGY | 45-54<br>ZNF258 | AAH29439 |
| 323 | ATPTSPIRVK | 856-865<br>FLNA | NP_001447.1 |
| 324 | AVLYQPLFDK | 107-116<br>NAP1L1 | NP_004528.1 |
| 325 | EVVDFIQSKI | 451-460<br>PPM1G | NP_817092 |
| 326 | AVQEFGLARFK | 142-152<br>PX19 | NP_037369.1 |
| 327 | EAIQDLWQW | 282-290<br>NPM1 | NP_002511.1 |
| 328 | GVIRSLMAF | 60-68<br>SF3B3 | NP_036558.2 |
| 329 | HIISGTCASW | 241-250<br>TXNIP | NP_006463.2 |
| 330 | GVIDVITKTW | 261-270<br>MFTC | NP_110407.2 |
| 331 | GVIDLIFEK | 600-608<br>EIF4G1 | NP_004944.2 |
| 332 | GVCHIFASF | 29-37<br>RPS14 | NP_005608.1 |
| 333 | GTYVSSVPR | 242-250<br>HLA-DOA | NP_002110.1 |
| 334 | GTAGLLEQWLK | 329-339<br>DC12 | NP_064572.1 |
| 335 | HVITGLLEHY | 133-142<br>SCRN2 | NP_612364.1 |

FIG.13O

| SEQ. ID NO: | Sequence | Position/Gene symbol | Acc. No. |
|---|---|---|---|
| 336 | GTADELVLHSW | 176-186 LYPLAL1 | NP_620149.1 |
| 337 | EIKEVILEF | 873-881 VPS13C | NP_060154 |
| 338 | EEASLLHQF | 741-749 SPTBN1 | NP_003119.1 |
| 339 | KLFIGGLSF | 15-23 HNRPA1 | NP_002127.1 |
| 340 | DWPAVRKW | 134-142 MASA | NP_067027.1 |
| 341 | DVTGWRQW | 200-208 TGFB1 | NP_000651.1 |
| 342 | DVKDYIQEY | 2500-2508 KIAA1554 | XP_290768.3 |
| 343 | DVIDNDSWRLW | 207-217 PAICS | NP_006443.1 |
| 344 | DVFSSKGMTRW | 90-100 RASSF6 | NP_803876.1 |
| 345 | DTVKKIESF | 3197-3205 RANBP2 | NP_006258.2 |
| 346 | DLPSNHVIDRW | 211-221 SKB1 | NP_006100.2 |
| 347 | DLIGHIVEF | 726-734 PUM2 | NP_056132.1 |
| 348 | DKESQLEAY | 106-114 LOC284680 | NP_872387.1 |
| 349 | EVIKLKGYTSW | 240-250 LDHA | NP_005557.1 |
| 350 | GSSDVIIHR | 519-527 KIAA1542 | XP_290536.2 |
| 351 | GTLDYILQR | 158-166 FTO | XP_051200.4 |
| 352 | EVDKRVHMTW | 326-335 PSMD13 | NP_002808.2 |
| 353 | SVPYFLFQHW | 197-206 SOAT1 | NP_003092.3 |
| 354 | SVEEISTLVQK | 93-103 MRPL43 | NP_115488.2 |
| 355 | STFQQMWISK | 352-361 ACTA2 | NP_001604.1 |
| 356 | TTIPHALLTW | 1533-1542 BIG1 | NP_006412.1 |
| 357 | SAFLLLGLFK | 419-428 TAPBP | NP_003181.3 |

FIG.13P

| SEQ. ID NO: | Sequence | Position/Gene symbol | Acc. No. |
|---|---|---|---|
| 358 | NIGDEALIGRW | 637-647 MAGED4 | NP_110428.2 |
| 359 | TVAFVPISGW | 187-196 EEF1A1 | NP_001393.1 |
| 360 | ETVNLRSLGF | 1930-1939 AIM1 | XP_166300.3 |
| 361 | MPKFSMPGF | 72-80 AHNAK | BAC87652.1 |
| 362 | EVMEIMSRF | 98-106 POLH | NP_006493.1 |
| 363 | EVMDVFLRF | 695-703 CSGlcA-T | XP_376724.1 |
| 364 | RLQEALNLF | 265-273 GNAS | NP_000507.1 |
| 365 | ETIDWKVFESW | 174-184 CD74 | NP_004346.1 |
| 366 | ELMEHGVVSW | 39-48 ELMO3 | NP_078988.1 |
| 367 | ASVAWAVLK | 2-10 CASPR3 | NP_387504.1 |
| 368 | SVSPVVHVR | 73-81 LOC92906 | NP_612403.2 |
| 369 | HVVDRDTEAW | 27-36 FLJ35220 | NP_775898.2 |
| 370 | ETITGLRVW | 6493-6501 NEB | NP_004534.1 |
| 371 | RQLEDILSTY | 77-86 DKFZp451J0118 | NP_787048.1 |
| 372 | AIAQAESLRYK | 98-108 RPS3 | NP_000996.2 |
| 373 | GVLQLGNIVFK | 345-355 MYH9 | NP_002464.1 |
| 374 | EVINALKQTW | 489-498 LIM | NP_006448.1 |
| 375 | STAAFFLLR | 407-415 SLC37A4 | NP_001458.1 |
| 376 | DIYNFPIHAF | 177-186 LOC84549 | NP_115898.2 |
| 377 | TVVERMLSNW | 1398-1407 PLXNB2 | BAA21571.1 |
| 378 | TKPWFASQIPF | 210-220 LOC345778 | XP_293971.3 |

FIG. 13Q

| SEQ. ID NO: | Sequence | Position/Gene symbol | Acc. No. |
|---|---|---|---|
| Sequences of RCC112 | | | |
| 379 | GRVDFAYKF | 111–119 PHC2 | NP_004418.2 |
| 380 | GRDLTDYLM | 182–190 ACTG1 | NP_001605.1 |
| 381 | GRISITGVGF | 101–110 MGC21644 | NP_612501.3 |
| 382 | GRIVTLISF | 262–270 MCL1 | NP_068779.1 |
| 383 | GRLDLQYAKL | 622–631 PLEC1 | NP_000436.1 |
| 384 | GRTNLIVNY | 18–26 ELAVL1 | NP_001410.2 |
| 385 | RYFDTAVSR | 5–13 HLA-A,-B or -C | AAC17722 |
| 386 | GRMVQVHEL | 170–178 SEC23A | NP_006355.2 |
| 387 | FLDASGAKLDY | 53–63 BZW1 | NP_055485.2 |
| 388 | ATDYHVRVY | 348–356 FAD104 | NP_073600.2 |
| 389 | ARLPWAGQL | 624–632 PBXIP1 | NP_065385.2 |
| 390 | YGMPRQIL | 192–199 TAGLN2 | NP_003555.1 |
| 391 | GRLLVATTF | 385–393 IARS | NP_002152.1 |
| 392 | AGGDWFTSR | 136–144 PPP2R1A | NP_055040.2 |
| 393 | GRAPISNPGM | 179–188 RPA2 | NP_002937 |
| 394 | GRMENLASYR | 308–317 PPP1R3C | NP_005389 |
| 395 | VLPKSRVEL | 89–97 HLA-DOA | BAA81787 |
| 396 | DAKIRIFDL | 28–36 RPL10 | NP_006004.1 |
| 397 | GRAMVARLGL | 2–11 CD24 | NP_037362.1 |
| 398 | FIDASRLVY | 612–620 CTNNA1 | NP_001894.1 |
| 399 | DPMKARVVL | 21–29 SRP9 | NP_003124.1 |

FIG.13R

| SEQ. ID NO: | Sequence | Position/Gene symbol | Acc. No. |
|---|---|---|---|
| 400 | FRFDPQFAL | 77-85<br>HLA-DQA1 | XP_371812 |
| 401 | DTDHYFLRY | 165-173<br>PIGT | NP_057021.2 |
| 402 | ELLIRKLPF | 60-68<br>HIST3H3 | NP_003484.1 |
| 403 | EAFVRHIL | 142-149<br>MYL6 | NP_066299.2 |
| 404 | RYFDTAMSR | 5-13<br>HLA-A,-B or -C | AAB48498.1 |
| 405 | GRVFIISKY | 416-424<br>FLJ31657 | NP_689971 |
| 406 | TFRPAAMLVER | 154-164<br>LAMB2 | NP_002283.2 |
| 407 | YLLEKSRAI | 257-265<br>MYH9 | NP_002464.1 |
| 408 | LSDLGKLSY | 353-361<br>MYST1 | NP_115564.1 |
| 409 | VTDSIRDEY | 258-266<br>DNM1L | NP_005681.1 |
| 410 | LTDRELEEY | 567-575<br>ADD1 | NP_001110.2 |
| 411 | LTDRGVMSY | 252-260<br>IRF3 | NP_001562.1 |
| 412 | KGLSVFLNR | 527-535<br>GPNMB | NP_002501.1 |
| 413 | VTDNRAFGY | 128-136<br>DAB2 | NP_001334.1 |
| 414 | STDVSDLLHQY | 257-267<br>PSMB8 | NP_004150.1 |
| 415 | RSLPFFSAR | 135-143<br>TRAPPC1 | NP_067033.1 |
| 416 | YRFMGTEAY | 378-386<br>SLC3A1 | NP_000332.1 |
| 417 | MPLLRQEEL | 394-402<br>EHD2 | NP_055416.2 |
| 418 | VTEIDQDKY | 2380-2388<br>FLNA | NP_001447.1 |
| 419 | MRHLGAFLF | 1-9<br>TCN2 | NP_000346.2 |
| 420 | TTEESLRNYY | 20-29<br>HNRPA2B1 | NP_002128.1 |
| 421 | MRTSYLLLF | 1-9<br>DEFB1 | NP_005209.1 |
| 422 | TVDQVKDLY | 882-890<br>CP | NP_000087.1 |

FIG.13S

| SEQ. ID NO: | Sequence | Position/Gene symbol | Acc. No. |
|---|---|---|---|
| 423 | MRYVASYLL | 1-9<br>RPLP2 | NP_000995.1 |
| 424 | VGLIRNLAL | 511-519<br>CTNNB1 | NP_001895.1 |
| 425 | GRLDAVLQR | 317-325<br>PML | NP_002666.1 |
| 426 | LLDQGQLNKY | 421-430<br>CLTC | NP_004850.1 |
| 427 | NRFAGFGIGL | 98-107<br>LOC91137 | NP_620128.1 |
| 428 | KRLGTLVVTY | 305-314<br>GBP4 | NP_443173.2 |
| 429 | KRGDVIYIL | 319-327<br>SCAP2 | NP_003921.2 |
| 430 | SRFDIPLGL | 1103-1111<br>PCF11 | NP_056969.2 |
| 431 | STDPSVLGKY | 101-110<br>HES1 | NP_005515.1 |
| 432 | SRFLKSDLF | 130-138<br>RGS10 | NP_002916.1 |
| 433 | VQKPSYYVR | 211-219<br>ADFP | NP_001113.2 |
| 434 | SRISLPLPNF | 409-418<br>VIM | NP_003371.1 |
| 435 | LRSGLPLLL | 231-239<br>MADHIP | NP_004790.1 |
| 436 | SFKDYIQER | 330-338<br>ETS2 | NP_005230.1 |
| 437 | HTQGPVDGSLY | 104-114<br>TENS1 | NP_073585.6 |
| 438 | STDKFKTDFY | 271-280<br>COPS6 | NP_006824.2 |
| Sequences of RCC115 | | | |
| 439 | GSHSMRYFF | 25-33<br>HLA-A | NP_002107 |
| 440 | GSHSMRYFFT | 25-34<br>HLA-A | NP_002107 |
| 441 | GSHSMRYFH | 25-33<br>HLA-B | I37515 |
| 442 | AAILGMHNL | 135-143<br>TMOD3 | NP_055362.1 |
| 443 | KLDPTKTTL | 275-283<br>NDRG1 | NP_006087.2 |

FIG.13T

| SEQ. ID NO: | Sequence | Position/Gene symbol | Acc. No. |
|---|---|---|---|
| 444 | FVHDLVLYL | 783-791 CLTCL1 | NP_001826.1 |
| 445 | FVHDLVL | 783-789 CLTCL1 | NP_001826.1 |
| 446 | VLIPKLPQL | 134-142 ORMDL3 | NP_644809.1 |
| 447 | NEITIPVTF | 177-185 HSPB1 | NP_001531.1 |
| 448 | YLADFLLTK | 255-263 SLC17A3 | NP_006623.1 |
| 449 | YLIPLLERL | 139-147 DDX6 | NP_004388.1 |
| 450 | NEVVTREY | 18-25 RPL31 | NP_000984.1 |
| 451 | DEFKIGELF | 145-153 PRKDC | NP_008835 |
| 452 | IQRTPKIQVYS | 21-31 B2M | NP_004039.1 |
| 453 | LTGPVMPVR | 150-158 RPL13 | NP_000968.2 |
| 454 | AVAIKAMAK | 146-154 EIF5A | NP_001961.1 |
| 455 | FVQMMTAK | 142-149 CALM1 | NP_008819.1 |
| 456 | ATDPNILGR | 4111-4119 PRKDC | NP_008835.5 |
| 457 | LLLLSIVIL | 212-220 EDG1 | NP_001391.2 |
| 458 | KLPNFGFWF | 376-385 G3BP | NP_005745.1 |
| 459 | KLSEIDVAL | 174-182 EFHD1 | NP_079478.1 |
| 10 | LAALPHSCL | 5-13 RGS5 | NP_003608.1 |
| 460 | YSIITPNILRL | 26-36 C3 | NP_000055.1 |
| 461 | ALPSRILLWK | 2-11 MGC3047 | NP_115724.1 |
| 462 | VKGFYPSDIAVE | 247-258 IGHG2 | AAB59393.1 |
| 463 | FLLDLSRSV | 92-100 GPR31 | NP_005290.1 |
| 464 | IIYKGGTSR | 545-553 GSN | NP_000168.1 |
| 465 | IVADHVASY | 3-11 MHC class II | AAC41957 |

FIG.13U

| SEQ. ID NO. | Sequence | Position/Gene symbol | Acc. No. |
|---|---|---|---|
| 466 | EVGGEALGRLL | 23-33<br>HBB | NP_000509.1 |
| 467 | RTGPPMGSRF | 175-184<br>WBSCR1 | NP_071496.1 |
| 468 | RQIQESVTF | 1305-1313<br>ANK2 | NP_001139.2 |
| 469 | RVAPEEHPV | 95-103<br>ACTB | NP_001092.1 |
| 470 | TLADLLALR | 1433-1441<br>DNAH11 | NP_003768.1 |
| 471 | RVAPEEHPVLLT | 95-106<br>ACTB | NP_001902.1 |
| 472 | TLADIIARL | 1487-1495<br>KIAA1305 | XP_370756.2 |
| 473 | RWEDGSPLNF | 142-151<br>KLRG1 | NP_005801.2 |
| 474 | YEVSQLKD | 468-475<br>CNDP2 | NP_060705.1 |
| 475 | YRDIPELQGF | 663-672<br>AACS | NP_076417 |
| 476 | YVDGTQFVRF | 51-60<br>HLA-A,-B or -C | BAA04965 |
| 477 | SLLDEFYKL | 184-192<br>M11S1 | NP_005889.3 |
| 478 | HGIDPTGTY | 28-36<br>TUBB5 | NP_006078.2 |
| 479 | SLDKFLASVSTVL | 125-137<br>HBA1 | NP_000549.1 |
| 480 | SIGERDLIFH | 289-298<br>TIMELESS | NP_003911.1 |
| 481 | SITSVFITK | 1788-1796<br>TRRAP | NP_003487.1 |
| 482 | FGEHLLESDLF | 28-38<br>CRYAB | NP_001876.1 |
| 483 | FLDPIKAYL | 76-84<br>GPR116 | NP_056049.3 |
| 484 | FLADPSAFVAA | 268-278<br>RPLP0 | NP_000993.1 |
| 485 | ITAPPSRVL | 20-28<br>SCD | NP_005054.2 |
| 486 | VLDELKNMKC | 170-179<br>CYFIP2 | NP_055191.1 |
| 487 | LLGPRLVLA | 23-31<br>TMP21 | NP_006818.2 |
| 488 | IIMPHNIYL | 251-259<br>SLC11A1 | NP_000569.2 |

FIG.13V

| SEQ. ID NO: | Sequence | Position/Gene symbol | Acc. No. |
|---|---|---|---|
| 489 | LVRMVLNG | 144-151 MYL6 | NP_034990 |
| 490 | RLYGPSSVSF | 133-142 SERPINH1 | NP_001226.2 |
| 491 | FEAPIKLVF | 236-244 HM13 | NP_110416.1 |
| 492 | IQPGAVKVY | 1472-1480 C3 | NP_000055.1 |
| 493 | VLAEVPTQL | 501-509 CPNE1 | NP_003906.1 |
| 494 | IMRAGMSSL | 521-529 CCT6A | NP_001753.1 |
| 495 | VSFSSGLKGMSL | 96-107 ATP5A1 | NP_004037.1 |
| 496 | ILNPDNSFEIL | 241-251 CANX | NP_001737.1 |
| 497 | VALEFALHL | 344-352 CABLES1 | NP_612384.1 |
| 498 | TVAVPLVGK | 22-30 MGC3067 | NP_077271.1 |
| 499 | TLSDLRVYL | 121-129 C20orf139 | NP_542763.1 |
| 500 | TLIDIMTRF | 35-43 HK1 | NP_000179.1 |
| Sequences of RCC116 | | | |
| 501 | HDFPRALIF | 64-72 CG018 | AAH22188 |
| 502 | GSHSMRYF | 25-32 HLA-A,-B or -C | BAA04965 |
| 503 | SLMDHTIPEV | 289-298 SDCBP | NP_005616.1 |
| 504 | SGVHTFPAVLQ | 155-165 Ig heavy chain | AAO22172 |
| 505 | FLVTVIHTL | 1065-1073 PLXNC1 | NP_005752.1 |
| 506 | TDGKVFQF | 24-31 RPL24 | NP_000977.1 |
| 507 | YDLLRNTNF | 246-254 DYRK1A | NP_001387.2 |
| 508 | ILYPKTLFL | 138-146 PPP3CA | NP_000935.1 |
| 509 | MRYVASYL | 1-8 RPLP2 | NP_000995.1 |
| 510 | FIWENIHTL | 3725-3733 BPAG1 | NP_056363.2 |

FIG.13W

| SEQ. ID NO: | Sequence | Position/Gene symbol | Acc. No. |
|---|---|---|---|
| 511 | RELPAWVSF | 125-133 MBC2 | NP_057107.1 |
| 512 | QDLNRIFPL | 81-89 PRG1 | NP_002718.2 |
| 513 | RDSIVAEL | 97-104 COPE | NP_009194.2 |
| 514 | ADVLKVEVF | 130-138 ITGB4BP | NP_002203.1 |
| 1187 | YDSIIYRM | 335-342 ATP6AP2 | NP_005756.2 |
| 515 | AMNPVEHPF | 203-211 RPL8 | NP_000964.1 |
| 516 | SELIRNVTL | 126-134 U5-116KD | NP_004238.2 |
| 517 | QDVARVLGF | 117-125 PNMA1 | NP_006020.3 |
| 518 | SDHIHIIAL | 215-223 OTUB1 | NP_060140.1 |
| 519 | ADSLRLQQL | 781-789 SPTAN1 | NP_003118.1 |
| 520 | LLDIRSEY | 466-473 ANXA11 | NP_001148.1 |
| 521 | VLFGLLREV | 663-671 DHX38 | NP_054722.2 |
| 522 | VAVGRALYY | 510-518 DDB1 | NP_001914.2 |
| 523 | MRFLAATFL | 1-9 NPC2 | NP_006423.1 |
| 524 | YTDPEVFKY | 398-406 PTGIS | NP_000952.1 |
| 525 | HDFLKYDFF | 232-240 SURF4 | NP_149351.1 |
| 526 | AIDQLHLEY | 525-533 ACTN4 | NP_004915.2 |
| 527 | SDLERVTSL | 316-324 FLJ21616 | NP_078843.2 |
| 528 | TLLPLRVFL | 128-136 FLJ90013 | NP_699196.1 |
| 529 | YSIITPNILR | 26-35 C3 | NP_000055.1 |
| 530 | FELQRNFQL | 19-27 ING4 | NP_057246.2 |
| 531 | LDLQRNYIF | 186-194 UNQ3030 | NP_940967.1 |
| 532 | RRLDPIPQL | 56-64 MGC8721 | NP_057211.4 |

FIG.13X

| SEQ. ID NO. | Sequence | Position/Gene symbol | Acc. No. |
|---|---|---|---|
| 533 | SLPIKESEIIDF | 85-96<br>RPS2 | NP_002943.2 |
| 534 | TELLRYYML | 292-300<br>SNX5 | NP_055241.1 |
| 535 | FIYHGEVPQA | 254-263<br>MHC2TA | NP_000237.1 |
| 536 | AEMLRSISF | 217-225<br>CSTF1 | NP_001315.1 |
| 537 | RLQEDPPVGV | 15-24<br>UBE2B | NP_003328.1 |
| 538 | AELERAAAL | 465-473<br>FLJ35453 | NP_689813.1 |
| 539 | YTDKIDRY | 107-114<br>TM4SF7 | NP_003262.1 |
| 540 | FLLPDVIRI | 329-337<br>TBC1D13 | NP_060671.2 |
| 541 | VELPHINLL | 169-177<br>FLJ10349 | NP_060536.2 |
| 542 | VMLDVPIRL | 725-733<br>RASAL2 | NP_004832.1 |
| 543 | SLLENLEKI | 209-216<br>HNRPC | NP_112604.1 |
| 544 | YADPVNAHY | 226-234<br>ROD1 | NP_005147.3 |
| 545 | AELLRGLSL | 165-173<br>FBXL5 | NP_036293.1 |
| 546 | TTEVHPELY | 51-59<br>SDBCAG84 | NP_057050.1 |
| 547 | RETNLDSLP | 424-432<br>VIM | NP_003371.1 |
| 548 | ELEDSTLRY | 543-551<br>PLEC1 | NP_000436.1 |
| Sequences of RCC130 | | | |
| 549 | FLDIYIFL | 84-91<br>LOC390875 | XP_372703.1 |
| 550 | TYTDRVFFL | 1282-1290<br>PLXNB2 | BAA21571.1 |
| 551 | SPHLANYFYF | 147-156<br>Symbol does not exist; Gene type: unnamed protein product | BAC87422 |
| 552 | SPRLPVGGF | 1921-1929<br>TRIP12 | XP_376178.1 |

FIG. 13Y

| SEQ. ID NO: | Sequence | Position/Gene symbol | Acc. No. |
|---|---|---|---|
| 553 | KLLDKVQAYS | 9-18<br>GJA1 | NP_000156.1 |
| 554 | AYQHLFYLL | 955-963<br>IQGAP3 | NP_839943.2 |
| 555 | KYILLMDIIA | 148-157<br>TBX3 | NP_005987.2 |
| 556 | RYSSMAASF | 82-90<br>MAP17 | NP_005755.1 |
| 557 | SPRAAEPVQL | 397-406<br>CA9 | NP_001207.1 |
| 558 | IYTSSVNRL | 535-543<br>COPB2 | NP_004757.1 |
| 559 | LYPQFMFHL | 576-584<br>SEC23A | NP_006355.2 |
| 560 | RYIPTAAAF | 415-423<br>SEC61A1 | NP_037468.1 |
| 561 | EYVKKIPV | 237-245<br>EIF2S3 | NP_001406.1 |
| 562 | SRVEAVYVL | 13-21<br>PADI2 | NP_031391.1 |
| 563 | MPRGVVVTL | 851-859<br>HECTD1 | NP_056197.1 |
| 564 | LPKPPGRGV | 341-349<br>FBXL6 | NP_036294.1 |
| 565 | RLWGEPVNL | 1665-1673<br>USP9X | NP_004643.2 |
| 566 | RLLDVLAPL | 14-22<br>COL18A1 | NP_569712.1 |
| 567 | LYILSSHDI | 474-482<br>FBXO24 | NP_277041.1 |
| 568 | TPMGPGRTV | 235-243<br>LGALS8 | NP_006490.3 |
| 569 | GPPGTGKTDVAVQI | 823-836<br>AQR | NP_055506.1 |
| 570 | NEIEDTFRQF | 46-55<br>ATP6V1F | NP_004222.2 |
| 571 | EEIDLRSVGW | 315-324<br>UNC93B1 | NP_112192.2 |
| 572 | KYQKGFSLW | 245-253<br>TRAM1 | NP_055109.1 |
| 573 | VYPDGIRHI | 519-527<br>SF3B3 | NP_036558.2 |
| 574 | KFIDTTSKF | 366-374<br>RPL3L | NP_005052.1 |
| 575 | FLDILNTLI | 1729-1737<br>DNAH8 | NP_001362.1 |

FIG.13Z-1

| SEQ. ID NO: | Sequence | Position/Gene symbol | Acc. No. |
|---|---|---|---|
| 576 | KYITQGQLLQF | 200-210 ELOVL5 | NP_068586.1 |
| 577 | KYLSVQGQLF | 344-353 MTCH1 | NP_055156.1 |
| 578 | RYFDEPVEL | 355-363 ARFGAP3 | NP_055385.2 |
| 579 | KYDEIFYNL | 452-460 EHD2 | NP_055416.2 |
| 580 | SYIEHIFEI | 61-69 PEA15 | NP_003759.1 |
| 581 | KFIDPIYQVW | 572-581 RRN3 | NP_060897.2 |
| 582 | LGYTEGALLAL | 1370-1380 PCDH15 | NP_149045.2 |
| 583 | KYPSPFFVF | 2-10 DHX9 | NP_085077.1 |
| 584 | EYPDRIMNTF | 158-167 TUBB4 | NP_006077.1 |
| 585 | VYISEHEHF | 107-115 CLPTM1 | NP_001285.1 |
| 586 | KYFLKPEVL | 167-176 KIAA1363 | NP_065843.2 |

Sequence of JY

| | | | |
|---|---|---|---|
| 15 | GPALGRSFL | 78-86 TNFSF7 | NP_001243.1 |

Sequences of the control peptides

| | | | |
|---|---|---|---|
| 20 | ELAGIGILTV | 26-35 MLANA (modified A27->L) | NP_005502.1 |
| 587 | ILKEPVHGV | 896-904 pol | NP_057849.4 |
| 588 | GILGFVFTL | 58-66 Symbol does not exist; Gene type: matrix protein M1 | S14616 |
| 589 | NLVPMVATV | 495-503 Symbol does not exist; Gene type: pp65 | P06725 |

FIG.13Z-2

| SEQ. ID NO: | Sequence | Position/Gene symbol | Acc. No. |
|---|---|---|---|
| 590 | LLDFVRFMGV | 284-293<br>Symbol does not exist; Gene type: EBNA-6 nuclear protein | P03204 |
| 591 | GLCTLVAML | 259-267<br>Symbol does not exist; Gene type: Immediate-early transactivator | NP_039857.1 |
| 592 | CLGGLLTMV | 294-302<br>Symbol does not exist; Gene type: latent membrane protein 2 | AAB59844.1 |
| 593 | APRTVALTA | 9-17<br>HLA-DPB1 | NP_002112 |

FIG.13Z-3

| SEQ. ID NO: | Sequence | Position/Gene type | Acc. No. |
|---|---|---|---|
| 594 | AAFPGASLY | 63-71<br>DAZ associated protein 2 | NM_014764 |
| 595 | AELATRALP | 137-145<br>junction placoglobin | NM_002230 |
| 596 | AFFAERLYY | 397-405<br>annexin A7 | NM_001156 |
| 597 | ALATLIHQV | 26-34<br>COP9 constitutive photomorphogenic homolog subunit 7A (Arabidopsis) | NM_016319 |
| 598 | ALAVIITSY | 318-326<br>ATPase, H+ transporting, lysosomal (vacuolar proton pump) membrane sector associated protein M8-9 | NM_005765 |
| 599 | ALQEMVHQV | 806-814<br>enhancer of filamentation 1 | NM_006403 |
| 600 | ALRDVRQQY | 268-276<br>vimentin | NM_003380 |
| 601 | AQNAVRLHY | 481-489<br>catenin (cadherin-associated protein), beta 1, 88kDa | NM_001904 |
| 602 | AQPGFFDRF | 1006-1014<br>collagen, type VI, alpha 2 (COL6A2), transcript variant 2C2 | NM_001849 |
| 603 | AVCEVALDY | 2260-2268<br>spectrin, beta, non-erythrocytic 1 | NM_003128 |
| 604 | AVLGAVVAV | 161-169<br>Cw1 antigen | M12679 |
| 605 | DAILEELSA | 154-162<br>hypothetical protein FLJ11749 | NM_024591 |
| 606 | EEHPTLLTEA | 101-110<br>actin, alpha 2, smooth muscle, aorta | NM_001613 |

FIG.14A

| SEQ. ID NO: | Sequence | Position/Gene type | Acc. No. |
|---|---|---|---|
| 607 | EEMPQVHTP | 715-723<br>MCM3 minichromosome maintenance deficient 3 (S. cerevisiae) | NM_002388 |
| 608 | EENFAVEA | 348-355<br>vimentin | NM_003380 |
| 609 | EENKLIYTP | 56-64<br>binder of Arl Two | NM_012106 |
| 610 | FAEGFVRAL | 110-118<br>v-jun sarcoma virus 17 oncogene homolog (avian | NM_002228 |
| 611 | FFGETSHNY | 235-243<br>matrin 3 | NM_018834 |
| 612 | FLPHMAYTY | 931-939<br>zinc finger homeobox 1b | NM_014795 |
| 613 | GEPRFISVGY | 42-51<br>major histocompatibility complex, class I, C | Z46810 |
| 614 | GLATDVQTV | 55-63<br>proteasome (prosome, macropain) subunit, beta type, 3 | NM_002795 |
| 615 | GLNDETYGY | 161-169<br>ATPase, Na+/K+ transporting, beta 1 polypeptide | NM_001677 |
| 616 | GQEFIRVGY | 103-111<br>anti-silencing function 1B | NM_018154 |
| 617 | GQFPGHNEF | 76-84<br>CDC42 effector protein (Rho GTPase binding) 3 | NM_006449 |
| 618 | GQPWVSVTV | 121-129<br>FLJ00063 | AC005912 |
| 619 | GYLHDFLKY | 254-262<br>mortality factor 4 like 2 | NM_012286 |

FIG.14B

| SEQ. ID NO: | Sequence | Position/Gene type | Acc. No. |
|---|---|---|---|
| 620 | HQITVLHVY | 137-145<br>homolog of yeast long chain polyunsaturated fatty acid elongation enzyme 2 | NM_021814 |
| 621 | HVIDVKFLY | 163-171<br>damage-specific DNA binding protein 1, 127kDa | NM_001923 |
| 622 | HVNDLFLQY | 484-492<br>KIAA1005 | AB023222 |
| 623 | IAMATVTAL | 249-257<br>aldolase A, fructose-bisphosphate | NM_000034 |
| 624 | IGIDLGTTY | 7-15<br>heat shock 70kDa protein 1A | NM_005345 |
| 625 | ILHDDEVTV | 15-23<br>ribosomal protein, large, P1 | NM_001003 |
| 626 | IQKESTLHL | 61-69<br>ubiquitin A-52 residue ribosomal protein fusion product 1 | NM_003333 |
| 627 | ISRELYEY | 70-77<br>clone MGC:39264 IMAGE:5087938 | BC022821 |
| 628 | KLHGVNINV | 59-67<br>RNA binding motif protein 4 | NM_002896 |
| 629 | KQMEQVAQF | 89-97<br>transgelin | NM_003186 |
| 630 | KVADMALHY | 296-304<br>chaperonin containing TCP1, subunit 8 (theta) | NM_006585 |
| 631 | LEEDSAREI | 68-76<br>LOC204689 | XM_119113 |
| 632 | LLAERDLYL | 576-584<br>transglutaminase 2 (C polypeptide, protein-glutamine-gamma-glutamyltransferase) | NM_004613 |

FIG.14C

| SEQ. ID NO: | Sequence | Position/Gene type | Acc. No. |
|---|---|---|---|
| 633 | LLDEEISRV | 44-52<br>RNA binding protein HQK-7 | AB067800 |
| 634 | LLYPTEITV | 830-838<br>integrin, alpha 3 (antigen CD49C,<br>alpha 3 subunit of VLA-3 receptor) | NM_002204 |
| 635 | LMDHTIPEV | 290-298<br>syndecan binding protein | NM_005625 |
| 636 | LQHPDVAAY | 229-237<br>catenin (cadherin-associated protein),<br>alpha 1, 102kDa | NM_001903 |
| 637 | MEDIKILIA | 632-640<br>hypoxia-inducible factor 1, alpha<br>subunit (basic helix-loop-helix<br>transcription factor) | NM_001530 |
| 638 | MEENFAVEA | 347-355<br>vimentin | NM_00380 |
| 639 | MQKEITAL | 313-320<br>actin, beta | NM_001101 |
| 640 | NEDLRSWTA | 151-159<br>HLA-G histocompatibility antigen,<br>class I, G | NM_002127 |
| 641 | NEIKDSWA | 673-681<br>eukaryotic translation elongation factor 2 | NM_001961 |
| 642 | NVTQVRAFY | 439-447<br>catalase | NM_001752 |
| 1188 | NYIDKVRFL | 116-124<br>vimentin | NM_003380 |
| 1189 | PTQELGLPAY | 392-401<br>seryl-tRNA synthetase 2 | NM_017827 |

FIG.14D

| SEQ. ID NO: | Sequence | Position/Gene type | Acc. No. |
|---|---|---|---|
| 643 | QEQSFVIRA | 422-430<br>integrin, beta 2 (antigen CD18 (p95), lymphocyte function-associated antigen 1; macrophage antigen 1 (mac-1) beta subunit) | NM_000211 |
| 644 | QQKLSRLQY | 636-644<br>integrin, alpha 3 (antigen CD49C, alpha 3 subunit of VLA-3 receptor) | NM_002204 |
| 645 | QVAEIVSKY | 217-225<br>integrin, alpha V (vitronectin receptor, alpha polypeptide antigen CD51) | NM_002210 |
| 646 | REHAPFLVA | 30-38<br>transport-secretion protein 2.2 | XM_208570 |
| 647 | RLAAAAAQSVY | 5-15<br>glutathione peroxidase I | NM_000581 |
| 648 | RLASYLDKV | 90-98<br>keratin 19 | Y00503 |
| 649 | RNADVFLKY | 1020-1028<br>triple functional domain (PTPRF interacting) | NM_007118 |
| 650 | RQGFVPAAY | 1012-1020<br>spectrin, alpha, non-erythrocytic 1 (alpha-fodrin) | NM_003127 |
| 651 | RVIEEAKTAF | 198-207<br>heme oxygenase (decycling) 1 | NM_002133 |
| 652 | RVQPKVTVY | 89-97<br>MHC class II antigen | AF450316 |
| 653 | RVYPEVTVY | 123-131<br>MHC HLA-DRB1*0411 | L42143 |
| 654 | SDHHIYL | 218-224<br>aldolase A, fructose-biphosphate | NM_000034 |

FIG.14E

| SEQ. ID NO: | Sequence | Position/Gene type | Acc. No. | |
|---|---|---|---|---|
| 655 | SHAILEALA | 204-212<br>F-box and leucine-rich repeat protein 8 | NM_018378 | S |
| 656 | SISGVTAAY | 728-736<br>IQ motif containing GTPase activating protein 1 | NM_003870 | S |
| 657 | SPVYVGRV | 216-223<br>transglutaminase 2 (C polypeptide, protein-glutamine-gamma-glutamyltransferase) | NM_004613 | S |
| 658 | SQFGTVTRF | 66-74<br>MKI67 (FHA domain) interacting nucleolar phosphoprotein | NM_032390 | S |
| 659 | SWNNHSYLY | 156-164<br>gamma-glutamyl carboxylase | NM_000821 | S |
| 660 | TFMDHVLRY | 700-708<br>ATP citrate lyase | NM_001096 | S |
| 661 | TLADLVHHV | 378-386<br>transformation/transcription domain-associated protein | NM_003496 | S |
| 662 | TLGALTVIDV | 1336-1345<br>hypothetical protein DKFZp434N074 | NM_017539 | S |
| 663 | TQMPDPKTF | 46-54<br>HSPC038 protein | NM_016096 | S |
| 664 | VEHPSLTSP | 170-178<br>HLA-DR beta gene, exon 2 | M15374 | S |
| 665 | VEPDHFKVA | 204-212<br>lectin, galactoside-binding, soluble, 3 (galectin 3) | NM_002306 | S |
| 666 | VEREVEQV | 64-71<br>EST reading frame +2 | A1278671 | S |
| 667 | VFIGTGATGATLY | 20-32<br>NADH dehydrogenase (ubiquinone) 1 alpha subcomplex, 4, 9kDa | NM_002489 | S |

FIG.14F

| SEQ. ID NO: | Sequence | Position/Gene type | Acc. No. |
|---|---|---|---|
| 68 | VLREIAEEY | 822-830<br>high density lipoprotein binding protein (vigilin) | NM_005336 |
| 669 | VLSLLSSVAL | 27-36<br>LOC153339 | XM_098362 |
| 670 | VLYDRVLKY | 484-492<br>signal recognition particle 68kDa | NM_014230 |
| 671 | VMDSKIVQV | 432-440<br>karyopherin alpha 6 (importin alpha 7) | NM_012316 |
| 672 | VQRTLMAL | 126-133<br>transgelin | NM_003186 |
| 673 | YFEYIEENKY | 238-247<br>heterogeneous nuclear ribonucleoprotein U (scaffold attachment factor A) | NM_004501 |
| 674 | YIFKERESF | 303-311<br>CGI-18 protein | NM_015947 |
| 675 | YVYEYPSRY | 164-172<br>enhancer of filamentation 1 | NM_006403 |
| 676 | YYRYPTGESY | 354-363<br>6-phosphofructo-2-kinase/fructose-2,6-biphosphatase 3 | NM_004566 |
| 677 | YYSNKAYQY | 230-238<br>human immune associatd nucleotide 2 | NM_024711 |
| 678 | SSLPTQLFK | 5-13<br>insulin-like growth factor 1 | NM_000618 |
| 679 | ATFPDTLYTY | 702-710<br>integrin, alpha 6 | NM_000210 |
| 680 | SIFDGRWAK | 107-116<br>putative membrane protein | NM_019026 |
| 681 | FRFENVNGY | 32-40<br>asparagine synthetase | NM_001673 |

FIG.14G

| SEQ. ID NO: | Sequence | Position/Gene type | Acc. No. |
|---|---|---|---|
| 682 | QRYGFSAVGF | 82-91<br>Rh type C glycoprotein | NM_016321 |
| 683 | ARLSLTYERL | 307-316<br>ATPase, H+ transporting, lysosomal interacting protein 1 | NM_001183 |
| 684 | GRYQVSWSL | 84-92<br>signal sequence receptor, delta | NM_006280 |
| 685 | KRFDDKYTL | 61-69<br>KIAA0102 | NM_014572 |
| 686 | TRWNKIVLK | 37-45<br>ubiquitin-like 5 | NM_024292 |
| 687 | LRFDGALNV | 242-250<br>tubulin, alpha 2 | NM_006001 |
| 688 | ARFSGNLLV | 310-318<br>protein transport protein SEC61 alpha subunit isoform 1 | NM_013336 |
| 689 | NRIKFVIKR | 491-499<br>general transcription factor II, I | NM_001518 |
| 690 | GRVFIIKSY | 410-418<br>high-glucose-regulated protein 8 | NM_016258 |
| 691 | SRFGNAFHL | 538-546<br>PRP8 pre-mRNA processing factor 8 homolog (yeast) | NM_006445 |
| 692 | GRTGGSWFK | 26-34<br>ATPase, Na+/K+ transporting, beta 1 polypeptide | NM_001677 |

FIG.14H

| SEQ. ID NO: | Sequence | Position/Gene symbol i | Acc.No. ii |
|---|---|---|---|
| 16 | NPPSMVAAGSVVAAV | 198-212 CCND1 | P24385 |
| 17 | SHYFKIIEDLRAQI | 126-139 KRT18 | P05783 |
| 693 | SGTQFVCETVIRSL | 644-657 M17S2 | Q14596 |
| 694 | SGTQFVCETVIRSLT | 644-658 M17S2 | Q14596 |
| 695 | LKPAFKKDGSTTAGN | 260-274 ACAA1 | P09110 |
| 696 | RDLTDYMKILTERGYS | 183-199 ACTG1 | P02571 |
| 697 | TDYLMKILTERGYS | 186-199 ACTG1 | P02571 |
| 698 | TDYLMKILTERGYSFT | 186-201 ACTG1 | P02571 |
| 699 | WISKQEYDESGPSIVHRKCF | 356-375 ACTG1 | P02571 |
| 700 | YPEEAYIADLDAKSGAS | 247-263 ACLY | P53396 |
| 701 | EGRSFLAFPTLRAYHTL | 1378-1394 AGRN | XP_372195 |
| 702 | GRSFLAFPTLRAYHT | 1379-1393 AGRN | XP_372195 |
| 703 | GRSFLAFPTLRAYHTL | 1379-1394 AGRN | XP_372195 |
| 704 | ISRAQFVPLPVSVSVE | 185-200 AHSG | P12763 |
| 705 | SPDLPKLKPDPNTLCDEF | 133-150 ALB | P02769 |
| 706 | APGKGILAADESTGSIA | 24-40 ALDOA | P04075 |
| 707 | DVPKWISIMTERSVPHLQ | 208-225 ANXA2 | P07355 |
| 708 | VPKWISIMTERSVPH | 209-223 ANXA2 | P07355 |
| 709 | SASYKADTVAKVQG | 1848-1861 APOB | P04114 |
| 710 | IVVYTGDRTVMGRIA | 257-271 ATP1A1 | P05023 |

FIG. 15A

| SEQ. ID NO: | Sequence | Position/Gene symbol[i] | Acc.No.[ii] |
|---|---|---|---|
| 711 | IVVYTGDRTVMGRIAT | 257-272 ATP1A1 | P05023 |
| 712 | FYLLYYTEFTPTEKDEY | 82-98 B2M | P61769 |
| 713 | FYLLYYTEFTPTEKDEYA | 82-99 B2M | P61769 |
| 714 | LLYYTEFTPTEK | 84-95 B2M | P61769 |
| 715 | LLYYTEFTPTEKD | 84-96 B2M | P61769 |
| 716 | LLYYTEFTPTEKDE | 84-97 B2M | P61769 |
| 717 | LLYYTEFTPTEKDEYA | 84-99 B2M | P61769 |
| 718 | YLLYYTEFTPTEK | 83-95 B2M | P61769 |
| 719 | YLLYYTEFTPTEKDE | 83-97 B2M | P61769 |
| 720 | YLLYYTEFTPTEKDEY | 83-98 B2M | P61769 |
| 721 | YLLYYTEFTPTEKDEYA | 83-99 B2M | P61769 |
| 722 | YTEFTPTEKDEY | 87-98 B2M | P61769 |
| 723 | YYTEFTPTEKDEY | 86-98 B2M | P61769 |
| 724 | TGKTPGAEIDFKYALIGTAVGVA | 74-96 C10orf128 | XP_378226 |
| 725 | TEEFEVTKTAVAHRPG | 138-153 C19orf10 | NP_061980 |
| 726 | RGYMEIEQSVKSFK | 173-186 C5orf15 | NP_064584 |
| 727 | IPWFVSDTTIHDFN | 285-298 C6orf211 | NP_078849 |
| 728 | IAYDVTYSLACVR | 306-318 CCR7 | P32248 |
| 729 | NIAYDVTYSLACVR | 305-318 CCR7 | P32248 |
| 730 | SLMVTNDGATILKN | 60-73 CCT2 | P78371 |

FIG.15B

| SEQ. ID NO: | Sequence | Position/Gene symbol[i] | Acc.No.[ii] |
|---|---|---|---|
| 731 | ATQYFADRDMFCAGRVP | 299-315 CCT7 | Q99832 |
| 732 | VATQYFADRDMFCAGRVP | 298-315 CCT7 | Q99832 |
| 733 | GPKPLFRRMSSLVGP | 26-40 MS4A1 | P11836 |
| 734 | GPKPLFRRMSSLVGPT | 26-41 MS4A1 | P11836 |
| 735 | GPKPLFRRMSSLVGPTQS | 26-43 MS4A1 | P11836 |
| 736 | SGPKPLFRRMSSLVGPTQS | 25-43 MS4A1 | P11836 |
| 737 | SGPKPLFRRMSSLVGPTQSF | 25-44 MS4A1 | P11836 |
| 738 | RDMFTLEDTL | 140-149 CD38 | P28907 |
| 739 | RDMFTLEDTLLG | 140-151 CD38 | P28907 |
| 740 | RDMFTLEDTLLGYLAD | 140-155 CD38 | P28907 |
| 741 | VQRDMFTLEDTL | 138-149 CD38 | P28907 |
| 742 | SPGEPQIIFCRSEAAHQG | 389-406 PTPRC | P08575 |
| 743 | SPGEPQIIFCRSEAAHQGVI | 389-408 PTPRC | P08575 |
| 744 | ATPLLMQALPMGALPQGP | 110-127 CD74 | P04233 |
| 745 | GHLKIMHDAIGFR | 160-172 CLN5 | O75503 |
| 746 | LGHLKIMHDAIGFR | 159-172 CLN5 | O75503 |
| 747 | NPPLFALDKDAPLRY | 47-61 CLSTN3 | Q9BQT9 |
| 748 | LEKIVLDNSVFSEHRN | 1008-1023 CLTCL1 | P53675 |
| 749 | GQRRFNLQKNFVGKVA | 177-192 COCH | O43405 |
| 750 | IGQRRFNLQKNFVGKVAL | 176-193 COCH | O43405 |

FIG.15C

| SEQ. ID NO: | Sequence | Position/ Gene symbol[i] | Acc.No.[ii] |
|---|---|---|---|
| 1190 | RRFNLQKNFVGKVA | 179-192 COCH | O43405 |
| 1191 | VPGTYKITASARGYN | 836-850 CPD | O75976 |
| 751 | LAKWVAIQSVSAWPE | 22-36 CNDP2 | Q96KP4 |
| 752 | VARFAAAATQQQTA | 404-417 CPNE3 | O75131 |
| 753 | WGALATISTLEAVR | 68-81 CREG | NP_003842 |
| 754 | VGVPYRITVTAVSASG | 385-400 IL27RA | NP_004834 |
| 755 | VPYRITVTAVSASG | 387-400 IL27RA | NP_004834 |
| 756 | DHNFVKAINAIQKSW | 171-185 CTSC | P53634 |
| 757 | KKVWYLQKLDTAYDDLG | 62-79 CTSC | P53634 |
| 758 | KYDHNFVKAINAIQKSWT | 169-186 CTSC | P53634 |
| 759 | SGMDYWIVKNSWGTGWG | 418-434 CTSC | P53634 |
| 760 | YDHNFVKAINAIQK | 170-183 CTSC | P53634 |
| 761 | YDHNFVKAINAIQKSWT | 170-186 CTSC | P53634 |
| 762 | IFSFYLSRDPDAQPG | 228-242 CTSD | P07339 |
| 763 | LSRDPDAQPGGE | 233-244 CTSD | P07339 |
| 764 | GKEYWLVKNSWGHN | 290-303 CTSS | P25774 |
| 765 | KNLKFVMLHNLEHSM | 54-68 CTSS | P25774 |
| 766 | TTAFQYIIDNKGID | 186-199 CTSS | P25774 |
| 767 | GTEYWIVRNSWGEPW | 253-267 CTSZ | Q9UBR2 |
| 768 | GYLPNQLFRTF | 730-740 DDX1 | Q92499 |

FIG.15D

| SEQ. ID NO: | Sequence | Position/ Gene symbol[i] | Acc.No.[ii] |
|---|---|---|---|
| 769 | IRFWDSGKVKEM | 367-379 DHX34 | Q14147 |
| 770 | MEKYNIEKDIAAYIK | 29-43 Dlc2 | NP_542408 |
| 771 | LPFGAQSTQRGHTE | 114-127 DPP7 | Q9UHL4 |
| 772 | SKYYVTIIDAPGHRD | 83-97 EEF1A1 | P04720 |
| 773 | IEKFEKEAAEMGKG | 39-52 EEF1A2 | Q05639 |
| 774 | IEKFEKEAAEMGKGS | 39-53 EEF1A2 | Q05639 |
| 775 | IEKFEKEAAEMGKGSF | 39-54 EEF1A2 | Q05639 |
| 776 | TIEKFEKEAAEMGKGSF | 38-54 EEF1A2 | Q05639 |
| 777 | DIDAIFKDLSIRSVR | 57-71 WBSCR1 | Q15057 |
| 778 | GVPLYRHIADLAGN | 126-139 ENO1 | P06733 |
| 779 | GVPLYRHIADLAGNSEV | 126-142 ENO1 | P06733 |
| 780 | IKEKYGKDATNVGDEG | 195-210 ENO1 | P06733 |
| 781 | IKEKYGKDATNVGDEGG | 195-211 ENO1 | P06733 |
| 782 | KEKYGKDATNVGDEGG | 196-211 ENO1 | P06733 |
| 783 | VIKEKYGKDATNVGDEGG | 194-211 ENO1 | P06733 |
| 784 | VPLYRHIADLAGN | 127-139 ENO1 | P06733 |
| 785 | VPLYRHIADLAGNSE | 127-141 ENO1 | P06733 |
| 786 | VPLYRHIADLAGNSEV | 127-142 ENO1 | P06733 |
| 787 | VPLYRHIADLAGNSEVI | 127-143 ENO1 | P06733 |
| 788 | LLQKLILWRVL | 305-315 FLJ32752 | NP_653267 |

FIG.15E

| SEQ. ID NO: | Sequence | Position/Gene symbol[i] | Acc.No.[ii] |
|---|---|---|---|
| 789 | LQNIIPASTGAAKAVG | 202-217 GAPD | P04406 |
| 790 | EPIEQKFVSISDLLVPK | 374-390 GDI2 | P50395 |
| 791 | AIFLFVDKTVPQSS | 75-88 GABARAPL2 | P60520 |
| 792 | AIFLFVDKTVPQSSL | 75-89 GABARAPL2 | P60520 |
| 793 | AIFLFVDKTVPQSSLT | 75-90 GABARAPL2 | P60520 |
| 794 | FVDKTVPQSSL | 79-89 GABARAPL2 | P60520 |
| 795 | LPSEKAIFLFVDKTVPQSSLT | 70-90 GABARAPL2 | P60520 |
| 796 | KVNLLKIKTELCKKEV | 1035-1050 GLG1 | Q92896 |
| 797 | LGKWCSEKTETGQE | 643-656 GLG1 | Q92896 |
| 798 | VNLLKIKTELCKKEV | 1036-1050 GLG1 | Q92896 |
| 799 | GNYRIESVLSSSG | 166-178 GM2A | P17900 |
| 800 | GNYRIESVLSSSGK | 166-179 GM2A | P17900 |
| 801 | LGCIKIAASLKGI | 181-193 GM2A | P17900 |
| 802 | RLGCIKIAASLKGI | 180-193 GM2A | P17900 |
| 803 | TGNYRIESVLSSSG | 165-178 GM2A | P17900 |
| 804 | TGNYRIESVLSSSGK | 165-179 GM2A | P17900 |
| 805 | TGNYRIESVLSSSGKR | 165-180 GM2A | P17900 |
| 806 | TTGNYRIESVLSSSG | 164-178 GM2A | P17900 |
| 807 | TTGNYRIESVLSSSGK | 164-179 GM2A | 17900 |
| 808 | VTRAFVAARTFAQGL | 211-225 GPC4 | O75487 |

FIG.15F

| SEQ. ID NO: | Sequence | Position/Gene symbol[i] | Acc.No.[ii] |
|---|---|---|---|
| 809 | DIFERIASEASRL | 68-80 HIST1H2BL | Q99880 |
| 810 | DIFERIASEASRLA | 68-81 HIST1H2BL | Q99880 |
| 811 | DIFERIASEASRLAH | 68-82 HIST1H2BL | Q99880 |
| 812 | DIFERIASEASRLAHY | 68-83 HIST1H2BL | Q99880 |
| 813 | VNDIFERIASEASRLAHYN | 66-84 HIST1H2BL | Q99880 |
| 814 | DDTQFVRFDSDAASQR | 53-68 HLA-A | CAA73716 |
| 815 | DDTQFVRFDSDAASQRME | 53-70 HLA-A | CAA73716 |
| 816 | DDTQFVRFDSDAASQRMEP | 53-71 HLA-A | CAA73716 |
| 817 | DDTQFVRFDSDAASQRMEPR | 53-72 HLA-A | CAA73716 |
| 818 | DTEFVRFDSDAASQRME | 54-70 HLA-A | CAA73716 |
| 819 | DTEFVRFDSDAASQRMEP | 54-71 HLA-A | CAA73716 |
| 820 | DTQFVRFDSDAASQ | 54-67 HLA-A | CAA73716 |
| 821 | DTQFVRFDSDAASQR | 54-68 HLA-A | CAA73716 |
| 822 | DTQFVRFDSDAASQRM | 54-69 HLA-A | CAA73716 |
| 823 | DTQFVRFDSDAASQRME | 54-70 HLA-A | CAA73716 |
| 824 | DTQFVRFDSDAASQRMEP | 54-71 HLA-A | CAA73716 |
| 825 | DTQFVRFDSDAASQRMEPRAP | 54-74 HLA-A | CAA73716 |
| 826 | FVRFDSDAASQR | 57-68 HLA-A | CAA73716 |
| 827 | FVRFDSDAASQRME | 57-70 HLA-A | CAA73716 |
| 828 | KHKWEAAHVAEQLR | 168-181 HLA-A | CAA73716 |

FIG. 15G

| SEQ. ID NO: | Sequence | Position/Gene symbol[i] | Acc.No.[ii] |
|---|---|---|---|
| 829 | QFVRFDSDAASQRME | 56-70 HLA-A | CAA73716 |
| 830 | TQFVRFDSDAASQ | 55-67 HLA-A | CAA73716 |
| 831 | TQFVRFDSDAASQR | 55-68 HLA-A | CAA73716 |
| 832 | TTKHKWEAAHVAEQLR | 166-181 HLA-A | CAA73716 |
| 833 | VDDTEFVREDSDAASQR | 52-68 HLA-A | CAA73716 |
| 834 | VDDTQFVRFDSDAASQRMEPRAPW | 52-75 HLA-A | CAA73716 |
| 835 | VDDTQFVRFDSDAASQRMEPRAPWIE | 52-77 HLA-A | CAA73716 |
| 836 | DLSSWTAADTAAQIT | 153-167 HLA-B | P30481 |
| 837 | DLSSWTAADTAAQITQ | 153-168 HLA-B | P30481 |
| 838 | DLSSWTAADTAAQITQRKW | 153-171 HLA-B | P30481 |
| 839 | DLSSWTAADTAAQITQRKWEAARVA | 153-177 HLA-B | P30481 |
| 840 | DTLFVRFDSDATSPRKEPRAP | 54-74 HLA-B | P30481 |
| 841 | EDLSSWTAADTAAQIT | 152-167 HLA-B | P30481 |
| 842 | EDLSSWTAADTAAQITQR | 152-169 HLA-B | P30481 |
| 843 | EDLSSWTAADTAAQITQRKW | 152-171 HLA-B | P30481 |
| 844 | EDLSSWTAADTAAQITQRKWE | 152-172 HLA-B | P30481 |
| 845 | EDLSSWTAADTAAQITQRKWEAARVA | 152-177 HLA-B | P30481 |
| 846 | GPEYWDRETQISKTNJ | 80-94 HLA-B | P30481 |
| 847 | KDYIALNEDLSSWTA | 145-159 HLA-B | P30481 |
| 848 | LNEDLSSWTAADTAAQITQRKWE | 150-172 HLA-B | P30481 |

FIG.15H

| SEQ. ID NO: | Sequence | Position/Gene symbol[i] | Acc.No.[ii] |
|---|---|---|---|
| 849 | LRWEPSSQSTVPIVGIVAG | 296-314 HLA-B | P30481 |
| 850 | LSSWTAADTAAEITERKWE | 154-172 HLA-B | P30481 |
| 851 | LSSWTAADTAAQITQR | 154-169 HLA-B | P30481 |
| 852 | LSSWTAADTAAQITQRKW | 154-171 HLA-B | P30481 |
| 853 | LSSWTAADTAAQITQRKWE | 154-172 HLA-B | P30481 |
| 854 | NEDLSSWTAADTAAQITQRK | 151-171 HLA-B | P30481 |
| 855 | TLFVRFDSDATSP | 55-67 HLA-B | P30481 |
| 856 | VDDTLFVRFDSDATSPRKEPRAP | 52-74 HLA-B | Q9TNN7 |
| 857 | DDTQFVQFDSDAASPR | 53-68 HLA-C | Q9TNN7 |
| 858 | DGKDYIALNEDLRSWT | 143-158 HLA-C | Q9TNN7 |
| 859 | DGKDYIALNEDLRSWTA | 143-159 HLA-C | Q9TNN7 |
| 860 | DGKDYIALNEDLRSWTAA | 143-160 HLA-C | Q9TNN7 |
| 861 | DTQFVQFDSDAASPR | 54-68 HLA-C | Q9TNN7 |
| 862 | DTQFVQFDSDAASPRG | 54-69 HLA-C | Q9TNN7 |
| 863 | DTQFVQFDSDAASPRGEPR | 54-72 HLA-C | Q9TNN7 |
| 864 | DTQFVQFDSDAASPRGEPRAP | 54-74 HLA-C | Q9TNN7 |
| 865 | DYIALNEDLRSWTA | 146-159 HLA-C | Q9TNN7 |
| 866 | FVQFDSDAASPRGEP | 54-71 HLA-C | Q9TNN7 |
| 867 | GKDYIALNEDLRSWT | 144-158 HLA-C | Q9TNN7 |
| 868 | GRLLRGYNQFAYDGK | 131-145 HLA-C | Q9TNN7 |

FIG. 15I

| SEQ. ID NO: | Sequence | Position/Gene symbol[i] | Acc.No.[ii] |
|---|---|---|---|
| 869 | KDYIALNEDLRSW | 145-157 HLA-C | Q9TNN7 |
| 870 | TQFVQFDSDAASPR | 55-68 HLA-C | Q9TNN7 |
| 871 | TQFVQFDSDAASPRGEPR | 55-72 HLA-C | Q9TNN7 |
| 872 | VDDTQFVQFDSDAASPRGEPR | 52-72 HLA-C | Q9TNN7 |
| 873 | VDDTQFVQFDSDAASPRGEPRAP | 52-74 HLA-C | Q9TNN7 |
| 874 | YVDDTQFVQFDSDAASPRGEPRAP | 51-74 HLA-C | Q9TNN7 |
| 875 | FGPTFVSAVDGLSFQ | 167-181 HLA-DMA | CAA54170 |
| 876 | NREEFVRFDSDVGEFR | 24-39 HLA-DPB1 | AAA36255 |
| 877 | REEFVRFDSDVGEFR | 25-39 HLA-DPB1 | AAA36255 |
| 878 | DVEVYRAVTPLGPPD | 35-49 HLA-DQB1 | CAA71450 |
| 879 | AQGALANIAVDKANLEI | 81-97 HLA-DRA | P01903 |
| 880 | IQAEFYLNPDQSGEF | 33-47 HLA-DRA | P01903 |
| 881 | GAGLFIYFRNQKGHS | 243-257 HLA-DRB1 | P13760 |
| 882 | HQEEYVRFDSDVGEYR | 62-77 HLA-DRB1 | P13760 |
| 883 | HQEEYVRFDSDVGEYRA | 62-78 HLA-DRB1 | P13760 |
| 884 | HQEEYVRFDSDVGEYRAV | 62-79 HLA-DRB1 | P13760 |
| 885 | QEEYVRFDSDVGEYR | 63-77 HLA-DRB1 | P13760 |
| 886 | YVRFDSDVGEY | 66-76 HLA-DRB1 | P13760 |
| 887 | DLRSWTAVDTAAQISEQ | 150-166 HLA-E | P13747 |
| 888 | LRSWTAVDTAAQIS | 151-164 HLA-E | P13747 |

FIG.15J

| SEQ. ID NO: | Sequence | Position/Gene symbol[i] | Acc.No.[ii] |
|---|---|---|---|
| 889 | LRSWTAVDTAAQISEQ | 151-166 HLA-E | P13747 |
| 890 | VDDTQFVRFDSDSACPRMEP | 52-71 HLA-G | P17693 |
| 891 | YVDDTQFVRFDSDSACPRMEPRAP | 51-74 HLA-G | P17693 |
| 892 | AIPFVIEKAVRSSIY | 146-160 HPCL2 | Q9UJ83 |
| 893 | AIPFVIEKAVRSSIYG | 146-161 HPCL2 | Q9UJ83 |
| 894 | NVLRIINEPTAAAIAY | 168-183 HSPA1B | P08107 |
| 895 | RIINEPTAAAIA | 171-182 HSPA1B | P08107 |
| 896 | RIINEPTAAAIAYG | 171-184 HSPA1B | P08107 |
| 897 | VLRIINEPTAAAIA | 169-182 HSPA1B | P08107 |
| 898 | VLRIINEPTAAAIAY | 169-183 HSPA1B | P08107 |
| 899 | VLRIINEPTAAAIAYG | 169-184 HSPA1B | P08107 |
| 900 | VMRIINEPTAAAIAYG | 195-210 HSPA5 | P11021 |
| 901 | VPTKKSQIFSTASDNQPTVT | 443-462 HSPA5 | P11021 |
| 902 | GERAMTKDNNLLGRFE | 447-462 HSPA6 | P17066 |
| 903 | ERAMTKDNNLLGKFEL | 446-461 HSPA8 | P11142 |
| 904 | GERAMTKDNNLLGKFE | 445-460 HSPA8 | P11142 |
| 905 | GERAMTKDNNLLGKFEL | 445-461 HSPA8 | P11142 |
| 906 | GILNVSAVDKSTGKE | 484-498 HSPA8 | P11142 |
| 907 | RAMTKDNNLLGKFE | 447-460 HSPA8 | P11142 |
| 908 | IPIIIHPIDRSVD | 109-121 MTP18 | NP_057582 |

FIG. 15K

| SEQ. ID NO: | Sequence | Position/Gene symbol [i] | Acc.No. [ii] |
|---|---|---|---|
| 909 | DRKMVGDVTGAQAY | 65-78 IFITM1 | P13164 |
| 910 | DRKMVGDVTGAQAYA | 65-79 IFITM1 | P13164 |
| 911 | LGFIAFAYSVKSRD | 52-65 IFITM1 | P13164 |
| 912 | LITFLCDRDAGVGFP | 726-740 IGF2R | P11717 |
| 913 | LITFLCDRDAGVGFPE | 726-741 IGF2R | P11717 |
| 914 | KNTLYLQMNSLKTEDTA | 29-45 IGH@ | AAM87802 |
| 915 | NTLYLQMNSLKTEDT | 30-44 IGH@ | AAM87802 |
| 916 | NTLYLQMNSLKTEDTA | 30-45 IGH@ | AAM87802 |
| 917 | TLYLQMNSLKTED | 31-43 IGH@ | AAM87802 |
| 918 | TLYLQMNSLKTEDT | 31-44 IGH@ | AAM87802 |
| 919 | TLYLQMNSLKTEDTA | 31-45 IGH@ | AAM87802 |
| 920 | YLQMNSLKTEDT | 33-43 IGH@ | AAM87802 |
| 921 | ESGPTTYKVTSTLTIKESDWL | 171-191 IGHM | P01871 |
| 922 | GPTTYKVTSTLTIK | 173-186 IGHM | P01871 |
| 923 | GPTTYKVTSTLTIKE | 173-187 IGHM | P01871 |
| 924 | SGPTTYKVTSTLTIK | 172-186 IGHM | P01871 |
| 925 | SGPTTYKVTSTLTIKESDWL | 172-191 IGHM | P01871 |
| 926 | EPRRYGSAAALPS | 68-80 IGHMBP2 | P38935 |
| 927 | HKSYSCQVTHEGSTV | 81-95 IGLC1 | P01842 |
| 928 | HKSYSCQVTHEGSTVE | 81-96 IGLC1 | P01842 |

FIG. 15L

| SEQ. ID NO: | Sequence | Position/Gene symbol[i] | Acc.No.[ii] |
|---|---|---|---|
| 929 | KSHKSYSCQVTHEGSTVE | 79-96 IGLC1 | P01842 |
| 930 | KSYSCQVTHEGST | 82-94 IGLC1 | P01842 |
| 931 | KSYSCQVTHEGSTV | 82-95 IGLC1 | P01842 |
| 932 | KSYSCQVTHEGSTVE | 82-96 IGLC1 | P01842 |
| 933 | KSYSCQVTHEGSTVEK | 82-97 IGLC1 | P01842 |
| 934 | SHKSYSCQVTHEGST | 80-94 IGLC1 | P01842 |
| 935 | SHKSYSCQVTHEGSTV | 80-95 IGLC1 | P01842 |
| 936 | SHKSYSCQVTHEGSTVE | 80-96 IGLC1 | P01842 |
| 937 | SHKSYSCQVTHEGSTVEKT | 80-98 IGLC1 | P01842 |
| 938 | TPEQWKSHKSYSCQVTHEGSTVE | 74-96 IGLC1 | P01842 |
| 939 | IEVWVEAENALGKVT | 194-208 IL6ST | P40189 |
| 940 | YPSHSFIGEESVAAGEK | 62-78 IMPA1 | P29218 |
| 941 | DTGSYRAQISTKTSAK | 103-118 SLAMF6 | CAC59749 |
| 942 | FSQFLGDPVEKAAQ | 411-424 KIAA0494 | O75071 |
| 943 | LPSSYEEALSLPSKTP | 236-250 LAPTM5 | Q13571 |
| 944 | LPSYEEALSLPSKTPE | 236-251 LAPTM5 | Q13571 |
| 945 | LPSYEEALSLPSKTPEG | 236-252 LAPTM5 | Q13571 |
| 946 | VVLPSYEEALSLPSKTPE | 234-251 LAPTM5 | Q13571 |
| 947 | GVPKDYTGEDVTPQN | 98-112 LGMN | Q99538 |
| 948 | VPKDYTGEDVTPQN | 99-112 LGMN | Q99538 |

FIG.15M

| SEQ. ID NO: | Sequence | Position/ Gene symbol[i] | Acc.No.[ii] |
|---|---|---|---|
| 949 | DVRKLYWLMKSSLNGDN | 902-918 LNPEP | Q9UIQ6 |
| 950 | KPTICSDQDNYCVT | 37-50 LY6E | Q16553 |
| 951 | LKPTICSDQDNYCVT | 36-50 LY6E | Q16553 |
| 952 | HPPELLFSASLPALG | 559-573 MAN2B1 | O00754 |
| 953 | VDYFLNVATAQGRYY | 292-306 MAN2B1 | O00754 |
| 954 | TPISEVYESEKDEDGFL | 92-108 MAP1LC3B | Q9GZQ8 |
| 955 | TPISEVYESEKDEDGFLY | 92-109 MAP1LC3B | Q9GZQ8 |
| 956 | SPDRVYINYYDMNAAN | 90-105 MIF | P14174 |
| 957 | VPDGFLSELTQQLAQ | 14-28 MIF | P14174 |
| 958 | DGRTFYIDHNSKITQ | 541-555 NEDD4L | NP_056092 |
| 959 | GPVGVFEWEAFARGT | 337-351 PGK1 | P00558 |
| 960 | RVVMRVDFNVPMKN | 17-30 PGK1 | P00558 |
| 961 | SPDDKYIYVADILAHEIH | 228-245 PON2 | Q15165 |
| 962 | LPGLAKQPSFRQYSG | 38-52 PPGB | P10619 |
| 963 | VSFELFADKVPKTAEN | 19-34 PPIA | P05092 |
| 964 | GPSYWCQNTETAAQ | 498-511 PSAP | P07602 |
| 965 | VPGFADDPTELACRV | 417-431 PTGFRN | Q9P2B2 |
| 966 | GALLVYDITSRETYN | 83-97 RAB4A | P20338 |
| 967 | LIPSYIRDSTVAVW | 78-92 RAB6B | Q9NRW1 |
| 968 | FPEPIKLDKNDRAKASA | 186-202 RAB7 | P51149 |

FIG.15N

| SEQ. ID NO: | Sequence | Position/Gene symbol[i] | Acc.No.[ii] |
|---|---|---|---|
| 969 | AFFTLARDIKAKMD | 161-174 RAB8A | P61006 |
| 970 | NAFFTLARDIKAKMD | 160-174 RAB8A | P61006 |
| 971 | LLQQISQHQEHF | 313-324 RAD23B | P54727 |
| 972 | TEQFTAMRDLYMKN | 61-74 RAP1A | P10113 |
| 973 | IPSVFIGESSANSLKD | 145-160 RNF13 | O43567 |
| 974 | ADRDTYRRSAVPPGAD | 122-137 RPS10 | P46783 |
| 975 | DRDTYRRSAVPPGAD | 123-137 RPS10 | P46783 |
| 976 | RDTYRRSAVPPGAD | 124-137 RPS10 | P46783 |
| 977 | LPPNWKYESSTASA | 134-147 RPS13 | P62277 |
| 978 | RTFHRAASSAAQGAF | 308-326 SCAMP2 | O15127 |
| 979 | SRTFHRAASSAAQGA | 309-325 SCAMP2 | O15127 |
| 980 | SSRTFHRAASSAAQGA | 310-325 SCAMP2 | O15127 |
| 981 | SSRTFHRAASSAAQGAF | 310-326 SCAMP2 | O15127 |
| 982 | YGSYSTQASAAAAT | 83-96 SCAMP3 | O14828 |
| 983 | YGSYSTQASAAAATA | 83-97 SCAMP3 | O14828 |
| 984 | YGSYSTQASAAAATAE | 83-98 SCAMP3 | O14828 |
| 985 | VPMYIGEISPTALR | 162-175 SLC2A14 | NP_703150 |
| 986 | ISIYSSERSVLQ | 519-530 SEMA7A | O75326 |
| 987 | VAAVFIAQLSQQSLDFVK | 396-413 SLC1A5 | Q15758 |
| 988 | TGALYRIGDLQAFQGHG | 120-136 SLC3A2 | P08195 |

FIG. 15O

| SEQ. ID NO: | Sequence | Position/Gene symbol[i] | Acc.No.[ii] |
|---|---|---|---|
| 989 | DYYKGEESNSSANK | 150-163 NAPB | Q9H115 |
| 990 | KPGIYRSNMDGSAAY | 899-913 SORL1 | Q92673 |
| 991 | RHPINEYYIADASEDQVF | 343-360 SORL1 | Q92673 |
| 992 | NPRKFNLDATELSIR | 74-88 STX6 | Q43752 |
| 993 | NPRKFNLDATELSIRK | 74-89 STX6 | Q43752 |
| 994 | NPRKFNLDATELSIRKA | 74-90 STX6 | Q43752 |
| 995 | GPPIGSFTLIDSEVSQL | 88-104 unnamed protein product | BAD18470 |
| 996 | NPKDVLVGADSVRAAITF | 134-151 SYNGR2 | O43760 |
| 997 | HKGEIRGASTPFQFR | 107-121 TAX1BP1 | NP_006015 |
| 998 | DVAFVKDQTVIQ | 555-566 TF | Q29443 |
| 999 | FVKDQTVIQNTD | 558-569 TF | Q29443 |
| 1000 | GDVAFVKDQTVIQ | 554-566 TF | Q29443 |
| 1001 | GDVAFVKDQTVIQNTD | 554-569 TF | Q29443 |
| 1002 | CPSDWKTDSTCRMVT | 353-367 TFRC | P02786 |
| 1003 | CPSDWKTDSTCRMVTS | 353-368 TFRC | P02786 |
| 1004 | CPSDWKTDSTCRMVTSE | 353-369 TFRC | P02786 |
| 1005 | FTYINLDKAVLGTSN | 479-493 TFRC | P02786 |
| 1006 | YVAYSKAATVTGKL | 219-232 TFRC | P02786 |
| 1007 | EIIHKALIDRNIQ | 62-74 TNFAIP3 | P21580 |

FIG.15P

| SEQ. ID NO: | Sequence | Position/ Gene symbol[i] | Acc.No.[ii] |
|---|---|---|---|
| 1008 | GPLSWYSDPGLAGVS | 105-119 TNFSF9 | P41273 |
| 1009 | LKPEFVDIINAKQ | 236-248 TPI1 | P60174 |
| 1010 | GSSYGSETSIPAAAH | 811-825 TTYH3 | XP_166523 |
| 1011 | AKFWEVISDEHGIDPT | 18-33 TUBB1 | P07437 |
| 1012 | EPYNATLSVHQL | 181-192 TUBB5 | P05218 |
| 1013 | EPYNATLSVHQLVE | 181-194 TUBB5 | P05218 |
| 1014 | DYNIQKESTLHLVLR | 58-72 UBA52 | P02248 |
| 1015 | SDYNIQKESTLHLV | 57-70 UBA52 | P02248 |
| 1016 | DKGAFRIEINFPAEYPFKPP | 47-66 UBE2L3 | P51966 |
| 1017 | KGAFRIEINFPAEYPFKPP | 48-66 UBE2L3 | P51966 |
| 1018 | NPPYDKGAFRIEINFPAEYPFKPP | 43-66 UBE2L3 | P51966 |
| 1019 | PPYDKGAFRIEINFPAEYPFKPP | 44-66 UBE2L3 | P51966 |
| 1020 | NPDTLSAMSNPRAMQ | 447-461 UBQLN1 | Q9UMX0 |
| 1021 | QLIYIPLPDEKSRVA | 640-654 VCP | P55072 |
| 1022 | AAKYQLDPTASISA | 248-261 VDAC2 | P45880 |
| 1023 | DPDPEDFADEQSLVGRFI | 478-495 VPS35 | Q96QK1 |
| 1024 | APSGFYIASGDVSGKL | 67-82 WDR1 | O75083 |
| 1025 | APSGFYIASGDVSGKLR | 67-83 WDR1 | O75083 |
| 1026 | RASWRIISSIEQKEE | 57-71 YWHAE | NP_006752 |

[i]:According to HUGO gene nomenclature
[ii]:Accession Number according to Entrez Protein Database (NCBI)

FIG.15Q

Peptide sequences aligned according to the motif of HLA-DRB1*0101.

| SEQ ID NO: | | | | -3 | -2 | -1 | 1 | 2 | 3 | 4 | 5 | 6 | 7 | 8 | 9 | +1 | +2 | +3 | Gene Symbol | Acc. Nr. | Position | SYFPEITHI Score |
|---|---|---|---|---|---|---|---|---|---|---|---|---|---|---|---|---|---|---|---|---|---|---|
| 8 | S | Q | D | I | K | G | I | Q | K | L | Y | G | K | R | S | | | | MMP7 | NP_002414 | 247-262 | 35 |
| 1027 | | N | D | D | K | P | I | T | P | E | T | A | E | K | L | A | R | D | CDC42 | NP_426359 | 132-148 | 26 |
| 1028 | | D | D | P | S | T | I | E | K | I | P | S | N | K | Q | K | P | | CDC42 | NP_426359 | 121-136 | 19 |
| 1029 | | | | | N | P | L | E | I | F | P | N | K | R | I | L | R | R | CDH3 | NP_001784 | 91-105 | 27 |
| 1030 | | | | E | T | G | W | L | L | M | S | K | Q | P | D | R | | H | CDH3 | NP_001784 | 163-175 | 19 |
| 1031 | | | | D | N | E | L | Q | E | M | N | A | F | L | G | S | K | | CLU | NP_001822 | 80-92 | 24 |
| 1032 | | A | A | G | L | L | Y | S | T | Y | R | A | T | L | K | S | H | | COL15A1 | NP_001846 | 1243-1257 | 24 |
| 1033 | A | P | S | L | R | D | Y | E | V | D | A | T | L | K | S | L | N | Q | COL1A2 | NP_000080 | 1125-1145 | 25 |
| 1034 | | | | G | P | V | V | R | E | L | Q | A | K | A | I | G | A | V | P | CTSD | NP_001900 | 303-319 | 26 |
| 1035 | | | | P | I | N | H | E | V | S | M | I | Q | W | G | I | S | D | G | CTSZ | NP_001327 | 239-253 | 33 |
| 1036 | V | P | D | D | R | D | F | E | P | S | L | G | P | V | C | P | F | R | | DCN | NP_001911 | 40-57 | 23 |
| 1037 | L | P | Q | S | V | Y | M | Y | K | P | M | S | D | R | S | V | P | S | EFEMP1 | NP_004096 | 389-408 | 30 |
| 1038 | | | | I | V | H | R | Y | V | L | I | T | E | R | S | V | P | A | EFEMP2 | NP_058634 | 343-358 | 30 |
| 1039 | | | | K | N | G | I | K | Y | V | L | K | G | R | P | C | K | | | EF5A | NP_001961 | 27-39 | 28 |
| 1040 | | | T | I | Y | K | F | K | E | K | V | E | A | L | P | P | | | FN1 | NP_002017 | 1930-1944 | 23 |
| 1041 | | | T | G | N | Y | I | N | L | K | E | K | G | S | L | K | D | Q | FN1 | NP_002017 | 2134-2147 | 20 |
| 1042 | | | Y | R | V | R | V | T | P | K | E | K | L | G | K | P | | | FN1 | NP_002017 | 1749-1764 | 21 |
| 1043 | | | L | S | N | R | Y | L | R | F | L | A | T | R | G | P | | | FN1 | NP_002017 | 659-674 | 24 |
| 1044 | | | I | N | N | S | L | R | F | L | R | T | K | P | N | S | L | | FN1 | NP_997640 | 1908-1919 | 26 |
| 1045 | | | | D | L | V | P | A | P | A | G | R | I | L | I | L | T | P | GDF15 | NP_004855 | 76-92 | 25 |
| 1046 | | | A | E | L | A | G | N | A | A | R | N | A | A | R | D | N | | H2AFJ | NP_808760 | 61-74 | 32 |
| 1047 | | | E | P | V | L | K | A | G | N | R | W | A | V | G | A | L | | HEXB | NP_000512 | 153-169 | 32 |
| 1048 | Y | T | A | E | I | L | E | L | A | G | N | A | A | R | D | N | K | | HIST3H2A | NP_254280 | 60-75 | 32 |
| 1049 | H | L | K | I | K | K | G | H | A | K | T | V | H | K | A | K | | | GFBP3 | NP_000589 | 166-181 | 25 |
| 1050 | P | S | I | | K | K | G | H | A | K | D | S | Q | | | | | | IGFBP3 | NP_000589 | 169-184 | 28 |

FIG.16A

Peptide sequences aligned according to the motif of HLA-DRB1*0101.

| SEQ ID NO: | Sequence | | | | | | | | | | | | | | | Symbol | Acc. Nr. | Position | SYFPEITHI Score |
|---|---|---|---|---|---|---|---|---|---|---|---|---|---|---|---|---|---|---|---|
| 1051 | | R | P | K | H | T | R | I | S | E | L | K | A | E | A | V | K | K | D | | | IGFBP5 | NP_000590 | 138-155 | 32 |
| 1052 | | | G | P | E | D | N | V | V | I | Y | L | K | A | S | R | A | G | N | P | E | ISLR | NP_005536 | 380-397 | 26 |
| 1053 | | | | S | R | P | V | I | N | I | K | P | T | I | T | V | G | T | P | N | | ITGA6 | NP_000201 | 464-479 | 32 |
| 1054 | L | D | L | S | F | N | Q | A | R | L | Q | P | S | G | L | P | V | | | | | LUM | NP_002336 | 189-205 | 30 |
| 1055 | | | | K | L | P | S | K | E | G | L | H | A | I | V | S | | | | | | MAP2K1IP1 | NP_068805 | 12-27 | 32 |
| 1056 | | | | D | T | S | T | L | E | M | M | H | A | P | R | C | G | | | | | MMP12 | NP_002417 | 80-93 | 23 |
| 1057 | D | Q | N | T | I | E | T | M | R | K | P | R | C | G | N | P | D | D | R | | | MMP2 | NP_004521 | 90-106 | 20 |
| 1058 | | | | N | P | G | E | Y | R | V | T | A | H | A | E | G | Y | P | S | | | AEBP1 | NP_001120 | 947-963 | 20 |
| 1059 | | | | | L | D | F | L | K | A | V | D | I | N | R | A | S | V | G | | | PLXDC2 | NP_116201 | 69-83 | 29 |
| 1060 | | | | | | | | H | G | E | A | L | N | T | N | G | V | V | H | V | I D R | POSTN | NP_006466 | 213-228 | 23 |
| 1061 | | | | | | | | I | E | A | K | K | L | H | E | L | R | P | G | | | RBM14 | NP_006319 | 50-63 | 32 |
| 1062 | D | P | G | V | L | | R | A | M | I | N | V | A | S | D | P | G | | | | | S100A11 | NP_005611 | 56-72 | 25 |
| 1063 | | | | N | D | E | R | M | E | I | R | A | S | A | P | I | P | | | | | SDCBP | NP_001007069 | 56-71 | 26 |
| 1064 | | | | | P | E | A | I | L | S | Q | E | A | Q | T | V | G | A | P | | | SDCBP | NP_001007068 | 29-41 | 24 |
| 1065 | | | | | | K | V | K | Y | A | I | P | V | T | N | P | H | | | | | SDCBP | NP_001007070 | 14-27 | 30 |
| 1066 | | | | | N | G | A | V | K | V | F | Q | A | T | R | N | P | A | | S | | SPP1 | NP_000573 | 185-201 | 19 |
| 1067 | | | | T | T | N | Y | V | K | A | I | H | P | L | Q | D | L | P | A | | | TGFBI | NP_000349 | 621-636 | 29 |
| 1068 | | | T | | T | T | Q | L | Y | T | D | R | T | E | K | L | R | E | E | | | TGFBI | NP_000349 | 116-131 | 23 |
| 1069 | | | | | | | | K | E | Y | L | I | A | R | T | P | G | | | | | TIMP2 | NP_003246 | 106-120 | 25 |
| 1070 | | | | G | | K | G | K | F | D | K | A | K | L | K | K | L | | | | T | TMSB10 | NP_066926 | 6-20 | 20 |
| 1071 | M | A | E | I | E | K | F | D | K | S | K | L | K | K | T | | | | | | | TMSB4Y | NP_004193 | 6-19 | 19 |
| 1072 | | V | V | S | I | E | Q | K | T | E | G | A | E | K | K | | | | | | | YWHAZ | NP_003397 | 61-75 | 22 |
| 1073 | | | | | I | S | K | I | K | K | A | H | G | K | A | | | | | | | IGFBP3 | NP_000589 | 169-181 | 25 |
| 16 | | H | S | N | P | P | S | M | V | A | A | G | S | V | V | A | | | | | V | CCND1 | NP_444284 | 198-212 | 24 |

FIG. 16B

| Internal Sequence ID | Antigen | Sequence | SEQ. ID NO: |
|---|---|---|---|
| IMA-MMP-001 | Matrix Metalloproteinase 7 | SQDDIKGIQKLYGKRS | 8 |
| IMA-ADF-002 | Adipophilin | VMAGDIYSV | 2 |
| IMA-ADF-001 | Adipophilin | SVASTITGV | 1 |
| IMA-APO-001 | Apolipoprotein L1 | ALADGVQKV | 3 |
| IMA-CCN-001 | Cyclin D1 | LLGATCMFV | 4 |
| IMA-GUC-001 | GUCY1A3 | SVFAGVVGV | 5 |
| IMA-K67-001 | KIAA0367 | ALFDGDPHL | 6 |
| IMA-MET-001 | c-met proto-oncogene | YVDPVITSI | 7 |
| IMA-MUC-001 | MUC1 | STAPPVHNV | 9 |
| IMA-RGS-001 | RGS-5 | LAALPHSCL | 10 |
| IMA-HBV-001 | HBV | FLPSDFFPSV | 1135 |

FIG.17

| SEQ.ID NO: | Sequence | Position/Gene | Acc. No. |
|---|---|---|---|
| | Patient RCC01 HLA-A*02 | | |
| 7 | YVDPVITSI | 654-662<br>met proto-oncogen | J02958 |
| 1 | SVASTITGV | 129-137<br>adipose differentiation-related protein | X97324 |
| 1075 | ALLNIKVKL | 365-373<br>keratin 18 | M26326 |
| 6 | ALFDGDPHL | 1-9<br>KIAA0367 | AB002365 |
| 1076 | RLLDYVVNI | 679-687<br>hypothetical protein FLJ20004 | AB040951 |
| 1077 | ALANGIEEV | 101-109<br>apolipoprotein L, 3 | AY014906 |
| 1078 | QLIDKVWQL | 593-601<br>SEC14 (S. cerevisiae)-like 1 | D67029 |
| 1079 | ALSDLEITL | 389-397<br>mitogen inducible 2 | Z24725 |
| 1080 | ILDTGTIQL | 174-182<br>kidney and liver-specific gen | AB013094 |
| 1081 | SLLGGDVVSV | 27-36<br>delta sleep inducing peptide, immunoreactor | AF153603 |
| 1082 | FLDGNELTL | 167-175<br>chloride intracellular channel 1 | U93205 |
| 1083 | NLLPKLHIV | 179-187<br>chloride intracellular channel 1 | U93205 |
| 1084 | ALASHLIEA | 507-515<br>EH-domain containing 2 | AF181263 |
| 1085 | SLYGGTITI | 296-304<br>hypothetical protein FLJ11189 | AK000697 |

FIG.18A

| SEQ. ID NO: | Sequence | Position/Gene | Acc. No. |
| --- | --- | --- | --- |
| 1086 | FLLDKKIGV | 218-226<br>chaperonin containing TCP1, subunit 2 (beta) | AF026166 |
| 1192 | FLDGNEMTL | 178-186<br>chloride intracellular channel 4 | AF097330 |
| 1087 | AIVDKVPSV | 147-155<br>coat-protein gamma-cop | AF100756 |
| 1088 | DVASVIVTKL | 241-250<br>signal recognition particle 54kD | U51920 |
| 1089 | LASVSTVL | 130-137<br>hemoglobin, alpha 2 | AF230076 |
| 1090 | VMAPRTLVL | 3-11<br>HLA-A | |
| 1091 | LLFDRPMHV | 267-275<br>hnRNP M | L03532 |
| 1092 | MTSALPIIQK | 62-71<br>adipose differentiation-related protein | X97324 |
| 1093 | MAGDIYSVFR | 349-358<br>adipose differentiation-related protein | X97324 |
| 1094 | ETIPLTAEKL | 115-124<br>cyclin D1/PRAD1 | X59798 |
| 1095 | DVMVGPFKLR | 934-943<br>Akinase (PRKA) anchor protein 2 | AJ303079 |
| 1096 | TIIDILTKR | 64-72<br>annexin A1 | X05908 |
| 1097 | TIVNILTNR | 55-63<br>annexin A2 | BC001388 |
| 1098 | TIIDIITHR | 385-393<br>annexin A6 | J03578 |

FIG.18B

| SEQ. ID NO: | Sequence | Position/Gene | Acc. No. |
|---|---|---|---|
| 680 | SIFDGRVVAK | 107-116<br>putative membrane protein | AB020980 |
| 1099 | STIEYVIQR | 115-123<br>Sec23 (S. cerevisiae) homolog B | BC005032 |
| 1100 | ELIKPPTILR | 132-141<br>adaptor-related protein complex 3 | AF092092 |
| 1101 | EIAMATVTALR | 248-258<br>aldolase A, fructose-biphosphate | X12447 |
| 1102 | ETIGEILKK | 95-103<br>MRRNPK | BC000355 |
| 1103 | SLADIMAKR | 86-94<br>ribosomal protein L24 | BC000690 |
| 1104 | EEIAFLKKL | 229-237<br>vimentin | M14144 |
| 1105 | DEAAFLERL | 92-100<br>caldesmon 1 | M64110 |
| 1106 | DEMKVLVL | 545-522<br>spectrin, beta, non-erythrocytic 1 | M96803 |
| 1107 | DEVKFLTV | 191-198<br>annexin A4 | M82809 |
| 1108 | NENSLFKSL | 935-943<br>clathrin, heavy polypeptide (Hc) | D21260 |
| 1109 | DEFKVVVV | 373-380<br>coat protein, gamma-cop | AF100756 |
| 1110 | EEVKLIKKM | 137-145<br>ferritin, light polypeptide | M11147 |
| 1111 | DEVKLPAKL | 158-166<br>polymerase I and transcript release factor | AF312393 |

FIG.18C

| SEQ. ID NO: | Sequence | Position/Gene | Acc. No. |
|---|---|---|---|
| 1112 | TERELKVAY | 637-645<br>hypothetical protein FLJ20004 | AB040951 |
| 1113 | NEFSLKGVDF | 86-95<br>ets-1 | J04101 |
| 1114 | NEQDLGIQY | 169-177<br>catenin alpha 1 | D13866 |
| 1115 | EERIVELF | 306-313<br>signal transducer and activator of transcription 3 | BC000627 |
| 1116 | EEIREAFRVF | 84-93<br>calmodulin 3 | J04046 |
| 1117 | DEYIYRHFF | 344-352<br>cell cycle progression 8 protein | AF011794 |
| 1118 | DELELHQRF | 308-316<br>adenovirus 5 E1A binding protein | X86098 |
| 1119 | SEVKFTVTF | 80-88<br>galectin 2 | M87842 |
| 1120 | IETIINTF | 12-19<br>calgranulin B | M26311 |
| 1121 | KENPLQFKF | 61-69/72-80<br>villin 2 (ezrin)/(radixin) | J05021/<br>L02320 |
| 1122 | DEVRTLTY | 41-48<br>hnRNP methyltransferase, S. cerevisiae-like 2 | Y10807 |
| 1123 | GEAVVNRVF | 43-51<br>large multifunctional protease 2, LMP2 | Z14977 |
| 1124 | EEVLIPDQKY | 385-394<br>F-box and leucine-rich repeat protein 3A | AF126028 |
| 1125 | DEGRLY | 163-171<br>sterol O-acyltransferase 1 | L21934 |

FIG.18D

| SEQ. ID NO: | Sequence | Position/Gene | Acc. No. |
|---|---|---|---|
| 1126 | DEVELIHF | 838-845<br>chromatin-specific transcription elongation factor | AF152961 |
| 1127 | VEVLLNYAY | 83-91<br>NS 1-binding protein | AF205218 |
| 1128 | TENDIRVMF | 120-128<br>CUG triplet repeat, RNA-binding protein 1 | AF267534 |
| 1129 | LEGLTVVY | 62-69<br>coatomer protein complex subunit zeta 1 | AF151878 |
| 1130 | NELPTVAF | 192-199<br>hypothetical protein | AK001475 |
| 1131 | EEFGQAFSF | 77-85<br>MHC, class II, DP alpha 1 | X03100 |
| 1132 | VEAIFSKY | 33-40<br>hnRNP C (C1/C2) | M29063 |
| 1133 | DERTFHIFY | 277-285<br>myosin, heavy polypeptide 10, non-muscle | M69181 |
| 1193 | TEKVLAAVY | 206-214<br>aldolase B, fructose-bisphosphate | K01177 |
| 1194 | VESPLSVSF | 159-167<br>hypothetical protein FLJ22318 | AK025971 |
| 1195 | SEAGSHTLQW | MHC-I | |
| 1134 | DEGKVIRF | 56-63<br>EST reading frame-1 | BF431469 |
| Patient RCC13<br>HLA-A*02 | | | |
| 1196 | ALAAVVTEV | frameshift, DDX3 reading frame +2 | AF061337 |
| 1197 | TLIEDILGV | 209-217<br>transient receptor protein 4 associated protein | AL132825 |

FIG.18E

| SEQ. ID NO: | Sequence | Position/Gene | Acc. No. |
|---|---|---|---|
| 1198 | ALFGALFLA | 2-10<br>phospholipid transfer protein | L26232 |
| 1199 | VLATLVLLL | 72-80<br>EST | AA483794 |
| 1200 | TLDDLIAAV | 325-333<br>hypothetical protein FLJ10042 | AK000904 |
| 1201 | YLDNGVVFV | 316-324<br>damage-specific DNA binding protein 1 (127kD) | U18299 |
| 5 | SVFAGVVGV | 581-589<br>guanylate cyclase 1, soluble, alpha 3 | U58855 |
| 1202 | SLINVGLISV | 48-57<br>acidic protein rich in leucines | BC000476 |
| 3 | ALADGVQKV | 176-184<br>apolipoprotein L, 1) | AF323540 |

HLA-A*24

| 1203 | TYGEIFEKE | 107-115<br>NADH dehydrogenase (ubiquinone) 1, (B14.5b) | AF070652 |
|---|---|---|---|
| 1204 | YYMIGEQKF | 203-211<br>nicotinamide-n-methyltransferase | U08021 |

FIG.18F

COMBINATION THERAPY USING ACTIVE IMMUNOTHERAPY

RELATED APPLICATIONS

This application is a continuation of U.S. application Ser. No. 12/055,151, which was filed on Mar. 25, 2008, which claims priority to U.S. provisional application 60/908,012, which was filed on Mar. 26, 2007, the contents of which are incorporated herein by reference in their entireties.

BACKGROUND OF THE INVENTION

Although there have been great improvements in the diagnosis and treatment of cancer, many people die from cancer each year, and their deaths are typically due to metastases and cancers that are resistant to conventional therapies.

Most drug-mediated cancer therapies rely on chemotherapeutical agents, i.e. cytotoxic agents, selective for dividing cells. These agents are usually administered at or near maximum tolerated doses resulting in frequent dramatic toxicities that compromise the quality of life and have a severe effect on the immune response. However, such drugs almost inevitably do not kill all of the cancer cells in the patient since some of them acquire a resistance against the particular drug.

Anticancer drugs in general are more effective when used in combination. In particular, combination therapy is desirable in order to avoid an overlap of major toxicities, mechanism of action and resistance mechanism(s). The major advantages of combining chemotherapeutic drugs are that it may promote additive or possible synergistic effects through biochemical interactions and may also decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Various combination and treatment schemes were developed to overcome the developing drug resistance of cancer cells so that nowadays numerous combinations, mainly of conventional cytotoxic drugs, are used in current treatments. An extensive review of current medical practices may be found in "Oncologic Therapies" edited by E. E., Vokes and H. M. Golomb, published by Springer.

Kinase Inhibitors in Combination with Chemotherapeutics of Other Classes

Several references describe combinations of Sunitinib malate with other agents. For example, U.S. Patent Publication No. 2003-0216410 describes combinations of sunitinib malate with cyclooxygenase inhibitors. U.S. Patent Publication No. 2004-0152759 describes combinations of sunitinib malate with several agents, such as CPT-11 (topoisomerase inhibitor irinotecan, Camptosar™), the cytosceletal disruptor docetaxel and 5-fluorouracil (5-FU). However, no combinations with active immunotherapy are disclosed.

Kinase Inhibitors in Combination with Non-Specific Immunotherapy

Non-specific immunotherapy usually relies on molecule such as cytokines and interleukins to activate the immune system of a recipient in a non-specific manner so that an already present but weak immune response of the patient may be enhanced to reach beneficial levels. The rational behind this kind of treatment is the fact that tumor cells usually do not express MHC II and costimulators, which means that they usually do not activate helper T cells and no immune response ensues. Cytokine/interleukin treatment attempts to by-pass the need for helper T cells by providing cytokines for T cell growth and activation. Trials currently are under way to determine whether a combination of the TKI Genistein with interleukin-2 may be beneficial (Phase II Pilot Study of Genistein and High-Dose Interleukin-2 in Patients With Metastatic Malignant Melanoma or Renal Clear Cell Carcinoma NCT00276835).

While chemotherapeutics and their combinations are the mainstay of the majority of antitumor drug treatment strategies, other classes of drugs are being developed. They include specific active and passive immunotherapies. Additional combination therapies and treatment regimens encompassing these novel specific immunotherapies for the treatment of neoplastic cell growth, such as cancers are being developed.

Antigen-Specific Vaccination in Combination with Non-Specific Immunotherapy

Cytokines generally stimulate proliferation or differentiation of cells of the hematopoietic lineage or participate in the immune and inflammatory response mechanisms of the body. The interleukins are a family of cytokines that mediate immunological responses. Central to an immune response is the T cell, which produces many cytokines and plays a role in adaptive immunity to antigens. Cytokines produced by the T cell have been classified as type 1 and type 2 (Kelso, A. Immun. Cell Biol. 76:300-317, 1998). Type 1 cytokines include IL-2, IFN-γ, LT-α, and are involved in inflammatory responses, viral immunity, intracellular parasite immunity and allograft rejection. Type 2 cytokines include IL4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue. Cytokines such as GM-CSF are often used in lower doses as adjuvants in vaccination therapy.

Vaccination with tumor cells genetically engineered to produce interleukin (IL)-2 provides another strategy to enhance antitumor immune responses (Koppenhagen F J et al., Clin Cancer Res. 1998 (8):1881-1886).

Conventional Chemotherapeutics in Combination with Active Immunotherapy

Machiels et al. observed that cyclophosphamide, paclitaxel, and doxorubicin, when given in a defined sequence either before or after the whole-cell vaccine and by a different route of administration with a GM-CSF-secreting, neu-expressing whole-cell vaccine, enhanced the vaccine's potential to delay tumor growth in neu transgenic mice. In addition, it was shown that these drugs mediate their effects by enhancing the efficacy of the vaccine rather than via a direct cytolytic effect on cancer cells. Furthermore, paclitaxel and cyclophosphamide appear to amplify the T helper 1 neu-specific T-cell response. These findings suggest that the combined treatment with immune-modulating doses of DNA interfering chemotherapy and the GM-CSF-secreting neu vaccine can overcome immune tolerance and induce an antigen-specific antitumor immune response (Machiels et al. Cancer Res 2001 May 1; 61(9):3689-97).

Another study (C J Wheeler et al, Clin Cancer Res, 2004, Aug. 15, Clinical Responsiveness of Glioblastoma Multiforme to Chemotherapy after Vaccination) suggested that chemotherapy synergizes with previous therapeutic vaccination to generate a uniquely effective treatment that slows Globlastoma Multiforme (GBM) progression and significantly extends patient survival relative to individual therapies. Tumors treated with dendritic cell therapy were highly sensitive to subsequent chemotherapy suggesting that the vaccine either primes' the cell-death machinery or fundamentally alters the genetic or structural makeup of the tumor cells.

US2006-051354 suggests the use immunomodulator chemotherapeutic agents as adjuvants for vaccines. The inventors found that paclitaxel triggers the induction of MCP-1, a chemokine known to recruit dendritic cells (APC) at the injection site, a critical event for the induction of immune responses and therefore proposed to enhance immunogenicity of a vaccine by combining directly low-dose immunomodulator chemotherapeutic agents with the vaccine in one single administration. However, no combination treatment with therapeutical anti-neoplastic doses of a chemotherapeutic was disclosed.

Virtually all chemotherapeutics, including kinase inhibitors cause depression of the immune system when used in therapeutical doses, often by paralysing the bone marrow and leading to a decrease of white blood cells, red blood cells and platelets. Depending on their target, some monoclonal antibodies used in cancer therapy also have a detrimental effect on the immune system.

Thus, it was surprising to find, that small molecules, kinase inhibitors and antibodies that lead to a suppressed immune system do not prevent the desired immune response when used in combination with active immunotherapy.

SUMMARY OF THE INVENTION

The present invention provides a method of treating a neoplastic disorder in a mammal wherein the mammal, preferably human, is administered an active immunotherapy and at least one additional therapeutic agent.

In certain preferred embodiments, the active immunotherapy comprises a vaccine, which is preferably comprised of at least one protein, nucleic acid or fragment thereof, a peptide, cells or cellular extracts.

The additional therapeutic agent is selected from the group consisting of an immunoactive small molecule, an antibody, a kinase inhibitor or a combination thereof.

The kinase inhibitor is preferably a multi-kinase inhibitor and/or a tyrosine kinase inhibitor. The multi-kinase inhibitor and/or a tyrosine kinase inhibitor is preferably sunitinib malate and/or sorafenib tosylate or a pharmaceutically acceptable salt thereof.

In one embodiment, the active immunotherapy comprises administering to the mammal at least one vaccine and the therapeutic agent comprises administering a multi-kinase inhibitor and/or a tyrosine kinase inhibitor.

In other embodiments, the active immunotherapy comprises administering to the mammal at least one immunogenic peptide and the additional therapeutic agent comprises administering to the mammal a multi-kinase inhibitor and/or a tyrosine kinase inhibitor, preferably of the sunitinib and/or sorafenib type or a pharmaceutically acceptable salt or derivative thereof.

The methods of the invention may be used as a sole treatment or in an adjuvant or a neoadjuvant or a palliative therapy setting.

The active immunotherapy and the additional therapeutic agent may be administered simultaneously, sequentially or separately. The active immunotherapy may administered subcutaneously, intravenously, intradermally, intratumorally, intramuscularly, orally, or intranasal. The therapeutic agent may be administered subcutaneously, intravenously, intradermally, intramuscularly, orally, or intranasal.

In some embodiments, the routes of administration of the active immunotherapy and the route of administration of the additional therapeutic agent are different, and in other embodiments the routes of administration are the same. The active immunotherapy may be administered prior to and/or concurrently with the additional therapeutic agent.

In certain preferred embodiments, the present invention provides a method of treating cancer (preferably renal cancer) in a mammal comprising administering to the mammal a combination therapy comprising a vaccine and a multi-kinase inhibitor, wherein the vaccine comprises an isolated tumor associated peptide having the ability to bind to a molecule of the human major histocompatibility complex (MHC) class-I or class-II. Preferably the multi-kinase inhibitor is sunitinib malate and/or sorafenib tosylate or a pharmaceutically acceptable salt thereof. In a preferred embodiment, the vaccine comprises the following peptides: SEQ ID NO: 1 (SVASTITGV); SEQ ID NO: 2 (VMAGDIYSV); SEQ ID NO: 3 (ALADGVQKV); SEQ ID NO: 4 (LLGATCMFV); SEQ ID NO: 5 (SVFAGVVGV); SEQ ID NO: 6 (ALFDGD-PHL); SEQ ID NO: 7 (YVDPVITSI); SEQ ID NO: 8 (SQD-DIKGIQKLYGKRS); SEQ ID NO: 9 (STAPPVHNV); and SEQ ID NO: 10 (LAALPHSCL).

In another embodiment the vaccine comprises at least one peptide selected from the group consisting of SEQ ID NO: 1 (SVASTITGV); SEQ ID NO: 2 (VMAGDIYSV); SEQ ID NO: 3 (ALADGVQKV); SEQ ID NO: 4 (LLGATCMFV); SEQ ID NO: 5 (SVFAGVVGV); SEQ ID NO: 6 (ALFDGD-PHL); SEQ ID NO: 7 (YVDPVITSI); SEQ ID NO: 8 (SQD-DIKGIQKLYGKRS); SEQ ID NO: 9 (STAPPVHNV); and SEQ ID NO: 10 (LAALPHSCL).

In another embodiment, the vaccine comprises SEQ ID NO: 7 (YVDPVITSI); SEQ ID NO: 8 (SQDDIKGIQK-LYGKRS) and SEQ ID NO: 9 (STAPPVHNV).

BRIEF DESCRIPTION OF THE FIGURES

FIG. 1 depicts the percentage of highly-proliferated, CFSE-labeled C57BL/6 cells after 5 and 7 days allogenic stimulation with irradiated BALB/c splenocytes. CD4+ (left) and CD8+ (right) T-cells were analyzed separately. Means of duplicates with error bars representing half of the distance between measured values. Cells treated with 13 µM Sorafenib showed different morphology in flow cytometry, therefore the measured values are not comparable with the other treatment groups.

FIGS. 3A-D show the influence of Sorafenib and Subitinib on artificial APC mediated priming of human CD8+ T-cells. Readout was always HLA-tetramers for the antigen MLA-001 either by counting % Tetramer+ among CD8+ lymphocytes (upper panel) or by counting absolute number of Tetramer+ cells per well (lower panel). Shown are mean (filled bars) and standard deviation (error bars) of triplicate wells. Cells were stimulated with either high density pMHC (left panel) or low density pMHC (right panel) with antigens MLA-001 or negative control 1 antigen DDX5-001 as indicated. Final concentrations of TKIs in wells at timepoint of stimulation and medium exchange as indicated (Sorafenib or Sunitinib). Mock represents the DMSO control for TKIs.

FIGS. 5A-B are a schematic representation of the treatment schedules for combination treatment of mice. A. Treatment schedule with continuous TKI treatment during vaccination. B. Treatment schedule with vaccination after discontinuation of TKI treatment.

FIG. 11 provides a list of tumor associated antigens that are useful in the combination therapy of the present invention.

FIG. 12 provides a list of tumor associated antigens that are useful in the combination therapy of the present invention.

FIGS. 13A-Z3 provide a list of tumor associated antigens that are useful in the combination therapy of the present invention.

FIGS. 14A-H provide a list of tumor associated antigens that are useful in the combination therapy of the present invention.

FIGS. 15A-Q provide a list of tumor associated antigens that are useful in the combination therapy of the present invention.

FIGS. 16A-B provide a list of tumor associated antigens that are useful in the combination therapy of the present invention.

FIG. 17 provides a list of tumor associated antigens that are useful in the combination therapy of the present invention.

FIGS. 18A-F provide a list of tumor associated antigens that are useful in the combination therapy of the present invention.

DETAILED DESCRIPTION OF THE INVENTION

Figure 2:
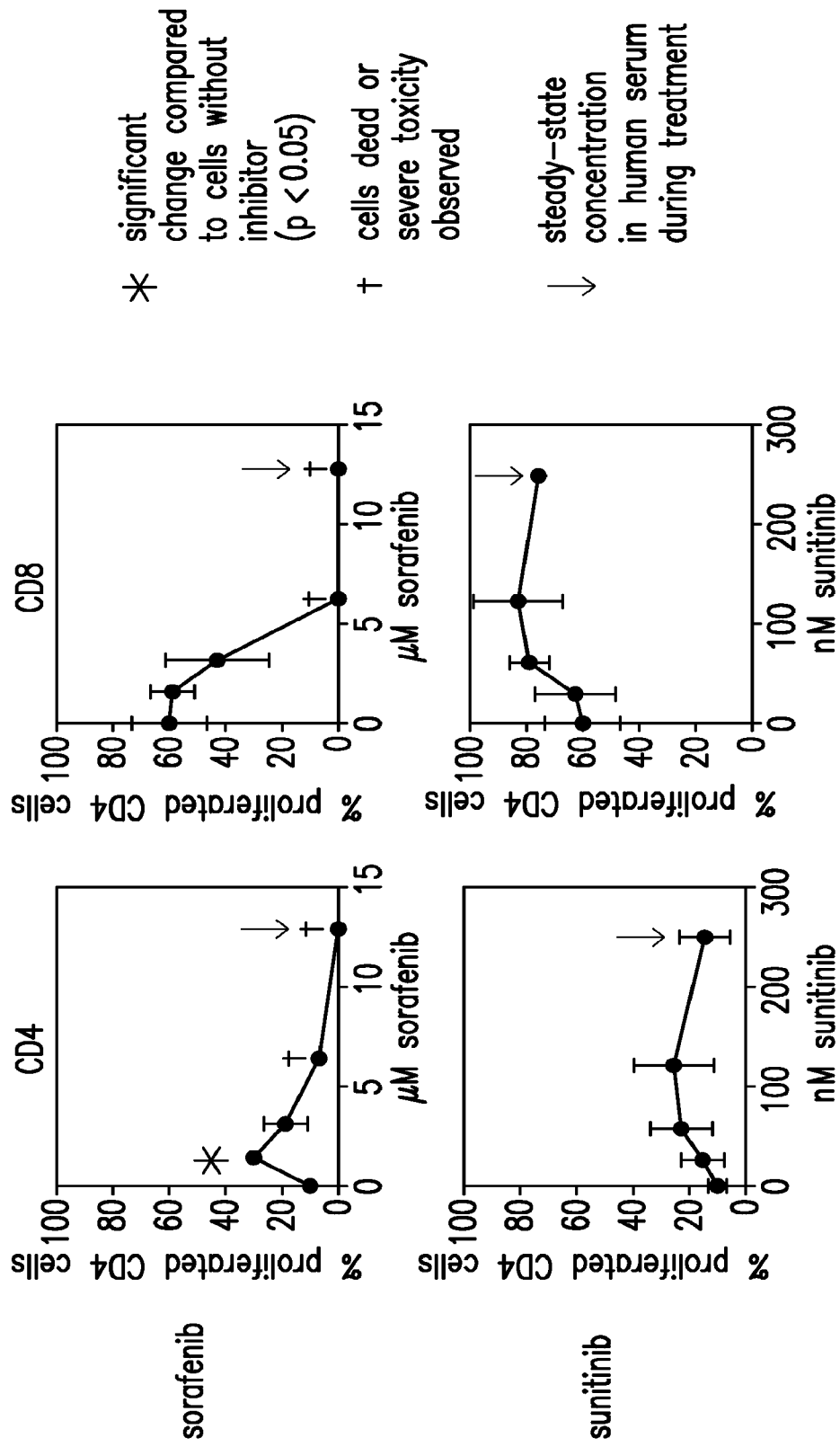
FIG. 2 depicts the proliferation of CD4 and CD8 cells in the presence of different concentrations of Sorafenib or Sunitinib. Means of triplicates with standard deviations are shown. Cells with 6.5 or 13 µM Sorafenib showed severe changes in morphology due to toxic effects of the drug.

The current invention refers to a method of treating a neoplastic disorder comprising administering to a mammal an active immunotherapy and at least one additional therapeutic agent selected from the group consisting of an immunoactive small molecule, an antibody, a kinase inhibitor or a combination thereof. The method of the present invention may be used in an adjuvant or a neoadjuvant or a palliative therapy setting or as a sole treatment. The active immunotherapy and the at least one additional therapeutic agent may target the same and/or different molecules and/or pathways in a neoplastic cell.

As used herein the term "adjuvant" therapy refers to treatment after surgical resection of the primary tumor. As used herein, the term "neoadjuvant therapy" refers to treatment prior to the surgical resection of a primary malignant tumor while "palliative" therapy is intended to relieve symptoms but is not expected to be a cure.

The term "neoplastic disorder" generally refers to one of a group of more than 100 diseases caused by the abnormal growth of cells that can spread to adjoining tissues or other parts of the body. In cancer this growth is uncontrolled and cells can form a solid tumor, in which the cancer cells are massed together, or exists as dispersed cells, as in leukemia. Normal cells divide (reproduce) until maturation is attained and then only as necessary for replacement of damaged or dead cells. Neoplastic cells are referred to as "malignant," if they divide endlessly, eventually crowding out nearby cells and spreading to other parts of the body. The tendency of cancer cells to spread from one organ to another or from one part of the body to another distinguishes them from benign tumor cells, which overgrow but do not spread to other organs or parts of the body. Malignant cancer cells eventually metastasize and spread to other parts of the body via the bloodstream or lymphatic system, where they can multiply and form new tumors. Benign neoplastic disorders are, for example, but not limited to psosiaris, uterine leiomyoma, melanocytic nevi, restinosis, and benign prostatic hyperplasia. Malignant neoplasias are, for example, cancer of the buccal cavity and pharynx, cancer of the digestive tract, cancer of the colon, rectum, and anus, cancer of the respiratory tract, breast cancer, cancer of the cervix uteri, vagina, and vulva, cancer of the uterine corpus and ovary, cancer of the male genital tract, cancer of the urinary tract, cancer of the bone and soft tissue, kaposi sarcoma, melanoma of the skin, eye melanoma, non-melanoma eye cancer, cancer of the brain and central nervous system, cancer of the thyroid and other endocrine glands, Hodgkin's Lymphoma, Non-Hodgkin's Lymphoma, and myeloma. Most preferably the neoplastic disorder treated by the method of the current invention is renal cancer, colorectal cancer, lung cancer, breast cancer, pancreatic cancer, prostate cancer, gastric cancer, GIST or Glioblastoma or a combination of one or more of the foregoing cancers.

"mammal" includes any mammal able to respond to active immunotherapy with an immune reaction. Preferred mammals include, but are not limited to humans, sport and pet animals, such as cats, dogs, horses, experimental animals such as e.g. rats, rabbits, mice, and livestock. Most preferably the mammal is a human.

In a preferred embodiment at least one additional therapeutic agent may be an immunoactive small molecule, an antibody, or a kinase inhibitor or a combination thereof.

Within the context of this invention, an immunoactive small molecule is a small molecule that may act synergistically with active immunotherapy approaches, in particular peptide-based therapeutic vaccines. Small molecules may, for example, act in such a way by:

reducing regulatory T cells in the periphery and in the tumor lesions by improving activation of professional APCs and/or helper and/or killer T cells and/or by biasing the immune response towards a TH1-type immune response (cytokine profile including e.g. IFN-gammma, IL-2 upregulation).

In preferred embodiments of the present invention the immunoactive small molecule is 1-MT, ABH, AMD3100, AZD2171, BEC, celebrex, CP-547632, CPA-7, cyclophosphamide, JSI-124, loxoribine, LY580276, NCX-4016, nor-NOHA, pazopanib, rofecoxib, S-27609, SB-505124, SD-208, Sildenafil, Tadalafil, Vardenafil, XL-999, and ZD2171.

The antibody may be a monoclonal or a polyclonal antibody or a fragment thereof, preferably a monoclonal antibody. Humanized and/or chimeric antibodies are included. The antibody may be conjugated or non-conjugated and may be directed at any target antigen of interest, in particular tumor-associated antigens. Examples of antibodies therapeutically active against neoplasia include, but are not limited to, anti-cancer antibodies such as 1D09C3, Abciximab, Alemtuzumab, Apolizumab, Avastin, Basiliximab, Bevacizumab, Cantuzumab, Cetuximab, Dacliximab, Eculizumab, Epratuzumab, Gemtuzumab Ozogamicin, Ibritumomab Tiuxetan, Infliximab, Labetuzumab, Mapatumumab, Matuzumab, Mepolizumab, Muromonab-Cd3, Nimotuzumab, Oregovomab, Palivizumab, Panitumumab, Panorex, Pertuzumab, Rituximab, Tositumomab, and Trastuzumab. Preferred therapeutic antibodies for use in the method of the present invention include anti-CD20 antibodies (e.g., Rituxan™, Bexxar™, Zevalin™), anti-Her2/neu antibodies (e.g., Herceptin™), anti-CD33 antibodies (e.g., Mylotarg™), anti-CD52 antibodies (e.g., Campath™), anti-CD22 antibodies, anti-CD25 antibodies, anti-CTLA-4 antibodies, anti-EGF-R antibodies (e.g. Erbitux™), anti-VEGF antibodies (e.g. Avastin™, VEGF Trap) anti-HLA-DR10β antibodies, anti-MUC1 antibodies, anti-CD40 antibodies (e.g. CP-870,893), anti-Treg cell antibodies (e.g. MDX-010, CP-675,206), anti-GITR antibodies, anti-CCL22 antibodies, and the like.

An antibody as contemplated herein includes any antibody specific to any region of a protein involved in the abnormal growth, differentiation, duplication, angiogenesis, metastasis, apoptosis and/or invasion of cells and the like.

The additional therapeutic agent of the invention is preferably a kinase inhibitor. Protein kinases are a family of enzymes that catalyse the phosphorylation of specific residues in proteins. In general, protein kinases fall into several groups; those that preferentially phosphorylate serine and/or threonine residues, those which preferentially phosphorylate tyrosine residues and those that phosphorylate both tyrosine and Ser/Thr residues. Protein kinases are key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis. Kinases such as c-Src, c-Abl, mitogen activated protein (MAP) kinase, phosphotidylinositol-3-kinase (PI3K) AKT, and the epidermal growth factor (EGF) receptor are commonly activated in cancer cells, and are known to contribute to tumorigenesis. Many of these occur in the same signaling pathway. For example, HER-kinase family members (HER1 EGFR, HER3, and HER4) transmit signals through MAP kinase and PI3 kinase to promote cell proliferation. Logically, a number of kinase inhibitors are currently being developed for anti-cancer therapy, in particular tyrosine kinase inhibitors (TKIs): cyclin-dependent kinase inhibitors, aurora kinase inhibitors, cell cycle checkpoint inhibitors, epidermal growth factor receptor (EGFR) inhibitors, FMS-like tyrosine kinase inhibitors, platelet-derived growth factor receptor (PDGFR) inhibitors, kinase insert domain inhibitors, inhibitors targeting the PI3K/Akt/mTOR pathway, inhibitors targeting the Ras-Raf-MEK-ERK (ERK) pathway, vascular endothelial growth factor receptor (VEGFR) kinase inhibitors, c-kit inhibitors and serine/threonine kinase inhibitors.

Kinase inhibitors useful in the method of the present invention include, but are not limited to, Lapatinib, AZD 2171, ET18OCH3, Indirubin-3'-oxime, NSC-154020, PD 169316, Quercetin, Roscovitine, Triciribine, ZD 1839, 5-Iodotubercidin, Adaphostin, Aloisine, Alsterpaullone, Aminogenistein, API-2, Apigenin, Arctigenin, ARRY-334543, Axitinib (AG-013736), AY-22989, AZD 2171, Bisindolylmaleimide IX, CCI-779, Chelerythrine, DMPQ, DRB, Edelfosine, ENMD-981693, Erbstatin analog, Erlotinib, Fasudil, Gefitinib (ZD1839), H-7, H-8, H-89, HA-100, HA-1004, HA-1077, HA-1100, Hydroxyfasudil, Kenpaullone, KN-62, KY12420, LFM-A13, Luteolin, LY294002, LY-294002, Mallotoxin, ML-9, MLN608, NSC-226080, NSC-231634, NSC-664704, NSC-680410, NU6102, Olomoucine, Oxindole I, PD 153035, PD 98059, Phloridzin, Piceatannol, Picropodophyllin, PK1, PP1, PP2, PTK787/ZK222584, PTK787/ZK-222584, Purvalanol A, Rapamune, Rapamycin, Ro 31-8220, Rottlerin, SB202190, SB203580, Sirolimus, SL327, SP600125, Staurosporine, STI-571, SU1498, SU4312, SU5416, SU5416 (Semaxanib), SU6656, SU6668, syk inhibitor, TBB, TCN, Tyrphostin AG 1024, Tyrphostin AG 490, Tyrphostin AG 825, Tyrphostin AG 957, U0126, W-7, Wortmannin, Y-27632, Zactima (ZD6474), ZM 252868. Recently approved TKIs for cancer therapy include, for example, Sorafenib and Sunitinib.

KIs currently under clinical investigation for use in anti-cancer therapies and/or novel indications are, for example, MK0457, VX-680, ZD6474, MLN8054, AZD2171, SNS-032, PTK787/ZK222584, Sorafinib (BAY43-9006), SU5416, SU6668 AMG706, Zactima (ZD6474), MP-412, Dasatinib, CEP-701, (Lestaurtinib), XL647, XL999, Tykerb, (Lapatinib), MLN518, (formerly known as CT53518), PKC412, STI571, AMN107, AEE 788, OSI-930, OSI-817, Sunitinib maleate (Sutent SU11248), Vatalanib (PTK787/ZK 222584), SNS-032, SNS-314 and Axitinib (AG-013736). Gefitinib and Erlotinib are two orally available EGFR-TKIs.

Thus, in a preferred embodiment of the present invention, the kinase inhibitor is a tyrosine kinase inhibitor, preferably a multi-kinase inhibitor. Within the context of this invention a multi-kinase inhibitor is an inhibitor that acts on more than one specific kinase. Multi-kinase inhibitors include the so-called DGF out-binders, such as imatinib, sorafenib, lapatinib, BIRB-796 and AZD-1152; other multi-kinase inhibitors are AMG706, Zactima (ZD6474), MP-412, sorafenib (BAY 43-9006), dasatinib, CEP-701 (lestaurtinib), XL647, XL999, Tykerb (lapatinib), MLN518, (formerly known as CT53518), PKC412, STI571, AEE 788, OSI-930, OSI-817, Sutent (sunitinib maleate), axitinib (AG-013736), erlotinib, gefitinib, axitinib, temsirolismus and nilotinib (AMN107).

Most preferred are Sunitinib and/or Sorafenib or a pharmaceutically acceptable salt or derivative, such as for example a malate or a tosylate thereof. The term "derivative" refers to a chemical modification still retaining kinase inhibitory function of the parent molecule. Examples for derivatives are disclosed e.g. in the patent applications mentioned below.

Sunitinib targets multiple receptor tyrosine kinase inhibitors, including PDGFR, KIT and VEGFR, and is a potent and selective anti-angiogenesis agent. Sunitinib or its L-malate salt is also referred to as SU11248, SU011248, Sunitinib malate (USAN/WHO designation) or SUTENT™ (L-malate salt).

The compound, its synthesis, and particular polymorphs are described in U.S. Pat. No. 6,573,293, U.S. Patent Publication Nos. 2003-0229229, 2003-0069298 and 2005-0059824, and in J. M. Manley, M. J. Kalman, B. G. Conway, C. C. Ball, J. L Havens and R. Vaidyanathan, "Early Amidation Approach to 3-[(4-amido)pyrrol-2-yl]-2-indolinones," J. Org. Chew. 68, 6447-6450 (2003). Preferred formulations of Sunitinib and its L-malate salt are described in PCT Publication No. WO 2004/024127. Preferred dosing regimens are described in U.S. patent application Ser. No. 10/991,244 published as U.S. Patent Publication No. 2005-0182122. The disclosures of these references are incorporated herein by reference in their entireties.

Sorafenib, is also a multi-kinase inhibitor, also known as BAY 43-9006. Sorafenib is a substituted omega carboxy diphenyl urea that inhibits RAF-1 activation, and thereby decreases RAF-1 dependent phosphorylation of MEK-1 and ERK-1, as described in US Patent Application No. 2003-0125359A1, WO 03/047523A2, and Wilhelm et al., Current Pharmaceutical Design, 8:2255-2257 (2002), each of which is herein incorporated by reference in its entirety, particularly in parts pertinent to its structure and properties, methods for making and using it, and other related molecules. Its chemical name is 4-(4-{3-[4-Chloro-3-(trifluoromethyl)phenyl]ureido}phenoxy)-N-methylpyrid-ine-2-carboxamide. A variety of derivatives have been produced. Among these are fluorinated derivatives described in US Patent Application 2005-0038080A1 and WO 2005/009961A2, which are herein incorporated by reference in their entireties, particularly as to these and other pharmaceutically active diphenyl urea compounds.

Currently different nonspecific immunotherapies are used to stimulate the immune system to improve or induce an immune response against neoplastic cells. Nonspecific immunotherapy refers to therapies that can stimulate the immune system by using a substance that activates or enhances immune cell function regardless of their antigen specificity. Nonspecific immunotherapies known in the art include, for example, Bacille Calmette-Guerin (BCG) therapy, cytokine therapy, cell therapy etc.

Antigen-specific immunotherapy refers to either adoptive transfer or vaccination. Adoptive transfer means the direct transfer of the actual components of the immune system that are already capable of producing a specific immune response, such as, for example, T cells or dendritic cells into the recipient. For example, isolated antigen-specific T cells from a cancer patient are expanded to large numbers in vitro, and re-infused back into the patient. Vaccination on the other hand involves the administration of one ore more particular antigen(s) to induce a specific immune response by the host (patient).

An active immunotherapy of the invention may be any immunotherapy that stimulates the intrinsic immune system of the recipient, non-specifically, antigen-specifically and/or multi-targeted. Preferably the active immunotherapy is a multi-targeted, antigen-specific immunotherapy.

In a preferred embodiment the method of the invention comprises an active immunotherapy, whereby at least one vaccine is administered to the mammal.

In whole-cell vaccines, the tumor cell itself is used to provide the broadest set of tumor-related antigens. The tumor cells in the composition should contain antigens that are also present in the tumor to be treated, so that the immune response elicited against the antigens in the composition is effected against the tumor. Generally, the cells are recovered from tumors, suspended in a preservation medium and frozen until used for the vaccine preparation. When needed, the cells are thawed, and then stored at temperatures ranging from about 0° C. (on ice) to room temperature until administration. Immunotherapy approaches using unmodified intact tumor cells prepared from tumors taken from the patient, i.e., autologous tumor cells, have been described in the literature (see, e.g., Berd et al., Cancer Research 1986; 46:2572-2577; Hoover et al., Cancer 1985; 55: 1236-1243; and U.S. Pat. No. 5,484,596).

Alternative vaccine compositions based on disrupted cells have also been suggested including, e.g., tumor membranes (see, e.g., Levin et al., In: Human Tumors in Short Term Culture Techniques and Clinical Applications, P. P. Dendy, Ed., 1976, Academic Press, London, pp. 277-280) or tumor peptides extracted from tumors (see, e.g., U.S. Pat. No. 5,550, 214 and U.S. Pat. No. 5,487,556).

The tumor cells can also be modified in some manner to alter or increase the immune response (see, e.g., Hostetler et al., Cancer Research 1989, 49:1207-1213, and Muller et al., Anticancer Research 1991; 11:925-930). Further examples for modifications and preparation methods are, for example, provided by US patent application 2007-0014775, 2006-0165668, 2002-0085997 or 2003-0170756.

One particular form of tumor cell modification that has a pronounced effect on immunotherapy is coupling of a hapten to the tumor cells. Such haptenized vaccines are described, for example, in WO 96/40173, WO 00/09140, and U.S. Pat. No. 6,333,028. Transducing the tumor with genes so that the tumor cell may act like an antigen presenting cell (Antonia S J et al. Phase I trial of a B7-1 (CD80) gene modified autologous tumor cell vaccine in combination with systemic interleukin-2 in patients with metastatic renal cell carcinoma. J Urol. 2002; 167:1995-2000) or may attract and stimulate local antigen-presenting cells (Simons et al. Bioactivity of autologous irradiated renal cell carcinoma vaccines generated by ex vivo granulocyte-macrophage colony-stimulating factor gene transfer. Cancer Res. 1997; 57:1537-1546) are two approaches.

A person skilled in the art will be able to determine the type of vaccine compositions and antigen modification suitable for a certain type and stage of tumor and/or the individual patient without undue experimentation using the general knowledge of the art and the references and suggestions disclosed in the present application.

In another embodiment the cell based vaccine employs non-tumor cells. The cells used for vaccination are antigen presenting cells (APCs), which may be isolated from the patient. These are loaded or pulsed with a tumor antigen ex vivo. The transfer of these pulsed APCs into the patient elicits a significant tumor-specific immune response that attacks the tumor cells. Currently, there are three different methods for pulsing or loading APCs. First, growing APCs in the presence of a tumor-associated protein; second, using genetic engineering techniques to introduce the gene that codes for a tumor-associated protein into APCs, and third, pulsing APCs with fragments (peptides) isolated from a tumor antigen or synthetic peptides.

The main advantage of APC-based vaccination is that dendritic cells (DCs) produce all the molecules required for eliciting an immune response, unlike other forms of cancer immunotherapy where adjuvants and co-stimulatory molecules are required to boost the ensuing immune response. The potency of DCs as vehicles for delivering antigen and achieving a tumor-specific immune response has been demonstrated in a number of clinical trials.

Thus, in a preferred embodiment of the present invention the method employs a vaccine that comprises cells or cellular extracts, preferably tumors cells or extracts thereof, which were derived from the same or a different mammal as the one to be treated by the inventive method. The cells are, for example, modified or unmodified tumor cells or APCs loaded or transfected with tumor antigen(s). The tumor antigen that is loaded or transfected includes the same proteins, nucleic acids and/or peptides that may be employed for direct vaccination (see below). The cells may also be T cells for adoptive transfer.

A trimolecular complex consisting of the components of T-cell-antigen receptor, an MHC (Major Histocompatibility Complex) molecule and the ligand thereof, which is a peptide fragment derived from a protein, plays a central role in the regulation of the specific (adaptive) immune response.

MHC class I and class II molecules (or the corresponding human molecules, the Human Leukocyte Antigene receptors, HLAs) are peptide receptors that allow the binding of millions of different ligands, with stringent specificity. The binding specifically provided by allele-specific peptide-binding motifs that have the following specificity criteria: the peptides have a defined length, which in the MHC class I haplotypes vary generally from eight to ten amino acids, while class II molecules bind peptides from a length of thirteen amino acids and above. Typically, two of the amino acid positions are so-called "anchors" which can only be occupied by a single amino acid or by amino acid groups with closely related physico-chemical properties defined by their side chains. The exact position of the anchor amino acids in the peptide and the requirements made on their properties vary with the MHC alleles. The C-terminus of the peptide ligands is frequently an aliphatic or a charged group. Examples for such peptide ligands, motifs, variants, as well as examples for extensions on the N- and/or C-terminal sides can be derived from public databases (Rammensee et al. SYFPEITHI: database for MHC ligands and peptide motifs Immunogenetics 1999, 50, 213-219.

Inside the cell, regular, degenerate and foreign gene products, e.g. viral proteins or tumor antigens, are broken down into small peptides. Peptides arising in the cytosol can be trimmed by cytosolic peptidases, as well as by proteolytic enzymes residing in the ER (after transfer of precursors into the ER through TAP). Peptides with a length of, on average, 8 to 10 amino acid residues fulfilling the binding requirements of the binding groove of expressed HLA alleles can then be presented by the respective HLA receptors on the cell surface. Some of those peptides constitute potential ligands for MHC molecules. Binding of the ligands to the MHC molecules provides the prerequisite for peptide presentation by MI-IC- molecules and the triggering of a cellular immune response. Thus, the introduction of a peptide may trigger an immune response. Since the immunogenic epitopes of a vast amount of proteins are known, protein fragments or synthetic peptides containing one or more epitopes may also be employed as vaccines.

In a preferred embodiment the method of the present invention employs a vaccine that comprises at least one protein, nucleic acid and/or fragment thereof derived from a tumor associated antigen (TAA) or cancer antigen. A TAA or cancer antigen is defined as an antigen that is selectively or abundantly expressed in cancer cells. See for example, the following applications directed to certain tumor associated peptides that bind to MHC-molecules useful in a vaccine and/or vaccines per se: Ser. No. 10/999,264 (filed Nov. 28, 2004) (claiming the peptide YVDPVITSI (SEQ ID NO:1)); Ser. No. 11/848,062 (filed Aug. 30, 2007) (claiming the peptide SVASTITGV (SEQ ID NO:2); Ser. No. 10/999,364 (Filed Aug. 30, 2007) (claiming the peptide ALFDGDPHL (SEQ ID NO:4) and others shown in FIG. 18)); 60/953,161 (filed Jul. 31, 2007) (claiming various peptides such as TGBI-001 and NOX-001 and others shown in FIG. 11); 60/953,109 (filed Jul. 31, 2007) (claiming various pharmaceutical compositions comprising peptides shown in FIG. 12); Ser. No. 11/596,802 (filed Nov. 17, 2006) (claiming various peptides shown in FIG. 13 and specifically the peptides FPSLREAAL, LAAL-PHSCL, GLASFKSFLK; SLLTSSKQLQK, IARNLTQQL and GPALGRSFL); Ser. No. 10/549,718 (filed Sep. 16, 2005) (claiming various peptides shown in FIG. 14); Ser. No. 11/664,627 (filed Apr. 2, 2007) (claiming various peptides shown in FIG. 15 and specifically the peptides NPPSM-VAAGSVVAAV and SHYFKIIEDLRAQI); U.S. Pat. No. 7,087,712 (issued Aug. 8, 2006) (claiming the MUC-1 peptide STAPPVHNV); Ser. No. 11/414,897 (filed May 1, 2006) (claiming the MUC-1 peptide LLLLTVLTV); Ser. No. 11/912,668 (filed Oct. 25, 2007) (claiming the peptides LLAARAIVAI and ALCNTDSPL); Ser. No. 11/912,670 (filed Oct. 25, 2007) (claiming various peptides shown in FIG. 16); and Ser. No. 12/065,725 (filed Mar. 4, 2008) (claiming various peptides shown in FIG. 17), all of which are herein incorporated by reference in their entirety.

The main advantage of a peptide-based vaccine is that it provides a method for monitoring a specific immune response for a particular antigen and thus allows the evaluation of the efficacy of vaccination. Other advantages include the bypassing of the need for antigen-presenting cells to process a whole cell before presenting the antigen to the immune system. In addition, administration of a peptide antigen does not carry the risk of introducing dangerous substances into the patient, unlike other vaccines that rely on tumor cells.

The protein, or fragment thereof or peptide may also be generated within the recipient mammal by introducing a nucleic acid encoding the peptide. The nucleic acid may be DNA, cDNA, PNA, CNA, RNA or a combination thereof. Methods for designing and introducing such a nucleic acid are well known in the art. An overview is provided by e.g. S. Pascolo: Vaccination with messenger RNA Methods Mol Med 2006, 127; 23-40; R. Stan, J D Wolchok and A D Cohen, DNA vaccines against cancer Hematol Oncol Clin North Am 2006, 3; 613-636 or A Mandavi and B J Monk Recent advances in human papillomavirus vaccines Curr Oncol Rep 2006, 6, 465-472. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptide encoded by the nucleic acid may be a fusion protein, for example with an epitope from tetanus toxoid, which stimulates CD4+ T cells. Clinical trials using polynucleotide vaccines in cancer have been reported (e.g. Restifo and Rosenberg, Developing recombinant and synthetic vaccines for the treatment of melanoma. Curr Opin Oncol. 1999 (1): 50-57).

A person skilled in the art will readily be able to determine the type of molecule for vaccination purposes, compositions suitable for a certain type and stage of tumor and/or the individual patient, as well as respective antigen modifications and/or delivery vehicles to enhance the immune response without undue experimentation using the general knowledge of the art and the references and suggestions disclosed in the present application.

Most preferably, the vaccine employed in the method of the invention comprises at least one peptide. Such a peptide comprises, for example, an epitope of a TAA, preferably an epitope that is capable of binding to a MHC molecule and generated in vivo by a tumor cell. Epitopes with these characteristics can be identified by methods described in WO03/100432, WO2005/076009, WO03/102023, WO2004/085461, WO2005/116051, U.S. Pat. No. 7,087,712, EP 04 013 790.3, WO2006/037421, WO2006/114307, EP 05 019 254.1, and EP 05 019 255.8, which are hereby incorporated by reference in their entireties.

In a particularly preferred embodiment the vaccine contains at least one of the peptides disclosed in EP 05 019 255.8, namely the peptides provided below:

| Peptide Code | SEQ ID NO | Peptide Sequence |
|---|---|---|
| ADF-001 | 1 | SVASTITGV |
| ADF-002 | 2 | VMAGDIYSV |
| APO-001 | 3 | ALADGVQKV |
| CCN-001 | 4 | LLGATCMFV |
| GUC-001 | 5 | SVFAGVVGV |
| K67-001 | 6 | ALFDGDPHL |
| MET-001 | 7 | YVDPVITSI |
| MMP-001 | 8 | SQDDIKGIQKLYGKRS |
| MUC-001 | 9 | STAPPVHNV |
| RGS-001 | 10 | LAALPHSCL |

In another embodiment, the vaccine contains one or more proteins containing at least one of the peptides mentioned above or one or more nucleic acids encoding at least one of the peptides mentioned above.

In another preferred embodiment, the vaccine contains at least one peptide selected from the group consisting of MET-001 (YVDPVITSI) (SEQ ID NO:7), MMP-001 (SQDDIKGIQKLYGKRS) (SEQ ID NO:8), and MUC-001 (STAPPVHNV) (SEQ ID NO:9) or one or more proteins containing at least one of the peptides selected from MET-001 (YVDPVITSI) (SEQ ID NO:7), MMP-001 (SQDDIKGIQKLYGKRS) (SEQ ID NO: 8), and MUC-001 (STAPPVHNV) (SEQ ID NO:9) or one or more nucleic acids encoding at least one of the peptides MET-001 (YVDPVITSI) (SEQ ID NO:7), MMP-001 (SQDDIKGIQKLYGKRS) (SEQ ID NO:8), and MUC-001 (STAPPVHNV) (SEQ ID NO:9).

In one aspect, the vaccine comprises at least one peptide, preferably two to 50, more preferably two to 25, even more preferably two to 15 and most preferably two, three, four, five, six, seven, eight, nine, ten or eleven peptides. The peptide(s) may be derived from one or more specific TAAs and may bind to MHC class I and/or class II molecules.

In one aspect of the invention, the method utilizes an active immunotherapy that comprises at least one vaccine in combination with at least one additional therapeutic agent comprising a multi-kinase inhibitor and/or a tyrosine kinase inhibitor. Preferred is the combination wherein at least one immunogenic peptide is administered to the mammal and said at least one additional therapeutic agent comprises a multi-kinase inhibitor and/or a tyrosine kinase inhibitor, preferably of the Sunitinib and/or Sorafenib type or a pharmaceutically acceptable salt or derivative thereof.

The exact combination of active immunotherapy and additional therapeutic agent in individual patients should take into account the patient's metabolism, the kind and stage of the disorder to be treated, and the biochemistry of the targets of the two arms of treatment. The setting of treatment (i.e. sole, adjuvant, neoadjuvant, palliative) needs also to be considered. Depending on these factors, the person skilled in the art will determine in which individual situation what kind of combination is the most promising. For example, in a situation where the tumor cells have gained resistance to certain therapeutic agents, the following combination treatment according to the method of the invention will involve TKIs and/or antibodies and targets for vaccination aiming at different key molecules/pathways than those involved in the resistance. The key molecule/pathway targets for TKI and active immunotherapy may be identical. In a different setting, for example, in neoadjuvant therapy, where there is a need for fast tumor shrinkage, it may be advantageous to get different key molecules/pathways with active immunotherapy and additional therapy. For an adjuvant therapy it may be advantageous to destroy any residual tumor cells. Beneficial combinations may also be suggested by studying the alteration of target presentation in cancer cell lines by additional therapeutic agent(s) as in Example 2, the in vitro alteration of T cell activation by said agent(s) as in Example 3, or the in vivo effects by animal experiments such as in Example 4. These procedures can also be used to determine the order of administration of the agents, i.e. before, simultaneously, or after vaccination.

In general, the success of vaccine strategies depends on the mode of antigen delivery, the choice of adjuvant, and the particular antigen being used.

The at least one additional therapeutic agent and/or active immunotherapy agent, i.e. the immunogenic protein, nucleic acid and/or peptide, can be administered by any means known to one of skill in the art (see Banga, A., "Parenteral Controlled Delivery of Therapeutic Peptides and Proteins," in Therapeutic Peptides and Proteins, Technomic Publishing Co., Inc., Lancaster, Pa., 1995, S. Pascolo: "Vaccination with messenger RNA Methods," Mol Med 2006, 127; 23-40; R. Stan, J D Wolchok and A D Cohen, "DNA vaccines against cancer," Hematol Oncol Clin North Am 2006, 3; 613-636 or A Mandavi and B Y Monk, "Recent advances in human papillomavirus vaccines," Curr Oncol Rep 2006, 6, 465-472) such as by intradermal, intramuscular, subcutaneous, intratumoral or intravenous injection. Other administration is contemplated such as mucosal, such as oral, nasal, or anal and dermal administration. For TKIs such as Sorafenib and Sunitinib, oral administration is preferred.

In one embodiment, administration of the active immunotherapy agent is by subcutaneous, intratumoral or intramuscular injection. To extend the time during which the peptide, nucleic acid and/or protein is available to stimulate a response, the agent can be provided as an implant, an oily injection, an oil-in-water emulsion, an water-in-oil emulsion, a suspension or as a particulate system. The particulate system, for example, can be a microparticle, a microcapsule, a microsphere, a nanocapsule, or similar particle. (see, e.g., Banga, supra) including controlled release devices and patches etc.

Controlled release antigen delivery systems may also be used. For example, WO 95/11008 (Genentech Inc.) discloses the use of PLGA (poly(DL-lactide-co-glycolide) microspheres for encapsulating an antigen. EP 0 686 030 teaches a method of potentiating an immune response by embedding an antigen in a biodegradable biopolymer and injecting it in the form of a dispersion to trigger a humoral and cellular response. Lipid-based systems disclosed in US patent application 2006-0275777, or virosomes may also be used. Preferred systems include those by Juvaris (e.g. JuvImmune™ or JuvaVax™). Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see, Kreuter, Colloidal Drug Delivery Systems, J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc., New York, N.Y., pp. 315-339, 1992). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In a preferred embodiment the additional therapeutic agent is administered orally while the active immunotherapeutic agent is administered intradermally, subcutaneously, intravenously, intratumorally or intramuscularly.

A person skilled in the art can readily determine the route of administration to choose depending of the type of composition, its solubility, dissolution, bioavailability, stability, the optional adjuvant(s) used etc. Formulations for the additional therapy by immunoactive small molecules, TKIs and/or antibodies are preferably those approved by drug regulatory authorities, but may also be adjusted to the particular combination with the active immunotherapy of the method of the invention. One of ordinary skill in the art would take into consideration the need to formulate the active ingredients of both therapeutic arms in a manner that does not cause severe toxicity in the individual, damage the individual to any appreciable degree or cause appreciable adverse side effects. The formulation and preparation of compositions is well-known to those skilled in the art of pharmaceutical formulation, and the descriptions herein are illustrative and not limiting. See, e.g., Genarro A R, Remington's Pharmaceutical Sciences, Easton, Pa.: Mack Publishing Company, 2000, 20th. ed.; Allen, Popovich and Ansel, 2005, Pharmaceutical Dosage Forms and Drug Delivery Systems 8th ed. Lippincott Williams & Wilkins;

In the method of the present invention, the active immunotherapy and at least one additional therapeutic agent can be administered simultaneously, sequentially (sequenced over time) or separately. For example, the active immunotherapy agent can be administered within the same hour or within the same day as the additional therapeutic agent to save visits to the medical practitioner, both agents may be administered on different days but within the same period of time, such as for example during the period of time of a chemotherapy regimen, or they may be administered separately, for example the active immunotherapy agent is administered some time, e.g. days, weeks or month after a therapy with the additional therapeutic agent(s) has been concluded. Also the additional therapeutic agent(s) may be administered days, weeks or month after the last vaccination took place.

Generally the routes of administration of the composition that effect the active immunotherapy and the route of administration of at least one additional therapeutic agent will be different, particularly in embodiments, wherein active immunotherapy is combined with treatment with an orally administered TKI. For instance, a vaccine may be administered intradermally, while the accompanying additional therapeutic agent such as e.g. a TKI like sunitinib or sorafenib, is given orally.

With certain combinations the routes of administration of the composition that effect the active immunotherapy and the route of administration of at least one additional therapeutic agent will be the same. This may be the case, for example, if the active immunotherapy is given intravenously and combined with an antibody as additional therapeutic agent, which has to be administered intravenously as well.

The treatment regimen with the active immunotherapy and the additional therapeutic agent in individual patients should take into account the patients height, weight, rate of absorption and metabolism of the medication in question, the type and stage of the disorder to be treated, and other pharmacological agents that are administered concurrently. Additionally, any synergistic or neutralizing effects of the two arms of treatment will be taken into consideration, so that synergistically acting treatment arms are preferably administered within a period of time that allows such synergies. In contrast, treatment arms having neutralizing effects will be administered separately so that the effects of the first arm of treatment have worn off, so they do not interfere with the second arm of treatment. The setting of treatment (i.e. sole, adjuvant, neoadjuvant, palliative) needs to be considered as well. Depending on these factors, the active immunotherapy may be administered prior to, concurrently with and/or after at least one additional therapeutic agent. For example, a patient receiving the treatment of the present invention might have renal cancer. A person skilled in the art may treat the patient first with a conventional chemotherapy consisting of several cycles of treatment with a TKI such as Sorafinib and, upon remission and recovery of the immune system, administer several boosts of a peptide vaccine to prevent or delay recurrence of a tumor. If Sunitinib is administered as the TKI, it may be of advantage to administer the vaccine concurrently, or concurrently and after the Sunitinib treatment, for example, since this particular TKI seems to inhibit regulatory T-cells (Tregs) limiting the immune response.

Treg cells represent a T-cell population that can functionally suppress an immune response by influencing the activity of other immune effector cells. The existence of Tregs was first established in 1971, when Gershon and Kondo transferred antigen-specific tolerance to antigen-naïve animals by transferring T-cells that had previously been exposed to the specific antigen. Several phenotypically distinct Tregs exist. The object of recent intensive research are CD4+ CD25+ Foxp3+ T cells, which also express high levels of glucocorticoid-induced TNFR-related protein (GITR). These Tregs are considered key mediators of peripheral tolerance. More recently, another type of Tregs (IL10+CCR7+) possibly involved in central priming suppression rather than in peripheral effector suppression, was described (Zou, 2005). CD4+ Foxp3+ Tregs suppress the execution of effector functions of T-cells in the periphery.

The active immunotherapy may be administered with or without adjuvant. Adjuvants are substances that non-specifically enhance or potentiate the immune response (e.g., immune responses mediated by CTLs and Helper-T ($T_H$) cells) to an antigen, and would thus be considered useful in the active immunotherapy of the present invention. Suitable adjuvants include, but are not limited to 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PepTel® vector system, PLG microparticles, resiquimod, SRL172, Virosomes and other Virus-like particles, YF-17 DBCG, Aquila's QS21 stimulon (Aquila Biotech, Worcester, Mass., USA), which is derived from saponin, mycobacterial extracts and synthetic bacterial cell wall mimics, and other proprietory adjuvants such as Ribi's Detox. Quil or Superfos. Adjuvants such as Freund's or GM-CSF are preferred. Other examples for adjuvants include cholera toxin, which acts locally as a mucosal adjuvant for the induction of peptide-specific CTLs following intranasal immunization of dendritic cells with CTL epitope peptides (Porgador et al., 1997; Porgador et al., 1998). Several immunological adjuvants (e.g., MF59) specific for dendritic cells and their preparation have been described previously (Dupis et al., 1998; Allison, 1997; Allison, 1998). Cytokines may also be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (Dupis et al., 1998; Allison, 1997; Allison, 1998; U.S. Pat. No. 5,849,589, specifically incorporated herein by reference in its entirety) and acting as immunoadjuvants (e.g., IL-12) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T-cell help. The TH1 bias induced by TLR9 stimulation is maintained even in the presence of vaccine adjuvants such as alum or incomplete Freund's adjuvant (IFA) that normally promote a TH2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the reduction of antigen doses by approximately two orders of magnitude, with comparable antibody responses to the full-dose vaccine without CpG in some experiments (Arthur M. Krieg, Therapeutic potential of Toll-like receptor 9 activation, Nature Reviews|Drug Discovery, 5, Jun. 2006, 471-484). U.S. Pat. No. 6,406,705 B1 describes the combined use of CpG oligonucleotides, non-nucleic acid adjuvants and an antigen to induce an antigen-specific immune response. Other examples of useful adjuvants include, but are not limited to, chemically modified CpGs (e.g. CpR, Idera), non-CpG bacterial DNA or RNA, as well as immunoactive small molecules (see above) that may act therapeutically and/or as an adjuvant. The amounts and concentrations of adjuvants and additives useful in the context of the present invention can readily be determined by the skilled artisan without undue experimentation.

The dosage of an active immunotherapy agent and an additional therapeutic agent will be tailored to each individual patient manifesting symptoms characteristic of a specific neoplastic disorder. For example, a patient receiving the treatment of the present invention might have renal cancer. A person skilled in the art will recognize that the optimal dose of a pharmaceutical agent to be administered will vary from one individual to another. Dosage in individual patients should take into account the patients height, weight, rate of absorption and metabolism of the medication in question, the stage of the disorder to be treated, and what other pharmacological agents are administered concurrently. The skilled artisan will adjust doses depending on tumor response and adverse effect profile. Generally, the dosage of the additional therapeutic agent(s) will be within the range approved by drug regulatory authorities and proven to be effective and save within clinical trial or below.

In a particularly preferred aspect of this embodiment, the invention provides a method of treating renal cell carcinoma in a patient, such as a human, by administering to the patient Sunitinib, for example in an amount of 25 to 75, preferably 25, 37.5, 50 or 62.5 mg daily, continuous (i.e., not intermittent) or intermittent dosing schedule for example on a 4/2, 4/1, 3/1 or 2/1 dosing schedule and a multi-target peptide vaccine, for example 50 µg to 1 mg of each peptide, preferably 200 µg to 600 µg of each peptide per patient and injection, preferably together with an adjuvant. In another embodiment, the invention provides a method of treating any of the earlier-recited cancers in a patient, such as a human, by administering to the patient Sorafinib in an amount of 200 mg or 400 mg, twice daily or once daily or once every two days.

One skilled in the art can readily determine the optimal dosage for a particular patient based on tumor response and adverse event profile. Those skilled in the art will appreciate that dosages may also be determined with guidance from Goodman & Gilman's The Pharmacological Basis of Therapeutics, McGraw-Hill Professional; 11th edition (2005).

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

EXAMPLES

The tyrosine kinase inhibitors (TKIs) Sorafenib and Sunitinib are multi-target kinase inhibitors recently approved for the treatment of advanced renal cell carcinoma (RCC) in the U.S. To gain preclinical knowledge on potential influence of TKIs on the effects caused by cancer vaccines, Sorafenib and Sunitinib treatment was combined with peptide vaccination.

Example 1

Quantification of Sorafenib and Sunitinib in Biological Fluids

Sunitinib malate and sorafenib tosylate were supplied by euroasia chemicals PVT. LTD., Mumbai (India).

1.1. Sample Preparation for Sunitinib Quantification

To quantify sunitinib in blood serum or in cell culture medium, 10 µl of 50% acetonitril (Acros, Geel, Belgium) was added to 50 µl serum or medium in brown glass tubes to protect the photo-unstable sunitinib from light, and mixed for 10 seconds. The proteins were precipitated with 40 µl 100% acetonitril (Acros, Geel, Belgium), centrifuged and filtered through a 0.2 µm PVDF filter. 10 µl was directly injected to the HPLC system.

1.2. HPLC-Conditions:

The HPLC system consisted of a Binary HPLC pump (Shimadzu LC10aVP), a Shimadzu SIL-10aVP autosampler, a Shimadzu CTO-10asVP column oven and a Shimadzu SPD10aVP detector. Data acquisition and analysis was performed using the Shimadzu Class-VP 7.3 software. Chromatographic separation was carried out on a reverse phase C18 column (Reprosil Pur ODS-3µ, 60×2 mm). To protect the analytical column a guard column has been used (Reprosil Pur ODS-5µ, 10×2 mm). Eluent A consisted of water (LCMS grade, Acros, Geel, Belgium), modified by 0.1% formic acid (Merck, Darmstadt, Germany) and eluent B was 80% acetonitril (Acros, Geel, Belgium) with 0.1% formic acid (Merck, Darmstadt, Germany).

The following gradient was used: 5 min 25% eluent B, 15 min 62.5% eluent B, 6 min 80% eluent B and 5 min 80% eluent B. The temperature of the autosampler was kept at 4° C. The temperature of the column was maintained at 30° C. The detection wavelength was set at 400 nm, the injection volume was 10 µl. The column was equilibrated with the mobile phase at a flow rate 0.5 ml/min.

1.3. Sample Preparation for Sorafenib Quantification

For Sorafenib analysis, 10 µl of 50% acetonitril (Acros, Geel, Belgium) was added to 50 serum or medium in 0.5 ml PCR tubes and mixed for 10 seconds. 10 mg $NH_4Cl$ (Roth, Karlsruhe, Germany) was added and mixed for 10 seconds. 60 µl acetonitril (Acros, Geel, Belgium) solution, containing Tolnaftate (Sigma, Steinheim, Germany) as internal standard was added and mixed for 1 minute. The mixture was centrifuged for 3 minutes at room temperature. After phase separation, 35 µl from the acetonitril phase was transferred into HPLC-vials and 10 µl were directly injected to the HPLC system.

1.4. HPLC-Conditions:

Sorafinib was analysed on the same system as sunitinib with Eluent A consisting of 20 mM $KH_2PO_4$-buffer (Sigma, Steinheim, Germany). Eluent B consisted of 80% acetonitril (Acros, Geel, Belgium), 20% 20 mM $KH_2PO_4$ (Sigma, Steinheim, Germany) and 0.01% phosphoric acid (Sigma, Steinheim, Germany). The following gradient was used: 5 min 20% eluent B, 5 min 32% eluent B, 20 min 56% eluent B and 10 min 80% eluent B. The temperature of the autosampler was kept at 4° C. The temperature of the column was maintained at 40° C. The detection wavelength was set at 265 nm, the injection volume was 10 µl. The column was equilibrated with the mobile phase at a flow rate 0.5 ml/min.

Using these methods, bioavailability of sorafenib and sunitinib in the mouse models at the used doses was confirmed to reach plasma levels shown by others to be effective in tumor growth inhibition. It could also be shown that the TKIs stability in the cell culture systems of choice was acceptable for the conduction of in vitro experiments. In vitro concentrations in later experiments were chosen to include steady state plasma concentrations of TKI treated patients.

Example 2

Alteration of Expression of Vaccination Relevant Genes During TKI Treatment 2.1. Alteration of Gene Expression Profiles of Human Tumor Cell Lines In Vitro Genome-wide mRNA expression was measured by Affymetrix microarrays. The human renal cell carcinoma cell line A498 was cultured in the presence of sorafenib and sunitinib. Gene expression for a selection of tumor associated antigens and genes involved in antigen presentation to T lymphocytes was compared with untreated cells to determine whether these tyrosine kinase inhibitors (TKIs) might have the potential to cause altered presentation of antigens in vitro.

The human renal cell carcinoma cell lines A498 and RCC068 were cultured in RPMI medium (5% FCS (Biochrom, Berlin, Germany), 5% HS (PromoCell, Heidelberg, Germany)). Human serum was added as a supply of ligands influencing signaling pathways, which might be altered by TKIs. 40 h after seeding, the experiment was started by addition of TKIs to the culture flasks. The following incubation periods (time points) were planned: 1 h, 6 h, 24 h, 14 days. For each time point 3 flasks of each cell line were prepared by containing either 0.1% DMSO alone as a control, 13 µM sorafenib (8.3 µg/ml sorafenib tosylate)+0.1% DMSO, or 250 nM sunitinib (133 ng/ml sunitinib malate). At each time point, cells were harvested by removing the culture medium and adding 1.25 ml TRI Reagent (Fermentas, St. Leon-Rot, Germany).

RNA was isolated according to standard protocols and further cleaned up by the RNeasy Mini Kit (QIAGEN, Hilden, Germany). For the 14 d time point, cells were trypsinized every 3-4 days and supplied with fresh medium containing fresh TKIs. Sorafenib cells were already harvested after 10 days since the TKI prevented cell growth. A normal medium control sample containing neither DMSO nor TKIs was harvested at 1 h for each cell line. Quality and quantity of RNA samples were assessed on an Agilent 2100 Bioanalyzer (Agilent, Waldbronn, Germany) using the RNA 6000 Pico LabChip Kit (Agilent).

Gene expression analysis was performed only for the 24 h time point (3 samples) and the normal medium control (1 sample) of the A498 cells by Affymetrix Human Genome HG-U133 Plus 2.0 oligonucleotide microarrays (Affymetrix, Santa Clara, Calif., USA).

All steps were carried out according to the Affymetrix manual. Briefly, double-stranded cDNA was synthesized from 8 µg of total RNA, using SuperScript RTII (Invitrogen, Karlsruhe, Germany) and the oligo-dTT7 primer (MWG Biotech, Ebersberg, Germany) as described in the manual. In vitro transcription was performed with the GeneChip IVT Labeling Kit (Affymetrix) followed by cRNA fragmentation, hybridization, and staining with streptavidin-phycoerythrin and biotinylated anti-streptavidin antibody (Molecular Probes, Leiden, Netherlands). Images were scanned with the Affymetrix Gene-Chip Scanner 3000 and data were analyzed with the GCOS software (Affymetrix), using default settings for all parameters. Pairwise comparisons were calculated using the normal medium control array as baseline. For normalization, 100 housekeeping genes provided by Affymetrix were used. Relative expression values were calculated from the signal log ratios given by the software and the expression level in the control sample was set to 100% for each gene.

mRNA expression was analyzed for possible vaccination target antigens as well as for proteins involved in antigen presentation to T cells, like HLA proteins themselves or members of the processing machinery like TAP1 or the immunoproteasomal subunits PSMB9 (LMP2) or PSMB8 (LMP7). The influence of DMSO addition alone or in combination with the TKIs sorafenib and sunitinib on the renal cell carcinoma cell line A498 after 24 h incubation was assessed by comparing these samples with the normal medium control cell line. Expression in the control was defined as 100%.

Result are summarized in Table 1.

TABLE 1

Relative expression of tumor associated antigens and genes involved in MHC-peptide presentation in A498 tumor cells.

| | % Expression relative to control | | |
|---|---|---|---|
| Gene | DMSO | Sorafenib | Sunitinib |
| Tumor associated antigens | | | |
| ADFP | 100 | 100 | 87 |
| APOL1 | 62 | 71 | 62 |
| CCND1 | 76 | 81 | 93 |
| GUCY1A3 | 115 | 44 | 57 |
| KIAA0367 | n.d. | n.d. | n.d. |
| MET | 81 | 62 | 41 |
| MMP7 | 71 | 25 | 31 |
| MUC1 | 76 | 107 | 54 |
| RGS5 | n.d. | n.d. | n.d. |
| MHC and processing related | | | |
| HLA-A | 93 | 100 | 93 |
| HLA-B | 87 | 87 | 76 |
| HLA-C | 100 | 87 | 87 |
| HLA-DPB1 | n.d. | n.d. | n.d. |
| HLA-DQB1 | n.d. | n.d. | n.d. |
| HLA-DRB1 | n.d. | n.d. | n.d. |
| TAP1 | 115 | 123 | 123 |
| PSMB9 | 107 | 123 | 132 |
| PSMB8 | 93 | 87 | 87 |

Expression values are given relative to the normal medium control (set to 100% for each gene) after 24 h incubation with DMSO, sorafenib, or sunitinib. "n.d."=gene was not reliably detected in the samples.

Many tested antigens are expressed only at relatively low levels in the A498 cell line compared with primary RCC samples (data not shown), further confirming that analyzing primary tissue rather than cell lines is highly relevant. KIAA0367 and RGS5 could not be detected at all in A498, and CCND1, GUCY1A3, MMP7, MUC1 showed very low levels as compared to expression in primary RCCs. For the majority of tumor associated antigen genes, no significant changes in gene expression have been detected. For three genes, GUCY1A3, MET and MMP7, expression levels were found to be moderately lower as compared to the DMSO control.

For proteins related to antigen presentation, no effects of TKI treatment on the tumor cell line A498 were observed. Expression of HLA-A, -B and -C was not altered under TKI treatment. Also expression of genes involved in antigen processing was not influenced. HLA class II genes are absent from the cell line despite their frequent detection in primary RCC samples (data not shown).

2.2. Alteration of Gene Expression Profiles in Primary Human Tumor Tissue In Vivo mRNA expression was measured as described in 1.1 except that mRNA from 20 primary clear cell renal cell carcinoma (ccRCC) samples of patients not treated with TKIs and 1 locally recurring ccRCC tumor sample of a patient having received sorafenib treatment (800 mg Nexavar™ per day starting 35 days before and stopping 2 days before surgery) previous to surgery were included in this analysis.

Tumor tissue specimens were snap-frozen in liquid nitrogen immediately after surgery and later homogenized with mortar and pestle under liquid nitrogen. Total RNA was prepared from these samples using TRIzol (Invitrogen) or TRI Reagent (Fermentas) followed by a cleanup with RNeasy (QIAGEN); both methods were performed according to the manufacturers' protocols. Quality and quantity of all RNA samples were assessed on an Agilent 2100 Bioanalyzer (Agilent) using the RNA 6000 Pico LabChip Kit (Agilent).

Gene expression analysis of the tumor samples was performed by Affymetrix Human Genome (HG) U133A or HG-U133 Plus 2.0 oligonucleotide microarrays (Affymetrix, Santa Clara, Calif., USA). A normal reference kidney sample was hybridized to both array types to achieve direct comparability of all samples.

All steps were carried out according to the Affymetrix manual. Briefly, double-stranded cDNA was synthesized from 5-8 μg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labeling Kit (ENZO Diagnostics, Inc., Farmingdale, N.Y., USA) for the U133A arrays or with the GeneChip IVT Labeling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. Pairwise comparisons were calculated using the respective normal reference kidney array as baseline. For normalization, 100 housekeeping genes provided by Affymetrix were used. Relative expression values were calculated from the signal log ratios given by the software and the normal kidney sample was arbitrarily set to 1.0.

The results are summarized in Table 2.

TABLE 2

Composite expression of tumor associated antigens and MHC related genes in primary ccRCC samples and expression in the RCC of one sorafenib patient.

| | ccRCC untreated | | Sorafenib patient |
|---|---|---|---|
| Gene | Mean | Range | Single value |
| Tumor associated antigen | | | |
| ADFP | 2.5 | 1-6.6 | 5.7 |
| APOL1 | 7.4 | 2.8-19.6 | 19.7 |
| CCND1 | 2.3 | 1-5.2 | 3.2 |
| GUCY1A3 | 2.0 | 1.1-3.5 | 0.5 |
| KIAA0367 | 1.7 | 0.6-4.8 | 1.2 |
| MET | 12.5 | 7.2-21.7 | 9.8 |
| MMP7 | 1.8 | 0.4-7.3 | 6.1 |
| MUC1 | 0.2 | 0.1-0.6 | 0.3 |
| RGS5 | 7.0 | 2.4-20.3 | 1.5 |

TABLE 2-continued

Composite expression of tumor associated antigens
and MHC related genes in primary ccRCC samples and
expression in the RCC of one sorafenib patient.

| Gene | ccRCC untreated | | Sorafenib patient |
| --- | --- | --- | --- |
| | Mean | Range | Single value |
| MHC and processing related | | | |
| HLA-A | 1.0 | 0.8-1.3 | 0.9 |
| HLA-B | 2.2 | 1.5-3.1 | 2.1 |
| HLA-C | 1.1 | 0.8-1.4 | 1.0 |
| HLA-DPB1 | 3.4 | 1.9-6.2 | 4.0 |
| HLA-DQB1 | 5.3 | 0.4-63.3 | 168.9 |
| HLA-DRB1 | 2.0 | 1.5-2.7 | 2.8 |
| TAP1 | 2.9 | 1.9-4.5 | 2.1 |
| PSMB9 | 4.4 | 2.2-8.6 | 5.7 |
| PSMB8 | 3.4 | 2.2-5.1 | 3.5 |

Expression values are given relative to a normal reference kidney sample. Mean expression for "untreated" (i.e. no TKI treatment) tumors was calculated as the geometric mean (by log transformation of the original values and re-transformation of the calculated mean) and "Range" designates the span between Mean minus Geometric Standard Deviation and Mean plus Geometric Standard Deviation.

As expected, mRNA expression shows a certain variation among primary ccRCC samples from patients having not received any TKI therapy. For the purpose of this experiment, the typical range of expression values was defined as the mean±one standard deviation for each gene (Table 2). The expression values of a patient RCC tumor sample treated with sorafenib previous to surgery lie within this range for most antigens considered in this experiment. Among the IMA901 target antigens, only GUCY1A3 and RGS5 expression is at the lower boundary of the range. Both genes are mainly involved in tumor angiogenesis. Downregulation of these two genes might reflect the effect of sorafenib on angiogenesis as reported recently (Murphy, D. A., S. et al. 2006. Inhibition of Tumor Endothelial ERK Activation, Angiogenesis, and Tumor Growth by Sorafenib (BAY43-9006). Am. J Pathol. 169:1875).

For proteins involved in antigen presentation to T cells, like HLA proteins themselves or members of the processing machinery like TAP1 or the immunoproteasomal subunits PSMB9 (LMP2) or PSMB8 (LMP7), only HLA-DQB1 seems to be an outlier.

In conclusion, data from this sample do not provide any evidence for a potential influence of sorafenib treatment on the expression profile of tumor associated antigens or their HLA presentation in vivo.

Example 3

In Vitro Alteration of T-Cell Activation by Kinase Inhibitors 3.1. Mouse T-Cell Activation To test whether the presence of sorafenib or sunitinib has an influence on mouse T-cell responses, alloreactive T-cells responses (CD4 and CD8) were assessed in mixed lymphocyte reactions (MLR).

Allogenic responses are the most potent and strong immune responses and they are easy to generate in the mouse system due to the availability of congenic mouse strains differing in their H2 alleles. Therefore, first hints on the influence of sunitinib and sorafenib on immune responses can be drawn from in vitro mixed lymphocyte cultures.

3.1.1. Mixed Lymphocyte Reaction Assay

CFSE-labeled spleen cells from C57BL/6 (H2-b) mice were co-cultured with irradiated splenocytes from BALB/c (H2-d) mice, resulting in the strong allogenic response and proliferation of the C57BL/6 T cells against H2-d MHC molecules. The proliferation of the T cells results in a diminished CFSE staining of the divided cells. Percentage of divided cells and their number of divisions can be analyzed by flow cytometry.

Spleen cells were prepared from 1 C57BL/6 mouse and 1 BALB/c mouse (Harlan Winkelmann GmbH, Borchen, Germany). BALB/c cells were irradiated with 33 Gy. Effectors (C57BL/6) were adjusted to 20 Mio cells/ml. A 2 mM 5(6)-Carboxyfluorescindiacetate-N-succinimidylester (CFSE, Fluka, Buchs, Switzerland) solution in PBS was freshly prepared from a 10 mM DMSO stock solution. The cell suspension was mixed 1:1 with the CFSE solution. After incubation at 37° C. for 4 min, reaction was stopped by addition of fetal calf serum (Biochrom, Berlin, Germany), and free CFSE was washed out. $2 \times 10^5$ stimulator cells (BALB/c) were plated into cavities of a 96-well round-bottom plate. $1 \times 10^5$ or $2 \times 10^5$ CFSE-labeled effector cells and tyrosine kinase inhibitors at two different concentrations were added. Appropriate positive and negative controls were included. All cultures were in 200 µl T-cell medium with 0.1% (v/v) DMSO for 5 or 7 days without further medium change. Thereafter, cells were stained with fluorescently labelled anti-CD4-PerCP and anti-CD8-FITC antibodies (both BD Biosciences, Heidelberg, Germany) and analyzed by flow cytometry.

The experiment described above was repeated with the exception that a 96-well flat-bottom plate was used for mixed lymphocyte reactions (MLRs), a syngenic control with irradiated C57BL/6 cells was included, more concentrations of inhibitors were assessed, and all groups were analyzed in triplicates.

During cultivation, half of the medium was replaced with fresh appropriate medium supplemented with final concentrations of tyrosine kinase inhibitors every day, and proliferation was analyzed at day 7 only. Additionally cells were stained for H2-Kb to clearly identify effector cells in a further dimension.

3.1.2. Results

Percentage of highly proliferated CD8 and CD4 cells are shown in FIG. 1. Cells in cultures with 13 µM sorafenib showed a clear change in morphology resembling apoptotic and/or necrotic cells due to putatively toxic effects of the drug and were therefore not comparable to the other treatment groups. For CD4 cells, an increased proliferation was observed for all cultures with tyrosine kinase inhibitor compared to the positive control (no inhibitor). CD8 proliferation was only slightly affected by 1.3 µM sorafenib and slightly increased for both sunitinib concentrations.

Proliferation of CD4 and CD8 cells in the presence of different concentrations of tyrosine kinase inhibitors are shown in FIG. 2. Tendency towards elevated proliferation of $CD4^+$ cells with both tyrosine kinase inhibitors was reproduced with even significant increase for 1.6 µM sorafenib. In addition, a slight increase in $CD8^+$ proliferation with sunitinib and a slight decrease with sorafenib was again observed. Sorafenib levels of 6.5 µM or greater induced toxic effects resulting in a dramatically changed morphology of cells in flow cytometry.

In summary, CD8 T-cell proliferation due to allogenic stimuli is not affected by sunitinib, but may be slightly decreased by sorafenib. In addition, sorafenib is toxic for cells in mixed lymphocyte reactions at concentration near the steady-state plasma level of treated patients. Observed changes were higher in the first experiment, most likely due to daily change of medium with cell-produced cytokine milieu during the second experiment.

In addition, sorafenib slightly reduced CD8+ T cell proliferation in response to allogenic stimuli, while CD4+ T-cell proliferation was increased. In contrast, CD4+ and CD8+ T-cell proliferation was not altered or even increased in the presence of sunitinib and no drug-related toxicity was observed in MLRs.

3.2. Human T-Cell Activation

To test whether the presence of TKIs has an influence on human T-cell activation in vitro, alloreactive T-cells responses (CD4 and CD8) were assessed in mixed lymphocyte reactions (MLR) using PBMCs of healthy human individuals. Two types of tests were performed.

3.2.1. Priming and Expansion of Isolated Human CD8+ Cells in the Presence of TKIs Six fresh buffy coats (HLA-A*02+, HBC-131 to -136) were obtained from the Katharinenhospital Stuttgart. PBMCs were isolated by standard density gradient isolation and incubated overnight in T-cell medium (TCM) for human in vitro priming consisting of RPMI-Glutamax (Invitrogen, Karlsruhe, Germany) supplemented with 10% heat inactivated human AB serum (PAA, Colbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Isolated CD8+ T-cells were incubated until use in TCM supplemented with 2.5 ng/ml IL-7 (PromoCell, Heidelberg, Germany) and 10 U/ml IL-2 (Chiron, Munich, Germany). Coating of pMHC/anti-CD28 coated beads, T-cell stimulations and readout was performed as described before with minor modifications. Briefly, 800000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). pMHC used were A*0201/MLA-001 (peptide ELAGIGILTV from modified Melan-A/MART-1) or negative control A*0201/DDX5-001 (YLLPAIVHI from DDX5). Stimulations were initiated in 96-well plates by co-incubating $1 \times 10^6$ CD8+ T-cells with $2 \times 10^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. TKIs (sorafenib tosylate or sunitinib malate) in DMSO or DMSO alone were added at indicated final concentrations to the well during stimulations and to the added medium during exchanges. Final concentration of DMSO was always 0.1%. This stimulation cycle was performed for a total of three times. Tetrameric analyses were then performed with fluorescent MHC tetramers plus Abs CD8-FITC clone SK1 (BD, Heidelberg, Germany) on a four-color FACSCalibur (BD). Total specific cell numbers per well were calculated by FACS analysis as follows: (specific cells counted)×(microspheres added per well)/(microspheres counted).

Figure 3A:
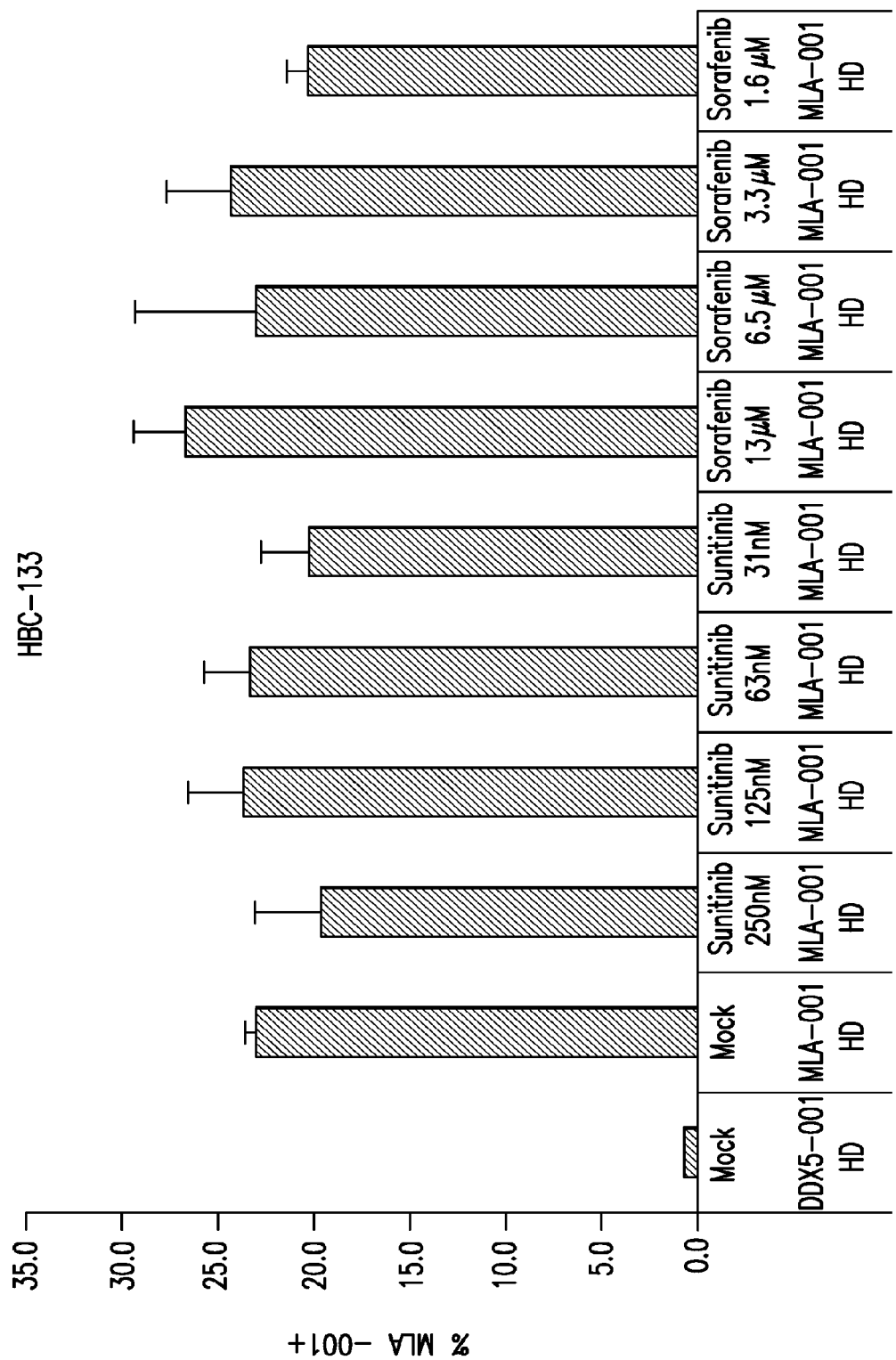
Figure 3B:
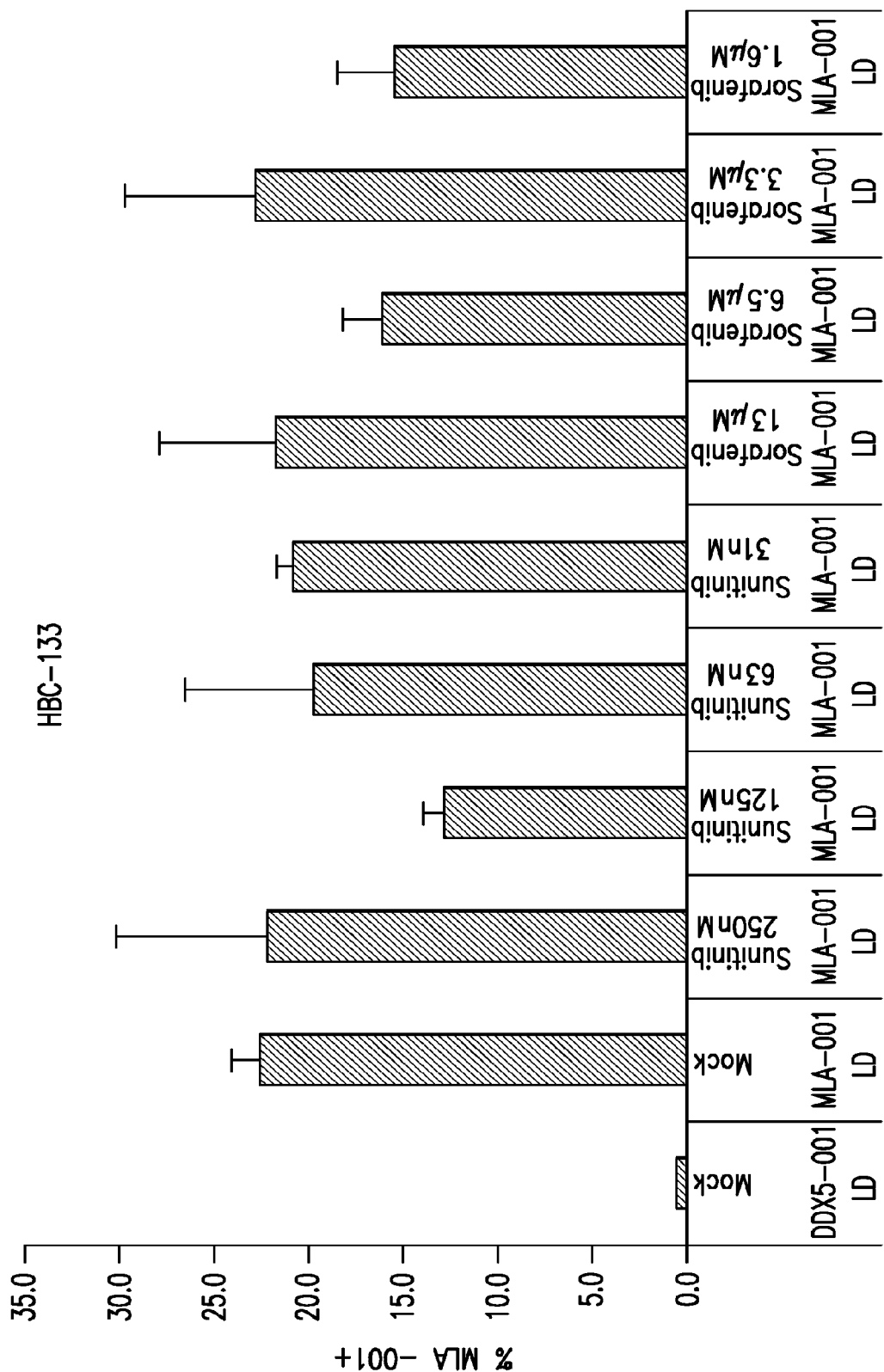
Figure 3C:
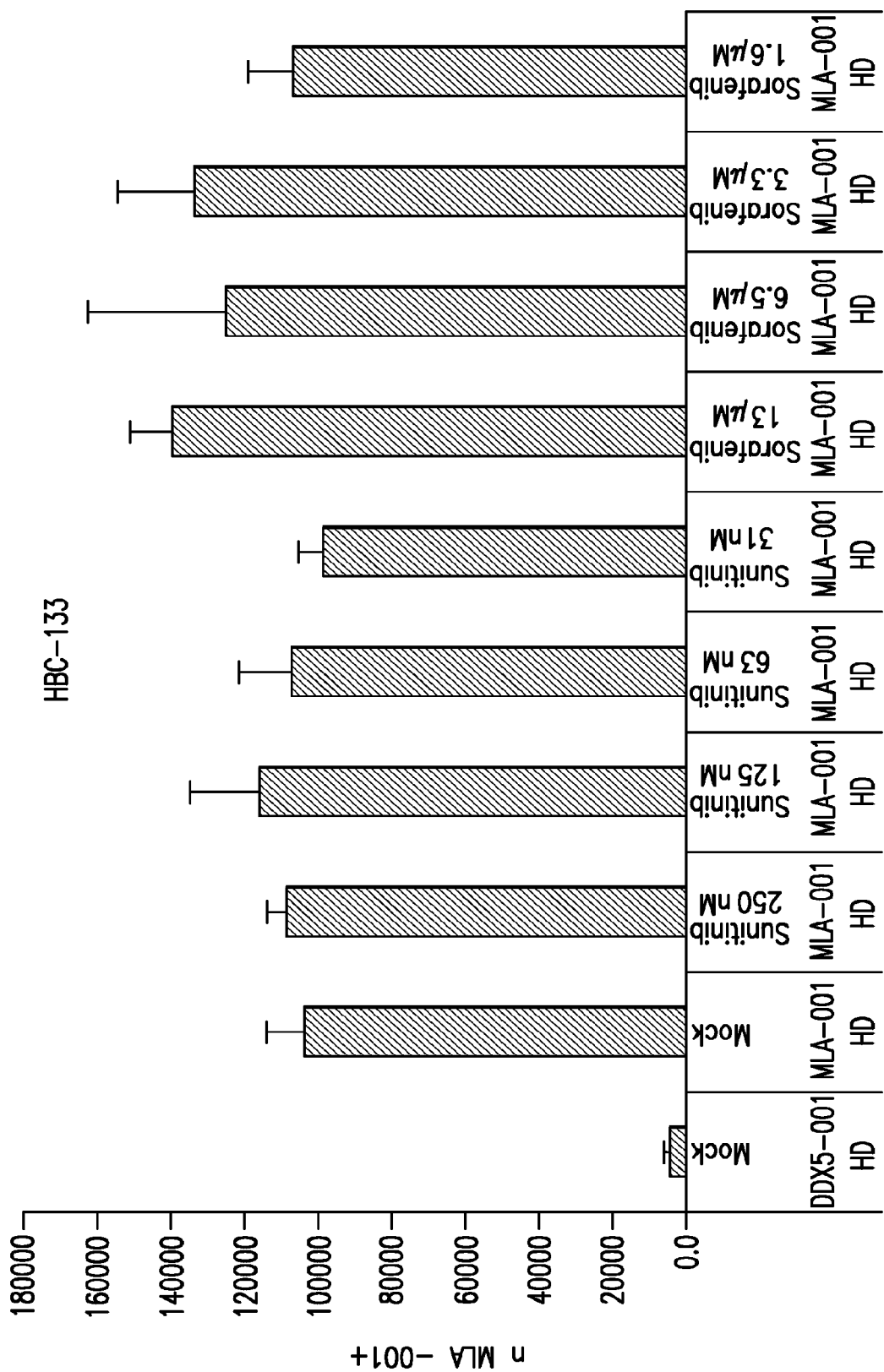

Evaluable results were available for three buffy coat donors of which one representative is shown in FIG. 3. aAPC priming with antigen A*0201/MLA-001 was successful in the presence of mock TKIs as compared to irrelevant stimulation with A*0201/DDX5-001. However, no concentration-dependent influence of sorafenib or sunitinib that was consistent between donors was seen on either the percentage of MLA-001 specific within CD8+ lymphocytes (upper panel) or their total number within wells (lower panel) after priming. Variations were higher after LD priming (right panel) as compared to HD priming (left panel), which can be readily explained by the expected lower precursor frequency of cells primed by LD stimulations within one well.

CD8+ T-cell priming and expansion is not altered by either sorafenib or sunitinib in this in vitro system in the absence of natural antigen presenting cells.

3.2.2. Proliferation of CD4+ and CD8+ Human PBMC Subsets in the Presence of TKIs Two fresh buffy coat (HLA-A*02+ and HLA-A*02−) were obtained from the Katharinenhospital Stuttgart. PBMCs were isolated by standard density gradient isolation and incubated overnight in T-cell medium (TCM) for human in vitro priming as in WP03 #4. Ca2+ and Mg2+ free PBS (Cambrex) washed HLA-A*02+ PBMCs were labeled at $1 \times 10^7$ cells/ml with 1 µM CFSE (Fluka, Buchs, Germany) at 37° C. for 4 minutes. Labeling was stopped by adding the same volume heat inactivated FCS (Invitrogen) and labeled cells were washed in TCM. Irradiation of target or feeder cells, if indicated, was performed at 33 Gy using a 1000 Elite gammacell (MDS Nordion, Ottawa, Canada). Stock solutions of sorafenib tosylate and sunitinib malate were prepared in DMSO (Merck, Darmstadt, Germany) and frozen aliquoted at −80° C. Mixed lymphocyte reactions were performed by coculturing $2 \times 10^5$ CFSE labeled effector plus $2 \times 10^5$ irradiated target cells as indicated per well of 96 well round bottom plates in 200 µl TCM in the presence of indicated concentrations of sorafenib, sunitinib or DMSO at 37° C. and 5% CO2 (day 1). On day 4, 100 µl supernatant was removed and 100 µl TCM supplemented with the original concentration of TKIs was added. On day 8, $3.75 \times 10^5$ unlabeled beads (T cell Activation/Expansion Kit, Miltenyi Biotech) were added to wells. Cells were washed in PBS containing 2% FCS (Invitrogen), 2 mM EDTA (Roth) and 0.02% sodium azide (Merck) (PFEA buffer) and stained with anti-HLA-A2 PE (AbD Serotec, Düsseldorf, Germany), anti-CD8 PerCP (BD) and anti-CD4 APC (BD). Cells were washed, fixed in PFEA containing 1% formaldehyde (Fluka) and analyzed on a FACSCalibur (BD). Data analysis was performed with FCS Express V3 (DeNovo Software).

Figure 4A:
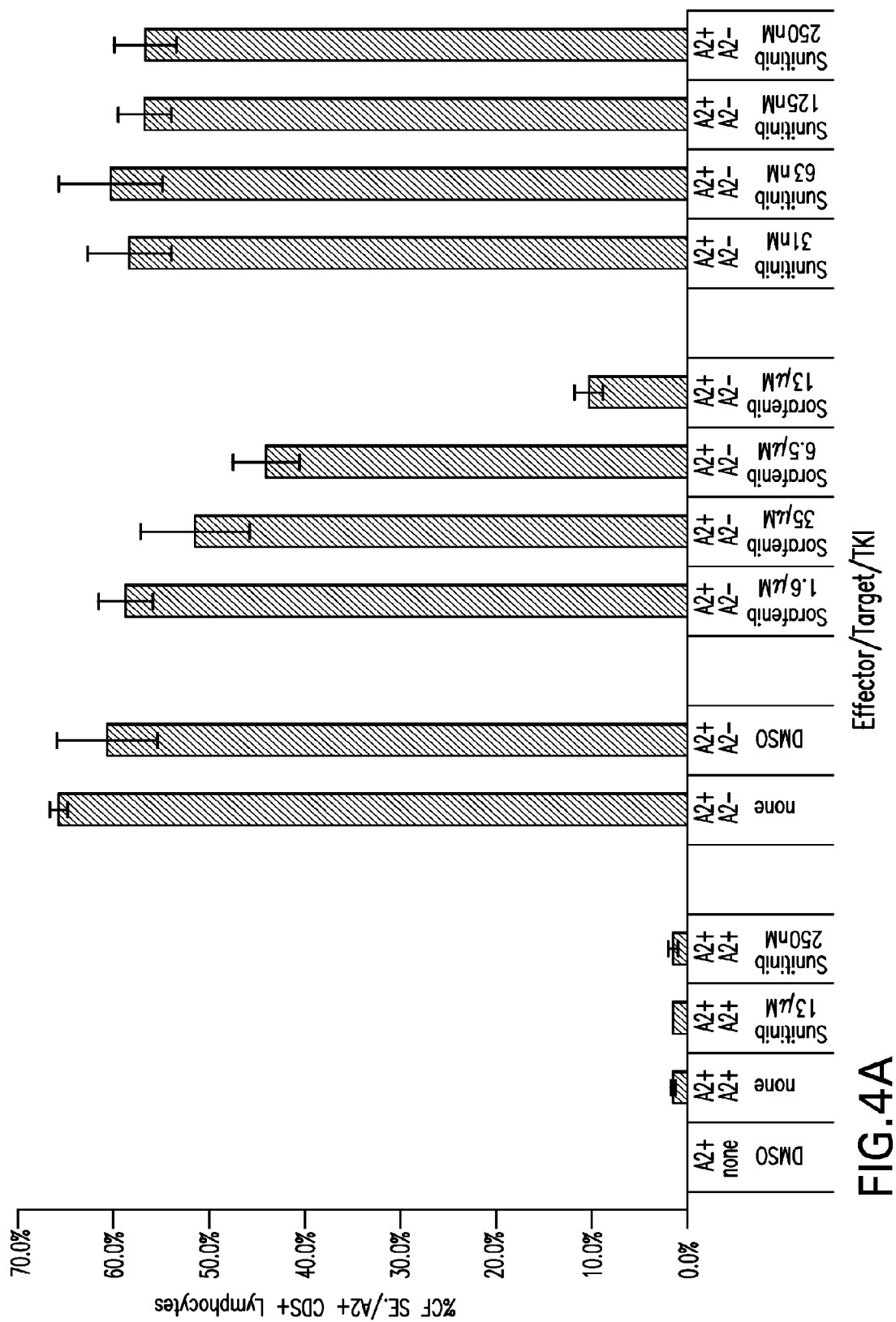
FIGS. 4A-B show the percentage of highly-proliferative, CFSE-labeled HlA-A *0201+ PBMCs after seven days allogenic stimulation with irradiated HLA-A*0201− PBMCs. CD4+ (upper panel) and CD8+ (lower panel) HLA-A2*0201+ cells were analyzed separately. Means of triplicate with error bars representing standard deviation. Labeling of horizontal axis (upper-, middle-, and lower label) represent effector cells, target cells and TKIs present, respectively. This figure shows that in the absence of target cells, or when autologous target cells were added, only baseline proliferation of effector cells was observed, which did not increase by the addition of sorafenib or sunitinib. In the presence of HLA-mismatched target cells, a prominent proliferation of CD8+ and CD4+ (presumably allo-reactive) effector cells could be detected. This proliferation did not change significantly in the presence of solvent (DMSO). However, increasing concentrations of sorafenib, but not sunitib, dramatically suppressed proliferation of CD8+ and CD4+ effector cells in this mixed lymphocyte reaction (MLR). Although absolute cell numbers were not determined, sufficient cells could be found in flow cytometry from all samples containing effector cells.
Figure 4B:
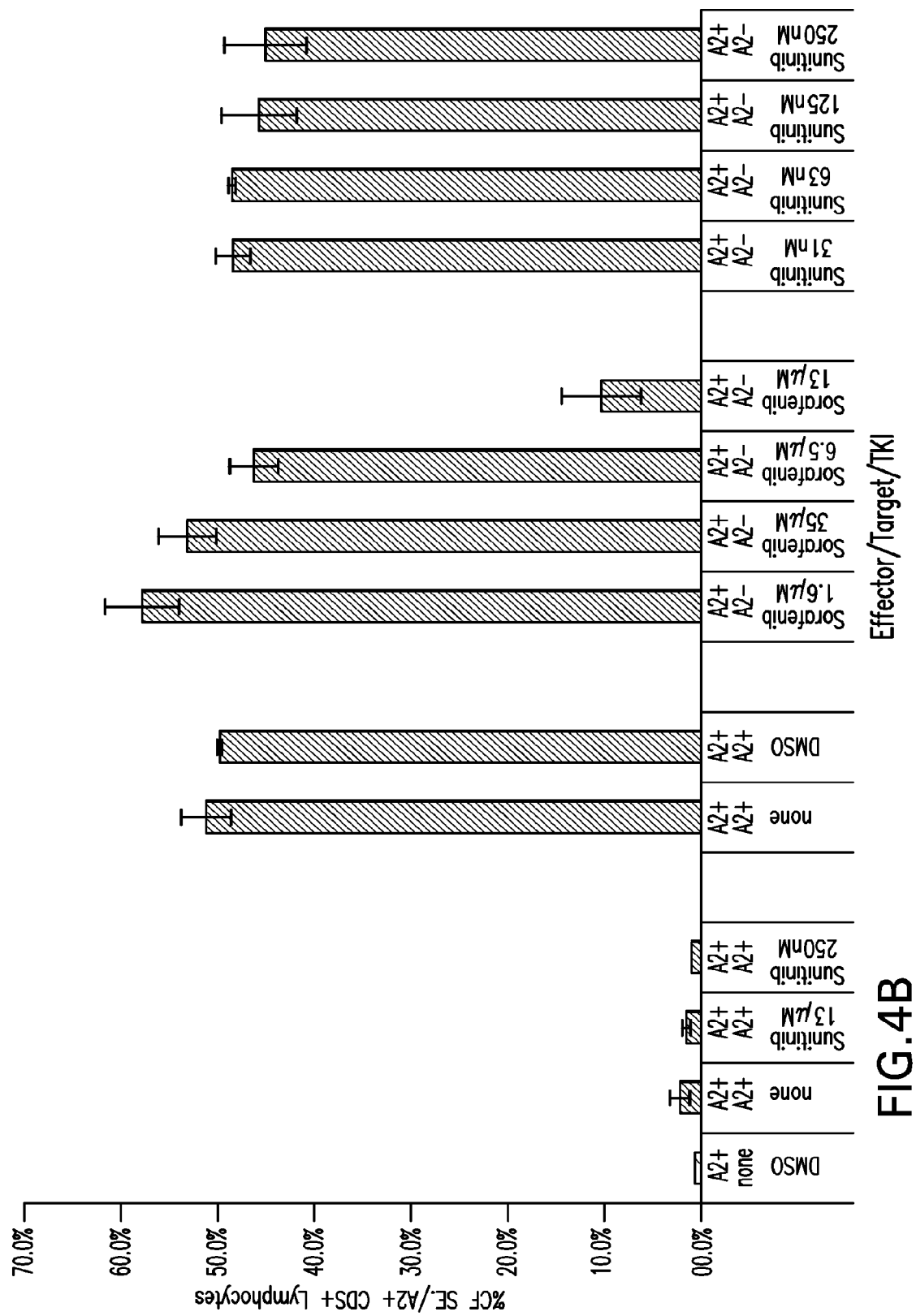

Summarized results are shown in FIG. 4 for CD8+ (upper panel) and CD4+ (lower panel) effector cells, respectively.

In the absence of target cells, or when autologous target cells were added, only baseline proliferation of effector cells was observed that did not increase by the addition of sorafenib or sunitinib. In the presence of HLA-mismatched target cells, a prominent proliferation of CD8+ and CD4+ (presumably allo-reactive) effector cells could be detected. This proliferation did not change significantly in the presence of solvent (DMSO). However, increasing concentrations of sorafenib suppressed proliferation of CD8+ and CD4+ effector cells in this MLR. Sunitinib did not have this effect. Although absolute cell numbers were not determined, sufficient cells could be found in flow cytometry from all samples containing effector cells.

No effect on the CD8+ and CD4+ T cell expansion in response to allogenic stimuli was detected in this system for sunitinib.

Example 4

In Vivo Alteration of Immune Cell and Vaccine Immunogenicity Populations in Mice by Kinase Inhibitors Immune responses are complex events that are dependent not only on several cell types, but also on the surrounding cytokine milieu and the architecture of tissues like skin and lymphoid organs that are the scene of immune response triggering. Therefore, it was the objective of these experiments to assess whether treatment with TKIs alters key cell populations in the immune response and the overall outcome of a peptide-vaccine triggered activation of the immune system. Therefore, mice were pre-treated for 2 weeks with TKIs applying dosages that have been shown to inhibit tumor growth. Thereafter, the mice were immunized with OVA-001 peptide under continued drug treatment before immune cell populations in spleen and blood and the triggered CD8$^+$ T-cell response were analyzed. Sunitinib did not alter the overall immunogenicity of the peptide vaccine in subtoxic dosages. Probable adverse effect of sunitinib on T-cell activation pathways might be compensated by reduced numbers of CD4$^+$ CD25$^+$ regulatory T-cells that was observed for sunitinib-treated mice in these experiments. All observed effects of the tyrosine kinase inhibitors were reversible, as after discontinuation of treatment cell populations and the immune response recovered quickly to normal levels.

4.1. Principle of Tests

Due to the potential inhibition of several key players in the activation pathways of T-cells by sorafenib and sunitinib, immune responses might be dramatically altered under the treatment with these drugs. Therefore, we assessed immune responses and immune cell populations during, and shortly after, the treatment with sorafenib or sunitinib in the mouse. The well-described H2-Kb restricted epitope SIINFEKL (OVA-001) from hen egg albumin was used for immunization of C57BL/6 mice. Evaluation of CD8+ T-cell responses was performed with a fluorescently labeled H2-Kb/SIINFEKL tetramer followed by flow cytometry analysis. With the same method, T-cell, B-cell, and NK cell populations in blood and spleen were assessed after staining with lineage specific antibodies. A pretreatment of 2 weeks before immunization was chosen, to allow cell populations to achieve a "near-steady-state" level. Although longer time spans are usually required for cell populations to reach full-steady state levels (up to 3 months), possible toxic effects of the drug and the stress caused to the animals by daily treatment argued against a prolonged drug treatment before first immunization. Plasma levels of tyrosine kinase inhibitors were analyzed routinely to ensure that drug application was reliable during the experiment.

4.2. Treatment of Mice

4.2.1. Animal Keeping

Female C57BL/6 mice (20-25 g, Harlan Winkelmann GmbH, Borchen, Germany) were used for all experiments described in this section. Animals were kept in the animal facility of the Dept. of Immunology at the University of Tuebingen. Animals were cared for by trained animal keepers and health status of animals was supervised by the veterinaries of the University of Tübingen. Feeding with drug was also performed in part by the local animal keepers after special training. All animals were supplied with water and food ad libitum. The described experiments were performed according to procedure no. IM1/06 approved by the Regierungsprasidium Tuebingen.

4.2.2. Drug Treatment

A liquid, viscous vehicle composed of 30% (w/v) Cremophor EL (Sigma, Deisenhofen, Germany), 30% (w/v) PEG 400 (Sigma, Deisenhofen, Germany), 10% ethanol p.a., 10% glucose was used. Sunitinib and sorafenib were suspended in vehicle according to the planned dosages in a way that 2.5 µl/kg body weight had to be applied to all mice, according to approx. 50 µl of suspension. Feasible aliquots were prepared from suspensions and from vehicle and stored until use at −20° C. in the dark. Thawed substance was stored at 4° C. and used within the next three days. Animals were weighed before start of treatment and thereafter weekly. The deduced dosage was applied daily using a 1 ml syringe with gavage into the backward cavity of the mouth of the animal without anesthesia. Drug delivery into blood plasma was controlled as described in example 1.

4.2.3. Immunization

Mice were immunized with 100 µl of a 1:1 water-in-oil suspension of 40 nmol CpG deoxyoligonucleotide 1668 (TIB MOLBIOL, Berlin, Germany), OVA-001 peptide (30 µg, SIINFEKL) and PBS in Incomplete Freund's Adjuvants (IFA)/Titermax (4:1; both from Sigma, Deisenhofen, Germany) s.c. under the dorsal skin (approx. 80 µl) and into the base of tail (approx. 20 µl). Negative control mice were immunized with peptide VSV-001 (RGYVYQGL) employing same composition of the vaccination cocktail. Negative and positive control mice were fed with vehicle only. One week after the first immunization, immune response was boosted by a second immunization with 30 µg peptide (OVA-001 or VSV-001), 25 nmol CpG deoxyoligonucleotide in 100 µl PBS.

4.2.4. Treatment Schedules 3 experiments were performed:

1) Immunization under continuous treatment with tyrosine kinase inhibitors. Pretreatment phase was two weeks (see FIG. 5A). Beside negative and positive control groups, groups treated with 15 and 60 mg/kg body weight sorafenib, and 20 and 80 mg/kg body weight sunitinib were included (6 mice per group). Analysis of the immune response was performed using the procedure described in example 3 with the following alterations:

Blood cells were not further purified by ficoll density centrifugation.

Staining for tetramer analysis: CD3e-PerCP was substituted by PerCP-labeled CD45R/B220 (exclusion of B cells).

Spleen cells well assessed for, CD4, Tregs, CD8 and memory subtypes, B cells and NK cells. PBMCs were analyzed for CD4, CD8, B cells and Tregs.

2) Immunization directly after discontinuation of treatment with tyrosine kinase inhibitors. Pretreatment phase was two weeks. First immunization was done 48 h after last drug treatment (see FIG. 5B).

Analysis of the immune response was performed using the procedure described in example 3 with the following alterations:

Staining for tetramer analysis: CD3e-PerCP was substituted by PerCP-labeled CD45R/B220 (exclusion of B cells).

Spleen cells were assessed for, CD4, Tregs, CD8 cells, B cells and NK cells. PBMCs were analyzed for CD4, CD8, B cells and Tregs.

3) The experimental design was identical to a) Beside negative and positive control groups, groups treated with 60 mg/kg body weight sorafenib, and 20 and 40 mg/kg body weight sunitinib were included (6 mice per group). For spleen cells, CD4, Tregs, CD8 cells, and B cells were assessed, for PBMCs CD4, CD8, B cells and Tregs were analyzed.

4.3. Analysis of Specific T-Cell Responses and Immune Cell Populations

4.3.1. Preparation of Blood Cells

One week after the boost immunization, mice were bled from the retrobulbar plexus under ether anesthesia and sacrificed without awakening by cervical dislocation. Blood was collected in tubes containing 40 µl of citrate phosphate dextrose (CPG, Sigma, Deisenhofen, Germany) to inhibit blood clotting. Single cell suspensions were prepared from spleens by passing cells through a 40 µm cell strainer (BD Biosciences). After lysis of erythrocytes, spleen cells were counted and stored in T-cell medium (see section 3.1.4.) until further use. Erythrocytes of blood cells were lysed with ACK (154 mM ammonium chloride, 19 mM potassium bicarbonate, 1 mM EDTA) and PBMC were further purified from contaminating erythrocytes by ficoll separation.

Splenocytes were stained with PE-labeled H2-Kb/OVA-001 tetramer, APC-labeled H2-Kb/VSV-001 (produced inhouse), CD8-FITC, and CD3e-PerCP (both BD Biosciences, Heidelberg, Germany) for analysis of induced peptide-specific T-cell responses. Splenocytes and PBMCs were further incubated with cell type-specific fluorecently-labeled antibodies (CD8, CD4, CD25, CD45R, CD19, NK1.1; all BD Biosciences, Heidelberg, Germany) for population analysis. Cells were measured by flow cytometry.

Figure 6:
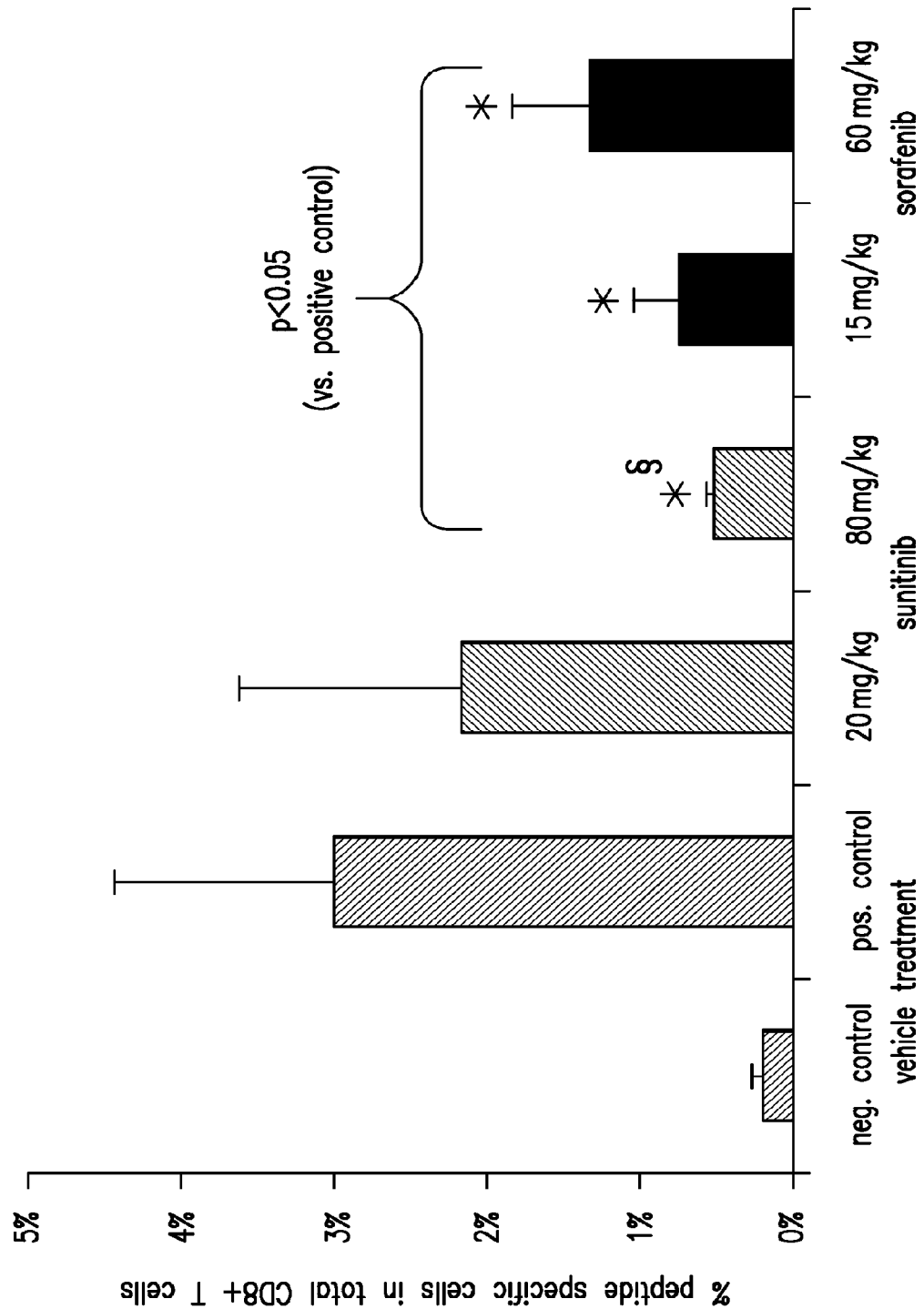
FIG. 6: OVA-001 specific T-cells in total CD8+ T-cells after 2 cycles of peptide immunizations during tyrosine kinase inhibitor treatment. Means with standard deviations are shown (n=6; n=4 for 15 mg/kg bw Sunitinib; n=2 for 80 mg/kg bw Sorafenib). *=significant reduced number of tetramer-positive cells (p<0.05 with unpaired, heteroscedastic student's t-test). §=toxic effects observed for this dosage: bad general condition, shrunken spleens, yellow discolored claws.

4.3.2. Results of Peptide Vaccination Under Continuous Tyrosine Kinase Inhibitor Treatment Frequency of specific T-cells from experiments 1) and 3) after two immunizations with OVA-001 peptide during treatment with sorafenib and sunitinib are shown in FIG. 6 Mice had been treated with tyrosine kinase inhibitors 2 weeks before and during the whole immunization phase. Serum analysis revealed acceptable drug delivery for all three experiments performed. Toxicity of drug treatment was observed for 40 mg/kg sunitinib (local loss of hairs around the eye) and for 80 mg/kg sunitinib (general bad condition; 2 out of 6 mice in experiment one died; and shrunken spleens in survivors). All OVA-001 immunized groups showed significantly elevated numbers of OVA-001 specific T-cells versus the VSV-001 immunized negative controls.

Both groups of mice treated with sorafenib and the high-dose sunitinib treated animals had a reduced immune response towards OVA-001 compared with vehicle treated controls. In contrast to all other groups, toxic effects of the drug were observed in the latter group with general bad conditions, death of 2 out of 6 animals, shrunken spleens (mean spleen cell number reduced to 20% of positive control for evaluable samples) and yellow discolored claws, leaving only 2 animals evaluable for tetramer analysis. Therefore, the reduced T-cell response in this group might be an indirect effect caused by general toxicity of the drug. Because variances and absolute results for the positive control groups were similar in both experiments, identical groups from the two experiments were pooled for statistical analysis to assess significance of the observed effects. Data are shown in table 3.

TABLE 3

Combined results from both experiments on CD8+ T-cell responses during tyrosine kinase treatment. Rational for summarizing identical groups were the similar absolute values and variances of the positive control of both experiments (3.0% ± 1.5% vs. 3.2% ± 2.1%).

| | | OVA-001 specific CD8+ T-cells | | |
|---|---|---|---|---|
| treatment | n | mean | stdev | p value vs. group 2 |
| vehicle, VSV-001 immunized | 9 | 0.17% | 0.06% | 0.0001 |
| vehicle, OVA-001 immunized (group 2) | 12 | 3.10% | 1.72% | N/A |
| sunitinib, 20 mg/kg bw, OVA-001 immunized | 12 | 3.47% | 2.09% | 0.66 |
| sunitinib, 40 mg/kg bw, OVA-001 immunized | 6 | 2.73% | 1.02% | 0.57 |
| sunitinib, 80 mg/kg bw, OVA-001 immunized | 2 | 0.51% | 0.03% | 0.0003 |
| sorafenib, 15 mg/kg bw, OVA-001 immunized | 4 | 0.72% | 0.30% | 0.0005 |
| sorafenib, 60 mg/kg bw, OVA-001 immunized | 12 | 1.81% | 1.08% | 0.04 | n indicates the number of evaluable animals per group.

This analysis clearly shows that an immune response could be induced even under continuous treatment with toxic doses of TKIs. Sunitinib does not impair CD8+ T-cell responses at intermediate dosages, but only at relatively high dosage of 80 mg/kg bw, most probably due to general toxicity. Sorafenib reduced specific T-cell responses at intermediate and high dosages without any observed toxic side effects. These results suggest that both substances may be combined with immune therapies based on T-cell responses.

Figure 7:
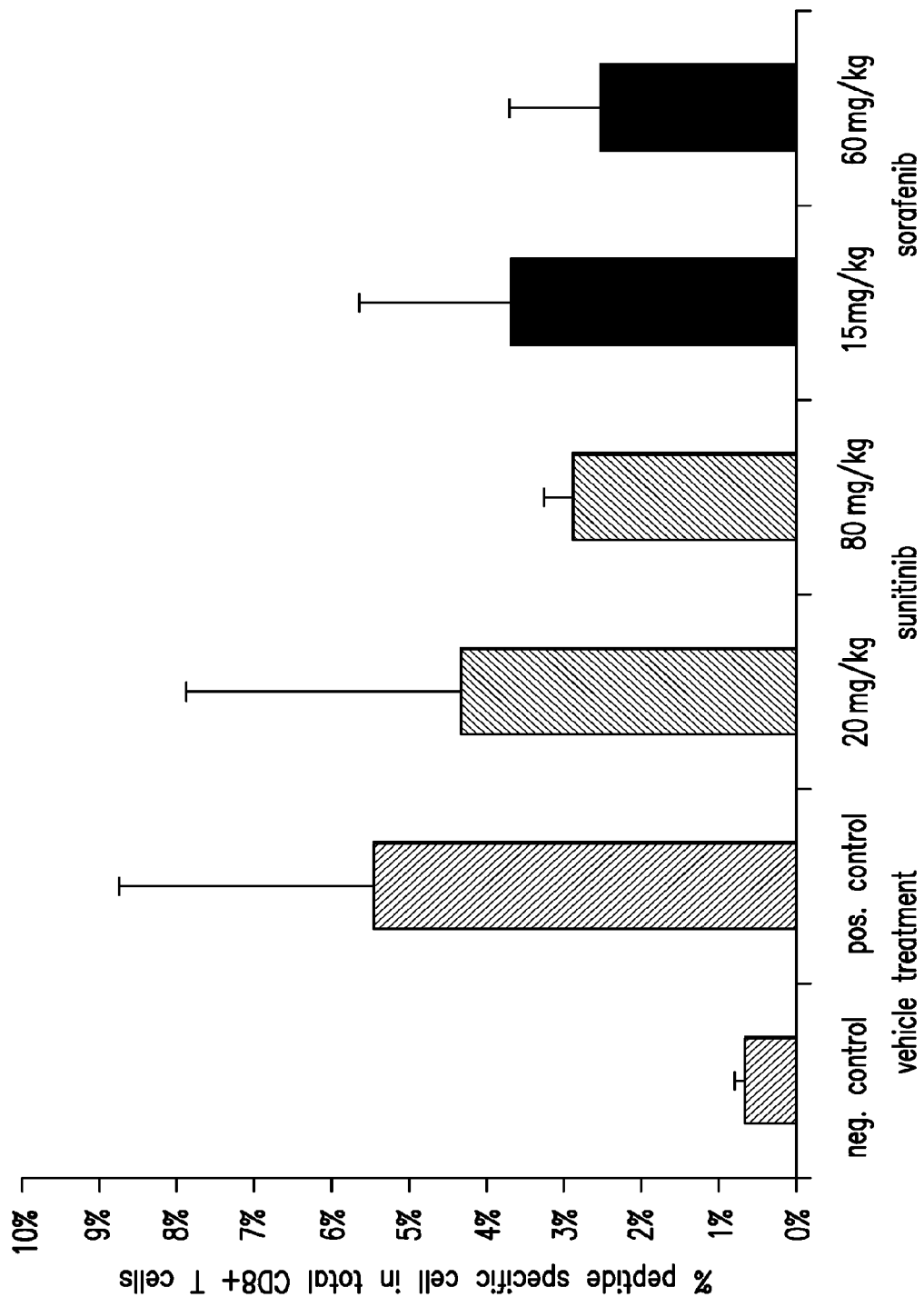
FIG. 7: OVA-001 specific T-cells in total CD8+ T-cells after 2 cycles of peptide immunization and tyrosine kinase inhibitor treatment stopped 48 h before first immunization. Mean values with standard deviations are shown (n=6).

4.3.3. Results of Peptide Vaccination after Discontinued Tyrosine Kinase Inhibitor Treatment In experiment 3), drug treatment was stopped 48 h before first immunization to analyze whether application of TKIs had any long-term effects on peptide-induced immune responses. Reduced numbers of OVA-001-specific T-cells were found for 80 mg/kg bw sunitinib and both sorafenib dosages, as in the experiments described above, but these differences were not significant (FIG. 7). Therefore, the observed slightly immunosuppressive influence of sorafenib and sunitinib is rapidly reversed after discontinuation of treatment.

4.4. Analysis of Immune Cell Populations Under Tyrosine Kinase Treatment

Figure 8:
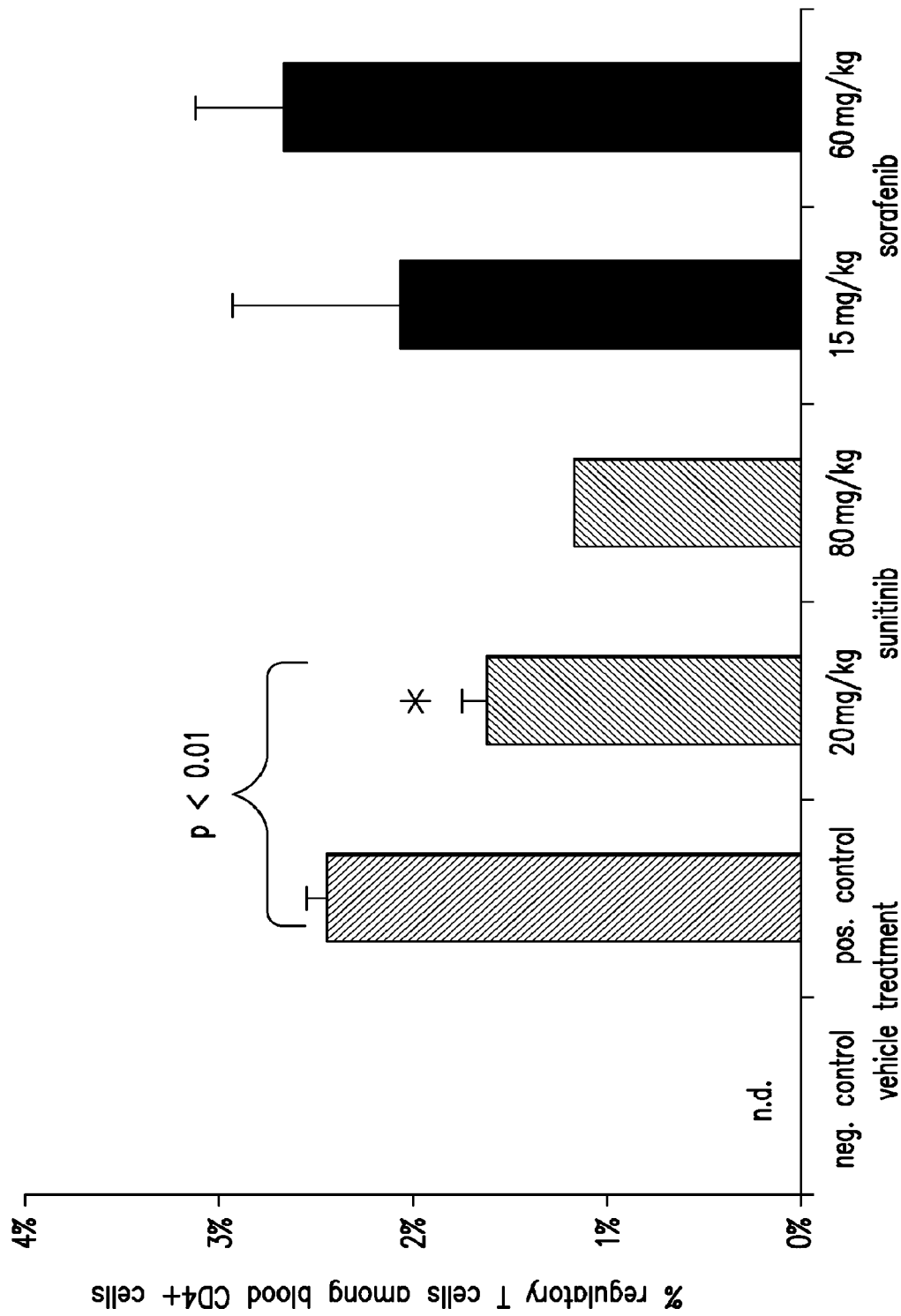
FIG. 8 shows the number of CD25+ cells among blood CD4+ cells after 4 weeks treatment with indicated tyrosine kinase inhibitor doses. The group of mice treated with 80 mglk:g body weight might not be directly comparable to the other groups due to the general toxicity observed for this treatment.
Figure 9:
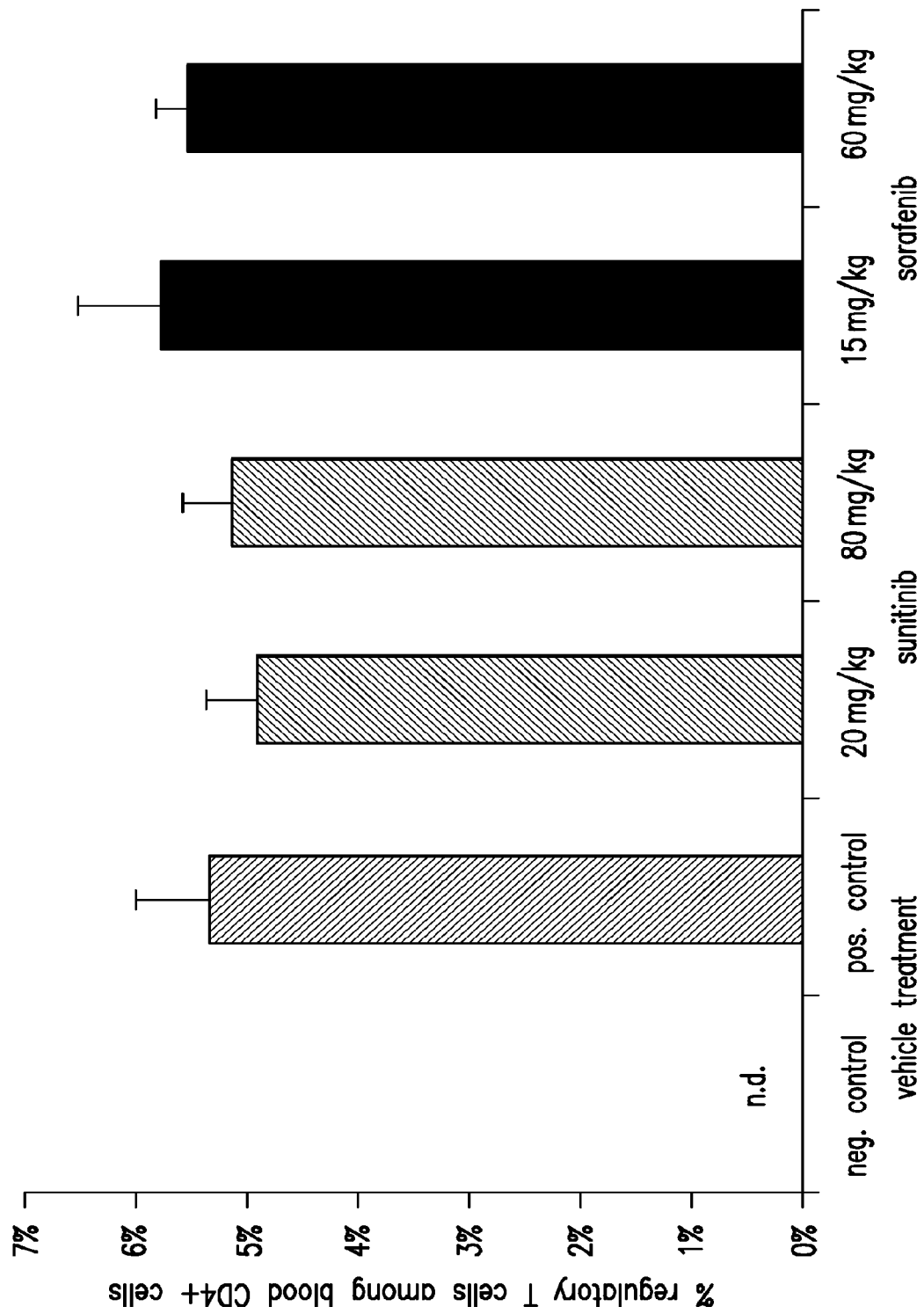
FIG. 9 shows the number of CD25+ cells among blood CD4+ cells after 2 weeks treatment with indicated tyrosine kinase inhibitor doses followed by 2 weeks recovery without treatment. Mean values with standard deviations are shown (n=3).

T cell subpopulations (CD4+, CD8+, Tregs), B cells and NK cells were analyzed in spleen and PBMCs of mice treated according to experiment 3). All mice treated with tyrosine kinase inhibitors showed reduced numbers of total splenocytes. For mice treated with high dose sunitinib elevated numbers of T-cells and B cells among splenocytes were observed, but might be explained by the general toxicity, already described above. Interestingly, a significantly reduced number of CD4+ CD25+ Tregs among total CD4+ cells was observed in PBMCs for mice treated with sunitinib, while Treg numbers in sorafenib treated mice were unchanged or even slightly elevated (FIG. 8). The reduced numbers of Tregs in sunitinib-treated mice recovered to normal levels during two weeks after discontinuation of treatment (treatment experiment 2) (FIG. 9). Absolute %-values for regulatory T cells among blood CD4+ cells between FIGS. 8 and 9 can not be compared because staining and FACS analysis was not done within one experiment for both analyses. However, the reduced number of Tregs during sunitinib treatment might favor the triggering of immune responses or may balance other adverse effects. This can in part explain that sunitinib does not have a negative effect on peptide-induced CD8+ T-cell responses. Interestingly, inflamed lesions of injections sites were frequently observed in mice treated with sunitinib, but not in other groups, supporting the suggestion that in these animals the barrier for activation of the immune system might be lower.

Example 5

Influence of Initial Treg Concentration on Vaccination Success in Humans

Regulatory T cells (Tregs) have been recently subject of renewed interest. Considerable experimental evidence now exists that shows that Tregs are a key mediator of peripheral tolerance in vivo, that they suppress T-cell functions in vitro, and that they are strongly implicated in cancer immunology, although the detailed molecular mechanisms are still subject of debate (for a review, see Beyer, M., and J. L. Schultze. 2006. Regulatory T cells in cancer. Blood 108:804.). Links of Tregs to cancer immunology are based on reports of increased Treg frequencies in cancer patients (Okita, R., T. Saeki, S. Takashima, Y. Yamaguchi, and T. Toge. 2005. CD4+ CD25+ regulatory T cells in the peripheral blood of patients with breast cancer and non-small cell lung cancer. Oncol. Rep. 14:1269); reports of correlation of Treg frequencies with prognosis; and reports that Treg depletion may lead to enhanced immune responses against cancer vaccines (Dannull, J., Z. Su, D. Rizzieri, B. K. Yang, D. Coleman, D. Yancey, A. Zhang, P. Dahm, N. Chao, E. Gilboa, and J. Vieweg. 2005. Enhancement of vaccine-mediated antitumor immunity in cancer patients after depletion of regulatory T cells. J Clin Invest 115:3623) and adoptive T-cell transfers in mice.

In a multicenter, open label, non controlled, single arm phase 1 study, patients suffering from renal cancer (RCC) were monitored prior and post vaccination with 578 µg of each of the peptides SEQ ID NO:1 to SEQ ID NO:10 (IMA901), which were purified by HPLC and ion exchange chromatography, dissolved in sodium hydrogen carbonate, and used for injection within 30 min after reconstitution at room temperature in combination with GM-CSF as adjuvant. Each vaccination consisted of an intradermal (i.d.) injection of rhuGM-CSF followed by an i.d. injection of IMA901. A total of 8 vaccinations was given. The last vaccination occurred in WEEK 10. A final evaluation took place after 4 weeks of follow-up.

Figure 10:
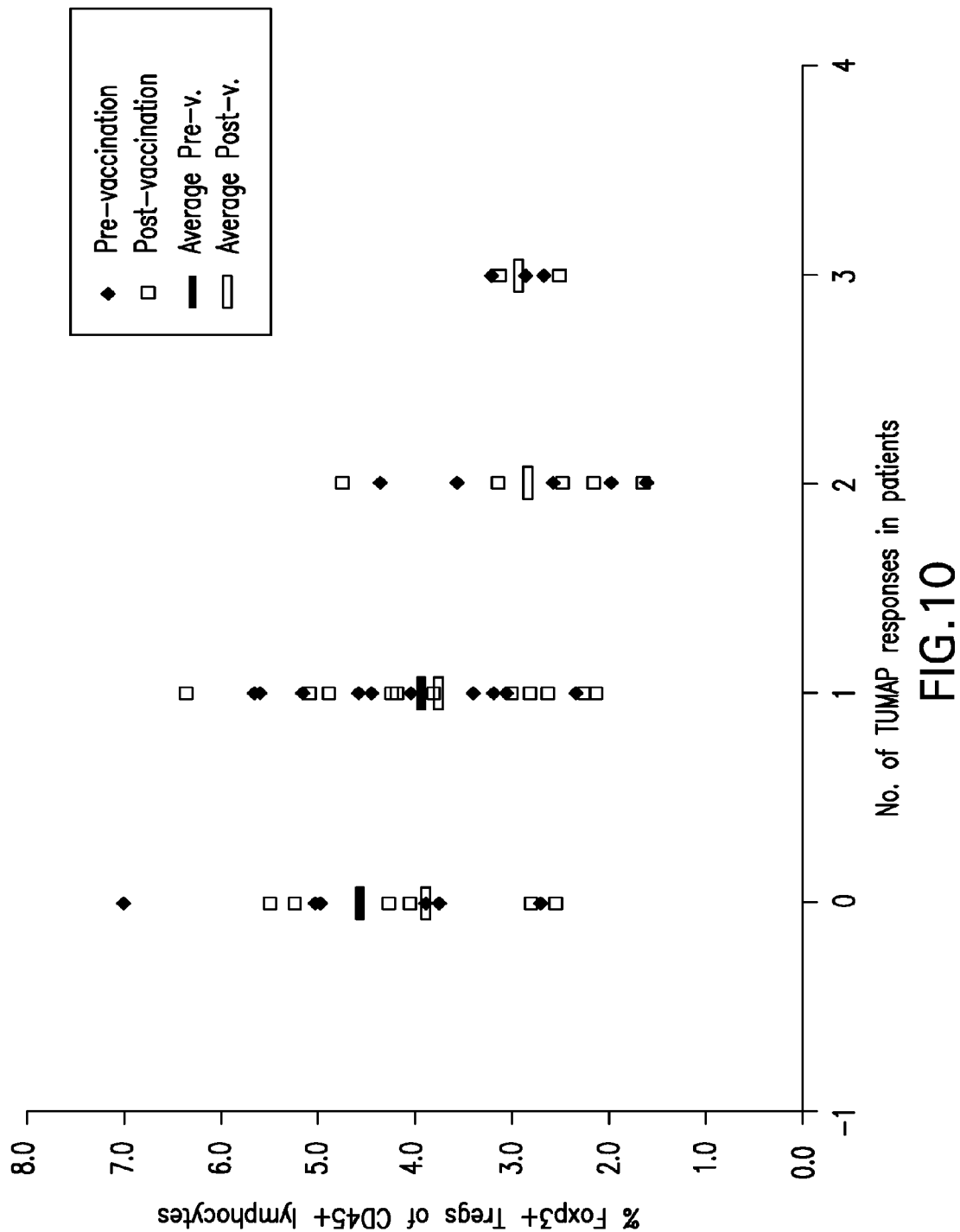
FIG. 10 shows the correlation of number of T-cell responses with frequency of regulatory T cells. Shown on the vertical axis are % of Foxp3+/CD45+ lymphocytes of tested pre- and post-vaccination timepoints (among 27 T-cell response evaluable patients). On the horizontal axis, the number of vaccine induced TUMAP responses per patient is indicated. Dot symbols represent individual patient samples and dashes represent averages. For two patient groups, averages of pre- and post-vaccination samples are overlaid and hence only one symbol is visible.

A newly available antibody against Foxp3 was used to quantify Tregs ex vivo from blood samples of the patients. For an optimal quality, it was considered crucial that all stainings were performed in parallel in one single experiment. Results are shown in FIG. 10. Although the individual post-vaccination Treg frequencies were closely linked to the pre-vaccination frequencies, there was a statistically significant (p=0.013) albeit slight overall reduction in Treg frequency post GM-CSF+IMA901 vaccination. This reduction appeared to be more prominent in patients responding to fewer peptides. Thus, the number of regulatory T cells pre-vaccination may be a new marker for the immunocompetence of RCC patients.

Finally and more importantly, there was a clear tendency that Treg frequencies correlate inversely with the number of responses against different peptides among patients. Patients with 2-3 peptide immune responses have significantly lower Treg levels than patients with 0-1 peptide responses (p=0.016 Wilcoxon Test, N=27 patients). A possible explanation for this observation is that the number of regulatory T cells prior to vaccination directly interferes with the in vivo T cell responses. Substances reducing the number regulatory T cells in a pre-vaccination setting may be favorable for the immunological and clinical outcome.

Consequently, these data support combination therapies of vaccines with an additional therapy arm that reduces the number of regulatory T cells previous to vaccination to enhance immunological outcome.

What is claimed is:

1. A method of treating a neoplastic disorder in a mammal comprising administering to the mammal a vaccine and sunitinib malate, wherein the vaccine comprises a plurality of isolated tumor associated peptides having the ability to bind to a molecule of the human major histocompatibility complex (MHC) class-I or class-II and the plurality of isolated tumor associated peptides consist of the following peptides: SEQ ID NO:1 (SVASTITGV); SEQ ID NO:2 (VMAGDIYSV); SEQ ID NO:3 (ALADGVQKV); SEQ ID NO:4 (LLGATCMFV); SEQ ID NO:5 (SVFAGVVGV); SEQ ID NO: 6 (ALFDGDPHL); SEQ ID NO:7 (YVDPVITSI); SEQ ID NO:8 (SQDDIKGIQKLYGKRS); SEQ ID NO:9 (STAPPVHNV); and SEQ ID NO:10 (LAALPHSCL).

2. The method of claim 1 wherein the neoplastic disorder is renal cancer.

3. The method of claim 1, wherein the method is used as a sole treatment, in an adjuvant, in a neoadjuvant or a palliative therapy setting.

4. The method of claim 1, wherein the vaccine and the sunitinib malate are administered simultaneously, sequentially or separately.

5. The method of claim 1, wherein the vaccine is administered subcutaneously, intravenously, intradermally, intratumorally, intramuscularly, orally, and nasal administration.

6. The method of claim 1, wherein the sunitinib malate is administered subcutaneously, intravenously, intradermally, intramuscularly, orally, and nasal administration.

7. The method of claim 1, wherein the routes of administration of the vaccine and the sunitinib malate are different.

8. The method of claim 1, wherein the routes of administration of the vaccine and the sunitinib malate are the same.

9. The method of claim 1, wherein the vaccine is administered prior to and/or concurrently with the sunitinib malate.

10. The method of claim 1, wherein the vaccine is administered concurrently and/or after the sunitinib malate.

11. The method of claim 1, wherein said neoplastic disorder expresses at least one peptide comprising a sequence selected from the group consisting of SEQ ID NO: 1 (SVASTITGV); SEQ ID NO: 2 (VMAGDIYSV); SEQ ID NO: 3 (ALADGVQKV); SEQ ID NO: 4 (LLGATCMFV); SEQ ID NO: 5 (SVFAGVVGV); SEQ ID NO: 6 (ALFDGDPHL); SEQ ID NO: 7 (YVDPVITSI); SEQ ID NO: 8 (SQDDIKGIQKLYGKRS); SEQ ID NO: 9 (STAPPVHNV); and SEQ ID NO: 10 (LAALPHSCL).

12. The method of claim 1, wherein said vaccine is administered together with an adjuvant.

13. The method of claim 1, wherein the neoplastic disorder is renal cell carcinoma, and wherein the sunitinib malate is administered in an amount of 25 to 75 mg, and wherein the vaccine is administered as a multi-target peptide vaccine comprising from 50 µg to 1 mg of each peptide.

14. The method of claim 13, wherein the sunitinib malate is administered in an amount of 25, 37.5, 50 or 62.5 mg on a daily, continuous, or intermittent dosing schedule.

15. The method of claim 14, wherein the sunitinib malate is administered on a 4/2, 4/1, 3/1 or 2/1 dosing schedule.

16. The method of claim 13, wherein said vaccine comprises from 200 µg to 600 µg of each peptide per patient and injection.

* * * * *

SEQUENCE LISTING

```
<160> NUMBER OF SEQ ID NOS: 1206

<210> SEQ ID NO 1
<211> LENGTH: 9
<212> TYPE: PRT
<213> ORGANISM: Homo sapiens

<400> SEQUENCE: 1

Ser Val Ala Ser Thr Ile Thr Gly Val
1               5

<210> SEQ ID NO 2
<211> LENGTH: 9
<212> TYPE: PRT
<213> ORGANISM: Homo sapiens

<400> SEQUENCE: 2

Val Met Ala Gly Asp Ile Tyr Ser Val
1               5

<210> SEQ ID NO 3
<211> LENGTH: 9
<212> TYPE: PRT
<213> ORGANISM: Homo sapiens

<400> SEQUENCE: 3

Ala Leu Ala Asp Gly Val Gln Lys Val
1               5
```

```
<210> SEQ ID NO 4
<211> LENGTH: 9
<212> TYPE: PRT
<213> ORGANISM: Homo sapiens

<400> SEQUENCE: 4

Leu Leu Gly Ala Thr Cys Met Phe Val
1               5

<210> SEQ ID NO 5
<211> LENGTH: 9
<212> TYPE: PRT
<213> ORGANISM: Homo sapiens

<400> SEQUENCE: 5

Ser Val Phe Ala Gly Val Val Gly Val
1               5

<210> SEQ ID NO 6
<211> LENGTH: 9
<212> TYPE: PRT
<213> ORGANISM: Homo sapiens

<400> SEQUENCE: 6

Ala Leu Phe Asp Gly Asp Pro His Leu
1               5

<210> SEQ ID NO 7
<211> LENGTH: 9
<212> TYPE: PRT
<213> ORGANISM: Homo sapiens

<400> SEQUENCE: 7

Tyr Val Asp Pro Val Ile Thr Ser Ile
1               5

<210> SEQ ID NO 8
<211> LENGTH: 16
<212> TYPE: PRT
<213> ORGANISM: Homo sapiens

<400> SEQUENCE: 8

Ser Gln Asp Asp Ile Lys Gly Ile Gln Lys Leu Tyr Gly Lys Arg Ser
1               5                   10                  15

<210> SEQ ID NO 9
<211> LENGTH: 9
<212> TYPE: PRT
<213> ORGANISM: Homo sapiens

<400> SEQUENCE: 9

Ser Thr Ala Pro Pro Val His Asn Val
1               5

<210> SEQ ID NO 10
<211> LENGTH: 9
<212> TYPE: PRT
<213> ORGANISM: Homo sapiens

<400> SEQUENCE: 10

Leu Ala Ala Leu Pro His Ser Cys Leu
1               5

<210> SEQ ID NO 11
<211> LENGTH: 9
```

<212> TYPE: PRT
<213> ORGANISM: Homo sapiens

<400> SEQUENCE: 11

Phe Pro Ser Leu Arg Glu Ala Ala Leu
1               5

<210> SEQ ID NO 12
<211> LENGTH: 10
<212> TYPE: PRT
<213> ORGANISM: Homo sapiens

<400> SEQUENCE: 12

Gly Leu Ala Ser Phe Lys Ser Phe Leu Lys
1               5                   10

<210> SEQ ID NO 13
<211> LENGTH: 11
<212> TYPE: PRT
<213> ORGANISM: Homo sapiens

<400> SEQUENCE: 13

Ser Leu Leu Thr Ser Ser Lys Gln Leu Gln Lys
1               5                   10

<210> SEQ ID NO 14
<211> LENGTH: 9
<212> TYPE: PRT
<213> ORGANISM: Homo sapiens

<400> SEQUENCE: 14

Ile Ala Arg Asn Leu Thr Gln Gln Leu
1               5

<210> SEQ ID NO 15
<211> LENGTH: 9
<212> TYPE: PRT
<213> ORGANISM: Homo sapiens

<400> SEQUENCE: 15

Gly Pro Ala Leu Gly Arg Ser Phe Leu
1               5

<210> SEQ ID NO 16
<211> LENGTH: 15
<212> TYPE: PRT
<213> ORGANISM: Homo sapiens

<400> SEQUENCE: 16

Asn Pro Pro Ser Met Val Ala Ala Gly Ser Val Val Ala Ala Val
1               5                   10                  15

<210> SEQ ID NO 17
<211> LENGTH: 14
<212> TYPE: PRT
<213> ORGANISM: Homo sapiens

<400> SEQUENCE: 17

Ser His Tyr Phe Lys Ile Ile Glu Asp Leu Arg Ala Gln Ile
1               5                   10

<210> SEQ ID NO 18
<211> LENGTH: 9
<212> TYPE: PRT
<213> ORGANISM: Homo sapiens

```
<400> SEQUENCE: 18

Leu Leu Leu Leu Thr Val Leu Thr Val
1               5

<210> SEQ ID NO 19
<211> LENGTH: 9
<212> TYPE: PRT
<213> ORGANISM: Homo sapiens

<400> SEQUENCE: 19

Ala Leu Cys Asn Thr Asp Ser Pro Leu
1               5

<210> SEQ ID NO 20
<211> LENGTH: 10
<212> TYPE: PRT
<213> ORGANISM: Homo sapiens

<400> SEQUENCE: 20

Glu Leu Ala Gly Ile Gly Ile Leu Thr Val
1               5                   10

<210> SEQ ID NO 21
<211> LENGTH: 9
<212> TYPE: PRT
<213> ORGANISM: Homo sapiens

<400> SEQUENCE: 21

Tyr Leu Leu Pro Ala Ile Val His Ile
1               5

<210> SEQ ID NO 22
<211> LENGTH: 8
<212> TYPE: PRT
<213> ORGANISM: Homo sapiens

<400> SEQUENCE: 22

Ser Ile Ile Asn Phe Glu Lys Leu
1               5

<210> SEQ ID NO 23
<211> LENGTH: 8
<212> TYPE: PRT
<213> ORGANISM: Homo sapiens

<400> SEQUENCE: 23

Arg Gly Tyr Val Tyr Gln Gly Leu
1               5

<210> SEQ ID NO 24
<211> LENGTH: 9
<212> TYPE: PRT
<213> ORGANISM: Homo sapiens

<400> SEQUENCE: 24

Ala Leu Ser Asn Leu Glu Val Thr Leu
1               5

<210> SEQ ID NO 25
<211> LENGTH: 9
<212> TYPE: PRT
<213> ORGANISM: Homo sapiens

<400> SEQUENCE: 25
```

```
Ile Leu Ala Pro Val Ile Leu Tyr Ile
1               5
```

<210> SEQ ID NO 26
<211> LENGTH: 10
<212> TYPE: PRT
<213> ORGANISM: Homo sapiens

<400> SEQUENCE: 26

```
Lys Leu Met Asp Leu Asp Val Glu Gln Leu
1               5                   10
```

<210> SEQ ID NO 27
<211> LENGTH: 9
<212> TYPE: PRT
<213> ORGANISM: Homo sapiens

<400> SEQUENCE: 27

```
Ser Met Ser Ala Asp Val Pro Leu Val
1               5
```

<210> SEQ ID NO 28
<211> LENGTH: 10
<212> TYPE: PRT
<213> ORGANISM: Homo sapiens

<400> SEQUENCE: 28

```
Lys Ile Phe Asp Glu Ile Leu Val Asn Ala
1               5                   10
```

<210> SEQ ID NO 29
<211> LENGTH: 10
<212> TYPE: PRT
<213> ORGANISM: Homo sapiens

<400> SEQUENCE: 29

```
Ala Ala Phe Val Glu Glu Leu Asp Lys Val
1               5                   10
```

<210> SEQ ID NO 30
<211> LENGTH: 14
<212> TYPE: PRT
<213> ORGANISM: Homo sapiens

<400> SEQUENCE: 30

```
Val Leu Leu Leu Val His Asn Leu Pro Gln His Leu Phe Gly
1               5                   10
```

<210> SEQ ID NO 31
<211> LENGTH: 10
<212> TYPE: PRT
<213> ORGANISM: Homo sapiens

<400> SEQUENCE: 31

```
Ala Leu Phe Val Arg Leu Leu Ala Leu Ala
1               5                   10
```

<210> SEQ ID NO 32
<211> LENGTH: 14
<212> TYPE: PRT
<213> ORGANISM: Homo sapiens

<400> SEQUENCE: 32

```
Gly Asp Lys Leu Glu Val Ser Leu Lys Asn Asn Val Val Ser
1               5                   10
```

-continued

```
1               5                   10
```

<210> SEQ ID NO 33
<211> LENGTH: 18
<212> TYPE: PRT
<213> ORGANISM: Homo sapiens

<400> SEQUENCE: 33

```
Gly Lys Lys Leu Arg Val Phe Val Tyr Arg Asn Ser Leu Cys Ile Glu
1               5                   10                  15

Asn Ser
```

<210> SEQ ID NO 34
<211> LENGTH: 17
<212> TYPE: PRT
<213> ORGANISM: Homo sapiens

<400> SEQUENCE: 34

```
Leu Lys Asn Asn Val Val Ser Val Asn Lys Glu Pro Val Ala Glu Pro
1               5                   10                  15

Asp
```

<210> SEQ ID NO 35
<211> LENGTH: 16
<212> TYPE: PRT
<213> ORGANISM: Homo sapiens

<400> SEQUENCE: 35

```
Lys Asn Asn Val Val Ser Val Asn Lys Glu Pro Val Ala Glu Pro Asp
1               5                   10                  15
```

<210> SEQ ID NO 36
<211> LENGTH: 13
<212> TYPE: PRT
<213> ORGANISM: Homo sapiens

<400> SEQUENCE: 36

```
Lys Asn Asn Val Val Ser Val Asn Lys Glu Pro Val Ala
1               5                   10
```

<210> SEQ ID NO 37
<211> LENGTH: 14
<212> TYPE: PRT
<213> ORGANISM: Homo sapiens

<400> SEQUENCE: 37

```
Leu Lys Asn Asn Val Val Ser Val Asn Lys Glu Pro Val Ala
1               5                   10
```

<210> SEQ ID NO 38
<211> LENGTH: 15
<212> TYPE: PRT
<213> ORGANISM: Homo sapiens

<400> SEQUENCE: 38

```
Asn Gly Val Ile His Tyr Ile Asp Glu Leu Leu Ile Pro Asp Ser
1               5                   10                  15
```

<210> SEQ ID NO 39
<211> LENGTH: 15
<212> TYPE: PRT
<213> ORGANISM: Homo sapiens

<400> SEQUENCE: 39

Gly Val Ile His Tyr Ile Asp Glu Leu Leu Ile Pro Asp Ser Ala
1               5                   10                  15

<210> SEQ ID NO 40
<211> LENGTH: 14
<212> TYPE: PRT
<213> ORGANISM: Homo sapiens

<400> SEQUENCE: 40

Leu Asn Arg Ile Leu Gly Asp Pro Glu Ala Leu Arg Asp Leu
1               5                   10

<210> SEQ ID NO 41
<211> LENGTH: 15
<212> TYPE: PRT
<213> ORGANISM: Homo sapiens

<400> SEQUENCE: 41

Thr Pro Pro Ile Asp Ala His Thr Arg Asn Leu Leu Arg Asn His
1               5                   10                  15

<210> SEQ ID NO 42
<211> LENGTH: 9
<212> TYPE: PRT
<213> ORGANISM: Homo sapiens

<400> SEQUENCE: 42

Ala Leu Thr Thr Leu Met His Gln Leu
1               5

<210> SEQ ID NO 43
<211> LENGTH: 9
<212> TYPE: PRT
<213> ORGANISM: Homo sapiens

<400> SEQUENCE: 43

Ser Leu Asp Pro Ser Ser Pro Gln Val
1               5

<210> SEQ ID NO 44
<211> LENGTH: 9
<212> TYPE: PRT
<213> ORGANISM: Homo sapiens

<400> SEQUENCE: 44

Ser Leu Trp Ala Gly Val Val Val Leu
1               5

<210> SEQ ID NO 45
<211> LENGTH: 9
<212> TYPE: PRT
<213> ORGANISM: Homo sapiens

<400> SEQUENCE: 45

Lys Leu Thr Asp Ile Gln Ile Glu Leu
1               5

<210> SEQ ID NO 46
<211> LENGTH: 9
<212> TYPE: PRT
<213> ORGANISM: Homo sapiens

<400> SEQUENCE: 46

Tyr Leu Ile His Phe Pro Val Ser Val

<210> SEQ ID NO 47
<211> LENGTH: 9
<212> TYPE: PRT
<213> ORGANISM: Homo sapiens

<400> SEQUENCE: 47

Ile Val Asp Asp Ile Thr Tyr Asn Val
1               5

<210> SEQ ID NO 48
<211> LENGTH: 16
<212> TYPE: PRT
<213> ORGANISM: Homo sapiens

<400> SEQUENCE: 48

Gly Ala Val Arg Phe Ser Asn Asn Pro Ala Leu Cys Asn Val Glu Ser
1               5                   10                  15

<210> SEQ ID NO 49
<211> LENGTH: 15
<212> TYPE: PRT
<213> ORGANISM: Homo sapiens

<400> SEQUENCE: 49

Ala Val Arg Phe Ser Asn Asn Pro Ala Leu Cys Asn Val Glu Ser
1               5                   10                  15

<210> SEQ ID NO 50
<211> LENGTH: 14
<212> TYPE: PRT
<213> ORGANISM: Homo sapiens

<400> SEQUENCE: 50

Ala Val Arg Phe Ser Asn Asn Pro Ala Leu Cys Asn Val Glu
1               5                   10

<210> SEQ ID NO 51
<211> LENGTH: 16
<212> TYPE: PRT
<213> ORGANISM: Homo sapiens

<400> SEQUENCE: 51

Asn Pro Thr Thr Tyr Gln Met Asp Val Asn Pro Glu Gly Lys Tyr Ser
1               5                   10                  15

<210> SEQ ID NO 52
<211> LENGTH: 13
<212> TYPE: PRT
<213> ORGANISM: Homo sapiens

<400> SEQUENCE: 52

Phe Lys Lys Ile Lys Val Leu Gly Ser Gly Ala Phe Gly
1               5                   10

<210> SEQ ID NO 53
<211> LENGTH: 18
<212> TYPE: PRT
<213> ORGANISM: Homo sapiens

<400> SEQUENCE: 53

Thr Thr Leu Ile Lys Glu Met Lys Ala Glu Phe Ile Lys Glu Ala Gln
1               5                   10                  15

Pro Gly

<210> SEQ ID NO 54
<211> LENGTH: 17
<212> TYPE: PRT
<213> ORGANISM: Homo sapiens

<400> SEQUENCE: 54

```
Thr Leu Ile Lys Glu Met Lys Ala Glu Phe Ile Lys Glu Ala Gln Pro
1               5                   10                  15

Gly
```

<210> SEQ ID NO 55
<211> LENGTH: 15
<212> TYPE: PRT
<213> ORGANISM: Homo sapiens

<400> SEQUENCE: 55

```
Thr Thr Leu Ile Lys Glu Met Lys Ala Glu Phe Ile Lys Glu Ala
1               5                   10                  15
```

<210> SEQ ID NO 56
<211> LENGTH: 14
<212> TYPE: PRT
<213> ORGANISM: Homo sapiens

<400> SEQUENCE: 56

```
Thr Leu Ile Lys Glu Met Lys Ala Glu Phe Ile Lys Glu Ala
1               5                   10
```

<210> SEQ ID NO 57
<211> LENGTH: 15
<212> TYPE: PRT
<213> ORGANISM: Homo sapiens

<400> SEQUENCE: 57

```
Ile Lys Glu Met Lys Ala Glu Phe Ile Lys Glu Ala Gln Pro Gly
1               5                   10                  15
```

<210> SEQ ID NO 58
<211> LENGTH: 14
<212> TYPE: PRT
<213> ORGANISM: Homo sapiens

<400> SEQUENCE: 58

```
Thr Thr Leu Ile Lys Glu Met Lys Ala Glu Phe Ile Lys Glu
1               5                   10
```

<210> SEQ ID NO 59
<211> LENGTH: 15
<212> TYPE: PRT
<213> ORGANISM: Homo sapiens

<400> SEQUENCE: 59

```
Val Lys Ser Lys Val Gln Tyr Leu Lys Asp Arg Gln Leu Ala Gly
1               5                   10                  15
```

<210> SEQ ID NO 60
<211> LENGTH: 15
<212> TYPE: PRT
<213> ORGANISM: Homo sapiens

<400> SEQUENCE: 60

```
Ser Arg Arg Thr Phe Ile Lys Ser Val Pro Pro Phe Leu Arg Thr
```

<210> SEQ ID NO 61
<211> LENGTH: 11
<212> TYPE: PRT
<213> ORGANISM: Homo sapiens

<400> SEQUENCE: 61

Lys Leu Gly Asp Phe Gly Leu Ala Thr Val Val
1               5                   10

<210> SEQ ID NO 62
<211> LENGTH: 9
<212> TYPE: PRT
<213> ORGANISM: Homo sapiens

<400> SEQUENCE: 62

Ser Leu Phe Asp Gln Val Val Lys Val
1               5

<210> SEQ ID NO 63
<211> LENGTH: 9
<212> TYPE: PRT
<213> ORGANISM: Homo sapiens

<400> SEQUENCE: 63

Ala Leu Leu Ser Glu Val Ile Gln Leu
1               5

<210> SEQ ID NO 64
<211> LENGTH: 9
<212> TYPE: PRT
<213> ORGANISM: Homo sapiens

<400> SEQUENCE: 64

Ile Leu Asp Gln Lys Ile Asn Glu Val
1               5

<210> SEQ ID NO 65
<211> LENGTH: 16
<212> TYPE: PRT
<213> ORGANISM: Homo sapiens

<400> SEQUENCE: 65

Ser Pro Gln Tyr Ser Trp Arg Ile Asn Gly Ile Pro Gln Gln His Thr
1               5                   10                  15

<210> SEQ ID NO 66
<211> LENGTH: 9
<212> TYPE: PRT
<213> ORGANISM: Homo sapiens

<400> SEQUENCE: 66

Thr Thr Ile Asp Ile Gly Val Lys Tyr
1               5

<210> SEQ ID NO 67
<211> LENGTH: 9
<212> TYPE: PRT
<213> ORGANISM: Homo sapiens

<400> SEQUENCE: 67

Ile His Ile Pro Ile Asn Asn Ile Ile
1               5

```
<210> SEQ ID NO 68
<211> LENGTH: 9
<212> TYPE: PRT
<213> ORGANISM: Homo sapiens

<400> SEQUENCE: 68

Tyr Gln Asp Leu Leu Asn Val Lys Leu
1               5

<210> SEQ ID NO 69
<211> LENGTH: 10
<212> TYPE: PRT
<213> ORGANISM: Homo sapiens

<400> SEQUENCE: 69

Leu Val Val Tyr Pro Trp Thr Gln Arg Phe
1               5                   10

<210> SEQ ID NO 70
<211> LENGTH: 9
<212> TYPE: PRT
<213> ORGANISM: Homo sapiens

<400> SEQUENCE: 70

Met His Leu Arg Gln Tyr Glu Leu Leu
1               5

<210> SEQ ID NO 71
<211> LENGTH: 9
<212> TYPE: PRT
<213> ORGANISM: Homo sapiens

<400> SEQUENCE: 71

Glu Ala Ile Glu Gln Ile Leu Lys Tyr
1               5

<210> SEQ ID NO 72
<211> LENGTH: 11
<212> TYPE: PRT
<213> ORGANISM: Homo sapiens

<400> SEQUENCE: 72

Asp Val Ala Glu Gly Asp Leu Ile Glu His Phe
1               5                   10

<210> SEQ ID NO 73
<211> LENGTH: 8
<212> TYPE: PRT
<213> ORGANISM: Homo sapiens

<400> SEQUENCE: 73

Asp Val Leu Gln Lys Ile Lys Tyr
1               5

<210> SEQ ID NO 74
<211> LENGTH: 10
<212> TYPE: PRT
<213> ORGANISM: Homo sapiens

<400> SEQUENCE: 74

Asp Ser Phe Pro Met Glu Ile Arg Gln Tyr
1               5                   10

<210> SEQ ID NO 75
```

```
<211> LENGTH: 9
<212> TYPE: PRT
<213> ORGANISM: Homo sapiens

<400> SEQUENCE: 75

Asp Val Ile Ser Asn Ile Glu Thr Phe
1               5

<210> SEQ ID NO 76
<211> LENGTH: 9
<212> TYPE: PRT
<213> ORGANISM: Homo sapiens

<400> SEQUENCE: 76

Asp Val Ile Arg Leu Ile Met Gln Tyr
1               5

<210> SEQ ID NO 77
<211> LENGTH: 9
<212> TYPE: PRT
<213> ORGANISM: Homo sapiens

<400> SEQUENCE: 77

Asp Val Ile Glu Arg Val Ile Gln Tyr
1               5

<210> SEQ ID NO 78
<211> LENGTH: 10
<212> TYPE: PRT
<213> ORGANISM: Homo sapiens

<400> SEQUENCE: 78

Asp Val Ile Ala Gln Gly Ile Gly Lys Leu
1               5                   10

<210> SEQ ID NO 79
<211> LENGTH: 10
<212> TYPE: PRT
<213> ORGANISM: Homo sapiens

<400> SEQUENCE: 79

Asp Val Phe Asn Glu Lys Gly Trp Asn Tyr
1               5                   10

<210> SEQ ID NO 80
<211> LENGTH: 9
<212> TYPE: PRT
<213> ORGANISM: Homo sapiens

<400> SEQUENCE: 80

Thr His Leu Asp Ser Val Thr Lys Ile
1               5

<210> SEQ ID NO 81
<211> LENGTH: 9
<212> TYPE: PRT
<213> ORGANISM: Homo sapiens

<400> SEQUENCE: 81

Asp Val Ala Gly Ile Ile Ala Asp Tyr
1               5

<210> SEQ ID NO 82
<211> LENGTH: 9
<212> TYPE: PRT
```

<213> ORGANISM: Homo sapiens

<400> SEQUENCE: 82

Thr Ala Ala Pro Phe Pro Phe His Leu
1               5

<210> SEQ ID NO 83
<211> LENGTH: 9
<212> TYPE: PRT
<213> ORGANISM: Homo sapiens

<400> SEQUENCE: 83

Asp Thr Leu Asp Lys Val Phe Thr Tyr
1               5

<210> SEQ ID NO 84
<211> LENGTH: 9
<212> TYPE: PRT
<213> ORGANISM: Homo sapiens

<400> SEQUENCE: 84

Asp Thr Ile Ser Pro Thr Leu Gly Phe
1               5

<210> SEQ ID NO 85
<211> LENGTH: 11
<212> TYPE: PRT
<213> ORGANISM: Homo sapiens

<400> SEQUENCE: 85

Asp Thr Gly Ile Leu Asp Ser Ile Gly Arg Phe
1               5                   10

<210> SEQ ID NO 86
<211> LENGTH: 9
<212> TYPE: PRT
<213> ORGANISM: Homo sapiens

<400> SEQUENCE: 86

Val Val Tyr Pro Trp Thr Gln Arg Phe
1               5

<210> SEQ ID NO 87
<211> LENGTH: 10
<212> TYPE: PRT
<213> ORGANISM: Homo sapiens

<400> SEQUENCE: 87

Glu Val Val Ala Gly Ile Lys Glu Tyr Phe
1               5                   10

<210> SEQ ID NO 88
<211> LENGTH: 9
<212> TYPE: PRT
<213> ORGANISM: Homo sapiens

<400> SEQUENCE: 88

Ser Ser Val Pro Gly Val Arg Leu Leu
1               5

<210> SEQ ID NO 89
<211> LENGTH: 11
<212> TYPE: PRT
<213> ORGANISM: Homo sapiens

```
<400> SEQUENCE: 89

Ser Val Val Asp Ala Ile Gly Ile Ser Arg Phe
1               5                   10

<210> SEQ ID NO 90
<211> LENGTH: 9
<212> TYPE: PRT
<213> ORGANISM: Homo sapiens

<400> SEQUENCE: 90

Glu Val Ile Pro Pro Met Lys Glu Phe
1               5

<210> SEQ ID NO 91
<211> LENGTH: 9
<212> TYPE: PRT
<213> ORGANISM: Homo sapiens

<400> SEQUENCE: 91

Glu Val Ile Pro Pro Tyr Tyr Ser Tyr
1               5

<210> SEQ ID NO 92
<211> LENGTH: 9
<212> TYPE: PRT
<213> ORGANISM: Homo sapiens

<400> SEQUENCE: 92

Glu Val Asn Gly Leu Ile Ser Met Tyr
1               5

<210> SEQ ID NO 93
<211> LENGTH: 10
<212> TYPE: PRT
<213> ORGANISM: Homo sapiens

<400> SEQUENCE: 93

Glu Val Ile Asp Leu Met Ile Lys Glu Tyr
1               5                   10

<210> SEQ ID NO 94
<211> LENGTH: 9
<212> TYPE: PRT
<213> ORGANISM: Homo sapiens

<400> SEQUENCE: 94

Glu Val Val Ala Gly Ile Lys Glu Tyr
1               5

<210> SEQ ID NO 95
<211> LENGTH: 9
<212> TYPE: PRT
<213> ORGANISM: Homo sapiens

<400> SEQUENCE: 95

Glu Val Phe Pro Leu Ala Met Asn Tyr
1               5

<210> SEQ ID NO 96
<211> LENGTH: 9
<212> TYPE: PRT
<213> ORGANISM: Homo sapiens

<400> SEQUENCE: 96
```

```
Glu Val Val Glu Arg Val Leu Thr Phe
1               5

<210> SEQ ID NO 97
<211> LENGTH: 10
<212> TYPE: PRT
<213> ORGANISM: Homo sapiens

<400> SEQUENCE: 97

Ser His Ser Pro Phe Gly Leu Asp Ser Phe
1               5                   10

<210> SEQ ID NO 98
<211> LENGTH: 9
<212> TYPE: PRT
<213> ORGANISM: Homo sapiens

<400> SEQUENCE: 98

Phe Gly Val Asp Arg Ala Ile Leu Tyr
1               5

<210> SEQ ID NO 99
<211> LENGTH: 9
<212> TYPE: PRT
<213> ORGANISM: Homo sapiens

<400> SEQUENCE: 99

Ser His Ser Asp Tyr Leu Leu Thr Ile
1               5

<210> SEQ ID NO 100
<211> LENGTH: 9
<212> TYPE: PRT
<213> ORGANISM: Homo sapiens

<400> SEQUENCE: 100

Ser His Leu Asp Tyr Asp Ile Thr Leu
1               5

<210> SEQ ID NO 101
<211> LENGTH: 9
<212> TYPE: PRT
<213> ORGANISM: Homo sapiens

<400> SEQUENCE: 101

Ser His Phe Val Ser Asp Val Val Ile
1               5

<210> SEQ ID NO 102
<211> LENGTH: 9
<212> TYPE: PRT
<213> ORGANISM: Homo sapiens

<400> SEQUENCE: 102

Glu Val Thr Glu Leu Leu Ala Arg Tyr
1               5

<210> SEQ ID NO 103
<211> LENGTH: 11
<212> TYPE: PRT
<213> ORGANISM: Homo sapiens

<400> SEQUENCE: 103

Glu Thr Ala Asp Thr Leu Met Gly Leu Arg Tyr
1               5                   10
```

```
<210> SEQ ID NO 104
<211> LENGTH: 9
<212> TYPE: PRT
<213> ORGANISM: Homo sapiens

<400> SEQUENCE: 104

Glu His Ala His Leu Ile Val Val Leu
1               5

<210> SEQ ID NO 105
<211> LENGTH: 9
<212> TYPE: PRT
<213> ORGANISM: Homo sapiens

<400> SEQUENCE: 105

Glu His Ser Leu Val Ile Asp Thr Leu
1               5

<210> SEQ ID NO 106
<211> LENGTH: 9
<212> TYPE: PRT
<213> ORGANISM: Homo sapiens

<400> SEQUENCE: 106

Glu Ile Ala Glu Ala Tyr Leu Gly Tyr
1               5

<210> SEQ ID NO 107
<211> LENGTH: 10
<212> TYPE: PRT
<213> ORGANISM: Homo sapiens

<400> SEQUENCE: 107

Glu Ile Tyr Gly Gly Ser Asp Ser Arg Phe
1               5                   10

<210> SEQ ID NO 108
<211> LENGTH: 9
<212> TYPE: PRT
<213> ORGANISM: Homo sapiens

<400> SEQUENCE: 108

Glu Leu Ile Ala Lys Ile Pro Asn Phe
1               5

<210> SEQ ID NO 109
<211> LENGTH: 9
<212> TYPE: PRT
<213> ORGANISM: Homo sapiens

<400> SEQUENCE: 109

Glu Val Ile Lys Asn Phe Ile Gln Tyr
1               5

<210> SEQ ID NO 110
<211> LENGTH: 11
<212> TYPE: PRT
<213> ORGANISM: Homo sapiens

<400> SEQUENCE: 110

Glu Thr Ala Asp Thr Leu Leu Ala Leu Arg Tyr
1               5                   10
```

```
<210> SEQ ID NO 111
<211> LENGTH: 10
<212> TYPE: PRT
<213> ORGANISM: Homo sapiens

<400> SEQUENCE: 111

Glu Val Val Ser Glu Pro Phe Arg Ser Phe
1               5                   10

<210> SEQ ID NO 112
<211> LENGTH: 10
<212> TYPE: PRT
<213> ORGANISM: Homo sapiens

<400> SEQUENCE: 112

Glu Thr Phe Asp Ala Gly Leu Gln Ala Phe
1               5                   10

<210> SEQ ID NO 113
<211> LENGTH: 9
<212> TYPE: PRT
<213> ORGANISM: Homo sapiens

<400> SEQUENCE: 113

Ser His Ser Gln Leu Met Gln Leu Ile
1               5

<210> SEQ ID NO 114
<211> LENGTH: 9
<212> TYPE: PRT
<213> ORGANISM: Homo sapiens

<400> SEQUENCE: 114

Glu Thr Val Arg Glu Leu Thr Glu Phe
1               5

<210> SEQ ID NO 115
<211> LENGTH: 9
<212> TYPE: PRT
<213> ORGANISM: Homo sapiens

<400> SEQUENCE: 115

Glu Val Ala Ala Thr Glu Ile Lys Met
1               5

<210> SEQ ID NO 116
<211> LENGTH: 9
<212> TYPE: PRT
<213> ORGANISM: Homo sapiens

<400> SEQUENCE: 116

Glu Val Ala Ala Val Leu Leu His Phe
1               5

<210> SEQ ID NO 117
<211> LENGTH: 9
<212> TYPE: PRT
<213> ORGANISM: Homo sapiens

<400> SEQUENCE: 117

Glu Val Phe Asp Lys Thr Tyr Gln Phe
1               5

<210> SEQ ID NO 118
<211> LENGTH: 9
```

```
<212> TYPE: PRT
<213> ORGANISM: Homo sapiens

<400> SEQUENCE: 118

Glu Leu Val Lys Arg Ile Leu Asn Phe
1               5

<210> SEQ ID NO 119
<211> LENGTH: 9
<212> TYPE: PRT
<213> ORGANISM: Homo sapiens

<400> SEQUENCE: 119

Ala His Asp Asp Gly Arg Trp Ser Leu
1               5

<210> SEQ ID NO 120
<211> LENGTH: 9
<212> TYPE: PRT
<213> ORGANISM: Homo sapiens

<400> SEQUENCE: 120

Ser Val Val Ser Val Ile Ser Arg Phe
1               5

<210> SEQ ID NO 121
<211> LENGTH: 9
<212> TYPE: PRT
<213> ORGANISM: Homo sapiens

<400> SEQUENCE: 121

Ser Val Val Glu Leu Ile Asn His Tyr
1               5

<210> SEQ ID NO 122
<211> LENGTH: 9
<212> TYPE: PRT
<213> ORGANISM: Homo sapiens

<400> SEQUENCE: 122

Ser Val Val Asp Leu Ile Asn His Tyr
1               5

<210> SEQ ID NO 123
<211> LENGTH: 9
<212> TYPE: PRT
<213> ORGANISM: Homo sapiens

<400> SEQUENCE: 123

Ala His Val Asp Leu Ile Glu Lys Leu
1               5

<210> SEQ ID NO 124
<211> LENGTH: 9
<212> TYPE: PRT
<213> ORGANISM: Homo sapiens

<400> SEQUENCE: 124

Phe His Asn Glu Leu Leu Thr Gln Leu
1               5

<210> SEQ ID NO 125
<211> LENGTH: 9
<212> TYPE: PRT
<213> ORGANISM: Homo sapiens
```

<400> SEQUENCE: 125

Ser Val Ile Glu Ala Val Ala His Phe
1               5

<210> SEQ ID NO 126
<211> LENGTH: 9
<212> TYPE: PRT
<213> ORGANISM: Homo sapiens

<400> SEQUENCE: 126

Gly His Phe Glu Lys Pro Leu Phe Leu
1               5

<210> SEQ ID NO 127
<211> LENGTH: 9
<212> TYPE: PRT
<213> ORGANISM: Homo sapiens

<400> SEQUENCE: 127

Gly His Asp Ala Ser Gln Ile Thr Leu
1               5

<210> SEQ ID NO 128
<211> LENGTH: 9
<212> TYPE: PRT
<213> ORGANISM: Homo sapiens

<400> SEQUENCE: 128

Ser Ala Val Asp Phe Ile Arg Thr Leu
1               5

<210> SEQ ID NO 129
<211> LENGTH: 9
<212> TYPE: PRT
<213> ORGANISM: Homo sapiens

<400> SEQUENCE: 129

Ile Ser Thr Pro Val Ile Arg Thr Phe
1               5

<210> SEQ ID NO 130
<211> LENGTH: 10
<212> TYPE: PRT
<213> ORGANISM: Homo sapiens

<400> SEQUENCE: 130

Gly Val Ile Glu Lys Leu Leu Thr Ser Tyr
1               5                   10

<210> SEQ ID NO 131
<211> LENGTH: 9
<212> TYPE: PRT
<213> ORGANISM: Homo sapiens

<400> SEQUENCE: 131

Ser His Asp Leu Thr Leu Val Asn Leu
1               5

<210> SEQ ID NO 132
<211> LENGTH: 9
<212> TYPE: PRT
<213> ORGANISM: Homo sapiens

<400> SEQUENCE: 132

Ser Ile Phe Lys Gln Pro Val Thr Lys
1               5

<210> SEQ ID NO 133
<211> LENGTH: 9
<212> TYPE: PRT
<213> ORGANISM: Homo sapiens

<400> SEQUENCE: 133

Lys Pro Asn Ala Asn Arg Ile Ala Leu
1               5

<210> SEQ ID NO 134
<211> LENGTH: 9
<212> TYPE: PRT
<213> ORGANISM: Homo sapiens

<400> SEQUENCE: 134

Lys Leu Tyr Glu Met Ile Leu Lys Arg
1               5

<210> SEQ ID NO 135
<211> LENGTH: 9
<212> TYPE: PRT
<213> ORGANISM: Homo sapiens

<400> SEQUENCE: 135

Ser Leu Phe Ser Arg Leu Phe Gly Lys
1               5

<210> SEQ ID NO 136
<211> LENGTH: 9
<212> TYPE: PRT
<213> ORGANISM: Homo sapiens

<400> SEQUENCE: 136

Lys Leu Phe Asp Lys Leu Leu Glu Tyr
1               5

<210> SEQ ID NO 137
<211> LENGTH: 12
<212> TYPE: PRT
<213> ORGANISM: Homo sapiens

<400> SEQUENCE: 137

Ser Leu Phe Pro Asn Ser Pro Lys Trp Thr Ser Lys
1               5                   10

<210> SEQ ID NO 138
<211> LENGTH: 9
<212> TYPE: PRT
<213> ORGANISM: Homo sapiens

<400> SEQUENCE: 138

Leu Glu Ser Leu Asp Gln Leu Glu Leu
1               5

<210> SEQ ID NO 139
<211> LENGTH: 10
<212> TYPE: PRT
<213> ORGANISM: Homo sapiens

<400> SEQUENCE: 139

Val Val Asn Lys Val Pro Leu Thr Gly Lys

<210> SEQ ID NO 140
<211> LENGTH: 9
<212> TYPE: PRT
<213> ORGANISM: Homo sapiens

<400> SEQUENCE: 140

Ser Val Tyr Asp Ser Val Leu Gln Lys
1               5

<210> SEQ ID NO 141
<211> LENGTH: 9
<212> TYPE: PRT
<213> ORGANISM: Homo sapiens

<400> SEQUENCE: 141

Ser Val Tyr Val Leu Val Arg Gln Lys
1               5

<210> SEQ ID NO 142
<211> LENGTH: 9
<212> TYPE: PRT
<213> ORGANISM: Homo sapiens

<400> SEQUENCE: 142

Ile Leu Glu Asn Ile Gln Arg Asn Lys
1               5

<210> SEQ ID NO 143
<211> LENGTH: 10
<212> TYPE: PRT
<213> ORGANISM: Homo sapiens

<400> SEQUENCE: 143

Gly Ser Tyr Asn Lys Val Phe Leu Ala Lys
1               5                   10

<210> SEQ ID NO 144
<211> LENGTH: 9
<212> TYPE: PRT
<213> ORGANISM: Homo sapiens

<400> SEQUENCE: 144

Thr Glu Ser Gly Leu Asn Val Thr Leu
1               5

<210> SEQ ID NO 145
<211> LENGTH: 9
<212> TYPE: PRT
<213> ORGANISM: Homo sapiens

<400> SEQUENCE: 145

Thr Glu His Gly Val Glu Val Val Leu
1               5

<210> SEQ ID NO 146
<211> LENGTH: 9
<212> TYPE: PRT
<213> ORGANISM: Homo sapiens

<400> SEQUENCE: 146

Thr Glu Ala Arg Phe Gly Ala Gln Leu
1               5

-continued

<210> SEQ ID NO 147
<211> LENGTH: 9
<212> TYPE: PRT
<213> ORGANISM: Homo sapiens

<400> SEQUENCE: 147

Thr Leu Ala Asp Ile Leu Leu Tyr Tyr
1               5

<210> SEQ ID NO 148
<211> LENGTH: 10
<212> TYPE: PRT
<213> ORGANISM: Homo sapiens

<400> SEQUENCE: 148

Leu Val Phe Pro Ser Glu Ile Val Gly Lys
1               5                   10

<210> SEQ ID NO 149
<211> LENGTH: 10
<212> TYPE: PRT
<213> ORGANISM: Homo sapiens

<400> SEQUENCE: 149

Val Leu Phe Gly Lys Ala Leu Asn Pro Lys
1               5                   10

<210> SEQ ID NO 150
<211> LENGTH: 9
<212> TYPE: PRT
<213> ORGANISM: Homo sapiens

<400> SEQUENCE: 150

Arg Pro Glu Leu Val Arg Pro Ala Leu
1               5

<210> SEQ ID NO 151
<211> LENGTH: 10
<212> TYPE: PRT
<213> ORGANISM: Homo sapiens

<400> SEQUENCE: 151

Val Pro Asn Gln Lys Arg Leu Thr Leu Leu
1               5                   10

<210> SEQ ID NO 152
<211> LENGTH: 9
<212> TYPE: PRT
<213> ORGANISM: Homo sapiens

<400> SEQUENCE: 152

Gln Leu Tyr Trp Ser His Pro Arg Lys
1               5

<210> SEQ ID NO 153
<211> LENGTH: 9
<212> TYPE: PRT
<213> ORGANISM: Homo sapiens

<400> SEQUENCE: 153

Ser Val Tyr Val Tyr Lys Val Leu Lys
1               5

<210> SEQ ID NO 154

```
<211> LENGTH: 9
<212> TYPE: PRT
<213> ORGANISM: Homo sapiens

<400> SEQUENCE: 154

Arg Glu Lys Leu Gln Glu Glu Met Leu
1               5

<210> SEQ ID NO 155
<211> LENGTH: 12
<212> TYPE: PRT
<213> ORGANISM: Homo sapiens

<400> SEQUENCE: 155

Arg Val Phe Ser Gly Leu Val Ser Thr Gly Leu Lys
1               5                   10

<210> SEQ ID NO 156
<211> LENGTH: 10
<212> TYPE: PRT
<213> ORGANISM: Homo sapiens

<400> SEQUENCE: 156

Lys Pro Arg Asp Val Ser Ser Val Glu Leu
1               5                   10

<210> SEQ ID NO 157
<211> LENGTH: 9
<212> TYPE: PRT
<213> ORGANISM: Homo sapiens

<400> SEQUENCE: 157

Asn Glu Phe Pro Glu Pro Ile Lys Leu
1               5

<210> SEQ ID NO 158
<211> LENGTH: 9
<212> TYPE: PRT
<213> ORGANISM: Homo sapiens

<400> SEQUENCE: 158

Lys Thr Tyr Gly Glu Ile Phe Glu Lys
1               5

<210> SEQ ID NO 159
<211> LENGTH: 9
<212> TYPE: PRT
<213> ORGANISM: Homo sapiens

<400> SEQUENCE: 159

Arg Ile Leu Phe Phe Asn Thr Pro Lys
1               5

<210> SEQ ID NO 160
<211> LENGTH: 9
<212> TYPE: PRT
<213> ORGANISM: Homo sapiens

<400> SEQUENCE: 160

Arg Val Phe Pro Trp Phe Ser Val Lys
1               5

<210> SEQ ID NO 161
<211> LENGTH: 9
<212> TYPE: PRT
```

-continued

```
<213> ORGANISM: Homo sapiens

<400> SEQUENCE: 161

Ser Glu Val Gln Asp Arg Val Met Leu
1               5

<210> SEQ ID NO 162
<211> LENGTH: 9
<212> TYPE: PRT
<213> ORGANISM: Homo sapiens

<400> SEQUENCE: 162

Ser Leu Trp Asp Arg Leu Ile Phe His
1               5

<210> SEQ ID NO 163
<211> LENGTH: 9
<212> TYPE: PRT
<213> ORGANISM: Homo sapiens

<400> SEQUENCE: 163

Lys Val Tyr Asn Ile Gln Ile Arg Tyr
1               5

<210> SEQ ID NO 164
<211> LENGTH: 9
<212> TYPE: PRT
<213> ORGANISM: Homo sapiens

<400> SEQUENCE: 164

Arg Leu Leu Glu Met Ile Leu Asn Lys
1               5

<210> SEQ ID NO 165
<211> LENGTH: 9
<212> TYPE: PRT
<213> ORGANISM: Homo sapiens

<400> SEQUENCE: 165

Ser Glu Asp Lys Lys Asn Ile Ile Leu
1               5

<210> SEQ ID NO 166
<211> LENGTH: 9
<212> TYPE: PRT
<213> ORGANISM: Homo sapiens

<400> SEQUENCE: 166

Tyr Glu Glu Leu Val Arg Met Val Leu
1               5

<210> SEQ ID NO 167
<211> LENGTH: 9
<212> TYPE: PRT
<213> ORGANISM: Homo sapiens

<400> SEQUENCE: 167

Gly Glu Ile Thr Gly Glu Val His Met
1               5

<210> SEQ ID NO 168
<211> LENGTH: 9
<212> TYPE: PRT
<213> ORGANISM: Homo sapiens
```

<400> SEQUENCE: 168

Ile Val Ala Gly Ser Leu Ile Thr Lys
1               5

<210> SEQ ID NO 169
<211> LENGTH: 12
<212> TYPE: PRT
<213> ORGANISM: Homo sapiens

<400> SEQUENCE: 169

Ala Pro Arg Ile Ile Thr Gly Pro Ala Pro Val Leu
1               5                   10

<210> SEQ ID NO 170
<211> LENGTH: 10
<212> TYPE: PRT
<213> ORGANISM: Homo sapiens

<400> SEQUENCE: 170

Phe Pro Asn Ser Pro Lys Trp Thr Ser Lys
1               5                   10

<210> SEQ ID NO 171
<211> LENGTH: 9
<212> TYPE: PRT
<213> ORGANISM: Homo sapiens

<400> SEQUENCE: 171

Phe Val Ile Glu Thr Ala Arg Gln Leu
1               5

<210> SEQ ID NO 172
<211> LENGTH: 10
<212> TYPE: PRT
<213> ORGANISM: Homo sapiens

<400> SEQUENCE: 172

Ile Glu Val Asp Gly Lys Gln Val Glu Leu
1               5                   10

<210> SEQ ID NO 173
<211> LENGTH: 9
<212> TYPE: PRT
<213> ORGANISM: Homo sapiens

<400> SEQUENCE: 173

Gly Glu Leu Thr Gly Glu Val Arg Met
1               5

<210> SEQ ID NO 174
<211> LENGTH: 10
<212> TYPE: PRT
<213> ORGANISM: Homo sapiens

<400> SEQUENCE: 174

Gly Glu Ser Asp Asp Ser Ile Leu Arg Leu
1               5                   10

<210> SEQ ID NO 175
<211> LENGTH: 12
<212> TYPE: PRT
<213> ORGANISM: Homo sapiens

<400> SEQUENCE: 175

```
Gly Glu Gly Asp Phe Leu Ala Glu Gly Gly Gly Val
1               5                   10

<210> SEQ ID NO 176
<211> LENGTH: 7
<212> TYPE: PRT
<213> ORGANISM: Homo sapiens

<400> SEQUENCE: 176

Asp Asn Phe Pro Gln Ser Leu
1               5

<210> SEQ ID NO 177
<211> LENGTH: 9
<212> TYPE: PRT
<213> ORGANISM: Homo sapiens

<400> SEQUENCE: 177

Gly Leu Thr Asp Val Ile Leu Tyr His
1               5

<210> SEQ ID NO 178
<211> LENGTH: 11
<212> TYPE: PRT
<213> ORGANISM: Homo sapiens

<400> SEQUENCE: 178

Ala Ala Leu Val Ala Ser Gly Val Ala Leu Tyr
1               5                   10

<210> SEQ ID NO 179
<211> LENGTH: 10
<212> TYPE: PRT
<213> ORGANISM: Homo sapiens

<400> SEQUENCE: 179

Ala Glu Ile Arg His Val Leu Val Thr Leu
1               5                   10

<210> SEQ ID NO 180
<211> LENGTH: 9
<212> TYPE: PRT
<213> ORGANISM: Homo sapiens

<400> SEQUENCE: 180

Ala Glu Pro Glu Glu Val Glu Val Leu
1               5

<210> SEQ ID NO 181
<211> LENGTH: 10
<212> TYPE: PRT
<213> ORGANISM: Homo sapiens

<400> SEQUENCE: 181

Ala Ile Ile Asp His Ile Phe Ala Ser Lys
1               5                   10

<210> SEQ ID NO 182
<211> LENGTH: 11
<212> TYPE: PRT
<213> ORGANISM: Homo sapiens

<400> SEQUENCE: 182

Ala Leu Leu Asp Gly Ser Asn Val Val Phe Lys
1               5                   10
```

```
<210> SEQ ID NO 183
<211> LENGTH: 9
<212> TYPE: PRT
<213> ORGANISM: Homo sapiens

<400> SEQUENCE: 183

Ala Met Leu Asp Thr Val Val Phe Lys
1               5

<210> SEQ ID NO 184
<211> LENGTH: 10
<212> TYPE: PRT
<213> ORGANISM: Homo sapiens

<400> SEQUENCE: 184

Ala Val Asn Ala His Ser Asn Ile Leu Lys
1               5                   10

<210> SEQ ID NO 185
<211> LENGTH: 9
<212> TYPE: PRT
<213> ORGANISM: Homo sapiens

<400> SEQUENCE: 185

Ala Pro Arg Pro Gly Val Leu Leu Leu
1               5

<210> SEQ ID NO 186
<211> LENGTH: 9
<212> TYPE: PRT
<213> ORGANISM: Homo sapiens

<400> SEQUENCE: 186

Glu Ala Phe Pro Leu Arg Val Ile Asp
1               5

<210> SEQ ID NO 187
<211> LENGTH: 9
<212> TYPE: PRT
<213> ORGANISM: Homo sapiens

<400> SEQUENCE: 187

Gly Val Ala Asp Lys Ile Leu Lys Lys
1               5

<210> SEQ ID NO 188
<211> LENGTH: 10
<212> TYPE: PRT
<213> ORGANISM: Homo sapiens

<400> SEQUENCE: 188

Ala Val Phe Pro Lys Pro Phe Val Glu Lys
1               5                   10

<210> SEQ ID NO 189
<211> LENGTH: 10
<212> TYPE: PRT
<213> ORGANISM: Homo sapiens

<400> SEQUENCE: 189

Val Val Tyr Val Gly Gly Ile Leu Thr Lys
1               5                   10
```

```
<210> SEQ ID NO 190
<211> LENGTH: 9
<212> TYPE: PRT
<213> ORGANISM: Homo sapiens

<400> SEQUENCE: 190

His Leu Glu Asp Ile Val Arg Gln Lys
1               5

<210> SEQ ID NO 191
<211> LENGTH: 10
<212> TYPE: PRT
<213> ORGANISM: Homo sapiens

<400> SEQUENCE: 191

Val Thr Leu Thr Leu Val Ile Leu Ser Tyr
1               5                   10

<210> SEQ ID NO 192
<211> LENGTH: 10
<212> TYPE: PRT
<213> ORGANISM: Homo sapiens

<400> SEQUENCE: 192

Ser Leu Leu Ser Leu Val Thr Gly Leu Lys
1               5                   10

<210> SEQ ID NO 193
<211> LENGTH: 9
<212> TYPE: PRT
<213> ORGANISM: Homo sapiens

<400> SEQUENCE: 193

Gln Thr Tyr Val Gly Ile Thr Glu Lys
1               5

<210> SEQ ID NO 194
<211> LENGTH: 9
<212> TYPE: PRT
<213> ORGANISM: Homo sapiens

<400> SEQUENCE: 194

His Glu Asp Lys Ile Arg Val Val Leu
1               5

<210> SEQ ID NO 195
<211> LENGTH: 9
<212> TYPE: PRT
<213> ORGANISM: Homo sapiens

<400> SEQUENCE: 195

Gln Ile Ser Ile Pro Phe Leu Leu Lys
1               5

<210> SEQ ID NO 196
<211> LENGTH: 9
<212> TYPE: PRT
<213> ORGANISM: Homo sapiens

<400> SEQUENCE: 196

Gly Leu Met Gly Phe Ile Val Tyr Lys
1               5

<210> SEQ ID NO 197
<211> LENGTH: 9
```

```
<212> TYPE: PRT
<213> ORGANISM: Homo sapiens

<400> SEQUENCE: 197

Phe Ala Asp Gln Glu Val Arg Ser Leu
1               5

<210> SEQ ID NO 198
<211> LENGTH: 9
<212> TYPE: PRT
<213> ORGANISM: Homo sapiens

<400> SEQUENCE: 198

Ile Val Ala Leu Ile Leu Ser Thr Lys
1               5

<210> SEQ ID NO 199
<211> LENGTH: 10
<212> TYPE: PRT
<213> ORGANISM: Homo sapiens

<400> SEQUENCE: 199

Gly Thr Tyr Ala Pro Ala Glu Val Pro Lys
1               5                   10

<210> SEQ ID NO 200
<211> LENGTH: 9
<212> TYPE: PRT
<213> ORGANISM: Homo sapiens

<400> SEQUENCE: 200

Gly Thr Met Thr Gly Met Leu Tyr Lys
1               5

<210> SEQ ID NO 201
<211> LENGTH: 9
<212> TYPE: PRT
<213> ORGANISM: Homo sapiens

<400> SEQUENCE: 201

Ser Leu Ala Glu Ile Leu Leu Lys Lys
1               5

<210> SEQ ID NO 202
<211> LENGTH: 9
<212> TYPE: PRT
<213> ORGANISM: Homo sapiens

<400> SEQUENCE: 202

Lys Leu Thr Tyr Ile Tyr Ile Gln Lys
1               5

<210> SEQ ID NO 203
<211> LENGTH: 10
<212> TYPE: PRT
<213> ORGANISM: Homo sapiens

<400> SEQUENCE: 203

Lys Leu Leu Asn Tyr Ala Pro Leu Glu Lys
1               5                   10

<210> SEQ ID NO 204
<211> LENGTH: 9
<212> TYPE: PRT
<213> ORGANISM: Homo sapiens
```

<400> SEQUENCE: 204

Gly Thr Leu Pro His Pro Leu Gln Arg
1               5

<210> SEQ ID NO 205
<211> LENGTH: 9
<212> TYPE: PRT
<213> ORGANISM: Homo sapiens

<400> SEQUENCE: 205

Gly Leu Tyr Glu Phe Phe Arg Ala Lys
1               5

<210> SEQ ID NO 206
<211> LENGTH: 9
<212> TYPE: PRT
<213> ORGANISM: Homo sapiens

<400> SEQUENCE: 206

Lys Glu Pro Glu Ile Asn Thr Thr Leu
1               5

<210> SEQ ID NO 207
<211> LENGTH: 9
<212> TYPE: PRT
<213> ORGANISM: Homo sapiens

<400> SEQUENCE: 207

His Ala Ser Asp Arg Ile Ile Ala Leu
1               5

<210> SEQ ID NO 208
<211> LENGTH: 9
<212> TYPE: PRT
<213> ORGANISM: Homo sapiens

<400> SEQUENCE: 208

Arg Pro Thr Leu Trp Ala Ala Ala Leu
1               5

<210> SEQ ID NO 209
<211> LENGTH: 9
<212> TYPE: PRT
<213> ORGANISM: Homo sapiens

<400> SEQUENCE: 209

Ala Pro Ser Pro Arg Pro Leu Ser Leu
1               5

<210> SEQ ID NO 210
<211> LENGTH: 10
<212> TYPE: PRT
<213> ORGANISM: Homo sapiens

<400> SEQUENCE: 210

Ala Ser Asp Phe Ile Thr Lys Met Asp Tyr
1               5                   10

<210> SEQ ID NO 211
<211> LENGTH: 9
<212> TYPE: PRT
<213> ORGANISM: Homo sapiens

<400> SEQUENCE: 211

```
Glu Glu Arg Val Ile Asn Glu Glu Tyr
1               5

<210> SEQ ID NO 212
<211> LENGTH: 10
<212> TYPE: PRT
<213> ORGANISM: Homo sapiens

<400> SEQUENCE: 212

Ala Thr Gly Ser Trp Asp Ser Phe Leu Lys
1               5                   10

<210> SEQ ID NO 213
<211> LENGTH: 9
<212> TYPE: PRT
<213> ORGANISM: Homo sapiens

<400> SEQUENCE: 213

Arg Met Phe Asp Met Gly Phe Glu Tyr
1               5

<210> SEQ ID NO 214
<211> LENGTH: 8
<212> TYPE: PRT
<213> ORGANISM: Homo sapiens

<400> SEQUENCE: 214

Ala Pro Leu Leu Arg Trp Val Leu
1               5

<210> SEQ ID NO 215
<211> LENGTH: 11
<212> TYPE: PRT
<213> ORGANISM: Homo sapiens

<400> SEQUENCE: 215

Ala Leu Arg Pro Ser Thr Ser Arg Ser Leu Tyr
1               5                   10

<210> SEQ ID NO 216
<211> LENGTH: 9
<212> TYPE: PRT
<213> ORGANISM: Homo sapiens

<400> SEQUENCE: 216

Arg Gln Ile Pro Tyr Thr Met Met Lys
1               5

<210> SEQ ID NO 217
<211> LENGTH: 9
<212> TYPE: PRT
<213> ORGANISM: Homo sapiens

<400> SEQUENCE: 217

Ala Glu Thr His Ile Val Leu Leu Phe
1               5

<210> SEQ ID NO 218
<211> LENGTH: 9
<212> TYPE: PRT
<213> ORGANISM: Homo sapiens

<400> SEQUENCE: 218

Arg Val His Ala Tyr Ile Ile Ser Tyr
```

```
1               5
```

```
<210> SEQ ID NO 219
<211> LENGTH: 11
<212> TYPE: PRT
<213> ORGANISM: Homo sapiens

<400> SEQUENCE: 219

Ala Val Ile Val Leu Val Glu Asn Phe Tyr Lys
1               5                   10

<210> SEQ ID NO 220
<211> LENGTH: 9
<212> TYPE: PRT
<213> ORGANISM: Homo sapiens

<400> SEQUENCE: 220

Ser Glu Glu Leu Leu Arg Glu His Tyr
1               5

<210> SEQ ID NO 221
<211> LENGTH: 9
<212> TYPE: PRT
<213> ORGANISM: Homo sapiens

<400> SEQUENCE: 221

Arg Ala Asp Gly Asn Phe Leu Leu Tyr
1               5

<210> SEQ ID NO 222
<211> LENGTH: 9
<212> TYPE: PRT
<213> ORGANISM: Homo sapiens

<400> SEQUENCE: 222

Ser Ile Asp Arg Thr Val Met Tyr Tyr
1               5

<210> SEQ ID NO 223
<211> LENGTH: 11
<212> TYPE: PRT
<213> ORGANISM: Homo sapiens

<400> SEQUENCE: 223

Glu Thr Asp Leu Leu Asp Ile Arg Ser Glu Tyr
1               5                   10

<210> SEQ ID NO 224
<211> LENGTH: 9
<212> TYPE: PRT
<213> ORGANISM: Homo sapiens

<400> SEQUENCE: 224

Glu Ser Tyr Glu Ala Leu Pro Gln His
1               5

<210> SEQ ID NO 225
<211> LENGTH: 9
<212> TYPE: PRT
<213> ORGANISM: Homo sapiens

<400> SEQUENCE: 225

Ser Glu Glu Glu Ile Arg Glu Ala Phe
1               5
```

```
<210> SEQ ID NO 226
<211> LENGTH: 9
<212> TYPE: PRT
<213> ORGANISM: Homo sapiens

<400> SEQUENCE: 226

Lys Val Met Gln Gln Asn Leu Val Tyr
1               5

<210> SEQ ID NO 227
<211> LENGTH: 8
<212> TYPE: PRT
<213> ORGANISM: Homo sapiens

<400> SEQUENCE: 227

Asp Glu Lys Ser Ile Ile Thr Tyr
1               5

<210> SEQ ID NO 228
<211> LENGTH: 8
<212> TYPE: PRT
<213> ORGANISM: Homo sapiens

<400> SEQUENCE: 228

Glu Glu Ile Glu Gly Phe Arg Tyr
1               5

<210> SEQ ID NO 229
<211> LENGTH: 9
<212> TYPE: PRT
<213> ORGANISM: Homo sapiens

<400> SEQUENCE: 229

Met Glu Asn Leu Phe Ile Asn Arg Phe
1               5

<210> SEQ ID NO 230
<211> LENGTH: 9
<212> TYPE: PRT
<213> ORGANISM: Homo sapiens

<400> SEQUENCE: 230

Met Glu Lys Ile Trp His His Thr Phe
1               5

<210> SEQ ID NO 231
<211> LENGTH: 10
<212> TYPE: PRT
<213> ORGANISM: Homo sapiens

<400> SEQUENCE: 231

Met Glu His Ala Met Glu Thr Met Met Phe
1               5                   10

<210> SEQ ID NO 232
<211> LENGTH: 8
<212> TYPE: PRT
<213> ORGANISM: Homo sapiens

<400> SEQUENCE: 232

Glu Glu Ile Phe Asn Leu Lys Phe
1               5

<210> SEQ ID NO 233
```

```
<211> LENGTH: 9
<212> TYPE: PRT
<213> ORGANISM: Homo sapiens

<400> SEQUENCE: 233

Leu Val Leu Met Val Leu Tyr Leu Ile
1               5

<210> SEQ ID NO 234
<211> LENGTH: 9
<212> TYPE: PRT
<213> ORGANISM: Homo sapiens

<400> SEQUENCE: 234

Glu Glu Leu Gln Gln Lys Val Ser Tyr
1               5

<210> SEQ ID NO 235
<211> LENGTH: 11
<212> TYPE: PRT
<213> ORGANISM: Homo sapiens

<400> SEQUENCE: 235

Leu Arg Val Ala Pro Glu Glu His Pro Val Leu
1               5                   10

<210> SEQ ID NO 236
<211> LENGTH: 9
<212> TYPE: PRT
<213> ORGANISM: Homo sapiens

<400> SEQUENCE: 236

Asp Gly His Leu Phe Gln Val Glu Tyr
1               5

<210> SEQ ID NO 237
<211> LENGTH: 9
<212> TYPE: PRT
<213> ORGANISM: Homo sapiens

<400> SEQUENCE: 237

Leu Ala Glu Leu Ala His Arg Glu Tyr
1               5

<210> SEQ ID NO 238
<211> LENGTH: 10
<212> TYPE: PRT
<213> ORGANISM: Homo sapiens

<400> SEQUENCE: 238

Asn Glu Ala Asp Val His Gly Ile Tyr Phe
1               5                   10

<210> SEQ ID NO 239
<211> LENGTH: 9
<212> TYPE: PRT
<213> ORGANISM: Homo sapiens

<400> SEQUENCE: 239

Lys Val Phe Gln Glu Pro Leu Phe Tyr
1               5

<210> SEQ ID NO 240
<211> LENGTH: 9
<212> TYPE: PRT
```

<213> ORGANISM: Homo sapiens

<400> SEQUENCE: 240

Gly Val Leu Ala Trp Val Lys Glu Lys
1               5

<210> SEQ ID NO 241
<211> LENGTH: 9
<212> TYPE: PRT
<213> ORGANISM: Homo sapiens

<400> SEQUENCE: 241

His Glu Ala Leu Leu Tyr Tyr Val Leu
1               5

<210> SEQ ID NO 242
<211> LENGTH: 8
<212> TYPE: PRT
<213> ORGANISM: Homo sapiens

<400> SEQUENCE: 242

His Glu Met Ile Ile Leu Lys Leu
1               5

<210> SEQ ID NO 243
<211> LENGTH: 9
<212> TYPE: PRT
<213> ORGANISM: Homo sapiens

<400> SEQUENCE: 243

Ile Val Pro Ala Asn Phe Pro Ser Leu
1               5

<210> SEQ ID NO 244
<211> LENGTH: 9
<212> TYPE: PRT
<213> ORGANISM: Homo sapiens

<400> SEQUENCE: 244

His Leu Asp Leu Gly Ile Leu Tyr Tyr
1               5

<210> SEQ ID NO 245
<211> LENGTH: 10
<212> TYPE: PRT
<213> ORGANISM: Homo sapiens

<400> SEQUENCE: 245

Ile Thr Asp Ser Ala Gly His Ile Leu Tyr
1               5                   10

<210> SEQ ID NO 246
<211> LENGTH: 10
<212> TYPE: PRT
<213> ORGANISM: Homo sapiens

<400> SEQUENCE: 246

His Thr Asp Asp Pro Leu Thr Trp Asp Tyr
1               5                   10

<210> SEQ ID NO 247
<211> LENGTH: 9
<212> TYPE: PRT
<213> ORGANISM: Homo sapiens

```
<400> SEQUENCE: 247

Ile Asp Gln Thr Ala Leu Ala Val Tyr
1               5

<210> SEQ ID NO 248
<211> LENGTH: 9
<212> TYPE: PRT
<213> ORGANISM: Homo sapiens

<400> SEQUENCE: 248

Leu Glu Asp Val Val Ile Glu Arg Tyr
1               5

<210> SEQ ID NO 249
<211> LENGTH: 9
<212> TYPE: PRT
<213> ORGANISM: Homo sapiens

<400> SEQUENCE: 249

Gln Ile Ala Ser Phe Ile Leu Leu Arg
1               5

<210> SEQ ID NO 250
<211> LENGTH: 8
<212> TYPE: PRT
<213> ORGANISM: Homo sapiens

<400> SEQUENCE: 250

Asp Glu His Tyr Ile Leu Thr Phe
1               5

<210> SEQ ID NO 251
<211> LENGTH: 10
<212> TYPE: PRT
<213> ORGANISM: Homo sapiens

<400> SEQUENCE: 251

Asp Glu Ile Gly Leu Pro Lys Ile Phe Tyr
1               5                   10

<210> SEQ ID NO 252
<211> LENGTH: 9
<212> TYPE: PRT
<213> ORGANISM: Homo sapiens

<400> SEQUENCE: 252

Asp Glu Ile Val Arg Ile Asn Gly Tyr
1               5

<210> SEQ ID NO 253
<211> LENGTH: 9
<212> TYPE: PRT
<213> ORGANISM: Homo sapiens

<400> SEQUENCE: 253

Asp Glu Lys Leu Leu Tyr Asp Thr Phe
1               5

<210> SEQ ID NO 254
<211> LENGTH: 10
<212> TYPE: PRT
<213> ORGANISM: Homo sapiens

<400> SEQUENCE: 254
```

Arg Ile Ile Glu Glu Thr Leu Ala Leu Lys
1               5                   10

<210> SEQ ID NO 255
<211> LENGTH: 9
<212> TYPE: PRT
<213> ORGANISM: Homo sapiens

<400> SEQUENCE: 255

Gly Thr Asp Glu Leu Arg Leu Leu Tyr
1               5

<210> SEQ ID NO 256
<211> LENGTH: 11
<212> TYPE: PRT
<213> ORGANISM: Homo sapiens

<400> SEQUENCE: 256

Asp Glu Leu Glu Ile Ile Glu Gly Met Lys Phe
1               5                   10

<210> SEQ ID NO 257
<211> LENGTH: 10
<212> TYPE: PRT
<213> ORGANISM: Homo sapiens

<400> SEQUENCE: 257

Gln Val Asp Pro Leu Ser Ala Leu Lys Tyr
1               5                   10

<210> SEQ ID NO 258
<211> LENGTH: 9
<212> TYPE: PRT
<213> ORGANISM: Homo sapiens

<400> SEQUENCE: 258

Asp Glu Leu His Tyr Leu Glu Val Tyr
1               5

<210> SEQ ID NO 259
<211> LENGTH: 10
<212> TYPE: PRT
<213> ORGANISM: Homo sapiens

<400> SEQUENCE: 259

Glu Glu Phe Glu Leu Leu Gly Lys Ala Tyr
1               5                   10

<210> SEQ ID NO 260
<211> LENGTH: 11
<212> TYPE: PRT
<213> ORGANISM: Homo sapiens

<400> SEQUENCE: 260

Gln Leu Glu Asp Gly Arg Thr Leu Ser Asp Tyr
1               5                   10

<210> SEQ ID NO 261
<211> LENGTH: 9
<212> TYPE: PRT
<213> ORGANISM: Homo sapiens

<400> SEQUENCE: 261

Asp Glu Phe Leu Trp Arg Glu Gln Phe
1               5

```
<210> SEQ ID NO 262
<211> LENGTH: 8
<212> TYPE: PRT
<213> ORGANISM: Homo sapiens

<400> SEQUENCE: 262

Asp Glu Met Leu Ser Arg Gly Phe
1               5

<210> SEQ ID NO 263
<211> LENGTH: 10
<212> TYPE: PRT
<213> ORGANISM: Homo sapiens

<400> SEQUENCE: 263

Asp Glu Pro Leu Leu Lys His Trp Glu Phe
1               5                   10

<210> SEQ ID NO 264
<211> LENGTH: 10
<212> TYPE: PRT
<213> ORGANISM: Homo sapiens

<400> SEQUENCE: 264

Pro Ser Arg Asp Ser Leu Pro Leu Pro Val
1               5                   10

<210> SEQ ID NO 265
<211> LENGTH: 11
<212> TYPE: PRT
<213> ORGANISM: Homo sapiens

<400> SEQUENCE: 265

Asn Leu Arg Glu Thr Asn Leu Asp Ser Leu Pro
1               5                   10

<210> SEQ ID NO 266
<211> LENGTH: 9
<212> TYPE: PRT
<213> ORGANISM: Homo sapiens

<400> SEQUENCE: 266

Asp Glu Val Lys Phe Leu Thr Val Leu
1               5

<210> SEQ ID NO 267
<211> LENGTH: 9
<212> TYPE: PRT
<213> ORGANISM: Homo sapiens

<400> SEQUENCE: 267

Asn Glu Val Glu Lys Thr Met Glu Tyr
1               5

<210> SEQ ID NO 268
<211> LENGTH: 10
<212> TYPE: PRT
<213> ORGANISM: Homo sapiens

<400> SEQUENCE: 268

Asp Glu Val Gln Val Val Arg Gly His Tyr
1               5                   10
```

<210> SEQ ID NO 269
<211> LENGTH: 9
<212> TYPE: PRT
<213> ORGANISM: Homo sapiens

<400> SEQUENCE: 269

Asp Glu Trp Leu Lys Pro Glu Leu Phe
1               5

<210> SEQ ID NO 270
<211> LENGTH: 9
<212> TYPE: PRT
<213> ORGANISM: Homo sapiens

<400> SEQUENCE: 270

Asp Glu Tyr Ser Leu Val Arg Glu Leu
1               5

<210> SEQ ID NO 271
<211> LENGTH: 9
<212> TYPE: PRT
<213> ORGANISM: Homo sapiens

<400> SEQUENCE: 271

Asn Glu Phe Glu Ala Thr Gln Lys Leu
1               5

<210> SEQ ID NO 272
<211> LENGTH: 9
<212> TYPE: PRT
<213> ORGANISM: Homo sapiens

<400> SEQUENCE: 272

Asp Glu Leu Gln Gln Pro Leu Glu Leu
1               5

<210> SEQ ID NO 273
<211> LENGTH: 11
<212> TYPE: PRT
<213> ORGANISM: Homo sapiens

<400> SEQUENCE: 273

Asp Val Val Met Thr Gln Ser Pro Leu Ser Leu
1               5                   10

<210> SEQ ID NO 274
<211> LENGTH: 9
<212> TYPE: PRT
<213> ORGANISM: Homo sapiens

<400> SEQUENCE: 274

Ser Glu Arg Glu Ala Ile Glu Val Phe
1               5

<210> SEQ ID NO 275
<211> LENGTH: 9
<212> TYPE: PRT
<213> ORGANISM: Homo sapiens

<400> SEQUENCE: 275

Arg Tyr Phe Tyr His Gln Glu Glu Tyr
1               5

<210> SEQ ID NO 276
<211> LENGTH: 9

```
<212> TYPE: PRT
<213> ORGANISM: Homo sapiens

<400> SEQUENCE: 276

Thr Ser Ala Leu Pro Ile Ile Gln Lys
1               5

<210> SEQ ID NO 277
<211> LENGTH: 11
<212> TYPE: PRT
<213> ORGANISM: Homo sapiens

<400> SEQUENCE: 277

Arg Val Gln Glu Ala Val Glu Ser Met Val Lys
1               5                   10

<210> SEQ ID NO 278
<211> LENGTH: 11
<212> TYPE: PRT
<213> ORGANISM: Homo sapiens

<400> SEQUENCE: 278

Thr Val Met Glu Leu Val Lys Ile Ile Tyr Lys
1               5                   10

<210> SEQ ID NO 279
<211> LENGTH: 9
<212> TYPE: PRT
<213> ORGANISM: Homo sapiens

<400> SEQUENCE: 279

Arg Leu Leu Gln Lys Val Leu Ala Tyr
1               5

<210> SEQ ID NO 280
<211> LENGTH: 9
<212> TYPE: PRT
<213> ORGANISM: Homo sapiens

<400> SEQUENCE: 280

Arg Ile His Phe Pro Leu Ala Thr Tyr
1               5

<210> SEQ ID NO 281
<211> LENGTH: 12
<212> TYPE: PRT
<213> ORGANISM: Homo sapiens

<400> SEQUENCE: 281

Val Gly Gly Leu Lys Asn Thr Leu Val His Arg Leu
1               5                   10

<210> SEQ ID NO 282
<211> LENGTH: 10
<212> TYPE: PRT
<213> ORGANISM: Homo sapiens

<400> SEQUENCE: 282

Gln Ala Gln Ala Asp Ser Leu Thr Val Tyr
1               5                   10

<210> SEQ ID NO 283
<211> LENGTH: 9
<212> TYPE: PRT
<213> ORGANISM: Homo sapiens
```

<400> SEQUENCE: 283

Val Leu Asp Pro Tyr Leu Leu Lys Tyr
1               5

<210> SEQ ID NO 284
<211> LENGTH: 10
<212> TYPE: PRT
<213> ORGANISM: Homo sapiens

<400> SEQUENCE: 284

Ile Phe Ser Pro Pro Phe Pro Leu Phe Tyr
1               5                   10

<210> SEQ ID NO 285
<211> LENGTH: 9
<212> TYPE: PRT
<213> ORGANISM: Homo sapiens

<400> SEQUENCE: 285

Thr Glu Leu Leu Leu Lys Glu Gly Phe
1               5

<210> SEQ ID NO 286
<211> LENGTH: 12
<212> TYPE: PRT
<213> ORGANISM: Homo sapiens

<400> SEQUENCE: 286

Gly Leu Phe Glu Val Gly Ala Gly Trp Ile Gly Lys
1               5                   10

<210> SEQ ID NO 287
<211> LENGTH: 9
<212> TYPE: PRT
<213> ORGANISM: Homo sapiens

<400> SEQUENCE: 287

Tyr Glu Tyr Lys Phe Gly Phe Glu Leu
1               5

<210> SEQ ID NO 288
<211> LENGTH: 9
<212> TYPE: PRT
<213> ORGANISM: Homo sapiens

<400> SEQUENCE: 288

Trp Pro Leu Trp Arg Leu Val Ser Leu
1               5

<210> SEQ ID NO 289
<211> LENGTH: 9
<212> TYPE: PRT
<213> ORGANISM: Homo sapiens

<400> SEQUENCE: 289

Tyr Ile Asp Glu Gln Phe Glu Arg Tyr
1               5

<210> SEQ ID NO 290
<211> LENGTH: 11
<212> TYPE: PRT
<213> ORGANISM: Homo sapiens

<400> SEQUENCE: 290

Tyr Leu Asp Glu Lys Leu Ala Leu Leu Asn Ala
1               5                   10

<210> SEQ ID NO 291
<211> LENGTH: 8
<212> TYPE: PRT
<213> ORGANISM: Homo sapiens

<400> SEQUENCE: 291

Asp Glu His Leu Ile Thr Phe Phe
1               5

<210> SEQ ID NO 292
<211> LENGTH: 8
<212> TYPE: PRT
<213> ORGANISM: Homo sapiens

<400> SEQUENCE: 292

Asp Asp Phe His Ile Tyr Val Tyr
1               5

<210> SEQ ID NO 293
<211> LENGTH: 9
<212> TYPE: PRT
<213> ORGANISM: Homo sapiens

<400> SEQUENCE: 293

Ala Pro Arg Thr Val Leu Leu Leu
1               5

<210> SEQ ID NO 294
<211> LENGTH: 11
<212> TYPE: PRT
<213> ORGANISM: Homo sapiens

<400> SEQUENCE: 294

Ala Pro Arg Thr Val Ala Leu Thr Ala Leu Leu
1               5                   10

<210> SEQ ID NO 295
<211> LENGTH: 10
<212> TYPE: PRT
<213> ORGANISM: Homo sapiens

<400> SEQUENCE: 295

Phe Thr Asp Val Asn Ser Ile Leu Arg Tyr
1               5                   10

<210> SEQ ID NO 296
<211> LENGTH: 9
<212> TYPE: PRT
<213> ORGANISM: Homo sapiens

<400> SEQUENCE: 296

Tyr Ser Glu Glu Glu Cys Arg Gln Tyr
1               5

<210> SEQ ID NO 297
<211> LENGTH: 9
<212> TYPE: PRT
<213> ORGANISM: Homo sapiens

<400> SEQUENCE: 297

Tyr Ser Glu Lys Ile Val Asp Met Tyr

```
<210> SEQ ID NO 298
<211> LENGTH: 10
<212> TYPE: PRT
<213> ORGANISM: Homo sapiens

<400> SEQUENCE: 298

Tyr Thr Asp Leu Leu Arg Leu Phe Glu Tyr
1               5                   10

<210> SEQ ID NO 299
<211> LENGTH: 9
<212> TYPE: PRT
<213> ORGANISM: Homo sapiens

<400> SEQUENCE: 299

Tyr Val Asp Pro Gln Phe Leu Thr Tyr
1               5

<210> SEQ ID NO 300
<211> LENGTH: 9
<212> TYPE: PRT
<213> ORGANISM: Homo sapiens

<400> SEQUENCE: 300

His Glu Arg Thr Phe Leu Leu Glu Tyr
1               5

<210> SEQ ID NO 301
<211> LENGTH: 12
<212> TYPE: PRT
<213> ORGANISM: Homo sapiens

<400> SEQUENCE: 301

Ser Leu Leu Thr Ser Ser Lys Gly Gln Leu Gln Lys
1               5                   10

<210> SEQ ID NO 302
<211> LENGTH: 10
<212> TYPE: PRT
<213> ORGANISM: Homo sapiens

<400> SEQUENCE: 302

Ser Pro Arg Glu Asn Ile Leu Val Ser Leu
1               5                   10

<210> SEQ ID NO 303
<211> LENGTH: 11
<212> TYPE: PRT
<213> ORGANISM: Homo sapiens

<400> SEQUENCE: 303

Asp Glu Val Asp Ile Lys Ser Arg Ala Ala Tyr
1               5                   10

<210> SEQ ID NO 304
<211> LENGTH: 9
<212> TYPE: PRT
<213> ORGANISM: Homo sapiens

<400> SEQUENCE: 304

Thr Ser Pro Ser Gln Ser Leu Phe Tyr
1               5
```

<210> SEQ ID NO 305
<211> LENGTH: 10
<212> TYPE: PRT
<213> ORGANISM: Homo sapiens

<400> SEQUENCE: 305

Tyr Thr Glu Thr Glu Pro Tyr His Asn Tyr
1               5                   10

<210> SEQ ID NO 306
<211> LENGTH: 15
<212> TYPE: PRT
<213> ORGANISM: Homo sapiens

<400> SEQUENCE: 306

Ser Ser Val Pro Gly Val Arg Leu Leu Gln Asp Ser Val Asp Phe
1               5                   10                  15

<210> SEQ ID NO 307
<211> LENGTH: 9
<212> TYPE: PRT
<213> ORGANISM: Homo sapiens

<400> SEQUENCE: 307

Val Ala Leu Ile Ser Pro Lys Asp Ile
1               5

<210> SEQ ID NO 308
<211> LENGTH: 10
<212> TYPE: PRT
<213> ORGANISM: Homo sapiens

<400> SEQUENCE: 308

Ser Thr Asp Lys Ala Glu Tyr Thr Phe Tyr
1               5                   10

<210> SEQ ID NO 309
<211> LENGTH: 9
<212> TYPE: PRT
<213> ORGANISM: Homo sapiens

<400> SEQUENCE: 309

Val Thr Glu Ile Phe Arg Gln Ala Phe
1               5

<210> SEQ ID NO 310
<211> LENGTH: 9
<212> TYPE: PRT
<213> ORGANISM: Homo sapiens

<400> SEQUENCE: 310

Ser Val Leu Ser Pro Leu Leu Asn Lys
1               5

<210> SEQ ID NO 311
<211> LENGTH: 10
<212> TYPE: PRT
<213> ORGANISM: Homo sapiens

<400> SEQUENCE: 311

Arg Ala Phe Ser Ser Leu Gly Leu Leu Lys
1               5                   10

<210> SEQ ID NO 312

```
<211> LENGTH: 10
<212> TYPE: PRT
<213> ORGANISM: Homo sapiens

<400> SEQUENCE: 312

Phe Ser Lys Leu Arg Pro Leu Ile Ser Lys
1               5                   10

<210> SEQ ID NO 313
<211> LENGTH: 9
<212> TYPE: PRT
<213> ORGANISM: Homo sapiens

<400> SEQUENCE: 313

Arg Thr Phe Thr Trp Leu Val Gly Lys
1               5

<210> SEQ ID NO 314
<211> LENGTH: 9
<212> TYPE: PRT
<213> ORGANISM: Homo sapiens

<400> SEQUENCE: 314

Lys Val Ala Asn Ile Ile Leu Ser Tyr
1               5

<210> SEQ ID NO 315
<211> LENGTH: 9
<212> TYPE: PRT
<213> ORGANISM: Homo sapiens

<400> SEQUENCE: 315

Thr Met Leu Ala Arg Leu Ala Ser Ala
1               5

<210> SEQ ID NO 316
<211> LENGTH: 9
<212> TYPE: PRT
<213> ORGANISM: Homo sapiens

<400> SEQUENCE: 316

His Glu Leu Pro Leu Pro His Ser Val
1               5

<210> SEQ ID NO 317
<211> LENGTH: 9
<212> TYPE: PRT
<213> ORGANISM: Homo sapiens

<400> SEQUENCE: 317

Ala Val Gln Arg Thr Leu Leu Glu Lys
1               5

<210> SEQ ID NO 318
<211> LENGTH: 13
<212> TYPE: PRT
<213> ORGANISM: Homo sapiens

<400> SEQUENCE: 318

Glu Thr Arg Pro Ala Gly Asp Gly Thr Phe Gln Lys Trp
1               5                   10

<210> SEQ ID NO 319
<211> LENGTH: 12
<212> TYPE: PRT
```

<213> ORGANISM: Homo sapiens

<400> SEQUENCE: 319

Ala Val Leu Ser Ile Leu Pro Ala Ile Phe Gln Lys
1               5                   10

<210> SEQ ID NO 320
<211> LENGTH: 9
<212> TYPE: PRT
<213> ORGANISM: Homo sapiens

<400> SEQUENCE: 320

Glu Ile Ala Gly His Ile Met Glu Phe
1               5

<210> SEQ ID NO 321
<211> LENGTH: 9
<212> TYPE: PRT
<213> ORGANISM: Homo sapiens

<400> SEQUENCE: 321

Glu Leu Ile Arg Thr Ile Met Gly Trp
1               5

<210> SEQ ID NO 322
<211> LENGTH: 10
<212> TYPE: PRT
<213> ORGANISM: Homo sapiens

<400> SEQUENCE: 322

Glu Val Phe Pro Leu Lys Val Phe Gly Tyr
1               5                   10

<210> SEQ ID NO 323
<211> LENGTH: 10
<212> TYPE: PRT
<213> ORGANISM: Homo sapiens

<400> SEQUENCE: 323

Ala Thr Pro Thr Ser Pro Ile Arg Val Lys
1               5                   10

<210> SEQ ID NO 324
<211> LENGTH: 10
<212> TYPE: PRT
<213> ORGANISM: Homo sapiens

<400> SEQUENCE: 324

Ala Val Leu Tyr Gln Pro Leu Phe Asp Lys
1               5                   10

<210> SEQ ID NO 325
<211> LENGTH: 10
<212> TYPE: PRT
<213> ORGANISM: Homo sapiens

<400> SEQUENCE: 325

Glu Val Val Asp Phe Ile Gln Ser Lys Ile
1               5                   10

<210> SEQ ID NO 326
<211> LENGTH: 11
<212> TYPE: PRT
<213> ORGANISM: Homo sapiens

<400> SEQUENCE: 326

Ala Val Gln Glu Phe Gly Leu Ala Arg Phe Lys
1               5                  10

<210> SEQ ID NO 327
<211> LENGTH: 9
<212> TYPE: PRT
<213> ORGANISM: Homo sapiens

<400> SEQUENCE: 327

Glu Ala Ile Gln Asp Leu Trp Gln Trp
1               5

<210> SEQ ID NO 328
<211> LENGTH: 9
<212> TYPE: PRT
<213> ORGANISM: Homo sapiens

<400> SEQUENCE: 328

Gly Val Ile Arg Ser Leu Met Ala Phe
1               5

<210> SEQ ID NO 329
<211> LENGTH: 10
<212> TYPE: PRT
<213> ORGANISM: Homo sapiens

<400> SEQUENCE: 329

His Ile Ile Ser Gly Thr Cys Ala Ser Trp
1               5                  10

<210> SEQ ID NO 330
<211> LENGTH: 10
<212> TYPE: PRT
<213> ORGANISM: Homo sapiens

<400> SEQUENCE: 330

Gly Val Ile Asp Val Ile Thr Lys Thr Trp
1               5                  10

<210> SEQ ID NO 331
<211> LENGTH: 9
<212> TYPE: PRT
<213> ORGANISM: Homo sapiens

<400> SEQUENCE: 331

Gly Val Ile Asp Leu Ile Phe Glu Lys
1               5

<210> SEQ ID NO 332
<211> LENGTH: 9
<212> TYPE: PRT
<213> ORGANISM: Homo sapiens

<400> SEQUENCE: 332

Gly Val Cys His Ile Phe Ala Ser Phe
1               5

<210> SEQ ID NO 333
<211> LENGTH: 9
<212> TYPE: PRT
<213> ORGANISM: Homo sapiens

<400> SEQUENCE: 333

```
Gly Thr Tyr Val Ser Ser Val Pro Arg
1               5

<210> SEQ ID NO 334
<211> LENGTH: 11
<212> TYPE: PRT
<213> ORGANISM: Homo sapiens

<400> SEQUENCE: 334

Gly Thr Ala Gly Leu Leu Glu Gln Trp Leu Lys
1               5                   10

<210> SEQ ID NO 335
<211> LENGTH: 10
<212> TYPE: PRT
<213> ORGANISM: Homo sapiens

<400> SEQUENCE: 335

His Val Ile Thr Gly Leu Leu Glu His Tyr
1               5                   10

<210> SEQ ID NO 336
<211> LENGTH: 11
<212> TYPE: PRT
<213> ORGANISM: Homo sapiens

<400> SEQUENCE: 336

Gly Thr Ala Asp Glu Leu Val Leu His Ser Trp
1               5                   10

<210> SEQ ID NO 337
<211> LENGTH: 9
<212> TYPE: PRT
<213> ORGANISM: Homo sapiens

<400> SEQUENCE: 337

Glu Ile Lys Glu Val Ile Leu Glu Phe
1               5

<210> SEQ ID NO 338
<211> LENGTH: 9
<212> TYPE: PRT
<213> ORGANISM: Homo sapiens

<400> SEQUENCE: 338

Glu Glu Ala Ser Leu Leu His Gln Phe
1               5

<210> SEQ ID NO 339
<211> LENGTH: 9
<212> TYPE: PRT
<213> ORGANISM: Homo sapiens

<400> SEQUENCE: 339

Lys Leu Phe Ile Gly Gly Leu Ser Phe
1               5

<210> SEQ ID NO 340
<211> LENGTH: 9
<212> TYPE: PRT
<213> ORGANISM: Homo sapiens

<400> SEQUENCE: 340

Asp Val Val Pro Ala Val Arg Lys Trp
1               5
```

```
<210> SEQ ID NO 341
<211> LENGTH: 9
<212> TYPE: PRT
<213> ORGANISM: Homo sapiens

<400> SEQUENCE: 341

Asp Val Thr Gly Val Val Arg Gln Trp
1               5

<210> SEQ ID NO 342
<211> LENGTH: 9
<212> TYPE: PRT
<213> ORGANISM: Homo sapiens

<400> SEQUENCE: 342

Asp Val Lys Asp Tyr Ile Gln Glu Tyr
1               5

<210> SEQ ID NO 343
<211> LENGTH: 11
<212> TYPE: PRT
<213> ORGANISM: Homo sapiens

<400> SEQUENCE: 343

Asp Val Ile Asp Asn Asp Ser Trp Arg Leu Trp
1               5                   10

<210> SEQ ID NO 344
<211> LENGTH: 11
<212> TYPE: PRT
<213> ORGANISM: Homo sapiens

<400> SEQUENCE: 344

Asp Val Phe Ser Ser Lys Gly Met Thr Arg Trp
1               5                   10

<210> SEQ ID NO 345
<211> LENGTH: 9
<212> TYPE: PRT
<213> ORGANISM: Homo sapiens

<400> SEQUENCE: 345

Asp Thr Val Lys Lys Ile Glu Ser Phe
1               5

<210> SEQ ID NO 346
<211> LENGTH: 11
<212> TYPE: PRT
<213> ORGANISM: Homo sapiens

<400> SEQUENCE: 346

Asp Leu Pro Ser Asn His Val Ile Asp Arg Trp
1               5                   10

<210> SEQ ID NO 347
<211> LENGTH: 9
<212> TYPE: PRT
<213> ORGANISM: Homo sapiens

<400> SEQUENCE: 347

Asp Leu Ile Gly His Ile Val Glu Phe
1               5
```

```
<210> SEQ ID NO 348
<211> LENGTH: 9
<212> TYPE: PRT
<213> ORGANISM: Homo sapiens

<400> SEQUENCE: 348

Asp Lys Glu Ser Gln Leu Glu Ala Tyr
1               5

<210> SEQ ID NO 349
<211> LENGTH: 11
<212> TYPE: PRT
<213> ORGANISM: Homo sapiens

<400> SEQUENCE: 349

Glu Val Ile Lys Leu Lys Gly Tyr Thr Ser Trp
1               5                   10

<210> SEQ ID NO 350
<211> LENGTH: 9
<212> TYPE: PRT
<213> ORGANISM: Homo sapiens

<400> SEQUENCE: 350

Gly Ser Ser Asp Val Ile Ile His Arg
1               5

<210> SEQ ID NO 351
<211> LENGTH: 9
<212> TYPE: PRT
<213> ORGANISM: Homo sapiens

<400> SEQUENCE: 351

Gly Thr Leu Asp Tyr Ile Leu Gln Arg
1               5

<210> SEQ ID NO 352
<211> LENGTH: 10
<212> TYPE: PRT
<213> ORGANISM: Homo sapiens

<400> SEQUENCE: 352

Glu Val Asp Lys Arg Val His Met Thr Trp
1               5                   10

<210> SEQ ID NO 353
<211> LENGTH: 10
<212> TYPE: PRT
<213> ORGANISM: Homo sapiens

<400> SEQUENCE: 353

Ser Val Pro Tyr Phe Leu Phe Gln His Trp
1               5                   10

<210> SEQ ID NO 354
<211> LENGTH: 11
<212> TYPE: PRT
<213> ORGANISM: Homo sapiens

<400> SEQUENCE: 354

Ser Val Glu Glu Ile Ser Thr Leu Val Gln Lys
1               5                   10

<210> SEQ ID NO 355
<211> LENGTH: 10
```

```
<212> TYPE: PRT
<213> ORGANISM: Homo sapiens

<400> SEQUENCE: 355

Ser Thr Phe Gln Gln Met Trp Ile Ser Lys
1               5                   10

<210> SEQ ID NO 356
<211> LENGTH: 10
<212> TYPE: PRT
<213> ORGANISM: Homo sapiens

<400> SEQUENCE: 356

Thr Thr Ile Pro His Ala Leu Leu Thr Trp
1               5                   10

<210> SEQ ID NO 357
<211> LENGTH: 10
<212> TYPE: PRT
<213> ORGANISM: Homo sapiens

<400> SEQUENCE: 357

Ser Ala Phe Leu Leu Leu Gly Leu Phe Lys
1               5                   10

<210> SEQ ID NO 358
<211> LENGTH: 11
<212> TYPE: PRT
<213> ORGANISM: Homo sapiens

<400> SEQUENCE: 358

Asn Ile Gly Asp Glu Ala Leu Ile Gly Arg Trp
1               5                   10

<210> SEQ ID NO 359
<211> LENGTH: 10
<212> TYPE: PRT
<213> ORGANISM: Homo sapiens

<400> SEQUENCE: 359

Thr Val Ala Phe Val Pro Ile Ser Gly Trp
1               5                   10

<210> SEQ ID NO 360
<211> LENGTH: 10
<212> TYPE: PRT
<213> ORGANISM: Homo sapiens

<400> SEQUENCE: 360

Glu Thr Val Asn Leu Arg Ser Leu Gly Phe
1               5                   10

<210> SEQ ID NO 361
<211> LENGTH: 9
<212> TYPE: PRT
<213> ORGANISM: Homo sapiens

<400> SEQUENCE: 361

Met Pro Lys Phe Ser Met Pro Gly Phe
1               5

<210> SEQ ID NO 362
<211> LENGTH: 9
<212> TYPE: PRT
<213> ORGANISM: Homo sapiens
```

<400> SEQUENCE: 362

Glu Val Met Glu Ile Met Ser Arg Phe
1               5

<210> SEQ ID NO 363
<211> LENGTH: 9
<212> TYPE: PRT
<213> ORGANISM: Homo sapiens

<400> SEQUENCE: 363

Glu Val Met Asp Val Phe Leu Arg Phe
1               5

<210> SEQ ID NO 364
<211> LENGTH: 9
<212> TYPE: PRT
<213> ORGANISM: Homo sapiens

<400> SEQUENCE: 364

Arg Leu Gln Glu Ala Leu Asn Leu Phe
1               5

<210> SEQ ID NO 365
<211> LENGTH: 11
<212> TYPE: PRT
<213> ORGANISM: Homo sapiens

<400> SEQUENCE: 365

Glu Thr Ile Asp Trp Lys Val Phe Glu Ser Trp
1               5                   10

<210> SEQ ID NO 366
<211> LENGTH: 10
<212> TYPE: PRT
<213> ORGANISM: Homo sapiens

<400> SEQUENCE: 366

Glu Leu Met Glu His Gly Val Val Ser Trp
1               5                   10

<210> SEQ ID NO 367
<211> LENGTH: 9
<212> TYPE: PRT
<213> ORGANISM: Homo sapiens

<400> SEQUENCE: 367

Ala Ser Val Ala Trp Ala Val Leu Lys
1               5

<210> SEQ ID NO 368
<211> LENGTH: 9
<212> TYPE: PRT
<213> ORGANISM: Homo sapiens

<400> SEQUENCE: 368

Ser Val Ser Pro Val Val His Val Arg
1               5

<210> SEQ ID NO 369
<211> LENGTH: 10
<212> TYPE: PRT
<213> ORGANISM: Homo sapiens

<400> SEQUENCE: 369

His Val Val Asp Arg Asp Thr Glu Ala Trp
1               5                   10

<210> SEQ ID NO 370
<211> LENGTH: 9
<212> TYPE: PRT
<213> ORGANISM: Homo sapiens

<400> SEQUENCE: 370

Glu Thr Ile Thr Gly Leu Arg Val Trp
1               5

<210> SEQ ID NO 371
<211> LENGTH: 10
<212> TYPE: PRT
<213> ORGANISM: Homo sapiens

<400> SEQUENCE: 371

Arg Gln Leu Glu Asp Ile Leu Ser Thr Tyr
1               5                   10

<210> SEQ ID NO 372
<211> LENGTH: 11
<212> TYPE: PRT
<213> ORGANISM: Homo sapiens

<400> SEQUENCE: 372

Ala Ile Ala Gln Ala Glu Ser Leu Arg Tyr Lys
1               5                   10

<210> SEQ ID NO 373
<211> LENGTH: 11
<212> TYPE: PRT
<213> ORGANISM: Homo sapiens

<400> SEQUENCE: 373

Gly Val Leu Gln Leu Gly Asn Ile Val Phe Lys
1               5                   10

<210> SEQ ID NO 374
<211> LENGTH: 10
<212> TYPE: PRT
<213> ORGANISM: Homo sapiens

<400> SEQUENCE: 374

Glu Val Ile Asn Ala Leu Lys Gln Thr Trp
1               5                   10

<210> SEQ ID NO 375
<211> LENGTH: 9
<212> TYPE: PRT
<213> ORGANISM: Homo sapiens

<400> SEQUENCE: 375

Ser Thr Ala Ala Phe Phe Leu Leu Arg
1               5

<210> SEQ ID NO 376
<211> LENGTH: 10
<212> TYPE: PRT
<213> ORGANISM: Homo sapiens

<400> SEQUENCE: 376

Asp Ile Tyr Asn Phe Pro Ile His Ala Phe

-continued

```
1               5                   10

<210> SEQ ID NO 377
<211> LENGTH: 10
<212> TYPE: PRT
<213> ORGANISM: Homo sapiens

<400> SEQUENCE: 377

Thr Val Val Glu Arg Met Leu Ser Asn Trp
1               5                   10

<210> SEQ ID NO 378
<211> LENGTH: 11
<212> TYPE: PRT
<213> ORGANISM: Homo sapiens

<400> SEQUENCE: 378

Thr Lys Pro Trp Phe Ala Ser Gln Ile Pro Phe
1               5                   10

<210> SEQ ID NO 379
<211> LENGTH: 9
<212> TYPE: PRT
<213> ORGANISM: Homo sapiens

<400> SEQUENCE: 379

Gly Arg Val Asp Phe Ala Tyr Lys Phe
1               5

<210> SEQ ID NO 380
<211> LENGTH: 9
<212> TYPE: PRT
<213> ORGANISM: Homo sapiens

<400> SEQUENCE: 380

Gly Arg Asp Leu Thr Asp Tyr Leu Met
1               5

<210> SEQ ID NO 381
<211> LENGTH: 10
<212> TYPE: PRT
<213> ORGANISM: Homo sapiens

<400> SEQUENCE: 381

Gly Arg Ile Ser Ile Thr Gly Val Gly Phe
1               5                   10

<210> SEQ ID NO 382
<211> LENGTH: 9
<212> TYPE: PRT
<213> ORGANISM: Homo sapiens

<400> SEQUENCE: 382

Gly Arg Ile Val Thr Leu Ile Ser Phe
1               5

<210> SEQ ID NO 383
<211> LENGTH: 10
<212> TYPE: PRT
<213> ORGANISM: Homo sapiens

<400> SEQUENCE: 383

Gly Arg Leu Asp Leu Gln Tyr Ala Lys Leu
1               5                   10
```

<210> SEQ ID NO 384
<211> LENGTH: 9
<212> TYPE: PRT
<213> ORGANISM: Homo sapiens

<400> SEQUENCE: 384

Gly Arg Thr Asn Leu Ile Val Asn Tyr
1               5

<210> SEQ ID NO 385
<211> LENGTH: 9
<212> TYPE: PRT
<213> ORGANISM: Homo sapiens

<400> SEQUENCE: 385

Arg Tyr Phe Asp Thr Ala Val Ser Arg
1               5

<210> SEQ ID NO 386
<211> LENGTH: 9
<212> TYPE: PRT
<213> ORGANISM: Homo sapiens

<400> SEQUENCE: 386

Gly Arg Met Val Gln Val His Glu Leu
1               5

<210> SEQ ID NO 387
<211> LENGTH: 11
<212> TYPE: PRT
<213> ORGANISM: Homo sapiens

<400> SEQUENCE: 387

Phe Leu Asp Ala Ser Gly Ala Lys Leu Asp Tyr
1               5                   10

<210> SEQ ID NO 388
<211> LENGTH: 9
<212> TYPE: PRT
<213> ORGANISM: Homo sapiens

<400> SEQUENCE: 388

Ala Thr Asp Tyr His Val Arg Val Tyr
1               5

<210> SEQ ID NO 389
<211> LENGTH: 9
<212> TYPE: PRT
<213> ORGANISM: Homo sapiens

<400> SEQUENCE: 389

Ala Arg Leu Pro Trp Ala Gly Gln Leu
1               5

<210> SEQ ID NO 390
<211> LENGTH: 8
<212> TYPE: PRT
<213> ORGANISM: Homo sapiens

<400> SEQUENCE: 390

Tyr Gly Met Pro Arg Gln Ile Leu
1               5

<210> SEQ ID NO 391

```
<211> LENGTH: 9
<212> TYPE: PRT
<213> ORGANISM: Homo sapiens

<400> SEQUENCE: 391

Gly Arg Leu Leu Val Ala Thr Thr Phe
1               5

<210> SEQ ID NO 392
<211> LENGTH: 9
<212> TYPE: PRT
<213> ORGANISM: Homo sapiens

<400> SEQUENCE: 392

Ala Gly Gly Asp Trp Phe Thr Ser Arg
1               5

<210> SEQ ID NO 393
<211> LENGTH: 10
<212> TYPE: PRT
<213> ORGANISM: Homo sapiens

<400> SEQUENCE: 393

Gly Arg Ala Pro Ile Ser Asn Pro Gly Met
1               5                   10

<210> SEQ ID NO 394
<211> LENGTH: 10
<212> TYPE: PRT
<213> ORGANISM: Homo sapiens

<400> SEQUENCE: 394

Gly Arg Met Glu Asn Leu Ala Ser Tyr Arg
1               5                   10

<210> SEQ ID NO 395
<211> LENGTH: 9
<212> TYPE: PRT
<213> ORGANISM: Homo sapiens

<400> SEQUENCE: 395

Val Leu Pro Lys Ser Arg Val Glu Leu
1               5

<210> SEQ ID NO 396
<211> LENGTH: 9
<212> TYPE: PRT
<213> ORGANISM: Homo sapiens

<400> SEQUENCE: 396

Asp Ala Lys Ile Arg Ile Phe Asp Leu
1               5

<210> SEQ ID NO 397
<211> LENGTH: 10
<212> TYPE: PRT
<213> ORGANISM: Homo sapiens

<400> SEQUENCE: 397

Gly Arg Ala Met Val Ala Arg Leu Gly Leu
1               5                   10

<210> SEQ ID NO 398
<211> LENGTH: 9
<212> TYPE: PRT
```

<213> ORGANISM: Homo sapiens

<400> SEQUENCE: 398

Phe Ile Asp Ala Ser Arg Leu Val Tyr
1               5

<210> SEQ ID NO 399
<211> LENGTH: 9
<212> TYPE: PRT
<213> ORGANISM: Homo sapiens

<400> SEQUENCE: 399

Asp Pro Met Lys Ala Arg Val Val Leu
1               5

<210> SEQ ID NO 400
<211> LENGTH: 9
<212> TYPE: PRT
<213> ORGANISM: Homo sapiens

<400> SEQUENCE: 400

Phe Arg Phe Asp Pro Gln Phe Ala Leu
1               5

<210> SEQ ID NO 401
<211> LENGTH: 9
<212> TYPE: PRT
<213> ORGANISM: Homo sapiens

<400> SEQUENCE: 401

Asp Thr Asp His Tyr Phe Leu Arg Tyr
1               5

<210> SEQ ID NO 402
<211> LENGTH: 9
<212> TYPE: PRT
<213> ORGANISM: Homo sapiens

<400> SEQUENCE: 402

Glu Leu Leu Ile Arg Lys Leu Pro Phe
1               5

<210> SEQ ID NO 403
<211> LENGTH: 8
<212> TYPE: PRT
<213> ORGANISM: Homo sapiens

<400> SEQUENCE: 403

Glu Ala Phe Val Arg His Ile Leu
1               5

<210> SEQ ID NO 404
<211> LENGTH: 9
<212> TYPE: PRT
<213> ORGANISM: Homo sapiens

<400> SEQUENCE: 404

Arg Tyr Phe Asp Thr Ala Met Ser Arg
1               5

<210> SEQ ID NO 405
<211> LENGTH: 9
<212> TYPE: PRT
<213> ORGANISM: Homo sapiens

```
<400> SEQUENCE: 405

Gly Arg Val Phe Ile Ile Ser Lys Tyr
1               5

<210> SEQ ID NO 406
<211> LENGTH: 11
<212> TYPE: PRT
<213> ORGANISM: Homo sapiens

<400> SEQUENCE: 406

Thr Phe Arg Pro Ala Ala Met Leu Val Glu Arg
1               5                   10

<210> SEQ ID NO 407
<211> LENGTH: 9
<212> TYPE: PRT
<213> ORGANISM: Homo sapiens

<400> SEQUENCE: 407

Tyr Leu Leu Glu Lys Ser Arg Ala Ile
1               5

<210> SEQ ID NO 408
<211> LENGTH: 9
<212> TYPE: PRT
<213> ORGANISM: Homo sapiens

<400> SEQUENCE: 408

Leu Ser Asp Leu Gly Lys Leu Ser Tyr
1               5

<210> SEQ ID NO 409
<211> LENGTH: 9
<212> TYPE: PRT
<213> ORGANISM: Homo sapiens

<400> SEQUENCE: 409

Val Thr Asp Ser Ile Arg Asp Glu Tyr
1               5

<210> SEQ ID NO 410
<211> LENGTH: 9
<212> TYPE: PRT
<213> ORGANISM: Homo sapiens

<400> SEQUENCE: 410

Leu Thr Asp Arg Glu Leu Glu Glu Tyr
1               5

<210> SEQ ID NO 411
<211> LENGTH: 9
<212> TYPE: PRT
<213> ORGANISM: Homo sapiens

<400> SEQUENCE: 411

Leu Thr Asp Arg Gly Val Met Ser Tyr
1               5

<210> SEQ ID NO 412
<211> LENGTH: 9
<212> TYPE: PRT
<213> ORGANISM: Homo sapiens

<400> SEQUENCE: 412
```

Lys Gly Leu Ser Val Phe Leu Asn Arg
1               5

<210> SEQ ID NO 413
<211> LENGTH: 9
<212> TYPE: PRT
<213> ORGANISM: Homo sapiens

<400> SEQUENCE: 413

Val Thr Asp Asn Arg Ala Phe Gly Tyr
1               5

<210> SEQ ID NO 414
<211> LENGTH: 11
<212> TYPE: PRT
<213> ORGANISM: Homo sapiens

<400> SEQUENCE: 414

Ser Thr Asp Val Ser Asp Leu Leu His Gln Tyr
1               5                   10

<210> SEQ ID NO 415
<211> LENGTH: 9
<212> TYPE: PRT
<213> ORGANISM: Homo sapiens

<400> SEQUENCE: 415

Arg Ser Leu Pro Phe Phe Ser Ala Arg
1               5

<210> SEQ ID NO 416
<211> LENGTH: 9
<212> TYPE: PRT
<213> ORGANISM: Homo sapiens

<400> SEQUENCE: 416

Tyr Arg Phe Met Gly Thr Glu Ala Tyr
1               5

<210> SEQ ID NO 417
<211> LENGTH: 9
<212> TYPE: PRT
<213> ORGANISM: Homo sapiens

<400> SEQUENCE: 417

Met Pro Leu Leu Arg Gln Glu Glu Leu
1               5

<210> SEQ ID NO 418
<211> LENGTH: 9
<212> TYPE: PRT
<213> ORGANISM: Homo sapiens

<400> SEQUENCE: 418

Val Thr Glu Ile Asp Gln Asp Lys Tyr
1               5

<210> SEQ ID NO 419
<211> LENGTH: 9
<212> TYPE: PRT
<213> ORGANISM: Homo sapiens

<400> SEQUENCE: 419

Met Arg His Leu Gly Ala Phe Leu Phe
1               5

```
<210> SEQ ID NO 420
<211> LENGTH: 10
<212> TYPE: PRT
<213> ORGANISM: Homo sapiens

<400> SEQUENCE: 420

Thr Thr Glu Glu Ser Leu Arg Asn Tyr Tyr
1               5                   10

<210> SEQ ID NO 421
<211> LENGTH: 9
<212> TYPE: PRT
<213> ORGANISM: Homo sapiens

<400> SEQUENCE: 421

Met Arg Thr Ser Tyr Leu Leu Leu Phe
1               5

<210> SEQ ID NO 422
<211> LENGTH: 9
<212> TYPE: PRT
<213> ORGANISM: Homo sapiens

<400> SEQUENCE: 422

Thr Val Asp Gln Val Lys Asp Leu Tyr
1               5

<210> SEQ ID NO 423
<211> LENGTH: 9
<212> TYPE: PRT
<213> ORGANISM: Homo sapiens

<400> SEQUENCE: 423

Met Arg Tyr Val Ala Ser Tyr Leu Leu
1               5

<210> SEQ ID NO 424
<211> LENGTH: 9
<212> TYPE: PRT
<213> ORGANISM: Homo sapiens

<400> SEQUENCE: 424

Val Gly Leu Ile Arg Asn Leu Ala Leu
1               5

<210> SEQ ID NO 425
<211> LENGTH: 9
<212> TYPE: PRT
<213> ORGANISM: Homo sapiens

<400> SEQUENCE: 425

Gly Arg Leu Asp Ala Val Leu Gln Arg
1               5

<210> SEQ ID NO 426
<211> LENGTH: 10
<212> TYPE: PRT
<213> ORGANISM: Homo sapiens

<400> SEQUENCE: 426

Leu Leu Asp Gln Gly Gln Leu Asn Lys Tyr
1               5                   10
```

<210> SEQ ID NO 427
<211> LENGTH: 10
<212> TYPE: PRT
<213> ORGANISM: Homo sapiens

<400> SEQUENCE: 427

Asn Arg Phe Ala Gly Phe Gly Ile Gly Leu
1               5                   10

<210> SEQ ID NO 428
<211> LENGTH: 10
<212> TYPE: PRT
<213> ORGANISM: Homo sapiens

<400> SEQUENCE: 428

Lys Arg Leu Gly Thr Leu Val Val Thr Tyr
1               5                   10

<210> SEQ ID NO 429
<211> LENGTH: 9
<212> TYPE: PRT
<213> ORGANISM: Homo sapiens

<400> SEQUENCE: 429

Lys Arg Gly Asp Val Ile Tyr Ile Leu
1               5

<210> SEQ ID NO 430
<211> LENGTH: 9
<212> TYPE: PRT
<213> ORGANISM: Homo sapiens

<400> SEQUENCE: 430

Ser Arg Phe Asp Ile Pro Leu Gly Leu
1               5

<210> SEQ ID NO 431
<211> LENGTH: 10
<212> TYPE: PRT
<213> ORGANISM: Homo sapiens

<400> SEQUENCE: 431

Ser Thr Asp Pro Ser Val Leu Gly Lys Tyr
1               5                   10

<210> SEQ ID NO 432
<211> LENGTH: 9
<212> TYPE: PRT
<213> ORGANISM: Homo sapiens

<400> SEQUENCE: 432

Ser Arg Phe Leu Lys Ser Asp Leu Phe
1               5

<210> SEQ ID NO 433
<211> LENGTH: 9
<212> TYPE: PRT
<213> ORGANISM: Homo sapiens

<400> SEQUENCE: 433

Val Gln Lys Pro Ser Tyr Tyr Val Arg
1               5

<210> SEQ ID NO 434
<211> LENGTH: 10

<212> TYPE: PRT
<213> ORGANISM: Homo sapiens

<400> SEQUENCE: 434

Ser Arg Ile Ser Leu Pro Leu Pro Asn Phe
1               5                   10

<210> SEQ ID NO 435
<211> LENGTH: 9
<212> TYPE: PRT
<213> ORGANISM: Homo sapiens

<400> SEQUENCE: 435

Leu Arg Ser Gly Leu Pro Leu Leu Leu
1               5

<210> SEQ ID NO 436
<211> LENGTH: 9
<212> TYPE: PRT
<213> ORGANISM: Homo sapiens

<400> SEQUENCE: 436

Ser Phe Lys Asp Tyr Ile Gln Glu Arg
1               5

<210> SEQ ID NO 437
<211> LENGTH: 11
<212> TYPE: PRT
<213> ORGANISM: Homo sapiens

<400> SEQUENCE: 437

His Thr Gln Gly Pro Val Asp Gly Ser Leu Tyr
1               5                   10

<210> SEQ ID NO 438
<211> LENGTH: 10
<212> TYPE: PRT
<213> ORGANISM: Homo sapiens

<400> SEQUENCE: 438

Ser Thr Asp Lys Phe Lys Thr Asp Phe Tyr
1               5                   10

<210> SEQ ID NO 439
<211> LENGTH: 9
<212> TYPE: PRT
<213> ORGANISM: Homo sapiens

<400> SEQUENCE: 439

Gly Ser His Ser Met Arg Tyr Phe Phe
1               5

<210> SEQ ID NO 440
<211> LENGTH: 10
<212> TYPE: PRT
<213> ORGANISM: Homo sapiens

<400> SEQUENCE: 440

Gly Ser His Ser Met Arg Tyr Phe Phe Thr
1               5                   10

<210> SEQ ID NO 441
<211> LENGTH: 9
<212> TYPE: PRT
<213> ORGANISM: Homo sapiens

<400> SEQUENCE: 441

Gly Ser His Ser Met Arg Tyr Phe His
1               5

<210> SEQ ID NO 442
<211> LENGTH: 9
<212> TYPE: PRT
<213> ORGANISM: Homo sapiens

<400> SEQUENCE: 442

Ala Ala Ile Leu Gly Met His Asn Leu
1               5

<210> SEQ ID NO 443
<211> LENGTH: 9
<212> TYPE: PRT
<213> ORGANISM: Homo sapiens

<400> SEQUENCE: 443

Lys Leu Asp Pro Thr Lys Thr Thr Leu
1               5

<210> SEQ ID NO 444
<211> LENGTH: 9
<212> TYPE: PRT
<213> ORGANISM: Homo sapiens

<400> SEQUENCE: 444

Phe Val His Asp Leu Val Leu Tyr Leu
1               5

<210> SEQ ID NO 445
<211> LENGTH: 7
<212> TYPE: PRT
<213> ORGANISM: Homo sapiens

<400> SEQUENCE: 445

Phe Val His Asp Leu Val Leu
1               5

<210> SEQ ID NO 446
<211> LENGTH: 9
<212> TYPE: PRT
<213> ORGANISM: Homo sapiens

<400> SEQUENCE: 446

Val Leu Ile Pro Lys Leu Pro Gln Leu
1               5

<210> SEQ ID NO 447
<211> LENGTH: 9
<212> TYPE: PRT
<213> ORGANISM: Homo sapiens

<400> SEQUENCE: 447

Asn Glu Ile Thr Ile Pro Val Thr Phe
1               5

<210> SEQ ID NO 448
<211> LENGTH: 9
<212> TYPE: PRT
<213> ORGANISM: Homo sapiens

<400> SEQUENCE: 448

Tyr Leu Ala Asp Phe Leu Leu Thr Lys
1               5

<210> SEQ ID NO 449
<211> LENGTH: 9
<212> TYPE: PRT
<213> ORGANISM: Homo sapiens

<400> SEQUENCE: 449

Tyr Leu Ile Pro Leu Leu Glu Arg Leu
1               5

<210> SEQ ID NO 450
<211> LENGTH: 8
<212> TYPE: PRT
<213> ORGANISM: Homo sapiens

<400> SEQUENCE: 450

Asn Glu Val Val Thr Arg Glu Tyr
1               5

<210> SEQ ID NO 451
<211> LENGTH: 9
<212> TYPE: PRT
<213> ORGANISM: Homo sapiens

<400> SEQUENCE: 451

Asp Glu Phe Lys Ile Gly Glu Leu Phe
1               5

<210> SEQ ID NO 452
<211> LENGTH: 11
<212> TYPE: PRT
<213> ORGANISM: Homo sapiens

<400> SEQUENCE: 452

Ile Gln Arg Thr Pro Lys Ile Gln Val Tyr Ser
1               5                   10

<210> SEQ ID NO 453
<211> LENGTH: 9
<212> TYPE: PRT
<213> ORGANISM: Homo sapiens

<400> SEQUENCE: 453

Leu Thr Gly Pro Val Met Pro Val Arg
1               5

<210> SEQ ID NO 454
<211> LENGTH: 9
<212> TYPE: PRT
<213> ORGANISM: Homo sapiens

<400> SEQUENCE: 454

Ala Val Ala Ile Lys Ala Met Ala Lys
1               5

<210> SEQ ID NO 455
<211> LENGTH: 8
<212> TYPE: PRT
<213> ORGANISM: Homo sapiens

<400> SEQUENCE: 455

Phe Val Gln Met Met Thr Ala Lys

<210> SEQ ID NO 456
<211> LENGTH: 9
<212> TYPE: PRT
<213> ORGANISM: Homo sapiens

<400> SEQUENCE: 456

Ala Thr Asp Pro Asn Ile Leu Gly Arg
1               5

<210> SEQ ID NO 457
<211> LENGTH: 9
<212> TYPE: PRT
<213> ORGANISM: Homo sapiens

<400> SEQUENCE: 457

Leu Leu Leu Leu Ser Ile Val Ile Leu
1               5

<210> SEQ ID NO 458
<211> LENGTH: 10
<212> TYPE: PRT
<213> ORGANISM: Homo sapiens

<400> SEQUENCE: 458

Lys Leu Pro Asn Phe Gly Phe Val Val Phe
1               5                   10

<210> SEQ ID NO 459
<211> LENGTH: 9
<212> TYPE: PRT
<213> ORGANISM: Homo sapiens

<400> SEQUENCE: 459

Lys Leu Ser Glu Ile Asp Val Ala Leu
1               5

<210> SEQ ID NO 460
<211> LENGTH: 11
<212> TYPE: PRT
<213> ORGANISM: Homo sapiens

<400> SEQUENCE: 460

Tyr Ser Ile Ile Thr Pro Asn Ile Leu Arg Leu
1               5                   10

<210> SEQ ID NO 461
<211> LENGTH: 10
<212> TYPE: PRT
<213> ORGANISM: Homo sapiens

<400> SEQUENCE: 461

Ala Leu Pro Ser Arg Ile Leu Leu Trp Lys
1               5                   10

<210> SEQ ID NO 462
<211> LENGTH: 12
<212> TYPE: PRT
<213> ORGANISM: Homo sapiens

<400> SEQUENCE: 462

Val Lys Gly Phe Tyr Pro Ser Asp Ile Ala Val Glu
1               5                   10

<210> SEQ ID NO 463
<211> LENGTH: 9
<212> TYPE: PRT
<213> ORGANISM: Homo sapiens

<400> SEQUENCE: 463

Phe Leu Leu Asp Leu Ser Arg Ser Val
1               5

<210> SEQ ID NO 464
<211> LENGTH: 9
<212> TYPE: PRT
<213> ORGANISM: Homo sapiens

<400> SEQUENCE: 464

Ile Ile Tyr Lys Gly Gly Thr Ser Arg
1               5

<210> SEQ ID NO 465
<211> LENGTH: 9
<212> TYPE: PRT
<213> ORGANISM: Homo sapiens

<400> SEQUENCE: 465

Ile Val Ala Asp His Val Ala Ser Tyr
1               5

<210> SEQ ID NO 466
<211> LENGTH: 11
<212> TYPE: PRT
<213> ORGANISM: Homo sapiens

<400> SEQUENCE: 466

Glu Val Gly Gly Glu Ala Leu Gly Arg Leu Leu
1               5                   10

<210> SEQ ID NO 467
<211> LENGTH: 10
<212> TYPE: PRT
<213> ORGANISM: Homo sapiens

<400> SEQUENCE: 467

Arg Thr Gly Pro Pro Met Gly Ser Arg Phe
1               5                   10

<210> SEQ ID NO 468
<211> LENGTH: 9
<212> TYPE: PRT
<213> ORGANISM: Homo sapiens

<400> SEQUENCE: 468

Arg Gln Ile Gln Glu Ser Val Thr Phe
1               5

<210> SEQ ID NO 469
<211> LENGTH: 9
<212> TYPE: PRT
<213> ORGANISM: Homo sapiens

<400> SEQUENCE: 469

Arg Val Ala Pro Glu Glu His Pro Val
1               5

<210> SEQ ID NO 470

```
<211> LENGTH: 9
<212> TYPE: PRT
<213> ORGANISM: Homo sapiens

<400> SEQUENCE: 470

Thr Leu Ala Asp Leu Leu Ala Leu Arg
1               5

<210> SEQ ID NO 471
<211> LENGTH: 12
<212> TYPE: PRT
<213> ORGANISM: Homo sapiens

<400> SEQUENCE: 471

Arg Val Ala Pro Glu Glu His Pro Val Leu Leu Thr
1               5                   10

<210> SEQ ID NO 472
<211> LENGTH: 9
<212> TYPE: PRT
<213> ORGANISM: Homo sapiens

<400> SEQUENCE: 472

Thr Leu Ala Asp Ile Ile Ala Arg Leu
1               5

<210> SEQ ID NO 473
<211> LENGTH: 10
<212> TYPE: PRT
<213> ORGANISM: Homo sapiens

<400> SEQUENCE: 473

Arg Trp Glu Asp Gly Ser Pro Leu Asn Phe
1               5                   10

<210> SEQ ID NO 474
<211> LENGTH: 8
<212> TYPE: PRT
<213> ORGANISM: Homo sapiens

<400> SEQUENCE: 474

Tyr Glu Val Ser Gln Leu Lys Asp
1               5

<210> SEQ ID NO 475
<211> LENGTH: 10
<212> TYPE: PRT
<213> ORGANISM: Homo sapiens

<400> SEQUENCE: 475

Tyr Arg Asp Ile Pro Glu Leu Gln Gly Phe
1               5                   10

<210> SEQ ID NO 476
<211> LENGTH: 10
<212> TYPE: PRT
<213> ORGANISM: Homo sapiens

<400> SEQUENCE: 476

Tyr Val Asp Gly Thr Gln Phe Val Arg Phe
1               5                   10

<210> SEQ ID NO 477
<211> LENGTH: 9
<212> TYPE: PRT
```

<213> ORGANISM: Homo sapiens

<400> SEQUENCE: 477

Ser Leu Leu Asp Glu Phe Tyr Lys Leu
1               5

<210> SEQ ID NO 478
<211> LENGTH: 9
<212> TYPE: PRT
<213> ORGANISM: Homo sapiens

<400> SEQUENCE: 478

His Gly Ile Asp Pro Thr Gly Thr Tyr
1               5

<210> SEQ ID NO 479
<211> LENGTH: 13
<212> TYPE: PRT
<213> ORGANISM: Homo sapiens

<400> SEQUENCE: 479

Ser Leu Asp Lys Phe Leu Ala Ser Val Ser Thr Val Leu
1               5                   10

<210> SEQ ID NO 480
<211> LENGTH: 10
<212> TYPE: PRT
<213> ORGANISM: Homo sapiens

<400> SEQUENCE: 480

Ser Ile Gly Glu Arg Asp Leu Ile Phe His
1               5                   10

<210> SEQ ID NO 481
<211> LENGTH: 9
<212> TYPE: PRT
<213> ORGANISM: Homo sapiens

<400> SEQUENCE: 481

Ser Ile Thr Ser Val Phe Ile Thr Lys
1               5

<210> SEQ ID NO 482
<211> LENGTH: 11
<212> TYPE: PRT
<213> ORGANISM: Homo sapiens

<400> SEQUENCE: 482

Phe Gly Glu His Leu Leu Glu Ser Asp Leu Phe
1               5                   10

<210> SEQ ID NO 483
<211> LENGTH: 9
<212> TYPE: PRT
<213> ORGANISM: Homo sapiens

<400> SEQUENCE: 483

Phe Leu Asp Pro Ile Lys Ala Tyr Leu
1               5

<210> SEQ ID NO 484
<211> LENGTH: 11
<212> TYPE: PRT
<213> ORGANISM: Homo sapiens

```
<400> SEQUENCE: 484

Phe Leu Ala Asp Pro Ser Ala Phe Val Ala Ala
1               5                   10

<210> SEQ ID NO 485
<211> LENGTH: 9
<212> TYPE: PRT
<213> ORGANISM: Homo sapiens

<400> SEQUENCE: 485

Ile Thr Ala Pro Pro Ser Arg Val Leu
1               5

<210> SEQ ID NO 486
<211> LENGTH: 10
<212> TYPE: PRT
<213> ORGANISM: Homo sapiens

<400> SEQUENCE: 486

Val Leu Asp Glu Leu Lys Asn Met Lys Cys
1               5                   10

<210> SEQ ID NO 487
<211> LENGTH: 9
<212> TYPE: PRT
<213> ORGANISM: Homo sapiens

<400> SEQUENCE: 487

Leu Leu Gly Pro Arg Leu Val Leu Ala
1               5

<210> SEQ ID NO 488
<211> LENGTH: 9
<212> TYPE: PRT
<213> ORGANISM: Homo sapiens

<400> SEQUENCE: 488

Ile Ile Met Pro His Asn Ile Tyr Leu
1               5

<210> SEQ ID NO 489
<211> LENGTH: 8
<212> TYPE: PRT
<213> ORGANISM: Mus musculus

<400> SEQUENCE: 489

Leu Val Arg Met Val Leu Asn Gly
1               5

<210> SEQ ID NO 490
<211> LENGTH: 10
<212> TYPE: PRT
<213> ORGANISM: Homo sapiens

<400> SEQUENCE: 490

Arg Leu Tyr Gly Pro Ser Ser Val Ser Phe
1               5                   10

<210> SEQ ID NO 491
<211> LENGTH: 9
<212> TYPE: PRT
<213> ORGANISM: Homo sapiens

<400> SEQUENCE: 491
```

```
Phe Glu Ala Pro Ile Lys Leu Val Phe
1               5

<210> SEQ ID NO 492
<211> LENGTH: 9
<212> TYPE: PRT
<213> ORGANISM: Homo sapiens

<400> SEQUENCE: 492

Ile Gln Pro Gly Ala Val Lys Val Tyr
1               5

<210> SEQ ID NO 493
<211> LENGTH: 9
<212> TYPE: PRT
<213> ORGANISM: Homo sapiens

<400> SEQUENCE: 493

Val Leu Ala Glu Val Pro Thr Gln Leu
1               5

<210> SEQ ID NO 494
<211> LENGTH: 9
<212> TYPE: PRT
<213> ORGANISM: Homo sapiens

<400> SEQUENCE: 494

Ile Met Arg Ala Gly Met Ser Ser Leu
1               5

<210> SEQ ID NO 495
<211> LENGTH: 12
<212> TYPE: PRT
<213> ORGANISM: Homo sapiens

<400> SEQUENCE: 495

Val Glu Phe Ser Ser Gly Leu Lys Gly Met Ser Leu
1               5                   10

<210> SEQ ID NO 496
<211> LENGTH: 11
<212> TYPE: PRT
<213> ORGANISM: Homo sapiens

<400> SEQUENCE: 496

Ile Leu Asn Pro Asp Asn Ser Phe Glu Ile Leu
1               5                   10

<210> SEQ ID NO 497
<211> LENGTH: 9
<212> TYPE: PRT
<213> ORGANISM: Homo sapiens

<400> SEQUENCE: 497

Val Ala Leu Glu Phe Ala Leu His Leu
1               5

<210> SEQ ID NO 498
<211> LENGTH: 9
<212> TYPE: PRT
<213> ORGANISM: Homo sapiens

<400> SEQUENCE: 498

Thr Val Ala Val Pro Leu Val Gly Lys
1               5
```

<210> SEQ ID NO 499
<211> LENGTH: 9
<212> TYPE: PRT
<213> ORGANISM: Homo sapiens

<400> SEQUENCE: 499

Thr Leu Ser Asp Leu Arg Val Tyr Leu
1               5

<210> SEQ ID NO 500
<211> LENGTH: 9
<212> TYPE: PRT
<213> ORGANISM: Homo sapiens

<400> SEQUENCE: 500

Thr Leu Ile Asp Ile Met Thr Arg Phe
1               5

<210> SEQ ID NO 501
<211> LENGTH: 9
<212> TYPE: PRT
<213> ORGANISM: Homo sapiens

<400> SEQUENCE: 501

His Asp Phe Pro Arg Ala Leu Ile Phe
1               5

<210> SEQ ID NO 502
<211> LENGTH: 8
<212> TYPE: PRT
<213> ORGANISM: Homo sapiens

<400> SEQUENCE: 502

Gly Ser His Ser Met Arg Tyr Phe
1               5

<210> SEQ ID NO 503
<211> LENGTH: 10
<212> TYPE: PRT
<213> ORGANISM: Homo sapiens

<400> SEQUENCE: 503

Ser Leu Met Asp His Thr Ile Pro Glu Val
1               5                   10

<210> SEQ ID NO 504
<211> LENGTH: 11
<212> TYPE: PRT
<213> ORGANISM: Homo sapiens

<400> SEQUENCE: 504

Ser Gly Val His Thr Phe Pro Ala Val Leu Gln
1               5                   10

<210> SEQ ID NO 505
<211> LENGTH: 9
<212> TYPE: PRT
<213> ORGANISM: Homo sapiens

<400> SEQUENCE: 505

Phe Leu Val Thr Val Ile His Thr Leu
1               5

```
<210> SEQ ID NO 506
<211> LENGTH: 8
<212> TYPE: PRT
<213> ORGANISM: Homo sapiens

<400> SEQUENCE: 506

Thr Asp Gly Lys Val Phe Gln Phe
1               5

<210> SEQ ID NO 507
<211> LENGTH: 9
<212> TYPE: PRT
<213> ORGANISM: Homo sapiens

<400> SEQUENCE: 507

Tyr Asp Leu Leu Arg Asn Thr Asn Phe
1               5

<210> SEQ ID NO 508
<211> LENGTH: 9
<212> TYPE: PRT
<213> ORGANISM: Homo sapiens

<400> SEQUENCE: 508

Ile Leu Tyr Pro Lys Thr Leu Phe Leu
1               5

<210> SEQ ID NO 509
<211> LENGTH: 8
<212> TYPE: PRT
<213> ORGANISM: Homo sapiens

<400> SEQUENCE: 509

Met Arg Tyr Val Ala Ser Tyr Leu
1               5

<210> SEQ ID NO 510
<211> LENGTH: 9
<212> TYPE: PRT
<213> ORGANISM: Homo sapiens

<400> SEQUENCE: 510

Phe Ile Trp Glu Asn Ile His Thr Leu
1               5

<210> SEQ ID NO 511
<211> LENGTH: 9
<212> TYPE: PRT
<213> ORGANISM: Homo sapiens

<400> SEQUENCE: 511

Arg Glu Leu Pro Ala Trp Val Ser Phe
1               5

<210> SEQ ID NO 512
<211> LENGTH: 9
<212> TYPE: PRT
<213> ORGANISM: Homo sapiens

<400> SEQUENCE: 512

Gln Asp Leu Asn Arg Ile Phe Pro Leu
1               5

<210> SEQ ID NO 513
<211> LENGTH: 8
```

```
<212> TYPE: PRT
<213> ORGANISM: Homo sapiens

<400> SEQUENCE: 513

Arg Asp Ser Ile Val Ala Glu Leu
1               5

<210> SEQ ID NO 514
<211> LENGTH: 9
<212> TYPE: PRT
<213> ORGANISM: Homo sapiens

<400> SEQUENCE: 514

Ala Asp Val Leu Lys Val Glu Val Phe
1               5

<210> SEQ ID NO 515
<211> LENGTH: 9
<212> TYPE: PRT
<213> ORGANISM: Homo sapiens

<400> SEQUENCE: 515

Ala Met Asn Pro Val Glu His Pro Phe
1               5

<210> SEQ ID NO 516
<211> LENGTH: 9
<212> TYPE: PRT
<213> ORGANISM: Homo sapiens

<400> SEQUENCE: 516

Ser Glu Leu Ile Arg Asn Val Thr Leu
1               5

<210> SEQ ID NO 517
<211> LENGTH: 9
<212> TYPE: PRT
<213> ORGANISM: Homo sapiens

<400> SEQUENCE: 517

Gln Asp Val Ala Arg Val Leu Gly Phe
1               5

<210> SEQ ID NO 518
<211> LENGTH: 9
<212> TYPE: PRT
<213> ORGANISM: Homo sapiens

<400> SEQUENCE: 518

Ser Asp His Ile His Ile Ile Ala Leu
1               5

<210> SEQ ID NO 519
<211> LENGTH: 9
<212> TYPE: PRT
<213> ORGANISM: Homo sapiens

<400> SEQUENCE: 519

Ala Asp Ser Leu Arg Leu Gln Gln Leu
1               5

<210> SEQ ID NO 520
<211> LENGTH: 8
<212> TYPE: PRT
<213> ORGANISM: Homo sapiens
```

```
<400> SEQUENCE: 520

Leu Leu Asp Ile Arg Ser Glu Tyr
1               5

<210> SEQ ID NO 521
<211> LENGTH: 9
<212> TYPE: PRT
<213> ORGANISM: Homo sapiens

<400> SEQUENCE: 521

Val Leu Phe Gly Leu Leu Arg Glu Val
1               5

<210> SEQ ID NO 522
<211> LENGTH: 9
<212> TYPE: PRT
<213> ORGANISM: Homo sapiens

<400> SEQUENCE: 522

Val Ala Val Gly Arg Ala Leu Tyr Tyr
1               5

<210> SEQ ID NO 523
<211> LENGTH: 9
<212> TYPE: PRT
<213> ORGANISM: Homo sapiens

<400> SEQUENCE: 523

Met Arg Phe Leu Ala Ala Thr Phe Leu
1               5

<210> SEQ ID NO 524
<211> LENGTH: 9
<212> TYPE: PRT
<213> ORGANISM: Homo sapiens

<400> SEQUENCE: 524

Tyr Thr Asp Pro Glu Val Phe Lys Tyr
1               5

<210> SEQ ID NO 525
<211> LENGTH: 9
<212> TYPE: PRT
<213> ORGANISM: Homo sapiens

<400> SEQUENCE: 525

His Asp Phe Leu Lys Tyr Asp Phe Phe
1               5

<210> SEQ ID NO 526
<211> LENGTH: 9
<212> TYPE: PRT
<213> ORGANISM: Homo sapiens

<400> SEQUENCE: 526

Ala Ile Asp Gln Leu His Leu Glu Tyr
1               5

<210> SEQ ID NO 527
<211> LENGTH: 9
<212> TYPE: PRT
<213> ORGANISM: Homo sapiens

<400> SEQUENCE: 527
```

Ser Asp Leu Glu Arg Val Thr Ser Leu
1               5

<210> SEQ ID NO 528
<211> LENGTH: 9
<212> TYPE: PRT
<213> ORGANISM: Homo sapiens

<400> SEQUENCE: 528

Thr Leu Leu Pro Leu Arg Val Phe Leu
1               5

<210> SEQ ID NO 529
<211> LENGTH: 10
<212> TYPE: PRT
<213> ORGANISM: Homo sapiens

<400> SEQUENCE: 529

Tyr Ser Ile Ile Thr Pro Asn Ile Leu Arg
1               5                   10

<210> SEQ ID NO 530
<211> LENGTH: 9
<212> TYPE: PRT
<213> ORGANISM: Homo sapiens

<400> SEQUENCE: 530

Phe Glu Leu Gln Arg Asn Phe Gln Leu
1               5

<210> SEQ ID NO 531
<211> LENGTH: 9
<212> TYPE: PRT
<213> ORGANISM: Homo sapiens

<400> SEQUENCE: 531

Leu Asp Leu Gln Arg Asn Tyr Ile Phe
1               5

<210> SEQ ID NO 532
<211> LENGTH: 9
<212> TYPE: PRT
<213> ORGANISM: Homo sapiens

<400> SEQUENCE: 532

Arg Arg Leu Asp Pro Ile Pro Gln Leu
1               5

<210> SEQ ID NO 533
<211> LENGTH: 12
<212> TYPE: PRT
<213> ORGANISM: Homo sapiens

<400> SEQUENCE: 533

Ser Leu Pro Ile Lys Glu Ser Glu Ile Ile Asp Phe
1               5                   10

<210> SEQ ID NO 534
<211> LENGTH: 9
<212> TYPE: PRT
<213> ORGANISM: Homo sapiens

<400> SEQUENCE: 534

Thr Glu Leu Leu Arg Tyr Tyr Met Leu

```
<210> SEQ ID NO 535
<211> LENGTH: 10
<212> TYPE: PRT
<213> ORGANISM: Homo sapiens

<400> SEQUENCE: 535

Phe Ile Tyr His Gly Glu Val Pro Gln Ala
1               5                   10

<210> SEQ ID NO 536
<211> LENGTH: 9
<212> TYPE: PRT
<213> ORGANISM: Homo sapiens

<400> SEQUENCE: 536

Ala Glu Met Leu Arg Ser Ile Ser Phe
1               5

<210> SEQ ID NO 537
<211> LENGTH: 10
<212> TYPE: PRT
<213> ORGANISM: Homo sapiens

<400> SEQUENCE: 537

Arg Leu Gln Glu Asp Pro Pro Val Gly Val
1               5                   10

<210> SEQ ID NO 538
<211> LENGTH: 9
<212> TYPE: PRT
<213> ORGANISM: Homo sapiens

<400> SEQUENCE: 538

Ala Glu Leu Glu Arg Ala Ala Ala Leu
1               5

<210> SEQ ID NO 539
<211> LENGTH: 8
<212> TYPE: PRT
<213> ORGANISM: Homo sapiens

<400> SEQUENCE: 539

Tyr Thr Asp Lys Ile Asp Arg Tyr
1               5

<210> SEQ ID NO 540
<211> LENGTH: 9
<212> TYPE: PRT
<213> ORGANISM: Homo sapiens

<400> SEQUENCE: 540

Phe Leu Leu Pro Asp Val Ile Arg Ile
1               5

<210> SEQ ID NO 541
<211> LENGTH: 9
<212> TYPE: PRT
<213> ORGANISM: Homo sapiens

<400> SEQUENCE: 541

Val Glu Leu Pro His Ile Asn Leu Leu
1               5
```

<210> SEQ ID NO 542
<211> LENGTH: 9
<212> TYPE: PRT
<213> ORGANISM: Homo sapiens

<400> SEQUENCE: 542

Val Met Leu Asp Val Pro Ile Arg Leu
1               5

<210> SEQ ID NO 543
<211> LENGTH: 9
<212> TYPE: PRT
<213> ORGANISM: Homo sapiens

<400> SEQUENCE: 543

Ser Leu Leu Glu Asn Leu Glu Lys Ile
1               5

<210> SEQ ID NO 544
<211> LENGTH: 9
<212> TYPE: PRT
<213> ORGANISM: Homo sapiens

<400> SEQUENCE: 544

Tyr Ala Asp Pro Val Asn Ala His Tyr
1               5

<210> SEQ ID NO 545
<211> LENGTH: 9
<212> TYPE: PRT
<213> ORGANISM: Homo sapiens

<400> SEQUENCE: 545

Ala Glu Leu Leu Arg Gly Leu Ser Leu
1               5

<210> SEQ ID NO 546
<211> LENGTH: 9
<212> TYPE: PRT
<213> ORGANISM: Homo sapiens

<400> SEQUENCE: 546

Thr Thr Glu Val His Pro Glu Leu Tyr
1               5

<210> SEQ ID NO 547
<211> LENGTH: 9
<212> TYPE: PRT
<213> ORGANISM: Homo sapiens

<400> SEQUENCE: 547

Arg Glu Thr Asn Leu Asp Ser Leu Pro
1               5

<210> SEQ ID NO 548
<211> LENGTH: 9
<212> TYPE: PRT
<213> ORGANISM: Homo sapiens

<400> SEQUENCE: 548

Glu Leu Glu Asp Ser Thr Leu Arg Tyr
1               5

<210> SEQ ID NO 549

```
<211> LENGTH: 8
<212> TYPE: PRT
<213> ORGANISM: Homo sapiens

<400> SEQUENCE: 549

Phe Leu Asp Ile Tyr Ile Phe Leu
1               5

<210> SEQ ID NO 550
<211> LENGTH: 9
<212> TYPE: PRT
<213> ORGANISM: Homo sapiens

<400> SEQUENCE: 550

Thr Tyr Thr Asp Arg Val Phe Phe Leu
1               5

<210> SEQ ID NO 551
<211> LENGTH: 10
<212> TYPE: PRT
<213> ORGANISM: Homo sapiens

<400> SEQUENCE: 551

Ser Pro His Leu Ala Asn Tyr Phe Tyr Phe
1               5                   10

<210> SEQ ID NO 552
<211> LENGTH: 9
<212> TYPE: PRT
<213> ORGANISM: Homo sapiens

<400> SEQUENCE: 552

Ser Pro Arg Leu Pro Val Gly Gly Phe
1               5

<210> SEQ ID NO 553
<211> LENGTH: 10
<212> TYPE: PRT
<213> ORGANISM: Homo sapiens

<400> SEQUENCE: 553

Lys Leu Leu Asp Lys Val Gln Ala Tyr Ser
1               5                   10

<210> SEQ ID NO 554
<211> LENGTH: 9
<212> TYPE: PRT
<213> ORGANISM: Homo sapiens

<400> SEQUENCE: 554

Ala Tyr Gln His Leu Phe Tyr Leu Leu
1               5

<210> SEQ ID NO 555
<211> LENGTH: 10
<212> TYPE: PRT
<213> ORGANISM: Homo sapiens

<400> SEQUENCE: 555

Lys Tyr Ile Leu Leu Met Asp Ile Ile Ala
1               5                   10

<210> SEQ ID NO 556
<211> LENGTH: 9
<212> TYPE: PRT
```

<213> ORGANISM: Homo sapiens

<400> SEQUENCE: 556

Arg Tyr Ser Ser Met Ala Ala Ser Phe
1               5

<210> SEQ ID NO 557
<211> LENGTH: 10
<212> TYPE: PRT
<213> ORGANISM: Homo sapiens

<400> SEQUENCE: 557

Ser Pro Arg Ala Ala Glu Pro Val Gln Leu
1               5                   10

<210> SEQ ID NO 558
<211> LENGTH: 9
<212> TYPE: PRT
<213> ORGANISM: Homo sapiens

<400> SEQUENCE: 558

Ile Tyr Thr Ser Ser Val Asn Arg Leu
1               5

<210> SEQ ID NO 559
<211> LENGTH: 9
<212> TYPE: PRT
<213> ORGANISM: Homo sapiens

<400> SEQUENCE: 559

Leu Tyr Pro Gln Phe Met Phe His Leu
1               5

<210> SEQ ID NO 560
<211> LENGTH: 9
<212> TYPE: PRT
<213> ORGANISM: Homo sapiens

<400> SEQUENCE: 560

Arg Tyr Ile Pro Thr Ala Ala Ala Phe
1               5

<210> SEQ ID NO 561
<211> LENGTH: 9
<212> TYPE: PRT
<213> ORGANISM: Homo sapiens

<400> SEQUENCE: 561

Glu Tyr Ile Val Lys Lys Ile Pro Val
1               5

<210> SEQ ID NO 562
<211> LENGTH: 9
<212> TYPE: PRT
<213> ORGANISM: Homo sapiens

<400> SEQUENCE: 562

Ser Arg Val Glu Ala Val Tyr Val Leu
1               5

<210> SEQ ID NO 563
<211> LENGTH: 9
<212> TYPE: PRT
<213> ORGANISM: Homo sapiens

```
<400> SEQUENCE: 563

Met Pro Arg Gly Val Val Thr Leu
1               5

<210> SEQ ID NO 564
<211> LENGTH: 9
<212> TYPE: PRT
<213> ORGANISM: Homo sapiens

<400> SEQUENCE: 564

Leu Pro Lys Pro Pro Gly Arg Gly Val
1               5

<210> SEQ ID NO 565
<211> LENGTH: 9
<212> TYPE: PRT
<213> ORGANISM: Homo sapiens

<400> SEQUENCE: 565

Arg Leu Trp Gly Glu Pro Val Asn Leu
1               5

<210> SEQ ID NO 566
<211> LENGTH: 9
<212> TYPE: PRT
<213> ORGANISM: Homo sapiens

<400> SEQUENCE: 566

Arg Leu Leu Asp Val Leu Ala Pro Leu
1               5

<210> SEQ ID NO 567
<211> LENGTH: 9
<212> TYPE: PRT
<213> ORGANISM: Homo sapiens

<400> SEQUENCE: 567

Leu Tyr Ile Leu Ser Ser His Asp Ile
1               5

<210> SEQ ID NO 568
<211> LENGTH: 9
<212> TYPE: PRT
<213> ORGANISM: Homo sapiens

<400> SEQUENCE: 568

Thr Pro Met Gly Pro Gly Arg Thr Val
1               5

<210> SEQ ID NO 569
<211> LENGTH: 14
<212> TYPE: PRT
<213> ORGANISM: Homo sapiens

<400> SEQUENCE: 569

Gly Pro Pro Gly Thr Gly Lys Thr Asp Val Ala Val Gln Ile
1               5                   10

<210> SEQ ID NO 570
<211> LENGTH: 10
<212> TYPE: PRT
<213> ORGANISM: Homo sapiens

<400> SEQUENCE: 570
```

Asn Glu Ile Glu Asp Thr Phe Arg Gln Phe
1               5                   10

<210> SEQ ID NO 571
<211> LENGTH: 10
<212> TYPE: PRT
<213> ORGANISM: Homo sapiens

<400> SEQUENCE: 571

Glu Glu Ile Asp Leu Arg Ser Val Gly Trp
1               5                   10

<210> SEQ ID NO 572
<211> LENGTH: 9
<212> TYPE: PRT
<213> ORGANISM: Homo sapiens

<400> SEQUENCE: 572

Lys Tyr Gln Lys Gly Phe Ser Leu Trp
1               5

<210> SEQ ID NO 573
<211> LENGTH: 9
<212> TYPE: PRT
<213> ORGANISM: Homo sapiens

<400> SEQUENCE: 573

Val Tyr Pro Asp Gly Ile Arg His Ile
1               5

<210> SEQ ID NO 574
<211> LENGTH: 9
<212> TYPE: PRT
<213> ORGANISM: Homo sapiens

<400> SEQUENCE: 574

Lys Phe Ile Asp Thr Thr Ser Lys Phe
1               5

<210> SEQ ID NO 575
<211> LENGTH: 9
<212> TYPE: PRT
<213> ORGANISM: Homo sapiens

<400> SEQUENCE: 575

Phe Leu Asp Ile Leu Asn Thr Leu Ile
1               5

<210> SEQ ID NO 576
<211> LENGTH: 11
<212> TYPE: PRT
<213> ORGANISM: Homo sapiens

<400> SEQUENCE: 576

Lys Tyr Ile Thr Gln Gly Gln Leu Leu Gln Phe
1               5                   10

<210> SEQ ID NO 577
<211> LENGTH: 10
<212> TYPE: PRT
<213> ORGANISM: Homo sapiens

<400> SEQUENCE: 577

Lys Tyr Leu Ser Val Gln Gly Gln Leu Phe
1               5                   10

<210> SEQ ID NO 578
<211> LENGTH: 9
<212> TYPE: PRT
<213> ORGANISM: Homo sapiens

<400> SEQUENCE: 578

Arg Tyr Phe Asp Glu Pro Val Glu Leu
1               5

<210> SEQ ID NO 579
<211> LENGTH: 9
<212> TYPE: PRT
<213> ORGANISM: Homo sapiens

<400> SEQUENCE: 579

Lys Tyr Asp Glu Ile Phe Tyr Asn Leu
1               5

<210> SEQ ID NO 580
<211> LENGTH: 9
<212> TYPE: PRT
<213> ORGANISM: Homo sapiens

<400> SEQUENCE: 580

Ser Tyr Ile Glu His Ile Phe Glu Ile
1               5

<210> SEQ ID NO 581
<211> LENGTH: 10
<212> TYPE: PRT
<213> ORGANISM: Homo sapiens

<400> SEQUENCE: 581

Lys Phe Ile Asp Pro Ile Tyr Gln Val Trp
1               5                   10

<210> SEQ ID NO 582
<211> LENGTH: 11
<212> TYPE: PRT
<213> ORGANISM: Homo sapiens

<400> SEQUENCE: 582

Leu Gly Tyr Thr Glu Gly Ala Leu Leu Ala Leu
1               5                   10

<210> SEQ ID NO 583
<211> LENGTH: 9
<212> TYPE: PRT
<213> ORGANISM: Homo sapiens

<400> SEQUENCE: 583

Lys Tyr Pro Ser Pro Phe Phe Val Phe
1               5

<210> SEQ ID NO 584
<211> LENGTH: 10
<212> TYPE: PRT
<213> ORGANISM: Homo sapiens

<400> SEQUENCE: 584

Glu Tyr Pro Asp Arg Ile Met Asn Thr Phe
1               5                   10

```
<210> SEQ ID NO 585
<211> LENGTH: 9
<212> TYPE: PRT
<213> ORGANISM: Homo sapiens

<400> SEQUENCE: 585

Val Tyr Ile Ser Glu His Glu His Phe
1               5

<210> SEQ ID NO 586
<211> LENGTH: 9
<212> TYPE: PRT
<213> ORGANISM: Homo sapiens

<400> SEQUENCE: 586

Lys Tyr Phe Leu Lys Pro Glu Val Leu
1               5

<210> SEQ ID NO 587
<211> LENGTH: 9
<212> TYPE: PRT
<213> ORGANISM: Human immunodeficiency virus 1

<400> SEQUENCE: 587

Ile Leu Lys Glu Pro Val His Gly Val
1               5

<210> SEQ ID NO 588
<211> LENGTH: 9
<212> TYPE: PRT
<213> ORGANISM: Influenza A virus

<400> SEQUENCE: 588

Gly Ile Leu Gly Phe Val Phe Thr Leu
1               5

<210> SEQ ID NO 589
<211> LENGTH: 9
<212> TYPE: PRT
<213> ORGANISM: Human herpesvirus 5

<400> SEQUENCE: 589

Asn Leu Val Pro Met Val Ala Thr Val
1               5

<210> SEQ ID NO 590
<211> LENGTH: 10
<212> TYPE: PRT
<213> ORGANISM: Human herpesvirus 4

<400> SEQUENCE: 590

Leu Leu Asp Phe Val Arg Phe Met Gly Val
1               5                   10

<210> SEQ ID NO 591
<211> LENGTH: 9
<212> TYPE: PRT
<213> ORGANISM: Human herpesvirus 4

<400> SEQUENCE: 591

Gly Leu Cys Thr Leu Val Ala Met Leu
1               5

<210> SEQ ID NO 592
<211> LENGTH: 9
```

<212> TYPE: PRT
<213> ORGANISM: Human herpesvirus 4

<400> SEQUENCE: 592

Cys Leu Gly Gly Leu Leu Thr Met Val
1               5

<210> SEQ ID NO 593
<211> LENGTH: 9
<212> TYPE: PRT
<213> ORGANISM: Homo sapiens

<400> SEQUENCE: 593

Ala Pro Arg Thr Val Ala Leu Thr Ala
1               5

<210> SEQ ID NO 594
<211> LENGTH: 9
<212> TYPE: PRT
<213> ORGANISM: Homo sapiens

<400> SEQUENCE: 594

Ala Ala Phe Pro Gly Ala Ser Leu Tyr
1               5

<210> SEQ ID NO 595
<211> LENGTH: 9
<212> TYPE: PRT
<213> ORGANISM: Homo sapiens

<400> SEQUENCE: 595

Ala Glu Leu Ala Thr Arg Ala Leu Pro
1               5

<210> SEQ ID NO 596
<211> LENGTH: 9
<212> TYPE: PRT
<213> ORGANISM: Homo sapiens

<400> SEQUENCE: 596

Ala Phe Phe Ala Glu Arg Leu Tyr Tyr
1               5

<210> SEQ ID NO 597
<211> LENGTH: 9
<212> TYPE: PRT
<213> ORGANISM: Homo sapiens

<400> SEQUENCE: 597

Ala Leu Ala Thr Leu Ile His Gln Val
1               5

<210> SEQ ID NO 598
<211> LENGTH: 9
<212> TYPE: PRT
<213> ORGANISM: Homo sapiens

<400> SEQUENCE: 598

Ala Leu Ala Val Ile Ile Thr Ser Tyr
1               5

<210> SEQ ID NO 599
<211> LENGTH: 9
<212> TYPE: PRT
<213> ORGANISM: Homo sapiens

<400> SEQUENCE: 599

Ala Leu Gln Glu Met Val His Gln Val
1               5

<210> SEQ ID NO 600
<211> LENGTH: 9
<212> TYPE: PRT
<213> ORGANISM: Homo sapiens

<400> SEQUENCE: 600

Ala Leu Arg Asp Val Arg Gln Gln Tyr
1               5

<210> SEQ ID NO 601
<211> LENGTH: 9
<212> TYPE: PRT
<213> ORGANISM: Homo sapiens

<400> SEQUENCE: 601

Ala Gln Asn Ala Val Arg Leu His Tyr
1               5

<210> SEQ ID NO 602
<211> LENGTH: 9
<212> TYPE: PRT
<213> ORGANISM: Homo sapiens

<400> SEQUENCE: 602

Ala Gln Pro Gly Phe Phe Asp Arg Phe
1               5

<210> SEQ ID NO 603
<211> LENGTH: 9
<212> TYPE: PRT
<213> ORGANISM: Homo sapiens

<400> SEQUENCE: 603

Ala Val Cys Glu Val Ala Leu Asp Tyr
1               5

<210> SEQ ID NO 604
<211> LENGTH: 9
<212> TYPE: PRT
<213> ORGANISM: Homo sapiens

<400> SEQUENCE: 604

Ala Val Leu Gly Ala Val Val Ala Val
1               5

<210> SEQ ID NO 605
<211> LENGTH: 9
<212> TYPE: PRT
<213> ORGANISM: Homo sapiens

<400> SEQUENCE: 605

Asp Ala Ile Leu Glu Glu Leu Ser Ala
1               5

<210> SEQ ID NO 606
<211> LENGTH: 10
<212> TYPE: PRT
<213> ORGANISM: Homo sapiens

<400> SEQUENCE: 606

Glu Glu His Pro Thr Leu Leu Thr Glu Ala
1               5                   10

<210> SEQ ID NO 607
<211> LENGTH: 9
<212> TYPE: PRT
<213> ORGANISM: Homo sapiens

<400> SEQUENCE: 607

Glu Glu Met Pro Gln Val His Thr Pro
1               5

<210> SEQ ID NO 608
<211> LENGTH: 8
<212> TYPE: PRT
<213> ORGANISM: Homo sapiens

<400> SEQUENCE: 608

Glu Glu Asn Phe Ala Val Glu Ala
1               5

<210> SEQ ID NO 609
<211> LENGTH: 9
<212> TYPE: PRT
<213> ORGANISM: Homo sapiens

<400> SEQUENCE: 609

Glu Glu Asn Lys Leu Ile Tyr Thr Pro
1               5

<210> SEQ ID NO 610
<211> LENGTH: 9
<212> TYPE: PRT
<213> ORGANISM: Homo sapiens

<400> SEQUENCE: 610

Phe Ala Glu Gly Phe Val Arg Ala Leu
1               5

<210> SEQ ID NO 611
<211> LENGTH: 9
<212> TYPE: PRT
<213> ORGANISM: Homo sapiens

<400> SEQUENCE: 611

Phe Phe Gly Glu Thr Ser His Asn Tyr
1               5

<210> SEQ ID NO 612
<211> LENGTH: 9
<212> TYPE: PRT
<213> ORGANISM: Homo sapiens

<400> SEQUENCE: 612

Phe Leu Pro His Met Ala Tyr Thr Tyr
1               5

<210> SEQ ID NO 613
<211> LENGTH: 10
<212> TYPE: PRT
<213> ORGANISM: Homo sapiens

<400> SEQUENCE: 613

Gly Glu Pro Arg Phe Ile Ser Val Gly Tyr

```
                1               5                    10
```

<210> SEQ ID NO 614
<211> LENGTH: 9
<212> TYPE: PRT
<213> ORGANISM: Homo sapiens

<400> SEQUENCE: 614

```
Gly Leu Ala Thr Asp Val Gln Thr Val
1               5
```

<210> SEQ ID NO 615
<211> LENGTH: 9
<212> TYPE: PRT
<213> ORGANISM: Homo sapiens

<400> SEQUENCE: 615

```
Gly Leu Asn Asp Glu Thr Tyr Gly Tyr
1               5
```

<210> SEQ ID NO 616
<211> LENGTH: 9
<212> TYPE: PRT
<213> ORGANISM: Homo sapiens

<400> SEQUENCE: 616

```
Gly Gln Glu Phe Ile Arg Val Gly Tyr
1               5
```

<210> SEQ ID NO 617
<211> LENGTH: 9
<212> TYPE: PRT
<213> ORGANISM: Homo sapiens

<400> SEQUENCE: 617

```
Gly Gln Phe Pro Gly His Asn Glu Phe
1               5
```

<210> SEQ ID NO 618
<211> LENGTH: 9
<212> TYPE: PRT
<213> ORGANISM: Homo sapiens

<400> SEQUENCE: 618

```
Gly Gln Pro Trp Val Ser Val Thr Val
1               5
```

<210> SEQ ID NO 619
<211> LENGTH: 9
<212> TYPE: PRT
<213> ORGANISM: Homo sapiens

<400> SEQUENCE: 619

```
Gly Tyr Leu His Asp Phe Leu Lys Tyr
1               5
```

<210> SEQ ID NO 620
<211> LENGTH: 9
<212> TYPE: PRT
<213> ORGANISM: Homo sapiens

<400> SEQUENCE: 620

```
His Gln Ile Thr Val Leu His Val Tyr
1               5
```

<210> SEQ ID NO 621
<211> LENGTH: 9
<212> TYPE: PRT
<213> ORGANISM: Homo sapiens

<400> SEQUENCE: 621

His Val Ile Asp Val Lys Phe Leu Tyr
1               5

<210> SEQ ID NO 622
<211> LENGTH: 9
<212> TYPE: PRT
<213> ORGANISM: Homo sapiens

<400> SEQUENCE: 622

His Val Asn Asp Leu Phe Leu Gln Tyr
1               5

<210> SEQ ID NO 623
<211> LENGTH: 9
<212> TYPE: PRT
<213> ORGANISM: Homo sapiens

<400> SEQUENCE: 623

Ile Ala Met Ala Thr Val Thr Ala Leu
1               5

<210> SEQ ID NO 624
<211> LENGTH: 9
<212> TYPE: PRT
<213> ORGANISM: Homo sapiens

<400> SEQUENCE: 624

Ile Gly Ile Asp Leu Gly Thr Thr Tyr
1               5

<210> SEQ ID NO 625
<211> LENGTH: 9
<212> TYPE: PRT
<213> ORGANISM: Homo sapiens

<400> SEQUENCE: 625

Ile Leu His Asp Asp Glu Val Thr Val
1               5

<210> SEQ ID NO 626
<211> LENGTH: 9
<212> TYPE: PRT
<213> ORGANISM: Homo sapiens

<400> SEQUENCE: 626

Ile Gln Lys Glu Ser Thr Leu His Leu
1               5

<210> SEQ ID NO 627
<211> LENGTH: 8
<212> TYPE: PRT
<213> ORGANISM: Homo sapiens

<400> SEQUENCE: 627

Ile Ser Arg Glu Leu Tyr Glu Tyr
1               5

<210> SEQ ID NO 628

```
<211> LENGTH: 9
<212> TYPE: PRT
<213> ORGANISM: Homo sapiens

<400> SEQUENCE: 628

Lys Leu His Gly Val Asn Ile Asn Val
1               5

<210> SEQ ID NO 629
<211> LENGTH: 9
<212> TYPE: PRT
<213> ORGANISM: Homo sapiens

<400> SEQUENCE: 629

Lys Gln Met Glu Gln Val Ala Gln Phe
1               5

<210> SEQ ID NO 630
<211> LENGTH: 9
<212> TYPE: PRT
<213> ORGANISM: Homo sapiens

<400> SEQUENCE: 630

Lys Val Ala Asp Met Ala Leu His Tyr
1               5

<210> SEQ ID NO 631
<211> LENGTH: 9
<212> TYPE: PRT
<213> ORGANISM: Homo sapiens

<400> SEQUENCE: 631

Leu Glu Glu Asp Ser Ala Arg Glu Ile
1               5

<210> SEQ ID NO 632
<211> LENGTH: 9
<212> TYPE: PRT
<213> ORGANISM: Homo sapiens

<400> SEQUENCE: 632

Leu Leu Ala Glu Arg Asp Leu Tyr Leu
1               5

<210> SEQ ID NO 633
<211> LENGTH: 9
<212> TYPE: PRT
<213> ORGANISM: Homo sapiens

<400> SEQUENCE: 633

Leu Leu Asp Glu Glu Ile Ser Arg Val
1               5

<210> SEQ ID NO 634
<211> LENGTH: 9
<212> TYPE: PRT
<213> ORGANISM: Homo sapiens

<400> SEQUENCE: 634

Leu Leu Tyr Pro Thr Glu Ile Thr Val
1               5

<210> SEQ ID NO 635
<211> LENGTH: 9
<212> TYPE: PRT
```

```
<213> ORGANISM: Homo sapiens

<400> SEQUENCE: 635

Leu Met Asp His Thr Ile Pro Glu Val
1               5

<210> SEQ ID NO 636
<211> LENGTH: 9
<212> TYPE: PRT
<213> ORGANISM: Homo sapiens

<400> SEQUENCE: 636

Leu Gln His Pro Asp Val Ala Ala Tyr
1               5

<210> SEQ ID NO 637
<211> LENGTH: 9
<212> TYPE: PRT
<213> ORGANISM: Homo sapiens

<400> SEQUENCE: 637

Met Glu Asp Ile Lys Ile Leu Ile Ala
1               5

<210> SEQ ID NO 638
<211> LENGTH: 9
<212> TYPE: PRT
<213> ORGANISM: Homo sapiens

<400> SEQUENCE: 638

Met Glu Glu Asn Phe Ala Val Glu Ala
1               5

<210> SEQ ID NO 639
<211> LENGTH: 8
<212> TYPE: PRT
<213> ORGANISM: Homo sapiens

<400> SEQUENCE: 639

Met Gln Lys Glu Ile Thr Ala Leu
1               5

<210> SEQ ID NO 640
<211> LENGTH: 9
<212> TYPE: PRT
<213> ORGANISM: Homo sapiens

<400> SEQUENCE: 640

Asn Glu Asp Leu Arg Ser Trp Thr Ala
1               5

<210> SEQ ID NO 641
<211> LENGTH: 9
<212> TYPE: PRT
<213> ORGANISM: Homo sapiens

<400> SEQUENCE: 641

Asn Glu Ile Lys Asp Ser Val Val Ala
1               5

<210> SEQ ID NO 642
<211> LENGTH: 9
<212> TYPE: PRT
<213> ORGANISM: Homo sapiens
```

```
<400> SEQUENCE: 642

Asn Val Thr Gln Val Arg Ala Phe Tyr
1               5

<210> SEQ ID NO 643
<211> LENGTH: 9
<212> TYPE: PRT
<213> ORGANISM: Homo sapiens

<400> SEQUENCE: 643

Gln Glu Gln Ser Phe Val Ile Arg Ala
1               5

<210> SEQ ID NO 644
<211> LENGTH: 9
<212> TYPE: PRT
<213> ORGANISM: Homo sapiens

<400> SEQUENCE: 644

Gln Gln Lys Leu Ser Arg Leu Gln Tyr
1               5

<210> SEQ ID NO 645
<211> LENGTH: 9
<212> TYPE: PRT
<213> ORGANISM: Homo sapiens

<400> SEQUENCE: 645

Gln Val Ala Glu Ile Val Ser Lys Tyr
1               5

<210> SEQ ID NO 646
<211> LENGTH: 9
<212> TYPE: PRT
<213> ORGANISM: Homo sapiens

<400> SEQUENCE: 646

Arg Glu His Ala Pro Phe Leu Val Ala
1               5

<210> SEQ ID NO 647
<211> LENGTH: 11
<212> TYPE: PRT
<213> ORGANISM: Homo sapiens

<400> SEQUENCE: 647

Arg Leu Ala Ala Ala Ala Ala Gln Ser Val Tyr
1               5                   10

<210> SEQ ID NO 648
<211> LENGTH: 9
<212> TYPE: PRT
<213> ORGANISM: Homo sapiens

<400> SEQUENCE: 648

Arg Leu Ala Ser Tyr Leu Asp Lys Val
1               5

<210> SEQ ID NO 649
<211> LENGTH: 9
<212> TYPE: PRT
<213> ORGANISM: Homo sapiens

<400> SEQUENCE: 649
```

Arg Asn Ala Asp Val Phe Leu Lys Tyr
1               5

<210> SEQ ID NO 650
<211> LENGTH: 9
<212> TYPE: PRT
<213> ORGANISM: Homo sapiens

<400> SEQUENCE: 650

Arg Gln Gly Phe Val Pro Ala Ala Tyr
1               5

<210> SEQ ID NO 651
<211> LENGTH: 10
<212> TYPE: PRT
<213> ORGANISM: Homo sapiens

<400> SEQUENCE: 651

Arg Val Ile Glu Glu Ala Lys Thr Ala Phe
1               5                   10

<210> SEQ ID NO 652
<211> LENGTH: 9
<212> TYPE: PRT
<213> ORGANISM: Homo sapiens

<400> SEQUENCE: 652

Arg Val Gln Pro Lys Val Thr Val Tyr
1               5

<210> SEQ ID NO 653
<211> LENGTH: 9
<212> TYPE: PRT
<213> ORGANISM: Homo sapiens

<400> SEQUENCE: 653

Arg Val Tyr Pro Glu Val Thr Val Tyr
1               5

<210> SEQ ID NO 654
<211> LENGTH: 7
<212> TYPE: PRT
<213> ORGANISM: Homo sapiens

<400> SEQUENCE: 654

Ser Asp His His Ile Tyr Leu
1               5

<210> SEQ ID NO 655
<211> LENGTH: 9
<212> TYPE: PRT
<213> ORGANISM: Homo sapiens

<400> SEQUENCE: 655

Ser His Ala Ile Leu Glu Ala Leu Ala
1               5

<210> SEQ ID NO 656
<211> LENGTH: 9
<212> TYPE: PRT
<213> ORGANISM: Homo sapiens

<400> SEQUENCE: 656

Ser Ile Ser Gly Val Thr Ala Ala Tyr
1               5

```
<210> SEQ ID NO 657
<211> LENGTH: 8
<212> TYPE: PRT
<213> ORGANISM: Homo sapiens

<400> SEQUENCE: 657

Ser Pro Val Tyr Val Gly Arg Val
1               5

<210> SEQ ID NO 658
<211> LENGTH: 9
<212> TYPE: PRT
<213> ORGANISM: Homo sapiens

<400> SEQUENCE: 658

Ser Gln Phe Gly Thr Val Thr Arg Phe
1               5

<210> SEQ ID NO 659
<211> LENGTH: 9
<212> TYPE: PRT
<213> ORGANISM: Homo sapiens

<400> SEQUENCE: 659

Ser Trp Asn Asn His Ser Tyr Leu Tyr
1               5

<210> SEQ ID NO 660
<211> LENGTH: 9
<212> TYPE: PRT
<213> ORGANISM: Homo sapiens

<400> SEQUENCE: 660

Thr Phe Met Asp His Val Leu Arg Tyr
1               5

<210> SEQ ID NO 661
<211> LENGTH: 9
<212> TYPE: PRT
<213> ORGANISM: Homo sapiens

<400> SEQUENCE: 661

Thr Leu Ala Asp Leu Val His His Val
1               5

<210> SEQ ID NO 662
<211> LENGTH: 10
<212> TYPE: PRT
<213> ORGANISM: Homo sapiens

<400> SEQUENCE: 662

Thr Leu Gly Ala Leu Thr Val Ile Asp Val
1               5                   10

<210> SEQ ID NO 663
<211> LENGTH: 9
<212> TYPE: PRT
<213> ORGANISM: Homo sapiens

<400> SEQUENCE: 663

Thr Gln Met Pro Asp Pro Lys Thr Phe
1               5
```

<210> SEQ ID NO 664
<211> LENGTH: 9
<212> TYPE: PRT
<213> ORGANISM: Homo sapiens

<400> SEQUENCE: 664

Val Glu His Pro Ser Leu Thr Ser Pro
1               5

<210> SEQ ID NO 665
<211> LENGTH: 9
<212> TYPE: PRT
<213> ORGANISM: Homo sapiens

<400> SEQUENCE: 665

Val Glu Pro Asp His Phe Lys Val Ala
1               5

<210> SEQ ID NO 666
<211> LENGTH: 8
<212> TYPE: PRT
<213> ORGANISM: Homo sapiens

<400> SEQUENCE: 666

Val Glu Arg Glu Val Glu Gln Val
1               5

<210> SEQ ID NO 667
<211> LENGTH: 13
<212> TYPE: PRT
<213> ORGANISM: Homo sapiens

<400> SEQUENCE: 667

Val Phe Ile Gly Thr Gly Ala Thr Gly Ala Thr Leu Tyr
1               5                   10

<210> SEQ ID NO 668
<211> LENGTH: 9
<212> TYPE: PRT
<213> ORGANISM: Homo sapiens

<400> SEQUENCE: 668

Val Leu Arg Glu Ile Ala Glu Glu Tyr
1               5

<210> SEQ ID NO 669
<211> LENGTH: 10
<212> TYPE: PRT
<213> ORGANISM: Homo sapiens

<400> SEQUENCE: 669

Val Leu Ser Leu Leu Ser Ser Val Ala Leu
1               5                   10

<210> SEQ ID NO 670
<211> LENGTH: 9
<212> TYPE: PRT
<213> ORGANISM: Homo sapiens

<400> SEQUENCE: 670

Val Leu Tyr Asp Arg Val Leu Lys Tyr
1               5

<210> SEQ ID NO 671
<211> LENGTH: 9

```
<212> TYPE: PRT
<213> ORGANISM: Homo sapiens

<400> SEQUENCE: 671

Val Met Asp Ser Lys Ile Val Gln Val
1               5

<210> SEQ ID NO 672
<211> LENGTH: 8
<212> TYPE: PRT
<213> ORGANISM: Homo sapiens

<400> SEQUENCE: 672

Val Gln Arg Thr Leu Met Ala Leu
1               5

<210> SEQ ID NO 673
<211> LENGTH: 10
<212> TYPE: PRT
<213> ORGANISM: Homo sapiens

<400> SEQUENCE: 673

Tyr Phe Glu Tyr Ile Glu Glu Asn Lys Tyr
1               5                   10

<210> SEQ ID NO 674
<211> LENGTH: 9
<212> TYPE: PRT
<213> ORGANISM: Homo sapiens

<400> SEQUENCE: 674

Tyr Ile Phe Lys Glu Arg Glu Ser Phe
1               5

<210> SEQ ID NO 675
<211> LENGTH: 9
<212> TYPE: PRT
<213> ORGANISM: Homo sapiens

<400> SEQUENCE: 675

Tyr Val Tyr Glu Tyr Pro Ser Arg Tyr
1               5

<210> SEQ ID NO 676
<211> LENGTH: 10
<212> TYPE: PRT
<213> ORGANISM: Homo sapiens

<400> SEQUENCE: 676

Tyr Tyr Arg Tyr Pro Thr Gly Glu Ser Tyr
1               5                   10

<210> SEQ ID NO 677
<211> LENGTH: 9
<212> TYPE: PRT
<213> ORGANISM: Homo sapiens

<400> SEQUENCE: 677

Tyr Tyr Ser Asn Lys Ala Tyr Gln Tyr
1               5

<210> SEQ ID NO 678
<211> LENGTH: 9
<212> TYPE: PRT
<213> ORGANISM: Homo sapiens
```

<400> SEQUENCE: 678

Ser Ser Leu Pro Thr Gln Leu Phe Lys
1               5

<210> SEQ ID NO 679
<211> LENGTH: 9
<212> TYPE: PRT
<213> ORGANISM: Homo sapiens

<400> SEQUENCE: 679

Ala Thr Phe Pro Asp Thr Leu Thr Tyr
1               5

<210> SEQ ID NO 680
<211> LENGTH: 10
<212> TYPE: PRT
<213> ORGANISM: Homo sapiens

<400> SEQUENCE: 680

Ser Ile Phe Asp Gly Arg Val Val Ala Lys
1               5                   10

<210> SEQ ID NO 681
<211> LENGTH: 9
<212> TYPE: PRT
<213> ORGANISM: Homo sapiens

<400> SEQUENCE: 681

Phe Arg Phe Glu Asn Val Asn Gly Tyr
1               5

<210> SEQ ID NO 682
<211> LENGTH: 10
<212> TYPE: PRT
<213> ORGANISM: Homo sapiens

<400> SEQUENCE: 682

Gln Arg Tyr Gly Phe Ser Ala Val Gly Phe
1               5                   10

<210> SEQ ID NO 683
<211> LENGTH: 10
<212> TYPE: PRT
<213> ORGANISM: Homo sapiens

<400> SEQUENCE: 683

Ala Arg Leu Ser Leu Thr Tyr Glu Arg Leu
1               5                   10

<210> SEQ ID NO 684
<211> LENGTH: 9
<212> TYPE: PRT
<213> ORGANISM: Homo sapiens

<400> SEQUENCE: 684

Gly Arg Tyr Gln Val Ser Trp Ser Leu
1               5

<210> SEQ ID NO 685
<211> LENGTH: 9
<212> TYPE: PRT
<213> ORGANISM: Homo sapiens

<400> SEQUENCE: 685

Lys Arg Phe Asp Asp Lys Tyr Thr Leu
1               5

<210> SEQ ID NO 686
<211> LENGTH: 9
<212> TYPE: PRT
<213> ORGANISM: Homo sapiens

<400> SEQUENCE: 686

Thr Arg Trp Asn Lys Ile Val Leu Lys
1               5

<210> SEQ ID NO 687
<211> LENGTH: 9
<212> TYPE: PRT
<213> ORGANISM: Homo sapiens

<400> SEQUENCE: 687

Leu Arg Phe Asp Gly Ala Leu Asn Val
1               5

<210> SEQ ID NO 688
<211> LENGTH: 9
<212> TYPE: PRT
<213> ORGANISM: Homo sapiens

<400> SEQUENCE: 688

Ala Arg Phe Ser Gly Asn Leu Leu Val
1               5

<210> SEQ ID NO 689
<211> LENGTH: 9
<212> TYPE: PRT
<213> ORGANISM: Homo sapiens

<400> SEQUENCE: 689

Asn Arg Ile Lys Phe Val Ile Lys Arg
1               5

<210> SEQ ID NO 690
<211> LENGTH: 9
<212> TYPE: PRT
<213> ORGANISM: Homo sapiens

<400> SEQUENCE: 690

Gly Arg Val Phe Ile Ile Lys Ser Tyr
1               5

<210> SEQ ID NO 691
<211> LENGTH: 9
<212> TYPE: PRT
<213> ORGANISM: Homo sapiens

<400> SEQUENCE: 691

Ser Arg Phe Gly Asn Ala Phe His Leu
1               5

<210> SEQ ID NO 692
<211> LENGTH: 9
<212> TYPE: PRT
<213> ORGANISM: Homo sapiens

<400> SEQUENCE: 692

Gly Arg Thr Gly Gly Ser Trp Phe Lys

-continued

```
<210> SEQ ID NO 693
<211> LENGTH: 14
<212> TYPE: PRT
<213> ORGANISM: Homo sapiens

<400> SEQUENCE: 693

Ser Gly Thr Gln Phe Val Cys Glu Thr Val Ile Arg Ser Leu
1               5                   10

<210> SEQ ID NO 694
<211> LENGTH: 15
<212> TYPE: PRT
<213> ORGANISM: Homo sapiens

<400> SEQUENCE: 694

Ser Gly Thr Gln Phe Val Cys Glu Thr Val Ile Arg Ser Leu Thr
1               5                   10                  15

<210> SEQ ID NO 695
<211> LENGTH: 15
<212> TYPE: PRT
<213> ORGANISM: Homo sapiens

<400> SEQUENCE: 695

Leu Lys Pro Ala Phe Lys Lys Asp Gly Ser Thr Thr Ala Gly Asn
1               5                   10                  15

<210> SEQ ID NO 696
<211> LENGTH: 17
<212> TYPE: PRT
<213> ORGANISM: Homo sapiens

<400> SEQUENCE: 696

Arg Asp Leu Thr Asp Tyr Leu Met Lys Ile Leu Thr Glu Arg Gly Tyr
1               5                   10                  15

Ser

<210> SEQ ID NO 697
<211> LENGTH: 14
<212> TYPE: PRT
<213> ORGANISM: Homo sapiens

<400> SEQUENCE: 697

Thr Asp Tyr Leu Met Lys Ile Leu Thr Glu Arg Gly Tyr Ser
1               5                   10

<210> SEQ ID NO 698
<211> LENGTH: 16
<212> TYPE: PRT
<213> ORGANISM: Homo sapiens

<400> SEQUENCE: 698

Thr Asp Tyr Leu Met Lys Ile Leu Thr Glu Arg Gly Tyr Ser Phe Thr
1               5                   10                  15

<210> SEQ ID NO 699
<211> LENGTH: 20
<212> TYPE: PRT
<213> ORGANISM: Homo sapiens

<400> SEQUENCE: 699

Trp Ile Ser Lys Gln Glu Tyr Asp Glu Ser Gly Pro Ser Ile Val His
1               5                   10                  15
```

```
1               5                  10                 15

Arg Lys Cys Phe
            20

<210> SEQ ID NO 700
<211> LENGTH: 17
<212> TYPE: PRT
<213> ORGANISM: Homo sapiens

<400> SEQUENCE: 700

Tyr Pro Glu Glu Ala Tyr Ile Ala Asp Leu Asp Ala Lys Ser Gly Ala
1               5                  10                 15

Ser

<210> SEQ ID NO 701
<211> LENGTH: 17
<212> TYPE: PRT
<213> ORGANISM: Homo sapiens

<400> SEQUENCE: 701

Glu Gly Arg Ser Phe Leu Ala Phe Pro Thr Leu Arg Ala Tyr His Thr
1               5                  10                 15

Leu

<210> SEQ ID NO 702
<211> LENGTH: 15
<212> TYPE: PRT
<213> ORGANISM: Homo sapiens

<400> SEQUENCE: 702

Gly Arg Ser Phe Leu Ala Phe Pro Thr Leu Arg Ala Tyr His Thr
1               5                  10                 15

<210> SEQ ID NO 703
<211> LENGTH: 16
<212> TYPE: PRT
<213> ORGANISM: Homo sapiens

<400> SEQUENCE: 703

Gly Arg Ser Phe Leu Ala Phe Pro Thr Leu Arg Ala Tyr His Thr Leu
1               5                  10                 15

<210> SEQ ID NO 704
<211> LENGTH: 16
<212> TYPE: PRT
<213> ORGANISM: Bos taurus

<400> SEQUENCE: 704

Ile Ser Arg Ala Gln Phe Val Pro Leu Pro Val Ser Val Ser Val Glu
1               5                  10                 15

<210> SEQ ID NO 705
<211> LENGTH: 18
<212> TYPE: PRT
<213> ORGANISM: Bos taurus

<400> SEQUENCE: 705

Ser Pro Asp Leu Pro Lys Leu Lys Pro Asp Pro Asn Thr Leu Cys Asp
1               5                  10                 15

Glu Phe

<210> SEQ ID NO 706
```

```
<211> LENGTH: 17
<212> TYPE: PRT
<213> ORGANISM: Homo sapiens

<400> SEQUENCE: 706

Ala Pro Gly Lys Gly Ile Leu Ala Ala Asp Glu Ser Thr Gly Ser Ile
1               5                   10                  15

Ala

<210> SEQ ID NO 707
<211> LENGTH: 18
<212> TYPE: PRT
<213> ORGANISM: Homo sapiens

<400> SEQUENCE: 707

Asp Val Pro Lys Trp Ile Ser Ile Met Thr Glu Arg Ser Val Pro His
1               5                   10                  15

Leu Gln

<210> SEQ ID NO 708
<211> LENGTH: 15
<212> TYPE: PRT
<213> ORGANISM: Homo sapiens

<400> SEQUENCE: 708

Val Pro Lys Trp Ile Ser Ile Met Thr Glu Arg Ser Val Pro His
1               5                   10                  15

<210> SEQ ID NO 709
<211> LENGTH: 14
<212> TYPE: PRT
<213> ORGANISM: Homo sapiens

<400> SEQUENCE: 709

Ser Ala Ser Tyr Lys Ala Asp Thr Val Ala Lys Val Gln Gly
1               5                   10

<210> SEQ ID NO 710
<211> LENGTH: 15
<212> TYPE: PRT
<213> ORGANISM: Homo sapiens

<400> SEQUENCE: 710

Ile Val Val Tyr Thr Gly Asp Arg Thr Val Met Gly Arg Ile Ala
1               5                   10                  15

<210> SEQ ID NO 711
<211> LENGTH: 16
<212> TYPE: PRT
<213> ORGANISM: Homo sapiens

<400> SEQUENCE: 711

Ile Val Val Tyr Thr Gly Asp Arg Thr Val Met Gly Arg Ile Ala Thr
1               5                   10                  15

<210> SEQ ID NO 712
<211> LENGTH: 17
<212> TYPE: PRT
<213> ORGANISM: Homo sapiens

<400> SEQUENCE: 712

Phe Tyr Leu Leu Tyr Tyr Thr Glu Phe Thr Pro Thr Glu Lys Asp Glu
1               5                   10                  15
```

Tyr

<210> SEQ ID NO 713
<211> LENGTH: 18
<212> TYPE: PRT
<213> ORGANISM: Homo sapiens

<400> SEQUENCE: 713

Phe Tyr Leu Leu Tyr Tyr Thr Glu Phe Thr Pro Thr Glu Lys Asp Glu
1               5                   10                  15

Tyr Ala

<210> SEQ ID NO 714
<211> LENGTH: 12
<212> TYPE: PRT
<213> ORGANISM: Homo sapiens

<400> SEQUENCE: 714

Leu Leu Tyr Tyr Thr Glu Phe Thr Pro Thr Glu Lys
1               5                   10

<210> SEQ ID NO 715
<211> LENGTH: 13
<212> TYPE: PRT
<213> ORGANISM: Homo sapiens

<400> SEQUENCE: 715

Leu Leu Tyr Tyr Thr Glu Phe Thr Pro Thr Glu Lys Asp
1               5                   10

<210> SEQ ID NO 716
<211> LENGTH: 14
<212> TYPE: PRT
<213> ORGANISM: Homo sapiens

<400> SEQUENCE: 716

Leu Leu Tyr Tyr Thr Glu Phe Thr Pro Thr Glu Lys Asp Glu
1               5                   10

<210> SEQ ID NO 717
<211> LENGTH: 16
<212> TYPE: PRT
<213> ORGANISM: Homo sapiens

<400> SEQUENCE: 717

Leu Leu Tyr Tyr Thr Glu Phe Thr Pro Thr Glu Lys Asp Glu Tyr Ala
1               5                   10                  15

<210> SEQ ID NO 718
<211> LENGTH: 13
<212> TYPE: PRT
<213> ORGANISM: Homo sapiens

<400> SEQUENCE: 718

Tyr Leu Leu Tyr Tyr Thr Glu Phe Thr Pro Thr Glu Lys
1               5                   10

<210> SEQ ID NO 719
<211> LENGTH: 15
<212> TYPE: PRT
<213> ORGANISM: Homo sapiens

<400> SEQUENCE: 719

Tyr Leu Leu Tyr Tyr Thr Glu Phe Thr Pro Thr Glu Lys Asp Glu

-continued

```
<210> SEQ ID NO 720
<211> LENGTH: 16
<212> TYPE: PRT
<213> ORGANISM: Homo sapiens

<400> SEQUENCE: 720

Tyr Leu Leu Tyr Tyr Thr Glu Phe Thr Pro Thr Glu Lys Asp Glu Tyr
1               5                   10                  15

<210> SEQ ID NO 721
<211> LENGTH: 17
<212> TYPE: PRT
<213> ORGANISM: Homo sapiens

<400> SEQUENCE: 721

Tyr Leu Leu Tyr Tyr Thr Glu Phe Thr Pro Thr Glu Lys Asp Glu Tyr
1               5                   10                  15

Ala

<210> SEQ ID NO 722
<211> LENGTH: 12
<212> TYPE: PRT
<213> ORGANISM: Homo sapiens

<400> SEQUENCE: 722

Tyr Thr Glu Phe Thr Pro Thr Glu Lys Asp Glu Tyr
1               5                   10

<210> SEQ ID NO 723
<211> LENGTH: 13
<212> TYPE: PRT
<213> ORGANISM: Homo sapiens

<400> SEQUENCE: 723

Tyr Tyr Thr Glu Phe Thr Pro Thr Glu Lys Asp Glu Tyr
1               5                   10

<210> SEQ ID NO 724
<211> LENGTH: 23
<212> TYPE: PRT
<213> ORGANISM: Homo sapiens

<400> SEQUENCE: 724

Thr Gly Lys Thr Pro Gly Ala Glu Ile Asp Phe Lys Tyr Ala Leu Ile
1               5                   10                  15

Gly Thr Ala Val Gly Val Ala
            20

<210> SEQ ID NO 725
<211> LENGTH: 16
<212> TYPE: PRT
<213> ORGANISM: Homo sapiens

<400> SEQUENCE: 725

Thr Glu Glu Phe Glu Val Thr Lys Thr Ala Val Ala His Arg Pro Gly
1               5                   10                  15

<210> SEQ ID NO 726
<211> LENGTH: 14
<212> TYPE: PRT
<213> ORGANISM: Homo sapiens
```

<400> SEQUENCE: 726

Arg Gly Tyr Met Glu Ile Glu Gln Ser Val Lys Ser Phe Lys
1               5                   10

<210> SEQ ID NO 727
<211> LENGTH: 14
<212> TYPE: PRT
<213> ORGANISM: Homo sapiens

<400> SEQUENCE: 727

Ile Pro Trp Phe Val Ser Asp Thr Thr Ile His Asp Phe Asn
1               5                   10

<210> SEQ ID NO 728
<211> LENGTH: 13
<212> TYPE: PRT
<213> ORGANISM: Homo sapiens

<400> SEQUENCE: 728

Ile Ala Tyr Asp Val Thr Tyr Ser Leu Ala Cys Val Arg
1               5                   10

<210> SEQ ID NO 729
<211> LENGTH: 14
<212> TYPE: PRT
<213> ORGANISM: Homo sapiens

<400> SEQUENCE: 729

Asn Ile Ala Tyr Asp Val Thr Tyr Ser Leu Ala Cys Val Arg
1               5                   10

<210> SEQ ID NO 730
<211> LENGTH: 14
<212> TYPE: PRT
<213> ORGANISM: Homo sapiens

<400> SEQUENCE: 730

Ser Leu Met Val Thr Asn Asp Gly Ala Thr Ile Leu Lys Asn
1               5                   10

<210> SEQ ID NO 731
<211> LENGTH: 17
<212> TYPE: PRT
<213> ORGANISM: Homo sapiens

<400> SEQUENCE: 731

Ala Thr Gln Tyr Phe Ala Asp Arg Asp Met Phe Cys Ala Gly Arg Val
1               5                   10                  15

Pro

<210> SEQ ID NO 732
<211> LENGTH: 18
<212> TYPE: PRT
<213> ORGANISM: Homo sapiens

<400> SEQUENCE: 732

Val Ala Thr Gln Tyr Phe Ala Asp Arg Asp Met Phe Cys Ala Gly Arg
1               5                   10                  15

Val Pro

<210> SEQ ID NO 733
<211> LENGTH: 15
<212> TYPE: PRT

```
<213> ORGANISM: Homo sapiens

<400> SEQUENCE: 733

Gly Pro Lys Pro Leu Phe Arg Arg Met Ser Ser Leu Val Gly Pro
1               5                   10                  15

<210> SEQ ID NO 734
<211> LENGTH: 16
<212> TYPE: PRT
<213> ORGANISM: Homo sapiens

<400> SEQUENCE: 734

Gly Pro Lys Pro Leu Phe Arg Arg Met Ser Ser Leu Val Gly Pro Thr
1               5                   10                  15

<210> SEQ ID NO 735
<211> LENGTH: 18
<212> TYPE: PRT
<213> ORGANISM: Homo sapiens

<400> SEQUENCE: 735

Gly Pro Lys Pro Leu Phe Arg Arg Met Ser Ser Leu Val Gly Pro Thr
1               5                   10                  15

Gln Ser

<210> SEQ ID NO 736
<211> LENGTH: 19
<212> TYPE: PRT
<213> ORGANISM: Homo sapiens

<400> SEQUENCE: 736

Ser Gly Pro Lys Pro Leu Phe Arg Arg Met Ser Ser Leu Val Gly Pro
1               5                   10                  15

Thr Gln Ser

<210> SEQ ID NO 737
<211> LENGTH: 20
<212> TYPE: PRT
<213> ORGANISM: Homo sapiens

<400> SEQUENCE: 737

Ser Gly Pro Lys Pro Leu Phe Arg Arg Met Ser Ser Leu Val Gly Pro
1               5                   10                  15

Thr Gln Ser Phe
            20

<210> SEQ ID NO 738
<211> LENGTH: 10
<212> TYPE: PRT
<213> ORGANISM: Homo sapiens

<400> SEQUENCE: 738

Arg Asp Met Phe Thr Leu Glu Asp Thr Leu
1               5                   10

<210> SEQ ID NO 739
<211> LENGTH: 12
<212> TYPE: PRT
<213> ORGANISM: Homo sapiens

<400> SEQUENCE: 739

Arg Asp Met Phe Thr Leu Glu Asp Thr Leu Leu Gly
1               5                   10
```

<210> SEQ ID NO 740
<211> LENGTH: 16
<212> TYPE: PRT
<213> ORGANISM: Homo sapiens

<400> SEQUENCE: 740

Arg Asp Met Phe Thr Leu Glu Asp Thr Leu Leu Gly Tyr Leu Ala Asp
1               5                   10                  15

<210> SEQ ID NO 741
<211> LENGTH: 12
<212> TYPE: PRT
<213> ORGANISM: Homo sapiens

<400> SEQUENCE: 741

Val Gln Arg Asp Met Phe Thr Leu Glu Asp Thr Leu
1               5                   10

<210> SEQ ID NO 742
<211> LENGTH: 18
<212> TYPE: PRT
<213> ORGANISM: Homo sapiens

<400> SEQUENCE: 742

Ser Pro Gly Glu Pro Gln Ile Ile Phe Cys Arg Ser Glu Ala Ala His
1               5                   10                  15

Gln Gly

<210> SEQ ID NO 743
<211> LENGTH: 20
<212> TYPE: PRT
<213> ORGANISM: Homo sapiens

<400> SEQUENCE: 743

Ser Pro Gly Glu Pro Gln Ile Ile Phe Cys Arg Ser Glu Ala Ala His
1               5                   10                  15

Gln Gly Val Ile
            20

<210> SEQ ID NO 744
<211> LENGTH: 18
<212> TYPE: PRT
<213> ORGANISM: Homo sapiens

<400> SEQUENCE: 744

Ala Thr Pro Leu Leu Met Gln Ala Leu Pro Met Gly Ala Leu Pro Gln
1               5                   10                  15

Gly Pro

<210> SEQ ID NO 745
<211> LENGTH: 13
<212> TYPE: PRT
<213> ORGANISM: Homo sapiens

<400> SEQUENCE: 745

Gly His Leu Lys Ile Met His Asp Ala Ile Gly Phe Arg
1               5                   10

<210> SEQ ID NO 746
<211> LENGTH: 14
<212> TYPE: PRT
<213> ORGANISM: Homo sapiens

```
<400> SEQUENCE: 746

Leu Gly His Leu Lys Ile Met His Asp Ala Ile Gly Phe Arg
1               5                   10

<210> SEQ ID NO 747
<211> LENGTH: 15
<212> TYPE: PRT
<213> ORGANISM: Homo sapiens

<400> SEQUENCE: 747

Asn Pro Pro Leu Phe Ala Leu Asp Lys Asp Ala Pro Leu Arg Tyr
1               5                   10                  15

<210> SEQ ID NO 748
<211> LENGTH: 16
<212> TYPE: PRT
<213> ORGANISM: Homo sapiens

<400> SEQUENCE: 748

Leu Glu Lys Ile Val Leu Asp Asn Ser Val Phe Ser Glu His Arg Asn
1               5                   10                  15

<210> SEQ ID NO 749
<211> LENGTH: 16
<212> TYPE: PRT
<213> ORGANISM: Homo sapiens

<400> SEQUENCE: 749

Gly Gln Arg Arg Phe Asn Leu Gln Lys Asn Phe Val Gly Lys Val Ala
1               5                   10                  15

<210> SEQ ID NO 750
<211> LENGTH: 18
<212> TYPE: PRT
<213> ORGANISM: Homo sapiens

<400> SEQUENCE: 750

Ile Gly Gln Arg Arg Phe Asn Leu Gln Lys Asn Phe Val Gly Lys Val
1               5                   10                  15

Ala Leu

<210> SEQ ID NO 751
<211> LENGTH: 15
<212> TYPE: PRT
<213> ORGANISM: Homo sapiens

<400> SEQUENCE: 751

Leu Ala Lys Trp Val Ala Ile Gln Ser Val Ser Ala Trp Pro Glu
1               5                   10                  15

<210> SEQ ID NO 752
<211> LENGTH: 14
<212> TYPE: PRT
<213> ORGANISM: Homo sapiens

<400> SEQUENCE: 752

Val Ala Arg Phe Ala Ala Ala Thr Gln Gln Gln Thr Ala
1               5                   10

<210> SEQ ID NO 753
<211> LENGTH: 14
<212> TYPE: PRT
<213> ORGANISM: Homo sapiens
```

<400> SEQUENCE: 753

Trp Gly Ala Leu Ala Thr Ile Ser Thr Leu Glu Ala Val Arg
1               5                   10

<210> SEQ ID NO 754
<211> LENGTH: 16
<212> TYPE: PRT
<213> ORGANISM: Homo sapiens

<400> SEQUENCE: 754

Val Gly Val Pro Tyr Arg Ile Thr Val Thr Ala Val Ser Ala Ser Gly
1               5                   10                  15

<210> SEQ ID NO 755
<211> LENGTH: 14
<212> TYPE: PRT
<213> ORGANISM: Homo sapiens

<400> SEQUENCE: 755

Val Pro Tyr Arg Ile Thr Val Thr Ala Val Ser Ala Ser Gly
1               5                   10

<210> SEQ ID NO 756
<211> LENGTH: 15
<212> TYPE: PRT
<213> ORGANISM: Homo sapiens

<400> SEQUENCE: 756

Asp His Asn Phe Val Lys Ala Ile Asn Ala Ile Gln Lys Ser Trp
1               5                   10                  15

<210> SEQ ID NO 757
<211> LENGTH: 18
<212> TYPE: PRT
<213> ORGANISM: Homo sapiens

<400> SEQUENCE: 757

Lys Lys Val Val Val Tyr Leu Gln Lys Leu Asp Thr Ala Tyr Asp Asp
1               5                   10                  15

Leu Gly

<210> SEQ ID NO 758
<211> LENGTH: 18
<212> TYPE: PRT
<213> ORGANISM: Homo sapiens

<400> SEQUENCE: 758

Lys Tyr Asp His Asn Phe Val Lys Ala Ile Asn Ala Ile Gln Lys Ser
1               5                   10                  15

Trp Thr

<210> SEQ ID NO 759
<211> LENGTH: 17
<212> TYPE: PRT
<213> ORGANISM: Homo sapiens

<400> SEQUENCE: 759

Ser Gly Met Asp Tyr Trp Ile Val Lys Asn Ser Trp Gly Thr Gly Trp
1               5                   10                  15

Gly

```
<210> SEQ ID NO 760
<211> LENGTH: 14
<212> TYPE: PRT
<213> ORGANISM: Homo sapiens

<400> SEQUENCE: 760

Tyr Asp His Asn Phe Val Lys Ala Ile Asn Ala Ile Gln Lys
1               5                   10

<210> SEQ ID NO 761
<211> LENGTH: 17
<212> TYPE: PRT
<213> ORGANISM: Homo sapiens

<400> SEQUENCE: 761

Tyr Asp His Asn Phe Val Lys Ala Ile Asn Ala Ile Gln Lys Ser Trp
1               5                   10                  15

Thr

<210> SEQ ID NO 762
<211> LENGTH: 15
<212> TYPE: PRT
<213> ORGANISM: Homo sapiens

<400> SEQUENCE: 762

Ile Phe Ser Phe Tyr Leu Ser Arg Asp Pro Asp Ala Gln Pro Gly
1               5                   10                  15

<210> SEQ ID NO 763
<211> LENGTH: 12
<212> TYPE: PRT
<213> ORGANISM: Homo sapiens

<400> SEQUENCE: 763

Leu Ser Arg Asp Pro Asp Ala Gln Pro Gly Gly Glu
1               5                   10

<210> SEQ ID NO 764
<211> LENGTH: 14
<212> TYPE: PRT
<213> ORGANISM: Homo sapiens

<400> SEQUENCE: 764

Gly Lys Glu Tyr Trp Leu Val Lys Asn Ser Trp Gly His Asn
1               5                   10

<210> SEQ ID NO 765
<211> LENGTH: 15
<212> TYPE: PRT
<213> ORGANISM: Homo sapiens

<400> SEQUENCE: 765

Lys Asn Leu Lys Phe Val Met Leu His Asn Leu Glu His Ser Met
1               5                   10                  15

<210> SEQ ID NO 766
<211> LENGTH: 14
<212> TYPE: PRT
<213> ORGANISM: Homo sapiens

<400> SEQUENCE: 766

Thr Thr Ala Phe Gln Tyr Ile Ile Asp Asn Lys Gly Ile Asp
1               5                   10
```

```
<210> SEQ ID NO 767
<211> LENGTH: 15
<212> TYPE: PRT
<213> ORGANISM: Homo sapiens

<400> SEQUENCE: 767

Gly Thr Glu Tyr Trp Ile Val Arg Asn Ser Trp Gly Glu Pro Trp
1               5                   10                  15

<210> SEQ ID NO 768
<211> LENGTH: 11
<212> TYPE: PRT
<213> ORGANISM: Homo sapiens

<400> SEQUENCE: 768

Gly Tyr Leu Pro Asn Gln Leu Phe Arg Thr Phe
1               5                   10

<210> SEQ ID NO 769
<211> LENGTH: 13
<212> TYPE: PRT
<213> ORGANISM: Homo sapiens

<400> SEQUENCE: 769

Ile Arg Phe Val Val Asp Ser Gly Lys Val Lys Glu Met
1               5                   10

<210> SEQ ID NO 770
<211> LENGTH: 15
<212> TYPE: PRT
<213> ORGANISM: Homo sapiens

<400> SEQUENCE: 770

Met Glu Lys Tyr Asn Ile Glu Lys Asp Ile Ala Ala Tyr Ile Lys
1               5                   10                  15

<210> SEQ ID NO 771
<211> LENGTH: 14
<212> TYPE: PRT
<213> ORGANISM: Homo sapiens

<400> SEQUENCE: 771

Leu Pro Phe Gly Ala Gln Ser Thr Gln Arg Gly His Thr Glu
1               5                   10

<210> SEQ ID NO 772
<211> LENGTH: 15
<212> TYPE: PRT
<213> ORGANISM: Homo sapiens

<400> SEQUENCE: 772

Ser Lys Tyr Tyr Val Thr Ile Ile Asp Ala Pro Gly His Arg Asp
1               5                   10                  15

<210> SEQ ID NO 773
<211> LENGTH: 14
<212> TYPE: PRT
<213> ORGANISM: Homo sapiens

<400> SEQUENCE: 773

Ile Glu Lys Phe Glu Lys Glu Ala Ala Glu Met Gly Lys Gly
1               5                   10

<210> SEQ ID NO 774
<211> LENGTH: 15
```

```
<212> TYPE: PRT
<213> ORGANISM: Homo sapiens

<400> SEQUENCE: 774

Ile Glu Lys Phe Glu Lys Glu Ala Ala Glu Met Gly Lys Gly Ser
1               5                   10                  15

<210> SEQ ID NO 775
<211> LENGTH: 16
<212> TYPE: PRT
<213> ORGANISM: Homo sapiens

<400> SEQUENCE: 775

Ile Glu Lys Phe Glu Lys Glu Ala Ala Glu Met Gly Lys Gly Ser Phe
1               5                   10                  15

<210> SEQ ID NO 776
<211> LENGTH: 17
<212> TYPE: PRT
<213> ORGANISM: Homo sapiens

<400> SEQUENCE: 776

Thr Ile Glu Lys Phe Glu Lys Glu Ala Ala Glu Met Gly Lys Gly Ser
1               5                   10                  15

Phe

<210> SEQ ID NO 777
<211> LENGTH: 15
<212> TYPE: PRT
<213> ORGANISM: Homo sapiens

<400> SEQUENCE: 777

Asp Ile Asp Ala Ile Phe Lys Asp Leu Ser Ile Arg Ser Val Arg
1               5                   10                  15

<210> SEQ ID NO 778
<211> LENGTH: 14
<212> TYPE: PRT
<213> ORGANISM: Homo sapiens

<400> SEQUENCE: 778

Gly Val Pro Leu Tyr Arg His Ile Ala Asp Leu Ala Gly Asn
1               5                   10

<210> SEQ ID NO 779
<211> LENGTH: 17
<212> TYPE: PRT
<213> ORGANISM: Homo sapiens

<400> SEQUENCE: 779

Gly Val Pro Leu Tyr Arg His Ile Ala Asp Leu Ala Gly Asn Ser Glu
1               5                   10                  15

Val

<210> SEQ ID NO 780
<211> LENGTH: 16
<212> TYPE: PRT
<213> ORGANISM: Homo sapiens

<400> SEQUENCE: 780

Ile Lys Glu Lys Tyr Gly Lys Asp Ala Thr Asn Val Gly Asp Glu Gly
1               5                   10                  15
```

-continued

```
<210> SEQ ID NO 781
<211> LENGTH: 17
<212> TYPE: PRT
<213> ORGANISM: Homo sapiens

<400> SEQUENCE: 781

Ile Lys Glu Lys Tyr Gly Lys Asp Ala Thr Asn Val Gly Asp Glu Gly
1               5                   10                  15

Gly

<210> SEQ ID NO 782
<211> LENGTH: 16
<212> TYPE: PRT
<213> ORGANISM: Homo sapiens

<400> SEQUENCE: 782

Lys Glu Lys Tyr Gly Lys Asp Ala Thr Asn Val Gly Asp Glu Gly Gly
1               5                   10                  15

<210> SEQ ID NO 783
<211> LENGTH: 18
<212> TYPE: PRT
<213> ORGANISM: Homo sapiens

<400> SEQUENCE: 783

Val Ile Lys Glu Lys Tyr Gly Lys Asp Ala Thr Asn Val Gly Asp Glu
1               5                   10                  15

Gly Gly

<210> SEQ ID NO 784
<211> LENGTH: 13
<212> TYPE: PRT
<213> ORGANISM: Homo sapiens

<400> SEQUENCE: 784

Val Pro Leu Tyr Arg His Ile Ala Asp Leu Ala Gly Asn
1               5                   10

<210> SEQ ID NO 785
<211> LENGTH: 15
<212> TYPE: PRT
<213> ORGANISM: Homo sapiens

<400> SEQUENCE: 785

Val Pro Leu Tyr Arg His Ile Ala Asp Leu Ala Gly Asn Ser Glu
1               5                   10                  15

<210> SEQ ID NO 786
<211> LENGTH: 16
<212> TYPE: PRT
<213> ORGANISM: Homo sapiens

<400> SEQUENCE: 786

Val Pro Leu Tyr Arg His Ile Ala Asp Leu Ala Gly Asn Ser Glu Val
1               5                   10                  15

<210> SEQ ID NO 787
<211> LENGTH: 17
<212> TYPE: PRT
<213> ORGANISM: Homo sapiens

<400> SEQUENCE: 787

Val Pro Leu Tyr Arg His Ile Ala Asp Leu Ala Gly Asn Ser Glu Val
1               5                   10                  15
```

Ile

<210> SEQ ID NO 788
<211> LENGTH: 11
<212> TYPE: PRT
<213> ORGANISM: Homo sapiens

<400> SEQUENCE: 788

Leu Leu Gln Lys Leu Ile Leu Trp Arg Val Leu
1               5                   10

<210> SEQ ID NO 789
<211> LENGTH: 16
<212> TYPE: PRT
<213> ORGANISM: Homo sapiens

<400> SEQUENCE: 789

Leu Gln Asn Ile Ile Pro Ala Ser Thr Gly Ala Ala Lys Ala Val Gly
1               5                   10                  15

<210> SEQ ID NO 790
<211> LENGTH: 17
<212> TYPE: PRT
<213> ORGANISM: Homo sapiens

<400> SEQUENCE: 790

Glu Pro Ile Glu Gln Lys Phe Val Ser Ile Ser Asp Leu Leu Val Pro
1               5                   10                  15

Lys

<210> SEQ ID NO 791
<211> LENGTH: 14
<212> TYPE: PRT
<213> ORGANISM: Homo sapiens

<400> SEQUENCE: 791

Ala Ile Phe Leu Phe Val Asp Lys Thr Val Pro Gln Ser Ser
1               5                   10

<210> SEQ ID NO 792
<211> LENGTH: 15
<212> TYPE: PRT
<213> ORGANISM: Homo sapiens

<400> SEQUENCE: 792

Ala Ile Phe Leu Phe Val Asp Lys Thr Val Pro Gln Ser Ser Leu
1               5                   10                  15

<210> SEQ ID NO 793
<211> LENGTH: 16
<212> TYPE: PRT
<213> ORGANISM: Homo sapiens

<400> SEQUENCE: 793

Ala Ile Phe Leu Phe Val Asp Lys Thr Val Pro Gln Ser Ser Leu Thr
1               5                   10                  15

<210> SEQ ID NO 794
<211> LENGTH: 11
<212> TYPE: PRT
<213> ORGANISM: Homo sapiens

<400> SEQUENCE: 794

```
Phe Val Asp Lys Thr Val Pro Gln Ser Ser Leu
1               5                   10
```

<210> SEQ ID NO 795
<211> LENGTH: 21
<212> TYPE: PRT
<213> ORGANISM: Homo sapiens

<400> SEQUENCE: 795

```
Leu Pro Ser Glu Lys Ala Ile Phe Leu Phe Val Asp Lys Thr Val Pro
1               5                   10                  15

Gln Ser Ser Leu Thr
            20
```

<210> SEQ ID NO 796
<211> LENGTH: 16
<212> TYPE: PRT
<213> ORGANISM: Homo sapiens

<400> SEQUENCE: 796

```
Lys Val Asn Leu Leu Lys Ile Lys Thr Glu Leu Cys Lys Lys Glu Val
1               5                   10                  15
```

<210> SEQ ID NO 797
<211> LENGTH: 14
<212> TYPE: PRT
<213> ORGANISM: Homo sapiens

<400> SEQUENCE: 797

```
Leu Gly Lys Trp Cys Ser Glu Lys Thr Glu Thr Gly Gln Glu
1               5                   10
```

<210> SEQ ID NO 798
<211> LENGTH: 15
<212> TYPE: PRT
<213> ORGANISM: Homo sapiens

<400> SEQUENCE: 798

```
Val Asn Leu Leu Lys Ile Lys Thr Glu Leu Cys Lys Lys Glu Val
1               5                   10                  15
```

<210> SEQ ID NO 799
<211> LENGTH: 13
<212> TYPE: PRT
<213> ORGANISM: Homo sapiens

<400> SEQUENCE: 799

```
Gly Asn Tyr Arg Ile Glu Ser Val Leu Ser Ser Ser Gly
1               5                   10
```

<210> SEQ ID NO 800
<211> LENGTH: 14
<212> TYPE: PRT
<213> ORGANISM: Homo sapiens

<400> SEQUENCE: 800

```
Gly Asn Tyr Arg Ile Glu Ser Val Leu Ser Ser Ser Gly Lys
1               5                   10
```

<210> SEQ ID NO 801
<211> LENGTH: 13
<212> TYPE: PRT
<213> ORGANISM: Homo sapiens

<400> SEQUENCE: 801

```
Leu Gly Cys Ile Lys Ile Ala Ala Ser Leu Lys Gly Ile
1               5                   10

<210> SEQ ID NO 802
<211> LENGTH: 14
<212> TYPE: PRT
<213> ORGANISM: Homo sapiens

<400> SEQUENCE: 802

Arg Leu Gly Cys Ile Lys Ile Ala Ala Ser Leu Lys Gly Ile
1               5                   10

<210> SEQ ID NO 803
<211> LENGTH: 14
<212> TYPE: PRT
<213> ORGANISM: Homo sapiens

<400> SEQUENCE: 803

Thr Gly Asn Tyr Arg Ile Glu Ser Val Leu Ser Ser Ser Gly
1               5                   10

<210> SEQ ID NO 804
<211> LENGTH: 15
<212> TYPE: PRT
<213> ORGANISM: Homo sapiens

<400> SEQUENCE: 804

Thr Gly Asn Tyr Arg Ile Glu Ser Val Leu Ser Ser Ser Gly Lys
1               5                   10                  15

<210> SEQ ID NO 805
<211> LENGTH: 16
<212> TYPE: PRT
<213> ORGANISM: Homo sapiens

<400> SEQUENCE: 805

Thr Gly Asn Tyr Arg Ile Glu Ser Val Leu Ser Ser Ser Gly Lys Arg
1               5                   10                  15

<210> SEQ ID NO 806
<211> LENGTH: 15
<212> TYPE: PRT
<213> ORGANISM: Homo sapiens

<400> SEQUENCE: 806

Thr Thr Gly Asn Tyr Arg Ile Glu Ser Val Leu Ser Ser Ser Gly
1               5                   10                  15

<210> SEQ ID NO 807
<211> LENGTH: 16
<212> TYPE: PRT
<213> ORGANISM: Homo sapiens

<400> SEQUENCE: 807

Thr Thr Gly Asn Tyr Arg Ile Glu Ser Val Leu Ser Ser Ser Gly Lys
1               5                   10                  15

<210> SEQ ID NO 808
<211> LENGTH: 15
<212> TYPE: PRT
<213> ORGANISM: Homo sapiens

<400> SEQUENCE: 808

Val Thr Arg Ala Phe Val Ala Ala Arg Thr Phe Ala Gln Gly Leu
```

-continued

```
1               5                   10                  15
```

<210> SEQ ID NO 809
<211> LENGTH: 13
<212> TYPE: PRT
<213> ORGANISM: Homo sapiens

<400> SEQUENCE: 809

```
Asp Ile Phe Glu Arg Ile Ala Ser Glu Ala Ser Arg Leu
1               5                   10
```

<210> SEQ ID NO 810
<211> LENGTH: 14
<212> TYPE: PRT
<213> ORGANISM: Homo sapiens

<400> SEQUENCE: 810

```
Asp Ile Phe Glu Arg Ile Ala Ser Glu Ala Ser Arg Leu Ala
1               5                   10
```

<210> SEQ ID NO 811
<211> LENGTH: 15
<212> TYPE: PRT
<213> ORGANISM: Homo sapiens

<400> SEQUENCE: 811

```
Asp Ile Phe Glu Arg Ile Ala Ser Glu Ala Ser Arg Leu Ala His
1               5                   10                  15
```

<210> SEQ ID NO 812
<211> LENGTH: 16
<212> TYPE: PRT
<213> ORGANISM: Homo sapiens

<400> SEQUENCE: 812

```
Asp Ile Phe Glu Arg Ile Ala Ser Glu Ala Ser Arg Leu Ala His Tyr
1               5                   10                  15
```

<210> SEQ ID NO 813
<211> LENGTH: 19
<212> TYPE: PRT
<213> ORGANISM: Homo sapiens

<400> SEQUENCE: 813

```
Val Asn Asp Ile Phe Glu Arg Ile Ala Ser Glu Ala Ser Arg Leu Ala
1               5                   10                  15

His Tyr Asn
```

<210> SEQ ID NO 814
<211> LENGTH: 16
<212> TYPE: PRT
<213> ORGANISM: Homo sapiens

<400> SEQUENCE: 814

```
Asp Asp Thr Gln Phe Val Arg Phe Asp Ser Asp Ala Ala Ser Gln Arg
1               5                   10                  15
```

<210> SEQ ID NO 815
<211> LENGTH: 18
<212> TYPE: PRT
<213> ORGANISM: Homo sapiens

<400> SEQUENCE: 815

```
Asp Asp Thr Gln Phe Val Arg Phe Asp Ser Asp Ala Ala Ser Gln Arg
```

```
1               5                   10                  15
Met Glu

<210> SEQ ID NO 816
<211> LENGTH: 19
<212> TYPE: PRT
<213> ORGANISM: Homo sapiens

<400> SEQUENCE: 816

Asp Asp Thr Gln Phe Val Arg Phe Asp Ser Asp Ala Ala Ser Gln Arg
1               5                   10                  15
Met Glu Pro

<210> SEQ ID NO 817
<211> LENGTH: 20
<212> TYPE: PRT
<213> ORGANISM: Homo sapiens

<400> SEQUENCE: 817

Asp Asp Thr Gln Phe Val Arg Phe Asp Ser Asp Ala Ala Ser Gln Arg
1               5                   10                  15
Met Glu Pro Arg
            20

<210> SEQ ID NO 818
<211> LENGTH: 17
<212> TYPE: PRT
<213> ORGANISM: Homo sapiens

<400> SEQUENCE: 818

Asp Thr Glu Phe Val Arg Phe Asp Ser Asp Ala Ala Ser Gln Arg Met
1               5                   10                  15
Glu

<210> SEQ ID NO 819
<211> LENGTH: 18
<212> TYPE: PRT
<213> ORGANISM: Homo sapiens

<400> SEQUENCE: 819

Asp Thr Glu Phe Val Arg Phe Asp Ser Asp Ala Ala Ser Gln Arg Met
1               5                   10                  15
Glu Pro

<210> SEQ ID NO 820
<211> LENGTH: 14
<212> TYPE: PRT
<213> ORGANISM: Homo sapiens

<400> SEQUENCE: 820

Asp Thr Gln Phe Val Arg Phe Asp Ser Asp Ala Ala Ser Gln
1               5                   10

<210> SEQ ID NO 821
<211> LENGTH: 15
<212> TYPE: PRT
<213> ORGANISM: Homo sapiens

<400> SEQUENCE: 821

Asp Thr Gln Phe Val Arg Phe Asp Ser Asp Ala Ala Ser Gln Arg
1               5                   10                  15
```

<210> SEQ ID NO 822
<211> LENGTH: 16
<212> TYPE: PRT
<213> ORGANISM: Homo sapiens

<400> SEQUENCE: 822

Asp Thr Gln Phe Val Arg Phe Asp Ser Asp Ala Ala Ser Gln Arg Met
1               5                   10                  15

<210> SEQ ID NO 823
<211> LENGTH: 17
<212> TYPE: PRT
<213> ORGANISM: Homo sapiens

<400> SEQUENCE: 823

Asp Thr Gln Phe Val Arg Phe Asp Ser Asp Ala Ala Ser Gln Arg Met
1               5                   10                  15

Glu

<210> SEQ ID NO 824
<211> LENGTH: 18
<212> TYPE: PRT
<213> ORGANISM: Homo sapiens

<400> SEQUENCE: 824

Asp Thr Gln Phe Val Arg Phe Asp Ser Asp Ala Ala Ser Gln Arg Met
1               5                   10                  15

Glu Pro

<210> SEQ ID NO 825
<211> LENGTH: 21
<212> TYPE: PRT
<213> ORGANISM: Homo sapiens

<400> SEQUENCE: 825

Asp Thr Gln Phe Val Arg Phe Asp Ser Asp Ala Ala Ser Gln Arg Met
1               5                   10                  15

Glu Pro Arg Ala Pro
            20

<210> SEQ ID NO 826
<211> LENGTH: 12
<212> TYPE: PRT
<213> ORGANISM: Homo sapiens

<400> SEQUENCE: 826

Phe Val Arg Phe Asp Ser Asp Ala Ala Ser Gln Arg
1               5                   10

<210> SEQ ID NO 827
<211> LENGTH: 14
<212> TYPE: PRT
<213> ORGANISM: Homo sapiens

<400> SEQUENCE: 827

Phe Val Arg Phe Asp Ser Asp Ala Ala Ser Gln Arg Met Glu
1               5                   10

<210> SEQ ID NO 828
<211> LENGTH: 14
<212> TYPE: PRT
<213> ORGANISM: Homo sapiens

```
<400> SEQUENCE: 828

Lys His Lys Trp Glu Ala Ala His Val Ala Glu Gln Leu Arg
1               5                   10

<210> SEQ ID NO 829
<211> LENGTH: 15
<212> TYPE: PRT
<213> ORGANISM: Homo sapiens

<400> SEQUENCE: 829

Gln Phe Val Arg Phe Asp Ser Asp Ala Ala Ser Gln Arg Met Glu
1               5                   10                  15

<210> SEQ ID NO 830
<211> LENGTH: 13
<212> TYPE: PRT
<213> ORGANISM: Homo sapiens

<400> SEQUENCE: 830

Thr Gln Phe Val Arg Phe Asp Ser Asp Ala Ala Ser Gln
1               5                   10

<210> SEQ ID NO 831
<211> LENGTH: 14
<212> TYPE: PRT
<213> ORGANISM: Homo sapiens

<400> SEQUENCE: 831

Thr Gln Phe Val Arg Phe Asp Ser Asp Ala Ala Ser Gln Arg
1               5                   10

<210> SEQ ID NO 832
<211> LENGTH: 16
<212> TYPE: PRT
<213> ORGANISM: Homo sapiens

<400> SEQUENCE: 832

Thr Thr Lys His Lys Trp Glu Ala Ala His Val Ala Glu Gln Leu Arg
1               5                   10                  15

<210> SEQ ID NO 833
<211> LENGTH: 17
<212> TYPE: PRT
<213> ORGANISM: Homo sapiens

<400> SEQUENCE: 833

Val Asp Asp Thr Glu Phe Val Arg Phe Asp Ser Asp Ala Ala Ser Gln
1               5                   10                  15

Arg

<210> SEQ ID NO 834
<211> LENGTH: 24
<212> TYPE: PRT
<213> ORGANISM: Homo sapiens

<400> SEQUENCE: 834

Val Asp Asp Thr Gln Phe Val Arg Phe Asp Ser Asp Ala Ala Ser Gln
1               5                   10                  15

Arg Met Glu Pro Arg Ala Pro Trp
            20

<210> SEQ ID NO 835
<211> LENGTH: 26
```

```
<212> TYPE: PRT
<213> ORGANISM: Homo sapiens

<400> SEQUENCE: 835

Val Asp Asp Thr Gln Phe Val Arg Phe Asp Ser Asp Ala Ala Ser Gln
1               5                   10                  15

Arg Met Glu Pro Arg Ala Pro Trp Ile Glu
            20                  25

<210> SEQ ID NO 836
<211> LENGTH: 15
<212> TYPE: PRT
<213> ORGANISM: Homo sapiens

<400> SEQUENCE: 836

Asp Leu Ser Ser Trp Thr Ala Ala Asp Thr Ala Ala Gln Ile Thr
1               5                   10                  15

<210> SEQ ID NO 837
<211> LENGTH: 16
<212> TYPE: PRT
<213> ORGANISM: Homo sapiens

<400> SEQUENCE: 837

Asp Leu Ser Ser Trp Thr Ala Ala Asp Thr Ala Ala Gln Ile Thr Gln
1               5                   10                  15

<210> SEQ ID NO 838
<211> LENGTH: 19
<212> TYPE: PRT
<213> ORGANISM: Homo sapiens

<400> SEQUENCE: 838

Asp Leu Ser Ser Trp Thr Ala Ala Asp Thr Ala Ala Gln Ile Thr Gln
1               5                   10                  15

Arg Lys Trp

<210> SEQ ID NO 839
<211> LENGTH: 25
<212> TYPE: PRT
<213> ORGANISM: Homo sapiens

<400> SEQUENCE: 839

Asp Leu Ser Ser Trp Thr Ala Ala Asp Thr Ala Ala Gln Ile Thr Gln
1               5                   10                  15

Arg Lys Trp Glu Ala Ala Arg Val Ala
            20                  25

<210> SEQ ID NO 840
<211> LENGTH: 21
<212> TYPE: PRT
<213> ORGANISM: Homo sapiens

<400> SEQUENCE: 840

Asp Thr Leu Phe Val Arg Phe Asp Ser Asp Ala Thr Ser Pro Arg Lys
1               5                   10                  15

Glu Pro Arg Ala Pro
            20

<210> SEQ ID NO 841
<211> LENGTH: 16
<212> TYPE: PRT
<213> ORGANISM: Homo sapiens
```

-continued

<400> SEQUENCE: 841

Glu Asp Leu Ser Ser Trp Thr Ala Ala Asp Thr Ala Ala Gln Ile Thr
1               5                   10                  15

<210> SEQ ID NO 842
<211> LENGTH: 18
<212> TYPE: PRT
<213> ORGANISM: Homo sapiens

<400> SEQUENCE: 842

Glu Asp Leu Ser Ser Trp Thr Ala Ala Asp Thr Ala Ala Gln Ile Thr
1               5                   10                  15

Gln Arg

<210> SEQ ID NO 843
<211> LENGTH: 20
<212> TYPE: PRT
<213> ORGANISM: Homo sapiens

<400> SEQUENCE: 843

Glu Asp Leu Ser Ser Trp Thr Ala Ala Asp Thr Ala Ala Gln Ile Thr
1               5                   10                  15

Gln Arg Lys Trp
            20

<210> SEQ ID NO 844
<211> LENGTH: 21
<212> TYPE: PRT
<213> ORGANISM: Homo sapiens

<400> SEQUENCE: 844

Glu Asp Leu Ser Ser Trp Thr Ala Ala Asp Thr Ala Ala Gln Ile Thr
1               5                   10                  15

Gln Arg Lys Trp Glu
            20

<210> SEQ ID NO 845
<211> LENGTH: 26
<212> TYPE: PRT
<213> ORGANISM: Homo sapiens

<400> SEQUENCE: 845

Glu Asp Leu Ser Ser Trp Thr Ala Ala Asp Thr Ala Ala Gln Ile Thr
1               5                   10                  15

Gln Arg Lys Trp Glu Ala Ala Arg Val Ala
            20                  25

<210> SEQ ID NO 846
<211> LENGTH: 15
<212> TYPE: PRT
<213> ORGANISM: Homo sapiens

<400> SEQUENCE: 846

Gly Pro Glu Tyr Trp Asp Arg Glu Thr Gln Ile Ser Lys Thr Asn
1               5                   10                  15

<210> SEQ ID NO 847
<211> LENGTH: 15
<212> TYPE: PRT
<213> ORGANISM: Homo sapiens

<400> SEQUENCE: 847

```
Lys Asp Tyr Ile Ala Leu Asn Glu Asp Leu Ser Ser Trp Thr Ala
1               5                   10                  15
```

<210> SEQ ID NO 848
<211> LENGTH: 23
<212> TYPE: PRT
<213> ORGANISM: Homo sapiens

<400> SEQUENCE: 848

```
Leu Asn Glu Asp Leu Ser Ser Trp Thr Ala Ala Asp Thr Ala Ala Gln
1               5                   10                  15

Ile Thr Gln Arg Lys Trp Glu
            20
```

<210> SEQ ID NO 849
<211> LENGTH: 19
<212> TYPE: PRT
<213> ORGANISM: Homo sapiens

<400> SEQUENCE: 849

```
Leu Arg Trp Glu Pro Ser Ser Gln Ser Thr Val Pro Ile Val Gly Ile
1               5                   10                  15

Val Ala Gly
```

<210> SEQ ID NO 850
<211> LENGTH: 19
<212> TYPE: PRT
<213> ORGANISM: Homo sapiens

<400> SEQUENCE: 850

```
Leu Ser Ser Trp Thr Ala Ala Asp Thr Ala Ala Glu Ile Thr Glu Arg
1               5                   10                  15

Lys Trp Glu
```

<210> SEQ ID NO 851
<211> LENGTH: 16
<212> TYPE: PRT
<213> ORGANISM: Homo sapiens

<400> SEQUENCE: 851

```
Leu Ser Ser Trp Thr Ala Ala Asp Thr Ala Ala Gln Ile Thr Gln Arg
1               5                   10                  15
```

<210> SEQ ID NO 852
<211> LENGTH: 18
<212> TYPE: PRT
<213> ORGANISM: Homo sapiens

<400> SEQUENCE: 852

```
Leu Ser Ser Trp Thr Ala Ala Asp Thr Ala Ala Gln Ile Thr Gln Arg
1               5                   10                  15

Lys Trp
```

<210> SEQ ID NO 853
<211> LENGTH: 19
<212> TYPE: PRT
<213> ORGANISM: Homo sapiens

<400> SEQUENCE: 853

```
Leu Ser Ser Trp Thr Ala Ala Asp Thr Ala Ala Gln Ile Thr Gln Arg
1               5                   10                  15
```

Lys Trp Glu

<210> SEQ ID NO 854
<211> LENGTH: 21
<212> TYPE: PRT
<213> ORGANISM: Homo sapiens

<400> SEQUENCE: 854

Asn Glu Asp Leu Ser Ser Trp Thr Ala Ala Asp Thr Ala Ala Gln Ile
1               5                   10                  15

Thr Gln Arg Lys Trp
            20

<210> SEQ ID NO 855
<211> LENGTH: 13
<212> TYPE: PRT
<213> ORGANISM: Homo sapiens

<400> SEQUENCE: 855

Thr Leu Phe Val Arg Phe Asp Ser Asp Ala Thr Ser Pro
1               5                   10

<210> SEQ ID NO 856
<211> LENGTH: 23
<212> TYPE: PRT
<213> ORGANISM: Homo sapiens

<400> SEQUENCE: 856

Val Asp Asp Thr Leu Phe Val Arg Phe Asp Ser Asp Ala Thr Ser Pro
1               5                   10                  15

Arg Lys Glu Pro Arg Ala Pro
            20

<210> SEQ ID NO 857
<211> LENGTH: 16
<212> TYPE: PRT
<213> ORGANISM: Homo sapiens

<400> SEQUENCE: 857

Asp Asp Thr Gln Phe Val Gln Phe Asp Ser Asp Ala Ala Ser Pro Arg
1               5                   10                  15

<210> SEQ ID NO 858
<211> LENGTH: 16
<212> TYPE: PRT
<213> ORGANISM: Homo sapiens

<400> SEQUENCE: 858

Asp Gly Lys Asp Tyr Ile Ala Leu Asn Glu Asp Leu Arg Ser Trp Thr
1               5                   10                  15

<210> SEQ ID NO 859
<211> LENGTH: 17
<212> TYPE: PRT
<213> ORGANISM: Homo sapiens

<400> SEQUENCE: 859

Asp Gly Lys Asp Tyr Ile Ala Leu Asn Glu Asp Leu Arg Ser Trp Thr
1               5                   10                  15

Ala

<210> SEQ ID NO 860
<211> LENGTH: 18

```
<212> TYPE: PRT
<213> ORGANISM: Homo sapiens

<400> SEQUENCE: 860

Asp Gly Lys Asp Tyr Ile Ala Leu Asn Glu Asp Leu Arg Ser Trp Thr
1               5                   10                  15

Ala Ala

<210> SEQ ID NO 861
<211> LENGTH: 15
<212> TYPE: PRT
<213> ORGANISM: Homo sapiens

<400> SEQUENCE: 861

Asp Thr Gln Phe Val Gln Phe Asp Ser Asp Ala Ala Ser Pro Arg
1               5                   10                  15

<210> SEQ ID NO 862
<211> LENGTH: 16
<212> TYPE: PRT
<213> ORGANISM: Homo sapiens

<400> SEQUENCE: 862

Asp Thr Gln Phe Val Gln Phe Asp Ser Asp Ala Ala Ser Pro Arg Gly
1               5                   10                  15

<210> SEQ ID NO 863
<211> LENGTH: 19
<212> TYPE: PRT
<213> ORGANISM: Homo sapiens

<400> SEQUENCE: 863

Asp Thr Gln Phe Val Gln Phe Asp Ser Asp Ala Ala Ser Pro Arg Gly
1               5                   10                  15

Glu Pro Arg

<210> SEQ ID NO 864
<211> LENGTH: 21
<212> TYPE: PRT
<213> ORGANISM: Homo sapiens

<400> SEQUENCE: 864

Asp Thr Gln Phe Val Gln Phe Asp Ser Asp Ala Ala Ser Pro Arg Gly
1               5                   10                  15

Glu Pro Arg Ala Pro
            20

<210> SEQ ID NO 865
<211> LENGTH: 14
<212> TYPE: PRT
<213> ORGANISM: Homo sapiens

<400> SEQUENCE: 865

Asp Tyr Ile Ala Leu Asn Glu Asp Leu Arg Ser Trp Thr Ala
1               5                   10

<210> SEQ ID NO 866
<211> LENGTH: 15
<212> TYPE: PRT
<213> ORGANISM: Homo sapiens

<400> SEQUENCE: 866

Phe Val Gln Phe Asp Ser Asp Ala Ala Ser Pro Arg Gly Glu Pro
```

-continued

```
1               5                   10                  15
```

<210> SEQ ID NO 867
<211> LENGTH: 15
<212> TYPE: PRT
<213> ORGANISM: Homo sapiens

<400> SEQUENCE: 867

```
Gly Lys Asp Tyr Ile Ala Leu Asn Glu Asp Leu Arg Ser Trp Thr
1               5                   10                  15
```

<210> SEQ ID NO 868
<211> LENGTH: 15
<212> TYPE: PRT
<213> ORGANISM: Homo sapiens

<400> SEQUENCE: 868

```
Gly Arg Leu Leu Arg Gly Tyr Asn Gln Phe Ala Tyr Asp Gly Lys
1               5                   10                  15
```

<210> SEQ ID NO 869
<211> LENGTH: 13
<212> TYPE: PRT
<213> ORGANISM: Homo sapiens

<400> SEQUENCE: 869

```
Lys Asp Tyr Ile Ala Leu Asn Glu Asp Leu Arg Ser Trp
1               5                   10
```

<210> SEQ ID NO 870
<211> LENGTH: 14
<212> TYPE: PRT
<213> ORGANISM: Homo sapiens

<400> SEQUENCE: 870

```
Thr Gln Phe Val Gln Phe Asp Ser Asp Ala Ala Ser Pro Arg
1               5                   10
```

<210> SEQ ID NO 871
<211> LENGTH: 18
<212> TYPE: PRT
<213> ORGANISM: Homo sapiens

<400> SEQUENCE: 871

```
Thr Gln Phe Val Gln Phe Asp Ser Asp Ala Ala Ser Pro Arg Gly Glu
1               5                   10                  15

Pro Arg
```

<210> SEQ ID NO 872
<211> LENGTH: 21
<212> TYPE: PRT
<213> ORGANISM: Homo sapiens

<400> SEQUENCE: 872

```
Val Asp Asp Thr Gln Phe Val Gln Phe Asp Ser Asp Ala Ala Ser Pro
1               5                   10                  15

Arg Gly Glu Pro Arg
                20
```

<210> SEQ ID NO 873
<211> LENGTH: 23
<212> TYPE: PRT
<213> ORGANISM: Homo sapiens -continued

<400> SEQUENCE: 873

Val Asp Asp Thr Gln Phe Val Gln Phe Asp Ser Asp Ala Ala Ser Pro
1               5                   10                  15

Arg Gly Glu Pro Arg Ala Pro
            20

<210> SEQ ID NO 874
<211> LENGTH: 24
<212> TYPE: PRT
<213> ORGANISM: Homo sapiens

<400> SEQUENCE: 874

Tyr Val Asp Asp Thr Gln Phe Val Gln Phe Asp Ser Asp Ala Ala Ser
1               5                   10                  15

Pro Arg Gly Glu Pro Arg Ala Pro
            20

<210> SEQ ID NO 875
<211> LENGTH: 15
<212> TYPE: PRT
<213> ORGANISM: Homo sapiens

<400> SEQUENCE: 875

Phe Gly Pro Thr Phe Val Ser Ala Val Asp Gly Leu Ser Phe Gln
1               5                   10                  15

<210> SEQ ID NO 876
<211> LENGTH: 16
<212> TYPE: PRT
<213> ORGANISM: Homo sapiens

<400> SEQUENCE: 876

Asn Arg Glu Glu Phe Val Arg Phe Asp Ser Asp Val Gly Glu Phe Arg
1               5                   10                  15

<210> SEQ ID NO 877
<211> LENGTH: 15
<212> TYPE: PRT
<213> ORGANISM: Homo sapiens

<400> SEQUENCE: 877

Arg Glu Glu Phe Val Arg Phe Asp Ser Asp Val Gly Glu Phe Arg
1               5                   10                  15

<210> SEQ ID NO 878
<211> LENGTH: 15
<212> TYPE: PRT
<213> ORGANISM: Homo sapiens

<400> SEQUENCE: 878

Asp Val Glu Val Tyr Arg Ala Val Thr Pro Leu Gly Pro Pro Asp
1               5                   10                  15

<210> SEQ ID NO 879
<211> LENGTH: 17
<212> TYPE: PRT
<213> ORGANISM: Homo sapiens

<400> SEQUENCE: 879

Ala Gln Gly Ala Leu Ala Asn Ile Ala Val Asp Lys Ala Asn Leu Glu
1               5                   10                  15

Ile

```
<210> SEQ ID NO 880
<211> LENGTH: 15
<212> TYPE: PRT
<213> ORGANISM: Homo sapiens

<400> SEQUENCE: 880

Ile Gln Ala Glu Phe Tyr Leu Asn Pro Asp Gln Ser Gly Glu Phe
1               5                   10                  15

<210> SEQ ID NO 881
<211> LENGTH: 15
<212> TYPE: PRT
<213> ORGANISM: Homo sapiens

<400> SEQUENCE: 881

Gly Ala Gly Leu Phe Ile Tyr Phe Arg Asn Gln Lys Gly His Ser
1               5                   10                  15

<210> SEQ ID NO 882
<211> LENGTH: 16
<212> TYPE: PRT
<213> ORGANISM: Homo sapiens

<400> SEQUENCE: 882

His Gln Glu Glu Tyr Val Arg Phe Asp Ser Asp Val Gly Glu Tyr Arg
1               5                   10                  15

<210> SEQ ID NO 883
<211> LENGTH: 17
<212> TYPE: PRT
<213> ORGANISM: Homo sapiens

<400> SEQUENCE: 883

His Gln Glu Glu Tyr Val Arg Phe Asp Ser Asp Val Gly Glu Tyr Arg
1               5                   10                  15

Ala

<210> SEQ ID NO 884
<211> LENGTH: 18
<212> TYPE: PRT
<213> ORGANISM: Homo sapiens

<400> SEQUENCE: 884

His Gln Glu Glu Tyr Val Arg Phe Asp Ser Asp Val Gly Glu Tyr Arg
1               5                   10                  15

Ala Val

<210> SEQ ID NO 885
<211> LENGTH: 15
<212> TYPE: PRT
<213> ORGANISM: Homo sapiens

<400> SEQUENCE: 885

Gln Glu Glu Tyr Val Arg Phe Asp Ser Asp Val Gly Glu Tyr Arg
1               5                   10                  15

<210> SEQ ID NO 886
<211> LENGTH: 11
<212> TYPE: PRT
<213> ORGANISM: Homo sapiens

<400> SEQUENCE: 886

Tyr Val Arg Phe Asp Ser Asp Val Gly Glu Tyr
```

```
                         1               5                   10

<210> SEQ ID NO 887
<211> LENGTH: 17
<212> TYPE: PRT
<213> ORGANISM: Homo sapiens

<400> SEQUENCE: 887

Asp Leu Arg Ser Trp Thr Ala Val Asp Thr Ala Ala Gln Ile Ser Glu
1               5                   10                  15

Gln

<210> SEQ ID NO 888
<211> LENGTH: 14
<212> TYPE: PRT
<213> ORGANISM: Homo sapiens

<400> SEQUENCE: 888

Leu Arg Ser Trp Thr Ala Val Asp Thr Ala Ala Gln Ile Ser
1               5                   10

<210> SEQ ID NO 889
<211> LENGTH: 16
<212> TYPE: PRT
<213> ORGANISM: Homo sapiens

<400> SEQUENCE: 889

Leu Arg Ser Trp Thr Ala Val Asp Thr Ala Ala Gln Ile Ser Glu Gln
1               5                   10                  15

<210> SEQ ID NO 890
<211> LENGTH: 20
<212> TYPE: PRT
<213> ORGANISM: Homo sapiens

<400> SEQUENCE: 890

Val Asp Asp Thr Gln Phe Val Arg Phe Asp Ser Asp Ser Ala Cys Pro
1               5                   10                  15

Arg Met Glu Pro
            20

<210> SEQ ID NO 891
<211> LENGTH: 24
<212> TYPE: PRT
<213> ORGANISM: Homo sapiens

<400> SEQUENCE: 891

Tyr Val Asp Asp Thr Gln Phe Val Arg Phe Asp Ser Asp Ser Ala Cys
1               5                   10                  15

Pro Arg Met Glu Pro Arg Ala Pro
            20

<210> SEQ ID NO 892
<211> LENGTH: 15
<212> TYPE: PRT
<213> ORGANISM: Homo sapiens

<400> SEQUENCE: 892

Ala Ile Pro Phe Val Ile Glu Lys Ala Val Arg Ser Ser Ile Tyr
1               5                   10                  15

<210> SEQ ID NO 893
<211> LENGTH: 16
```

```
<212> TYPE: PRT
<213> ORGANISM: Homo sapiens

<400> SEQUENCE: 893

Ala Ile Pro Phe Val Ile Glu Lys Ala Val Arg Ser Ser Ile Tyr Gly
1               5                   10                  15

<210> SEQ ID NO 894
<211> LENGTH: 16
<212> TYPE: PRT
<213> ORGANISM: Homo sapiens

<400> SEQUENCE: 894

Asn Val Leu Arg Ile Ile Asn Glu Pro Thr Ala Ala Ala Ile Ala Tyr
1               5                   10                  15

<210> SEQ ID NO 895
<211> LENGTH: 12
<212> TYPE: PRT
<213> ORGANISM: Homo sapiens

<400> SEQUENCE: 895

Arg Ile Ile Asn Glu Pro Thr Ala Ala Ala Ile Ala
1               5                   10

<210> SEQ ID NO 896
<211> LENGTH: 14
<212> TYPE: PRT
<213> ORGANISM: Homo sapiens

<400> SEQUENCE: 896

Arg Ile Ile Asn Glu Pro Thr Ala Ala Ala Ile Ala Tyr Gly
1               5                   10

<210> SEQ ID NO 897
<211> LENGTH: 14
<212> TYPE: PRT
<213> ORGANISM: Homo sapiens

<400> SEQUENCE: 897

Val Leu Arg Ile Ile Asn Glu Pro Thr Ala Ala Ala Ile Ala
1               5                   10

<210> SEQ ID NO 898
<211> LENGTH: 15
<212> TYPE: PRT
<213> ORGANISM: Homo sapiens

<400> SEQUENCE: 898

Val Leu Arg Ile Ile Asn Glu Pro Thr Ala Ala Ala Ile Ala Tyr
1               5                   10                  15

<210> SEQ ID NO 899
<211> LENGTH: 16
<212> TYPE: PRT
<213> ORGANISM: Homo sapiens

<400> SEQUENCE: 899

Val Leu Arg Ile Ile Asn Glu Pro Thr Ala Ala Ala Ile Ala Tyr Gly
1               5                   10                  15

<210> SEQ ID NO 900
<211> LENGTH: 16
<212> TYPE: PRT
<213> ORGANISM: Homo sapiens
```

<400> SEQUENCE: 900

Val Met Arg Ile Ile Asn Glu Pro Thr Ala Ala Ala Ile Ala Tyr Gly
1               5                   10                  15

<210> SEQ ID NO 901
<211> LENGTH: 20
<212> TYPE: PRT
<213> ORGANISM: Homo sapiens

<400> SEQUENCE: 901

Val Pro Thr Lys Lys Ser Gln Ile Phe Ser Thr Ala Ser Asp Asn Gln
1               5                   10                  15

Pro Thr Val Thr
            20

<210> SEQ ID NO 902
<211> LENGTH: 16
<212> TYPE: PRT
<213> ORGANISM: Homo sapiens

<400> SEQUENCE: 902

Gly Glu Arg Ala Met Thr Lys Asp Asn Asn Leu Leu Gly Arg Phe Glu
1               5                   10                  15

<210> SEQ ID NO 903
<211> LENGTH: 16
<212> TYPE: PRT
<213> ORGANISM: Homo sapiens

<400> SEQUENCE: 903

Glu Arg Ala Met Thr Lys Asp Asn Asn Leu Leu Gly Lys Phe Glu Leu
1               5                   10                  15

<210> SEQ ID NO 904
<211> LENGTH: 16
<212> TYPE: PRT
<213> ORGANISM: Homo sapiens

<400> SEQUENCE: 904

Gly Glu Arg Ala Met Thr Lys Asp Asn Asn Leu Leu Gly Lys Phe Glu
1               5                   10                  15

<210> SEQ ID NO 905
<211> LENGTH: 17
<212> TYPE: PRT
<213> ORGANISM: Homo sapiens

<400> SEQUENCE: 905

Gly Glu Arg Ala Met Thr Lys Asp Asn Asn Leu Leu Gly Lys Phe Glu
1               5                   10                  15

Leu

<210> SEQ ID NO 906
<211> LENGTH: 15
<212> TYPE: PRT
<213> ORGANISM: Homo sapiens

<400> SEQUENCE: 906

Gly Ile Leu Asn Val Ser Ala Val Asp Lys Ser Thr Gly Lys Glu
1               5                   10                  15

<210> SEQ ID NO 907

```
<211> LENGTH: 14
<212> TYPE: PRT
<213> ORGANISM: Homo sapiens

<400> SEQUENCE: 907

Arg Ala Met Thr Lys Asp Asn Asn Leu Leu Gly Lys Phe Glu
1               5                   10

<210> SEQ ID NO 908
<211> LENGTH: 13
<212> TYPE: PRT
<213> ORGANISM: Homo sapiens

<400> SEQUENCE: 908

Ile Pro Ile Ile Ile His Pro Ile Asp Arg Ser Val Asp
1               5                   10

<210> SEQ ID NO 909
<211> LENGTH: 14
<212> TYPE: PRT
<213> ORGANISM: Homo sapiens

<400> SEQUENCE: 909

Asp Arg Lys Met Val Gly Asp Val Thr Gly Ala Gln Ala Tyr
1               5                   10

<210> SEQ ID NO 910
<211> LENGTH: 15
<212> TYPE: PRT
<213> ORGANISM: Homo sapiens

<400> SEQUENCE: 910

Asp Arg Lys Met Val Gly Asp Val Thr Gly Ala Gln Ala Tyr Ala
1               5                   10                  15

<210> SEQ ID NO 911
<211> LENGTH: 14
<212> TYPE: PRT
<213> ORGANISM: Homo sapiens

<400> SEQUENCE: 911

Leu Gly Phe Ile Ala Phe Ala Tyr Ser Val Lys Ser Arg Asp
1               5                   10

<210> SEQ ID NO 912
<211> LENGTH: 15
<212> TYPE: PRT
<213> ORGANISM: Homo sapiens

<400> SEQUENCE: 912

Leu Ile Thr Phe Leu Cys Asp Arg Asp Ala Gly Val Gly Phe Pro
1               5                   10                  15

<210> SEQ ID NO 913
<211> LENGTH: 16
<212> TYPE: PRT
<213> ORGANISM: Homo sapiens

<400> SEQUENCE: 913

Leu Ile Thr Phe Leu Cys Asp Arg Asp Ala Gly Val Gly Phe Pro Glu
1               5                   10                  15

<210> SEQ ID NO 914
<211> LENGTH: 17
<212> TYPE: PRT
```

<213> ORGANISM: Homo sapiens

<400> SEQUENCE: 914

Lys Asn Thr Leu Tyr Leu Gln Met Asn Ser Leu Lys Thr Glu Asp Thr
1               5                   10                  15

Ala

<210> SEQ ID NO 915
<211> LENGTH: 15
<212> TYPE: PRT
<213> ORGANISM: Homo sapiens

<400> SEQUENCE: 915

Asn Thr Leu Tyr Leu Gln Met Asn Ser Leu Lys Thr Glu Asp Thr
1               5                   10                  15

<210> SEQ ID NO 916
<211> LENGTH: 16
<212> TYPE: PRT
<213> ORGANISM: Homo sapiens

<400> SEQUENCE: 916

Asn Thr Leu Tyr Leu Gln Met Asn Ser Leu Lys Thr Glu Asp Thr Ala
1               5                   10                  15

<210> SEQ ID NO 917
<211> LENGTH: 13
<212> TYPE: PRT
<213> ORGANISM: Homo sapiens

<400> SEQUENCE: 917

Thr Leu Tyr Leu Gln Met Asn Ser Leu Lys Thr Glu Asp
1               5                   10

<210> SEQ ID NO 918
<211> LENGTH: 14
<212> TYPE: PRT
<213> ORGANISM: Homo sapiens

<400> SEQUENCE: 918

Thr Leu Tyr Leu Gln Met Asn Ser Leu Lys Thr Glu Asp Thr
1               5                   10

<210> SEQ ID NO 919
<211> LENGTH: 15
<212> TYPE: PRT
<213> ORGANISM: Homo sapiens

<400> SEQUENCE: 919

Thr Leu Tyr Leu Gln Met Asn Ser Leu Lys Thr Glu Asp Thr Ala
1               5                   10                  15

<210> SEQ ID NO 920
<211> LENGTH: 12
<212> TYPE: PRT
<213> ORGANISM: Homo sapiens

<400> SEQUENCE: 920

Tyr Leu Gln Met Asn Ser Leu Lys Thr Glu Asp Thr
1               5                   10

<210> SEQ ID NO 921
<211> LENGTH: 21
<212> TYPE: PRT

<213> ORGANISM: Homo sapiens

<400> SEQUENCE: 921

Glu Ser Gly Pro Thr Thr Tyr Lys Val Thr Ser Thr Leu Thr Ile Lys
1               5                   10                  15

Glu Ser Asp Trp Leu
            20

<210> SEQ ID NO 922
<211> LENGTH: 14
<212> TYPE: PRT
<213> ORGANISM: Homo sapiens

<400> SEQUENCE: 922

Gly Pro Thr Thr Tyr Lys Val Thr Ser Thr Leu Thr Ile Lys
1               5                   10

<210> SEQ ID NO 923
<211> LENGTH: 15
<212> TYPE: PRT
<213> ORGANISM: Homo sapiens

<400> SEQUENCE: 923

Gly Pro Thr Thr Tyr Lys Val Thr Ser Thr Leu Thr Ile Lys Glu
1               5                   10                  15

<210> SEQ ID NO 924
<211> LENGTH: 15
<212> TYPE: PRT
<213> ORGANISM: Homo sapiens

<400> SEQUENCE: 924

Ser Gly Pro Thr Thr Tyr Lys Val Thr Ser Thr Leu Thr Ile Lys
1               5                   10                  15

<210> SEQ ID NO 925
<211> LENGTH: 20
<212> TYPE: PRT
<213> ORGANISM: Homo sapiens

<400> SEQUENCE: 925

Ser Gly Pro Thr Thr Tyr Lys Val Thr Ser Thr Leu Thr Ile Lys Glu
1               5                   10                  15

Ser Asp Trp Leu
            20

<210> SEQ ID NO 926
<211> LENGTH: 13
<212> TYPE: PRT
<213> ORGANISM: Homo sapiens

<400> SEQUENCE: 926

Glu Pro Arg Arg Tyr Gly Ser Ala Ala Ala Leu Pro Ser
1               5                   10

<210> SEQ ID NO 927
<211> LENGTH: 15
<212> TYPE: PRT
<213> ORGANISM: Homo sapiens

<400> SEQUENCE: 927

His Lys Ser Tyr Ser Cys Gln Val Thr His Glu Gly Ser Thr Val
1               5                   10                  15

```
<210> SEQ ID NO 928
<211> LENGTH: 16
<212> TYPE: PRT
<213> ORGANISM: Homo sapiens

<400> SEQUENCE: 928

His Lys Ser Tyr Ser Cys Gln Val Thr His Glu Gly Ser Thr Val Glu
1               5                   10                  15

<210> SEQ ID NO 929
<211> LENGTH: 18
<212> TYPE: PRT
<213> ORGANISM: Homo sapiens

<400> SEQUENCE: 929

Lys Ser His Lys Ser Tyr Ser Cys Gln Val Thr His Glu Gly Ser Thr
1               5                   10                  15

Val Glu

<210> SEQ ID NO 930
<211> LENGTH: 13
<212> TYPE: PRT
<213> ORGANISM: Homo sapiens

<400> SEQUENCE: 930

Lys Ser Tyr Ser Cys Gln Val Thr His Glu Gly Ser Thr
1               5                   10

<210> SEQ ID NO 931
<211> LENGTH: 14
<212> TYPE: PRT
<213> ORGANISM: Homo sapiens

<400> SEQUENCE: 931

Lys Ser Tyr Ser Cys Gln Val Thr His Glu Gly Ser Thr Val
1               5                   10

<210> SEQ ID NO 932
<211> LENGTH: 15
<212> TYPE: PRT
<213> ORGANISM: Homo sapiens

<400> SEQUENCE: 932

Lys Ser Tyr Ser Cys Gln Val Thr His Glu Gly Ser Thr Val Glu
1               5                   10                  15

<210> SEQ ID NO 933
<211> LENGTH: 16
<212> TYPE: PRT
<213> ORGANISM: Homo sapiens

<400> SEQUENCE: 933

Lys Ser Tyr Ser Cys Gln Val Thr His Glu Gly Ser Thr Val Glu Lys
1               5                   10                  15

<210> SEQ ID NO 934
<211> LENGTH: 15
<212> TYPE: PRT
<213> ORGANISM: Homo sapiens

<400> SEQUENCE: 934

Ser His Lys Ser Tyr Ser Cys Gln Val Thr His Glu Gly Ser Thr
1               5                   10                  15
```

```
<210> SEQ ID NO 935
<211> LENGTH: 16
<212> TYPE: PRT
<213> ORGANISM: Homo sapiens

<400> SEQUENCE: 935

Ser His Lys Ser Tyr Ser Cys Gln Val Thr His Glu Gly Ser Thr Val
1               5                   10                  15

<210> SEQ ID NO 936
<211> LENGTH: 17
<212> TYPE: PRT
<213> ORGANISM: Homo sapiens

<400> SEQUENCE: 936

Ser His Lys Ser Tyr Ser Cys Gln Val Thr His Glu Gly Ser Thr Val
1               5                   10                  15

Glu

<210> SEQ ID NO 937
<211> LENGTH: 19
<212> TYPE: PRT
<213> ORGANISM: Homo sapiens

<400> SEQUENCE: 937

Ser His Lys Ser Tyr Ser Cys Gln Val Thr His Glu Gly Ser Thr Val
1               5                   10                  15

Glu Lys Thr

<210> SEQ ID NO 938
<211> LENGTH: 23
<212> TYPE: PRT
<213> ORGANISM: Homo sapiens

<400> SEQUENCE: 938

Thr Pro Glu Gln Trp Lys Ser His Lys Ser Tyr Ser Cys Gln Val Thr
1               5                   10                  15

His Glu Gly Ser Thr Val Glu
            20

<210> SEQ ID NO 939
<211> LENGTH: 15
<212> TYPE: PRT
<213> ORGANISM: Homo sapiens

<400> SEQUENCE: 939

Ile Glu Val Trp Val Glu Ala Glu Asn Ala Leu Gly Lys Val Thr
1               5                   10                  15

<210> SEQ ID NO 940
<211> LENGTH: 17
<212> TYPE: PRT
<213> ORGANISM: Homo sapiens

<400> SEQUENCE: 940

Tyr Pro Ser His Ser Phe Ile Gly Glu Glu Ser Val Ala Ala Gly Glu
1               5                   10                  15

Lys

<210> SEQ ID NO 941
<211> LENGTH: 16
<212> TYPE: PRT
```

<213> ORGANISM: Homo sapiens

<400> SEQUENCE: 941

Asp Thr Gly Ser Tyr Arg Ala Gln Ile Ser Thr Lys Thr Ser Ala Lys
1               5                   10                  15

<210> SEQ ID NO 942
<211> LENGTH: 14
<212> TYPE: PRT
<213> ORGANISM: Homo sapiens

<400> SEQUENCE: 942

Phe Ser Gln Phe Leu Gly Asp Pro Val Glu Lys Ala Ala Gln
1               5                   10

<210> SEQ ID NO 943
<211> LENGTH: 15
<212> TYPE: PRT
<213> ORGANISM: Homo sapiens

<400> SEQUENCE: 943

Leu Pro Ser Tyr Glu Glu Ala Leu Ser Leu Pro Ser Lys Thr Pro
1               5                   10                  15

<210> SEQ ID NO 944
<211> LENGTH: 16
<212> TYPE: PRT
<213> ORGANISM: Homo sapiens

<400> SEQUENCE: 944

Leu Pro Ser Tyr Glu Glu Ala Leu Ser Leu Pro Ser Lys Thr Pro Glu
1               5                   10                  15

<210> SEQ ID NO 945
<211> LENGTH: 17
<212> TYPE: PRT
<213> ORGANISM: Homo sapiens

<400> SEQUENCE: 945

Leu Pro Ser Tyr Glu Glu Ala Leu Ser Leu Pro Ser Lys Thr Pro Glu
1               5                   10                  15

Gly

<210> SEQ ID NO 946
<211> LENGTH: 18
<212> TYPE: PRT
<213> ORGANISM: Homo sapiens

<400> SEQUENCE: 946

Val Val Leu Pro Ser Tyr Glu Glu Ala Leu Ser Leu Pro Ser Lys Thr
1               5                   10                  15

Pro Glu

<210> SEQ ID NO 947
<211> LENGTH: 15
<212> TYPE: PRT
<213> ORGANISM: Homo sapiens

<400> SEQUENCE: 947

Gly Val Pro Lys Asp Tyr Thr Gly Glu Asp Val Thr Pro Gln Asn
1               5                   10                  15

<210> SEQ ID NO 948

```
<211> LENGTH: 14
<212> TYPE: PRT
<213> ORGANISM: Homo sapiens

<400> SEQUENCE: 948

Val Pro Lys Asp Tyr Thr Gly Glu Asp Val Thr Pro Gln Asn
1               5                   10

<210> SEQ ID NO 949
<211> LENGTH: 17
<212> TYPE: PRT
<213> ORGANISM: Homo sapiens

<400> SEQUENCE: 949

Asp Val Arg Lys Leu Tyr Trp Leu Met Lys Ser Ser Leu Asn Gly Asp
1               5                   10                  15

Asn

<210> SEQ ID NO 950
<211> LENGTH: 14
<212> TYPE: PRT
<213> ORGANISM: Homo sapiens

<400> SEQUENCE: 950

Lys Pro Thr Ile Cys Ser Asp Gln Asp Asn Tyr Cys Val Thr
1               5                   10

<210> SEQ ID NO 951
<211> LENGTH: 15
<212> TYPE: PRT
<213> ORGANISM: Homo sapiens

<400> SEQUENCE: 951

Leu Lys Pro Thr Ile Cys Ser Asp Gln Asp Asn Tyr Cys Val Thr
1               5                   10                  15

<210> SEQ ID NO 952
<211> LENGTH: 15
<212> TYPE: PRT
<213> ORGANISM: Homo sapiens

<400> SEQUENCE: 952

His Pro Pro Glu Leu Leu Phe Ser Ala Ser Leu Pro Ala Leu Gly
1               5                   10                  15

<210> SEQ ID NO 953
<211> LENGTH: 15
<212> TYPE: PRT
<213> ORGANISM: Homo sapiens

<400> SEQUENCE: 953

Val Asp Tyr Phe Leu Asn Val Ala Thr Ala Gln Gly Arg Tyr Tyr
1               5                   10                  15

<210> SEQ ID NO 954
<211> LENGTH: 17
<212> TYPE: PRT
<213> ORGANISM: Homo sapiens

<400> SEQUENCE: 954

Thr Pro Ile Ser Glu Val Tyr Glu Ser Glu Lys Asp Glu Asp Gly Phe
1               5                   10                  15

Leu
```

<210> SEQ ID NO 955
<211> LENGTH: 18
<212> TYPE: PRT
<213> ORGANISM: Homo sapiens

<400> SEQUENCE: 955

Thr Pro Ile Ser Glu Val Tyr Glu Ser Glu Lys Asp Glu Asp Gly Phe
1               5                   10                  15
Leu Tyr

<210> SEQ ID NO 956
<211> LENGTH: 16
<212> TYPE: PRT
<213> ORGANISM: Homo sapiens

<400> SEQUENCE: 956

Ser Pro Asp Arg Val Tyr Ile Asn Tyr Tyr Asp Met Asn Ala Ala Asn
1               5                   10                  15

<210> SEQ ID NO 957
<211> LENGTH: 15
<212> TYPE: PRT
<213> ORGANISM: Homo sapiens

<400> SEQUENCE: 957

Val Pro Asp Gly Phe Leu Ser Glu Leu Thr Gln Gln Leu Ala Gln
1               5                   10                  15

<210> SEQ ID NO 958
<211> LENGTH: 15
<212> TYPE: PRT
<213> ORGANISM: Homo sapiens

<400> SEQUENCE: 958

Asp Gly Arg Thr Phe Tyr Ile Asp His Asn Ser Lys Ile Thr Gln
1               5                   10                  15

<210> SEQ ID NO 959
<211> LENGTH: 15
<212> TYPE: PRT
<213> ORGANISM: Homo sapiens

<400> SEQUENCE: 959

Gly Pro Val Gly Val Phe Glu Trp Glu Ala Phe Ala Arg Gly Thr
1               5                   10                  15

<210> SEQ ID NO 960
<211> LENGTH: 14
<212> TYPE: PRT
<213> ORGANISM: Homo sapiens

<400> SEQUENCE: 960

Arg Val Val Met Arg Val Asp Phe Asn Val Pro Met Lys Asn
1               5                   10

<210> SEQ ID NO 961
<211> LENGTH: 18
<212> TYPE: PRT
<213> ORGANISM: Homo sapiens

<400> SEQUENCE: 961

Ser Pro Asp Asp Lys Tyr Ile Tyr Val Ala Asp Ile Leu Ala His Glu
1               5                   10                  15

Ile His

<210> SEQ ID NO 962
<211> LENGTH: 15
<212> TYPE: PRT
<213> ORGANISM: Homo sapiens

<400> SEQUENCE: 962

Leu Pro Gly Leu Ala Lys Gln Pro Ser Phe Arg Gln Tyr Ser Gly
1               5                   10                  15

<210> SEQ ID NO 963
<211> LENGTH: 16
<212> TYPE: PRT
<213> ORGANISM: Homo sapiens

<400> SEQUENCE: 963

Val Ser Phe Glu Leu Phe Ala Asp Lys Val Pro Lys Thr Ala Glu Asn
1               5                   10                  15

<210> SEQ ID NO 964
<211> LENGTH: 14
<212> TYPE: PRT
<213> ORGANISM: Homo sapiens

<400> SEQUENCE: 964

Gly Pro Ser Tyr Trp Cys Gln Asn Thr Glu Thr Ala Ala Gln
1               5                   10

<210> SEQ ID NO 965
<211> LENGTH: 15
<212> TYPE: PRT
<213> ORGANISM: Homo sapiens

<400> SEQUENCE: 965

Val Pro Gly Phe Ala Asp Asp Pro Thr Glu Leu Ala Cys Arg Val
1               5                   10                  15

<210> SEQ ID NO 966
<211> LENGTH: 15
<212> TYPE: PRT
<213> ORGANISM: Homo sapiens

<400> SEQUENCE: 966

Gly Ala Leu Leu Val Tyr Asp Ile Thr Ser Arg Glu Thr Tyr Asn
1               5                   10                  15

<210> SEQ ID NO 967
<211> LENGTH: 15
<212> TYPE: PRT
<213> ORGANISM: Homo sapiens

<400> SEQUENCE: 967

Leu Ile Pro Ser Tyr Ile Arg Asp Ser Thr Val Ala Val Val Val
1               5                   10                  15

<210> SEQ ID NO 968
<211> LENGTH: 17
<212> TYPE: PRT
<213> ORGANISM: Homo sapiens

<400> SEQUENCE: 968

Phe Pro Glu Pro Ile Lys Leu Asp Lys Asn Asp Arg Ala Lys Ala Ser
1               5                   10                  15

Ala

<210> SEQ ID NO 969
<211> LENGTH: 14
<212> TYPE: PRT
<213> ORGANISM: Homo sapiens

<400> SEQUENCE: 969

Ala Phe Phe Thr Leu Ala Arg Asp Ile Lys Ala Lys Met Asp
1               5                   10

<210> SEQ ID NO 970
<211> LENGTH: 15
<212> TYPE: PRT
<213> ORGANISM: Homo sapiens

<400> SEQUENCE: 970

Asn Ala Phe Phe Thr Leu Ala Arg Asp Ile Lys Ala Lys Met Asp
1               5                   10                  15

<210> SEQ ID NO 971
<211> LENGTH: 12
<212> TYPE: PRT
<213> ORGANISM: Homo sapiens

<400> SEQUENCE: 971

Leu Leu Gln Gln Ile Ser Gln His Gln Glu His Phe
1               5                   10

<210> SEQ ID NO 972
<211> LENGTH: 14
<212> TYPE: PRT
<213> ORGANISM: Homo sapiens

<400> SEQUENCE: 972

Thr Glu Gln Phe Thr Ala Met Arg Asp Leu Tyr Met Lys Asn
1               5                   10

<210> SEQ ID NO 973
<211> LENGTH: 16
<212> TYPE: PRT
<213> ORGANISM: Homo sapiens

<400> SEQUENCE: 973

Ile Pro Ser Val Phe Ile Gly Glu Ser Ser Ala Asn Ser Leu Lys Asp
1               5                   10                  15

<210> SEQ ID NO 974
<211> LENGTH: 16
<212> TYPE: PRT
<213> ORGANISM: Homo sapiens

<400> SEQUENCE: 974

Ala Asp Arg Asp Thr Tyr Arg Arg Ser Ala Val Pro Pro Gly Ala Asp
1               5                   10                  15

<210> SEQ ID NO 975
<211> LENGTH: 15
<212> TYPE: PRT
<213> ORGANISM: Homo sapiens

<400> SEQUENCE: 975

Asp Arg Asp Thr Tyr Arg Arg Ser Ala Val Pro Pro Gly Ala Asp
1               5                   10                  15

```
<210> SEQ ID NO 976
<211> LENGTH: 14
<212> TYPE: PRT
<213> ORGANISM: Homo sapiens

<400> SEQUENCE: 976

Arg Asp Thr Tyr Arg Arg Ser Ala Val Pro Pro Gly Ala Asp
1               5                   10

<210> SEQ ID NO 977
<211> LENGTH: 14
<212> TYPE: PRT
<213> ORGANISM: Homo sapiens

<400> SEQUENCE: 977

Leu Pro Pro Asn Trp Lys Tyr Glu Ser Ser Thr Ala Ser Ala
1               5                   10

<210> SEQ ID NO 978
<211> LENGTH: 15
<212> TYPE: PRT
<213> ORGANISM: Homo sapiens

<400> SEQUENCE: 978

Arg Thr Phe His Arg Ala Ala Ser Ser Ala Ala Gln Gly Ala Phe
1               5                   10                  15

<210> SEQ ID NO 979
<211> LENGTH: 15
<212> TYPE: PRT
<213> ORGANISM: Homo sapiens

<400> SEQUENCE: 979

Ser Arg Thr Phe His Arg Ala Ala Ser Ser Ala Ala Gln Gly Ala
1               5                   10                  15

<210> SEQ ID NO 980
<211> LENGTH: 16
<212> TYPE: PRT
<213> ORGANISM: Homo sapiens

<400> SEQUENCE: 980

Ser Ser Arg Thr Phe His Arg Ala Ala Ser Ser Ala Ala Gln Gly Ala
1               5                   10                  15

<210> SEQ ID NO 981
<211> LENGTH: 17
<212> TYPE: PRT
<213> ORGANISM: Homo sapiens

<400> SEQUENCE: 981

Ser Ser Arg Thr Phe His Arg Ala Ala Ser Ser Ala Ala Gln Gly Ala
1               5                   10                  15

Phe

<210> SEQ ID NO 982
<211> LENGTH: 14
<212> TYPE: PRT
<213> ORGANISM: Homo sapiens

<400> SEQUENCE: 982

Tyr Gly Ser Tyr Ser Thr Gln Ala Ser Ala Ala Ala Ala Thr
1               5                   10
```

```
<210> SEQ ID NO 983
<211> LENGTH: 15
<212> TYPE: PRT
<213> ORGANISM: Homo sapiens

<400> SEQUENCE: 983

Tyr Gly Ser Tyr Ser Thr Gln Ala Ser Ala Ala Ala Thr Ala
1               5                   10                  15

<210> SEQ ID NO 984
<211> LENGTH: 16
<212> TYPE: PRT
<213> ORGANISM: Homo sapiens

<400> SEQUENCE: 984

Tyr Gly Ser Tyr Ser Thr Gln Ala Ser Ala Ala Ala Thr Ala Glu
1               5                   10                  15

<210> SEQ ID NO 985
<211> LENGTH: 14
<212> TYPE: PRT
<213> ORGANISM: Homo sapiens

<400> SEQUENCE: 985

Val Pro Met Tyr Ile Gly Glu Ile Ser Pro Thr Ala Leu Arg
1               5                   10

<210> SEQ ID NO 986
<211> LENGTH: 12
<212> TYPE: PRT
<213> ORGANISM: Homo sapiens

<400> SEQUENCE: 986

Ile Ser Ile Tyr Ser Ser Glu Arg Ser Val Leu Gln
1               5                   10

<210> SEQ ID NO 987
<211> LENGTH: 18
<212> TYPE: PRT
<213> ORGANISM: Homo sapiens

<400> SEQUENCE: 987

Val Ala Ala Val Phe Ile Ala Gln Leu Ser Gln Gln Ser Leu Asp Phe
1               5                   10                  15

Val Lys

<210> SEQ ID NO 988
<211> LENGTH: 17
<212> TYPE: PRT
<213> ORGANISM: Homo sapiens

<400> SEQUENCE: 988

Thr Gly Ala Leu Tyr Arg Ile Gly Asp Leu Gln Ala Phe Gln Gly His
1               5                   10                  15

Gly

<210> SEQ ID NO 989
<211> LENGTH: 14
<212> TYPE: PRT
<213> ORGANISM: Homo sapiens

<400> SEQUENCE: 989

Asp Tyr Tyr Lys Gly Glu Glu Ser Asn Ser Ser Ala Asn Lys
```

<210> SEQ ID NO 990
<211> LENGTH: 15
<212> TYPE: PRT
<213> ORGANISM: Homo sapiens

<400> SEQUENCE: 990

Lys Pro Gly Ile Tyr Arg Ser Asn Met Asp Gly Ser Ala Ala Tyr
1               5                   10                  15

<210> SEQ ID NO 991
<211> LENGTH: 18
<212> TYPE: PRT
<213> ORGANISM: Homo sapiens

<400> SEQUENCE: 991

Arg His Pro Ile Asn Glu Tyr Tyr Ile Ala Asp Ala Ser Glu Asp Gln
1               5                   10                  15

Val Phe

<210> SEQ ID NO 992
<211> LENGTH: 15
<212> TYPE: PRT
<213> ORGANISM: Homo sapiens

<400> SEQUENCE: 992

Asn Pro Arg Lys Phe Asn Leu Asp Ala Thr Glu Leu Ser Ile Arg
1               5                   10                  15

<210> SEQ ID NO 993
<211> LENGTH: 16
<212> TYPE: PRT
<213> ORGANISM: Homo sapiens

<400> SEQUENCE: 993

Asn Pro Arg Lys Phe Asn Leu Asp Ala Thr Glu Leu Ser Ile Arg Lys
1               5                   10                  15

<210> SEQ ID NO 994
<211> LENGTH: 17
<212> TYPE: PRT
<213> ORGANISM: Homo sapiens

<400> SEQUENCE: 994

Asn Pro Arg Lys Phe Asn Leu Asp Ala Thr Glu Leu Ser Ile Arg Lys
1               5                   10                  15

Ala

<210> SEQ ID NO 995
<211> LENGTH: 17
<212> TYPE: PRT
<213> ORGANISM: Homo sapiens

<400> SEQUENCE: 995

Gly Pro Pro Ile Gly Ser Phe Thr Leu Ile Asp Ser Glu Val Ser Gln
1               5                   10                  15

Leu

<210> SEQ ID NO 996
<211> LENGTH: 18
<212> TYPE: PRT
<213> ORGANISM: Homo sapiens -continued

<400> SEQUENCE: 996

Asn Pro Lys Asp Val Leu Val Gly Ala Asp Ser Val Arg Ala Ala Ile
1               5                   10                  15

Thr Phe

<210> SEQ ID NO 997
<211> LENGTH: 15
<212> TYPE: PRT
<213> ORGANISM: Homo sapiens

<400> SEQUENCE: 997

His Lys Gly Glu Ile Arg Gly Ala Ser Thr Pro Phe Gln Phe Arg
1               5                   10                  15

<210> SEQ ID NO 998
<211> LENGTH: 12
<212> TYPE: PRT
<213> ORGANISM: Bos taurus

<400> SEQUENCE: 998

Asp Val Ala Phe Val Lys Asp Gln Thr Val Ile Gln
1               5                   10

<210> SEQ ID NO 999
<211> LENGTH: 12
<212> TYPE: PRT
<213> ORGANISM: Bos taurus

<400> SEQUENCE: 999

Phe Val Lys Asp Gln Thr Val Ile Gln Asn Thr Asp
1               5                   10

<210> SEQ ID NO 1000
<211> LENGTH: 13
<212> TYPE: PRT
<213> ORGANISM: Bos taurus

<400> SEQUENCE: 1000

Gly Asp Val Ala Phe Val Lys Asp Gln Thr Val Ile Gln
1               5                   10

<210> SEQ ID NO 1001
<211> LENGTH: 16
<212> TYPE: PRT
<213> ORGANISM: Bos taurus

<400> SEQUENCE: 1001

Gly Asp Val Ala Phe Val Lys Asp Gln Thr Val Ile Gln Asn Thr Asp
1               5                   10                  15

<210> SEQ ID NO 1002
<211> LENGTH: 15
<212> TYPE: PRT
<213> ORGANISM: Homo sapiens

<400> SEQUENCE: 1002

Cys Pro Ser Asp Trp Lys Thr Asp Ser Thr Cys Arg Met Val Thr
1               5                   10                  15

<210> SEQ ID NO 1003
<211> LENGTH: 16
<212> TYPE: PRT
<213> ORGANISM: Homo sapiens

```
<400> SEQUENCE: 1003

Cys Pro Ser Asp Trp Lys Thr Asp Ser Thr Cys Arg Met Val Thr Ser
1               5                   10                  15

<210> SEQ ID NO 1004
<211> LENGTH: 17
<212> TYPE: PRT
<213> ORGANISM: Homo sapiens

<400> SEQUENCE: 1004

Cys Pro Ser Asp Trp Lys Thr Asp Ser Thr Cys Arg Met Val Thr Ser
1               5                   10                  15

Glu

<210> SEQ ID NO 1005
<211> LENGTH: 15
<212> TYPE: PRT
<213> ORGANISM: Homo sapiens

<400> SEQUENCE: 1005

Phe Thr Tyr Ile Asn Leu Asp Lys Ala Val Leu Gly Thr Ser Asn
1               5                   10                  15

<210> SEQ ID NO 1006
<211> LENGTH: 14
<212> TYPE: PRT
<213> ORGANISM: Homo sapiens

<400> SEQUENCE: 1006

Tyr Val Ala Tyr Ser Lys Ala Ala Thr Val Thr Gly Lys Leu
1               5                   10

<210> SEQ ID NO 1007
<211> LENGTH: 13
<212> TYPE: PRT
<213> ORGANISM: Homo sapiens

<400> SEQUENCE: 1007

Glu Ile Ile His Lys Ala Leu Ile Asp Arg Asn Ile Gln
1               5                   10

<210> SEQ ID NO 1008
<211> LENGTH: 15
<212> TYPE: PRT
<213> ORGANISM: Homo sapiens

<400> SEQUENCE: 1008

Gly Pro Leu Ser Trp Tyr Ser Asp Pro Gly Leu Ala Gly Val Ser
1               5                   10                  15

<210> SEQ ID NO 1009
<211> LENGTH: 13
<212> TYPE: PRT
<213> ORGANISM: Homo sapiens

<400> SEQUENCE: 1009

Leu Lys Pro Glu Phe Val Asp Ile Ile Asn Ala Lys Gln
1               5                   10

<210> SEQ ID NO 1010
<211> LENGTH: 15
<212> TYPE: PRT
<213> ORGANISM: Homo sapiens
```

<400> SEQUENCE: 1010

Gly Ser Ser Tyr Gly Ser Glu Thr Ser Ile Pro Ala Ala Ala His
1               5                   10                  15

<210> SEQ ID NO 1011
<211> LENGTH: 16
<212> TYPE: PRT
<213> ORGANISM: Homo sapiens

<400> SEQUENCE: 1011

Ala Lys Phe Trp Glu Val Ile Ser Asp Glu His Gly Ile Asp Pro Thr
1               5                   10                  15

<210> SEQ ID NO 1012
<211> LENGTH: 12
<212> TYPE: PRT
<213> ORGANISM: Homo sapiens

<400> SEQUENCE: 1012

Glu Pro Tyr Asn Ala Thr Leu Ser Val His Gln Leu
1               5                   10

<210> SEQ ID NO 1013
<211> LENGTH: 14
<212> TYPE: PRT
<213> ORGANISM: Homo sapiens

<400> SEQUENCE: 1013

Glu Pro Tyr Asn Ala Thr Leu Ser Val His Gln Leu Val Glu
1               5                   10

<210> SEQ ID NO 1014
<211> LENGTH: 15
<212> TYPE: PRT
<213> ORGANISM: Homo sapiens

<400> SEQUENCE: 1014

Asp Tyr Asn Ile Gln Lys Glu Ser Thr Leu His Leu Val Leu Arg
1               5                   10                  15

<210> SEQ ID NO 1015
<211> LENGTH: 14
<212> TYPE: PRT
<213> ORGANISM: Homo sapiens

<400> SEQUENCE: 1015

Ser Asp Tyr Asn Ile Gln Lys Glu Ser Thr Leu His Leu Val
1               5                   10

<210> SEQ ID NO 1016
<211> LENGTH: 20
<212> TYPE: PRT
<213> ORGANISM: Homo sapiens

<400> SEQUENCE: 1016

Asp Lys Gly Ala Phe Arg Ile Glu Ile Asn Phe Pro Ala Glu Tyr Pro
1               5                   10                  15

Phe Lys Pro Pro
            20

<210> SEQ ID NO 1017
<211> LENGTH: 19
<212> TYPE: PRT

-continued

<213> ORGANISM: Homo sapiens

<400> SEQUENCE: 1017

Lys Gly Ala Phe Arg Ile Glu Ile Asn Phe Pro Ala Glu Tyr Pro Phe
1               5                   10                  15

Lys Pro Pro

<210> SEQ ID NO 1018
<211> LENGTH: 24
<212> TYPE: PRT
<213> ORGANISM: Homo sapiens

<400> SEQUENCE: 1018

Asn Pro Pro Tyr Asp Lys Gly Ala Phe Arg Ile Glu Ile Asn Phe Pro
1               5                   10                  15

Ala Glu Tyr Pro Phe Lys Pro Pro
            20

<210> SEQ ID NO 1019
<211> LENGTH: 23
<212> TYPE: PRT
<213> ORGANISM: Homo sapiens

<400> SEQUENCE: 1019

Pro Pro Tyr Asp Lys Gly Ala Phe Arg Ile Glu Ile Asn Phe Pro Ala
1               5                   10                  15

Glu Tyr Pro Phe Lys Pro Pro
            20

<210> SEQ ID NO 1020
<211> LENGTH: 15
<212> TYPE: PRT
<213> ORGANISM: Homo sapiens

<400> SEQUENCE: 1020

Asn Pro Asp Thr Leu Ser Ala Met Ser Asn Pro Arg Ala Met Gln
1               5                   10                  15

<210> SEQ ID NO 1021
<211> LENGTH: 15
<212> TYPE: PRT
<213> ORGANISM: Homo sapiens

<400> SEQUENCE: 1021

Gln Leu Ile Tyr Ile Pro Leu Pro Asp Glu Lys Ser Arg Val Ala
1               5                   10                  15

<210> SEQ ID NO 1022
<211> LENGTH: 14
<212> TYPE: PRT
<213> ORGANISM: Homo sapiens

<400> SEQUENCE: 1022

Ala Ala Lys Tyr Gln Leu Asp Pro Thr Ala Ser Ile Ser Ala
1               5                   10

<210> SEQ ID NO 1023
<211> LENGTH: 18
<212> TYPE: PRT
<213> ORGANISM: Homo sapiens

<400> SEQUENCE: 1023

Asp Pro Asp Pro Glu Asp Phe Ala Asp Glu Gln Ser Leu Val Gly Arg

```
                1               5                    10                   15
Phe Ile

<210> SEQ ID NO 1024
<211> LENGTH: 16
<212> TYPE: PRT
<213> ORGANISM: Homo sapiens

<400> SEQUENCE: 1024

Ala Pro Ser Gly Phe Tyr Ile Ala Ser Gly Asp Val Ser Gly Lys Leu
1               5                   10                  15

<210> SEQ ID NO 1025
<211> LENGTH: 17
<212> TYPE: PRT
<213> ORGANISM: Homo sapiens

<400> SEQUENCE: 1025

Ala Pro Ser Gly Phe Tyr Ile Ala Ser Gly Asp Val Ser Gly Lys Leu
1               5                   10                  15

Arg

<210> SEQ ID NO 1026
<211> LENGTH: 15
<212> TYPE: PRT
<213> ORGANISM: Homo sapiens

<400> SEQUENCE: 1026

Arg Ala Ser Trp Arg Ile Ile Ser Ser Ile Glu Gln Lys Glu Glu
1               5                   10                  15

<210> SEQ ID NO 1027
<211> LENGTH: 17
<212> TYPE: PRT
<213> ORGANISM: Homo sapiens

<400> SEQUENCE: 1027

Asn Lys Gln Lys Pro Ile Thr Pro Glu Thr Ala Glu Lys Leu Ala Arg
1               5                   10                  15

Asp

<210> SEQ ID NO 1028
<211> LENGTH: 16
<212> TYPE: PRT
<213> ORGANISM: Homo sapiens

<400> SEQUENCE: 1028

Asp Asp Pro Ser Thr Ile Glu Lys Leu Ala Lys Asn Lys Gln Lys Pro
1               5                   10                  15

<210> SEQ ID NO 1029
<211> LENGTH: 15
<212> TYPE: PRT
<213> ORGANISM: Homo sapiens

<400> SEQUENCE: 1029

Asn Pro Leu Lys Ile Phe Pro Ser Lys Arg Ile Leu Arg Arg His
1               5                   10                  15

<210> SEQ ID NO 1030
<211> LENGTH: 13
<212> TYPE: PRT
<213> ORGANISM: Homo sapiens
```

```
<400> SEQUENCE: 1030

Glu Thr Gly Trp Leu Leu Leu Asn Lys Pro Leu Asp Arg
1               5                   10

<210> SEQ ID NO 1031
<211> LENGTH: 13
<212> TYPE: PRT
<213> ORGANISM: Homo sapiens

<400> SEQUENCE: 1031

Asp Asn Glu Leu Gln Glu Met Ser Asn Gln Gly Ser Lys
1               5                   10

<210> SEQ ID NO 1032
<211> LENGTH: 15
<212> TYPE: PRT
<213> ORGANISM: Homo sapiens

<400> SEQUENCE: 1032

Ala Ala Gly Leu Leu Ser Thr Tyr Arg Ala Phe Leu Ser Ser His
1               5                   10                  15

<210> SEQ ID NO 1033
<211> LENGTH: 21
<212> TYPE: PRT
<213> ORGANISM: Homo sapiens

<400> SEQUENCE: 1033

Ala Pro Ser Leu Arg Pro Lys Asp Tyr Glu Val Asp Ala Thr Leu Lys
1               5                   10                  15

Ser Leu Asn Asn Gln
            20

<210> SEQ ID NO 1034
<211> LENGTH: 17
<212> TYPE: PRT
<213> ORGANISM: Homo sapiens

<400> SEQUENCE: 1034

Gly Pro Val Asp Glu Val Arg Glu Leu Gln Lys Ala Ile Gly Ala Val
1               5                   10                  15

Pro

<210> SEQ ID NO 1035
<211> LENGTH: 15
<212> TYPE: PRT
<213> ORGANISM: Homo sapiens

<400> SEQUENCE: 1035

Ile Asn His Val Val Ser Val Ala Gly Trp Gly Ile Ser Asp Gly
1               5                   10                  15

<210> SEQ ID NO 1036
<211> LENGTH: 18
<212> TYPE: PRT
<213> ORGANISM: Homo sapiens

<400> SEQUENCE: 1036

Val Pro Asp Asp Arg Asp Phe Glu Pro Ser Leu Gly Pro Val Cys Pro
1               5                   10                  15

Phe Arg
```

```
<210> SEQ ID NO 1037
<211> LENGTH: 20
<212> TYPE: PRT
<213> ORGANISM: Homo sapiens

<400> SEQUENCE: 1037

Leu Pro Gln Ser Ile Val Tyr Lys Tyr Met Ser Ile Arg Ser Asp Arg
1               5                   10                  15

Ser Val Pro Ser
            20

<210> SEQ ID NO 1038
<211> LENGTH: 16
<212> TYPE: PRT
<213> ORGANISM: Homo sapiens

<400> SEQUENCE: 1038

Ile Val His Arg Tyr Met Thr Ile Thr Ser Glu Arg Ser Val Pro Ala
1               5                   10                  15

<210> SEQ ID NO 1039
<211> LENGTH: 13
<212> TYPE: PRT
<213> ORGANISM: Homo sapiens

<400> SEQUENCE: 1039

Lys Asn Gly Phe Val Val Leu Lys Gly Arg Pro Cys Lys
1               5                   10

<210> SEQ ID NO 1040
<211> LENGTH: 15
<212> TYPE: PRT
<213> ORGANISM: Homo sapiens

<400> SEQUENCE: 1040

Ile Thr Gly Tyr Ile Ile Lys Tyr Glu Lys Pro Gly Ser Pro Pro
1               5                   10                  15

<210> SEQ ID NO 1041
<211> LENGTH: 14
<212> TYPE: PRT
<213> ORGANISM: Homo sapiens

<400> SEQUENCE: 1041

Gly Ala Thr Tyr Asn Ile Ile Val Glu Ala Leu Lys Asp Gln
1               5                   10

<210> SEQ ID NO 1042
<211> LENGTH: 16
<212> TYPE: PRT
<213> ORGANISM: Homo sapiens

<400> SEQUENCE: 1042

Leu Thr Gly Tyr Arg Val Arg Val Thr Pro Lys Glu Lys Thr Gly Pro
1               5                   10                  15

<210> SEQ ID NO 1043
<211> LENGTH: 16
<212> TYPE: PRT
<213> ORGANISM: Homo sapiens

<400> SEQUENCE: 1043

Ile Pro Gly His Leu Asn Ser Tyr Thr Ile Lys Gly Leu Lys Pro Gly
1               5                   10                  15
```

<210> SEQ ID NO 1044
<211> LENGTH: 12
<212> TYPE: PRT
<213> ORGANISM: Homo sapiens

<400> SEQUENCE: 1044

Asn Leu Arg Phe Leu Ala Thr Thr Pro Asn Ser Leu
1               5                   10

<210> SEQ ID NO 1045
<211> LENGTH: 17
<212> TYPE: PRT
<213> ORGANISM: Homo sapiens

<400> SEQUENCE: 1045

Ser Asn Thr Asp Leu Val Pro Ala Pro Ala Val Arg Ile Leu Thr Pro
1               5                   10                  15

Glu

<210> SEQ ID NO 1046
<211> LENGTH: 14
<212> TYPE: PRT
<213> ORGANISM: Homo sapiens

<400> SEQUENCE: 1046

Ala Glu Ile Leu Glu Leu Ala Gly Asn Ala Ala Arg Asp Asn
1               5                   10

<210> SEQ ID NO 1047
<211> LENGTH: 17
<212> TYPE: PRT
<213> ORGANISM: Homo sapiens

<400> SEQUENCE: 1047

Val Lys Glu Pro Val Ala Val Leu Lys Ala Asn Arg Val Trp Gly Ala
1               5                   10                  15

Leu

<210> SEQ ID NO 1048
<211> LENGTH: 16
<212> TYPE: PRT
<213> ORGANISM: Homo sapiens

<400> SEQUENCE: 1048

Thr Ala Glu Ile Leu Glu Leu Ala Gly Asn Ala Ala Arg Asp Asn Lys
1               5                   10                  15

<210> SEQ ID NO 1049
<211> LENGTH: 16
<212> TYPE: PRT
<213> ORGANISM: Homo sapiens

<400> SEQUENCE: 1049

His Pro Leu His Ser Lys Ile Ile Ile Lys Lys Gly His Ala Lys
1               5                   10                  15

<210> SEQ ID NO 1050
<211> LENGTH: 16
<212> TYPE: PRT
<213> ORGANISM: Homo sapiens

<400> SEQUENCE: 1050

His Ser Lys Ile Ile Ile Lys Lys Gly His Ala Lys Asp Ser Gln
1               5                   10                  15

<210> SEQ ID NO 1051
<211> LENGTH: 18
<212> TYPE: PRT
<213> ORGANISM: Homo sapiens

<400> SEQUENCE: 1051

Arg Pro Lys His Thr Arg Ile Ser Glu Leu Lys Ala Glu Ala Val Lys
1               5                   10                  15

Lys Asp

<210> SEQ ID NO 1052
<211> LENGTH: 18
<212> TYPE: PRT
<213> ORGANISM: Homo sapiens

<400> SEQUENCE: 1052

Gly Pro Glu Asp Asn Val Val Ile Ile Tyr Leu Ser Arg Ala Gly Asn
1               5                   10                  15

Pro Glu

<210> SEQ ID NO 1053
<211> LENGTH: 16
<212> TYPE: PRT
<213> ORGANISM: Homo sapiens

<400> SEQUENCE: 1053

Ser Arg Pro Val Ile Asn Ile Gln Lys Thr Ile Thr Val Thr Pro Asn
1               5                   10                  15

<210> SEQ ID NO 1054
<211> LENGTH: 17
<212> TYPE: PRT
<213> ORGANISM: Homo sapiens

<400> SEQUENCE: 1054

Leu Asp Leu Ser Phe Asn Gln Ile Ala Arg Leu Pro Ser Gly Leu Pro
1               5                   10                  15

Val

<210> SEQ ID NO 1055
<211> LENGTH: 16
<212> TYPE: PRT
<213> ORGANISM: Homo sapiens

<400> SEQUENCE: 1055

Lys Leu Pro Ser Val Glu Gly Leu His Ala Ile Val Val Ser Asp Arg
1               5                   10                  15

<210> SEQ ID NO 1056
<211> LENGTH: 14
<212> TYPE: PRT
<213> ORGANISM: Homo sapiens

<400> SEQUENCE: 1056

Asp Thr Ser Thr Leu Glu Met Met His Ala Pro Arg Cys Gly
1               5                   10

<210> SEQ ID NO 1057
<211> LENGTH: 17
<212> TYPE: PRT

```
<213> ORGANISM: Homo sapiens

<400> SEQUENCE: 1057

Asp Gln Asn Thr Ile Glu Thr Met Arg Lys Pro Arg Cys Gly Asn Pro
1               5                   10                  15

Asp

<210> SEQ ID NO 1058
<211> LENGTH: 17
<212> TYPE: PRT
<213> ORGANISM: Homo sapiens

<400> SEQUENCE: 1058

Asn Pro Gly Glu Tyr Arg Val Thr Ala His Ala Glu Gly Tyr Thr Pro
1               5                   10                  15

Ser

<210> SEQ ID NO 1059
<211> LENGTH: 15
<212> TYPE: PRT
<213> ORGANISM: Homo sapiens

<400> SEQUENCE: 1059

Leu Asp Phe Leu Lys Ala Val Asp Thr Asn Arg Ala Ser Val Gly
1               5                   10                  15

<210> SEQ ID NO 1060
<211> LENGTH: 16
<212> TYPE: PRT
<213> ORGANISM: Homo sapiens

<400> SEQUENCE: 1060

His Gly Asn Gln Ile Ala Thr Asn Gly Val Val His Val Ile Asp Arg
1               5                   10                  15

<210> SEQ ID NO 1061
<211> LENGTH: 14
<212> TYPE: PRT
<213> ORGANISM: Homo sapiens

<400> SEQUENCE: 1061

Arg Ala Ile Glu Ala Leu His Gly His Glu Leu Arg Pro Gly
1               5                   10

<210> SEQ ID NO 1062
<211> LENGTH: 17
<212> TYPE: PRT
<213> ORGANISM: Homo sapiens

<400> SEQUENCE: 1062

Asp Pro Gly Val Leu Asp Arg Met Met Lys Lys Leu Asp Thr Asn Ser
1               5                   10                  15

Asp

<210> SEQ ID NO 1063
<211> LENGTH: 16
<212> TYPE: PRT
<213> ORGANISM: Homo sapiens

<400> SEQUENCE: 1063

Asn Glu Glu Glu Ile Arg Ala Asn Val Ala Val Val Ser Gly Ala Pro
1               5                   10                  15
```

```
<210> SEQ ID NO 1064
<211> LENGTH: 13
<212> TYPE: PRT
<213> ORGANISM: Homo sapiens

<400> SEQUENCE: 1064

Pro Ala Ile Leu Ser Glu Ala Ser Ala Pro Ile Pro His
1               5                   10

<210> SEQ ID NO 1065
<211> LENGTH: 14
<212> TYPE: PRT
<213> ORGANISM: Homo sapiens

<400> SEQUENCE: 1065

Lys Val Ile Gln Ala Gln Thr Ala Phe Ser Ala Asn Pro Ala
1               5                   10

<210> SEQ ID NO 1066
<211> LENGTH: 17
<212> TYPE: PRT
<213> ORGANISM: Homo sapiens

<400> SEQUENCE: 1066

Asn Gly Ala Tyr Lys Ala Ile Pro Val Ala Gln Asp Leu Asn Ala Pro
1               5                   10                  15

Ser

<210> SEQ ID NO 1067
<211> LENGTH: 16
<212> TYPE: PRT
<213> ORGANISM: Homo sapiens

<400> SEQUENCE: 1067

Thr Asn Gly Val Val His Val Ile Thr Asn Val Leu Gln Pro Pro Ala
1               5                   10                  15

<210> SEQ ID NO 1068
<211> LENGTH: 16
<212> TYPE: PRT
<213> ORGANISM: Homo sapiens

<400> SEQUENCE: 1068

Thr Thr Thr Gln Leu Tyr Thr Asp Arg Thr Glu Lys Leu Arg Pro Glu
1               5                   10                  15

<210> SEQ ID NO 1069
<211> LENGTH: 15
<212> TYPE: PRT
<213> ORGANISM: Homo sapiens

<400> SEQUENCE: 1069

Gly Lys Lys Glu Tyr Leu Ile Ala Gly Lys Ala Glu Gly Asp Gly
1               5                   10                  15

<210> SEQ ID NO 1070
<211> LENGTH: 15
<212> TYPE: PRT
<213> ORGANISM: Homo sapiens

<400> SEQUENCE: 1070

Met Gly Glu Ile Ala Ser Phe Asp Lys Ala Lys Leu Lys Lys Thr
1               5                   10                  15
```

<210> SEQ ID NO 1071
<211> LENGTH: 14
<212> TYPE: PRT
<213> ORGANISM: Homo sapiens

<400> SEQUENCE: 1071

Met Ala Glu Ile Glu Lys Phe Asp Lys Ser Lys Leu Lys Lys
1               5                   10

<210> SEQ ID NO 1072
<211> LENGTH: 15
<212> TYPE: PRT
<213> ORGANISM: Homo sapiens

<400> SEQUENCE: 1072

Val Val Ser Ser Ile Glu Gln Lys Thr Glu Gly Ala Glu Lys Lys
1               5                   10                  15

<210> SEQ ID NO 1073
<211> LENGTH: 13
<212> TYPE: PRT
<213> ORGANISM: Homo sapiens

<400> SEQUENCE: 1073

His Ser Lys Ile Ile Ile Ile Lys Lys Gly His Ala Lys
1               5                   10

<210> SEQ ID NO 1074
<211> LENGTH: 9
<212> TYPE: PRT
<213> ORGANISM: Homo sapiens

<400> SEQUENCE: 1074

Ser Val Ala Ser Thr Ile Thr Gly Val
1               5

<210> SEQ ID NO 1075
<211> LENGTH: 9
<212> TYPE: PRT
<213> ORGANISM: Homo sapiens

<400> SEQUENCE: 1075

Ala Leu Leu Asn Ile Lys Val Lys Leu
1               5

<210> SEQ ID NO 1076
<211> LENGTH: 9
<212> TYPE: PRT
<213> ORGANISM: Homo sapiens

<400> SEQUENCE: 1076

Arg Leu Leu Asp Tyr Val Val Asn Ile
1               5

<210> SEQ ID NO 1077
<211> LENGTH: 9
<212> TYPE: PRT
<213> ORGANISM: Homo sapiens

<400> SEQUENCE: 1077

Ala Leu Ala Asn Gly Ile Glu Glu Val
1               5

<210> SEQ ID NO 1078

```
<211> LENGTH: 9
<212> TYPE: PRT
<213> ORGANISM: Homo sapiens

<400> SEQUENCE: 1078

Gln Leu Ile Asp Lys Val Trp Gln Leu
1               5

<210> SEQ ID NO 1079
<211> LENGTH: 9
<212> TYPE: PRT
<213> ORGANISM: Homo sapiens

<400> SEQUENCE: 1079

Ala Leu Ser Asp Leu Glu Ile Thr Leu
1               5

<210> SEQ ID NO 1080
<211> LENGTH: 9
<212> TYPE: PRT
<213> ORGANISM: Homo sapiens

<400> SEQUENCE: 1080

Ile Leu Asp Thr Gly Thr Ile Gln Leu
1               5

<210> SEQ ID NO 1081
<211> LENGTH: 10
<212> TYPE: PRT
<213> ORGANISM: Homo sapiens

<400> SEQUENCE: 1081

Ser Leu Leu Gly Gly Asp Val Val Ser Val
1               5                   10

<210> SEQ ID NO 1082
<211> LENGTH: 9
<212> TYPE: PRT
<213> ORGANISM: Homo sapiens

<400> SEQUENCE: 1082

Phe Leu Asp Gly Asn Glu Leu Thr Leu
1               5

<210> SEQ ID NO 1083
<211> LENGTH: 9
<212> TYPE: PRT
<213> ORGANISM: Homo sapiens

<400> SEQUENCE: 1083

Asn Leu Leu Pro Lys Leu His Ile Val
1               5

<210> SEQ ID NO 1084
<211> LENGTH: 9
<212> TYPE: PRT
<213> ORGANISM: Homo sapiens

<400> SEQUENCE: 1084

Ala Leu Ala Ser His Leu Ile Glu Ala
1               5

<210> SEQ ID NO 1085
<211> LENGTH: 9
<212> TYPE: PRT
```

<213> ORGANISM: Homo sapiens

<400> SEQUENCE: 1085

Ser Leu Tyr Gly Gly Thr Ile Thr Ile
1               5

<210> SEQ ID NO 1086
<211> LENGTH: 9
<212> TYPE: PRT
<213> ORGANISM: Homo sapiens

<400> SEQUENCE: 1086

Phe Leu Leu Asp Lys Lys Ile Gly Val
1               5

<210> SEQ ID NO 1087
<211> LENGTH: 9
<212> TYPE: PRT
<213> ORGANISM: Homo sapiens

<400> SEQUENCE: 1087

Ala Ile Val Asp Lys Val Pro Ser Val
1               5

<210> SEQ ID NO 1088
<211> LENGTH: 10
<212> TYPE: PRT
<213> ORGANISM: Homo sapiens

<400> SEQUENCE: 1088

Asp Val Ala Ser Val Ile Val Thr Lys Leu
1               5                   10

<210> SEQ ID NO 1089
<211> LENGTH: 8
<212> TYPE: PRT
<213> ORGANISM: Homo sapiens

<400> SEQUENCE: 1089

Leu Ala Ser Val Ser Thr Val Leu
1               5

<210> SEQ ID NO 1090
<211> LENGTH: 9
<212> TYPE: PRT
<213> ORGANISM: Homo sapiens

<400> SEQUENCE: 1090

Val Met Ala Pro Arg Thr Leu Val Leu
1               5

<210> SEQ ID NO 1091
<211> LENGTH: 9
<212> TYPE: PRT
<213> ORGANISM: Homo sapiens

<400> SEQUENCE: 1091

Leu Leu Phe Asp Arg Pro Met His Val
1               5

<210> SEQ ID NO 1092
<211> LENGTH: 10
<212> TYPE: PRT
<213> ORGANISM: Homo sapiens

```
<400> SEQUENCE: 1092

Met Thr Ser Ala Leu Pro Ile Ile Gln Lys
1               5                   10

<210> SEQ ID NO 1093
<211> LENGTH: 10
<212> TYPE: PRT
<213> ORGANISM: Homo sapiens

<400> SEQUENCE: 1093

Met Ala Gly Asp Ile Tyr Ser Val Phe Arg
1               5                   10

<210> SEQ ID NO 1094
<211> LENGTH: 10
<212> TYPE: PRT
<213> ORGANISM: Homo sapiens

<400> SEQUENCE: 1094

Glu Thr Ile Pro Leu Thr Ala Glu Lys Leu
1               5                   10

<210> SEQ ID NO 1095
<211> LENGTH: 10
<212> TYPE: PRT
<213> ORGANISM: Homo sapiens

<400> SEQUENCE: 1095

Asp Val Met Val Gly Pro Phe Lys Leu Arg
1               5                   10

<210> SEQ ID NO 1096
<211> LENGTH: 9
<212> TYPE: PRT
<213> ORGANISM: Homo sapiens

<400> SEQUENCE: 1096

Thr Ile Ile Asp Ile Leu Thr Lys Arg
1               5

<210> SEQ ID NO 1097
<211> LENGTH: 9
<212> TYPE: PRT
<213> ORGANISM: Homo sapiens

<400> SEQUENCE: 1097

Thr Ile Val Asn Ile Leu Thr Asn Arg
1               5

<210> SEQ ID NO 1098
<211> LENGTH: 9
<212> TYPE: PRT
<213> ORGANISM: Homo sapiens

<400> SEQUENCE: 1098

Thr Ile Ile Asp Ile Ile Thr His Arg
1               5

<210> SEQ ID NO 1099
<211> LENGTH: 9
<212> TYPE: PRT
<213> ORGANISM: Homo sapiens

<400> SEQUENCE: 1099
```

```
Ser Thr Ile Glu Tyr Val Ile Gln Arg
1               5
```

<210> SEQ ID NO 1100
<211> LENGTH: 10
<212> TYPE: PRT
<213> ORGANISM: Homo sapiens

<400> SEQUENCE: 1100

```
Glu Leu Ile Lys Pro Pro Thr Ile Leu Arg
1               5                   10
```

<210> SEQ ID NO 1101
<211> LENGTH: 11
<212> TYPE: PRT
<213> ORGANISM: Homo sapiens

<400> SEQUENCE: 1101

```
Glu Ile Ala Met Ala Thr Val Thr Ala Leu Arg
1               5                   10
```

<210> SEQ ID NO 1102
<211> LENGTH: 9
<212> TYPE: PRT
<213> ORGANISM: Homo sapiens

<400> SEQUENCE: 1102

```
Glu Thr Ile Gly Glu Ile Leu Lys Lys
1               5
```

<210> SEQ ID NO 1103
<211> LENGTH: 9
<212> TYPE: PRT
<213> ORGANISM: Homo sapiens

<400> SEQUENCE: 1103

```
Ser Leu Ala Asp Ile Met Ala Lys Arg
1               5
```

<210> SEQ ID NO 1104
<211> LENGTH: 9
<212> TYPE: PRT
<213> ORGANISM: Homo sapiens

<400> SEQUENCE: 1104

```
Glu Glu Ile Ala Phe Leu Lys Lys Leu
1               5
```

<210> SEQ ID NO 1105
<211> LENGTH: 9
<212> TYPE: PRT
<213> ORGANISM: Homo sapiens

<400> SEQUENCE: 1105

```
Asp Glu Ala Ala Phe Leu Glu Arg Leu
1               5
```

<210> SEQ ID NO 1106
<211> LENGTH: 8
<212> TYPE: PRT
<213> ORGANISM: Homo sapiens

<400> SEQUENCE: 1106

```
Asp Glu Met Lys Val Leu Val Leu
1               5
```

<210> SEQ ID NO 1107
<211> LENGTH: 8
<212> TYPE: PRT
<213> ORGANISM: Homo sapiens

<400> SEQUENCE: 1107

Asp Glu Val Lys Phe Leu Thr Val
1               5

<210> SEQ ID NO 1108
<211> LENGTH: 9
<212> TYPE: PRT
<213> ORGANISM: Homo sapiens

<400> SEQUENCE: 1108

Asn Glu Asn Ser Leu Phe Lys Ser Leu
1               5

<210> SEQ ID NO 1109
<211> LENGTH: 8
<212> TYPE: PRT
<213> ORGANISM: Homo sapiens

<400> SEQUENCE: 1109

Asp Glu Phe Lys Val Val Val Val
1               5

<210> SEQ ID NO 1110
<211> LENGTH: 9
<212> TYPE: PRT
<213> ORGANISM: Homo sapiens

<400> SEQUENCE: 1110

Glu Glu Val Lys Leu Ile Lys Lys Met
1               5

<210> SEQ ID NO 1111
<211> LENGTH: 9
<212> TYPE: PRT
<213> ORGANISM: Homo sapiens

<400> SEQUENCE: 1111

Asp Glu Val Lys Leu Pro Ala Lys Leu
1               5

<210> SEQ ID NO 1112
<211> LENGTH: 9
<212> TYPE: PRT
<213> ORGANISM: Homo sapiens

<400> SEQUENCE: 1112

Thr Glu Arg Glu Leu Lys Val Ala Tyr
1               5

<210> SEQ ID NO 1113
<211> LENGTH: 10
<212> TYPE: PRT
<213> ORGANISM: Homo sapiens

<400> SEQUENCE: 1113

Asn Glu Phe Ser Leu Lys Gly Val Asp Phe
1               5                   10

<210> SEQ ID NO 1114
<211> LENGTH: 9
<212> TYPE: PRT
<213> ORGANISM: Homo sapiens

<400> SEQUENCE: 1114

Asn Glu Gln Asp Leu Gly Ile Gln Tyr
1               5

<210> SEQ ID NO 1115
<211> LENGTH: 8
<212> TYPE: PRT
<213> ORGANISM: Homo sapiens

<400> SEQUENCE: 1115

Glu Glu Arg Ile Val Glu Leu Phe
1               5

<210> SEQ ID NO 1116
<211> LENGTH: 10
<212> TYPE: PRT
<213> ORGANISM: Homo sapiens

<400> SEQUENCE: 1116

Glu Glu Ile Arg Glu Ala Phe Arg Val Phe
1               5                   10

<210> SEQ ID NO 1117
<211> LENGTH: 9
<212> TYPE: PRT
<213> ORGANISM: Homo sapiens

<400> SEQUENCE: 1117

Asp Glu Tyr Ile Tyr Arg His Phe Phe
1               5

<210> SEQ ID NO 1118
<211> LENGTH: 9
<212> TYPE: PRT
<213> ORGANISM: Homo sapiens

<400> SEQUENCE: 1118

Asp Glu Leu Glu Leu His Gln Arg Phe
1               5

<210> SEQ ID NO 1119
<211> LENGTH: 9
<212> TYPE: PRT
<213> ORGANISM: Homo sapiens

<400> SEQUENCE: 1119

Ser Glu Val Lys Phe Thr Val Thr Phe
1               5

<210> SEQ ID NO 1120
<211> LENGTH: 8
<212> TYPE: PRT
<213> ORGANISM: Homo sapiens

<400> SEQUENCE: 1120

Ile Glu Thr Ile Ile Asn Thr Phe
1               5

<210> SEQ ID NO 1121
<211> LENGTH: 9

```
<212> TYPE: PRT
<213> ORGANISM: Homo sapiens

<400> SEQUENCE: 1121

Lys Glu Asn Pro Leu Gln Phe Lys Phe
1               5

<210> SEQ ID NO 1122
<211> LENGTH: 8
<212> TYPE: PRT
<213> ORGANISM: Homo sapiens

<400> SEQUENCE: 1122

Asp Glu Val Arg Thr Leu Thr Tyr
1               5

<210> SEQ ID NO 1123
<211> LENGTH: 9
<212> TYPE: PRT
<213> ORGANISM: Homo sapiens

<400> SEQUENCE: 1123

Gly Glu Ala Val Val Asn Arg Val Phe
1               5

<210> SEQ ID NO 1124
<211> LENGTH: 10
<212> TYPE: PRT
<213> ORGANISM: Homo sapiens

<400> SEQUENCE: 1124

Glu Glu Val Leu Ile Pro Asp Gln Lys Tyr
1               5                   10

<210> SEQ ID NO 1125
<211> LENGTH: 9
<212> TYPE: PRT
<213> ORGANISM: Homo sapiens

<400> SEQUENCE: 1125

Asp Glu Gly Arg Leu Val Leu Glu Phe
1               5

<210> SEQ ID NO 1126
<211> LENGTH: 8
<212> TYPE: PRT
<213> ORGANISM: Homo sapiens

<400> SEQUENCE: 1126

Asp Glu Val Glu Leu Ile His Phe
1               5

<210> SEQ ID NO 1127
<211> LENGTH: 9
<212> TYPE: PRT
<213> ORGANISM: Homo sapiens

<400> SEQUENCE: 1127

Val Glu Val Leu Leu Asn Tyr Ala Tyr
1               5

<210> SEQ ID NO 1128
<211> LENGTH: 9
<212> TYPE: PRT
<213> ORGANISM: Homo sapiens
```

<400> SEQUENCE: 1128

Thr Glu Asn Asp Ile Arg Val Met Phe
1               5

<210> SEQ ID NO 1129
<211> LENGTH: 8
<212> TYPE: PRT
<213> ORGANISM: Homo sapiens

<400> SEQUENCE: 1129

Leu Glu Gly Leu Thr Val Val Tyr
1               5

<210> SEQ ID NO 1130
<211> LENGTH: 8
<212> TYPE: PRT
<213> ORGANISM: Homo sapiens

<400> SEQUENCE: 1130

Asn Glu Leu Pro Thr Val Ala Phe
1               5

<210> SEQ ID NO 1131
<211> LENGTH: 9
<212> TYPE: PRT
<213> ORGANISM: Homo sapiens

<400> SEQUENCE: 1131

Glu Glu Phe Gly Gln Ala Phe Ser Phe
1               5

<210> SEQ ID NO 1132
<211> LENGTH: 8
<212> TYPE: PRT
<213> ORGANISM: Homo sapiens

<400> SEQUENCE: 1132

Val Glu Ala Ile Phe Ser Lys Tyr
1               5

<210> SEQ ID NO 1133
<211> LENGTH: 9
<212> TYPE: PRT
<213> ORGANISM: Homo sapiens

<400> SEQUENCE: 1133

Asp Glu Arg Thr Phe His Ile Phe Tyr
1               5

<210> SEQ ID NO 1134
<211> LENGTH: 8
<212> TYPE: PRT
<213> ORGANISM: Homo sapiens

<400> SEQUENCE: 1134

Asp Glu Gly Lys Val Ile Arg Phe
1               5

<210> SEQ ID NO 1135
<211> LENGTH: 10
<212> TYPE: PRT
<213> ORGANISM: Homo sapiens

<400> SEQUENCE: 1135

```
Phe Leu Pro Ser Asp Phe Phe Pro Ser Val
1               5                   10

<210> SEQ ID NO 1136
<211> LENGTH: 9
<212> TYPE: PRT
<213> ORGANISM: Homo sapiens

<400> SEQUENCE: 1136

Tyr Leu Ser Gly Ala Asp Leu Asn Leu
1               5

<210> SEQ ID NO 1137
<211> LENGTH: 9
<212> TYPE: PRT
<213> ORGANISM: Homo sapiens

<400> SEQUENCE: 1137

Tyr Leu Ser Gly Ala Asn Leu Asn Leu
1               5

<210> SEQ ID NO 1138
<211> LENGTH: 11
<212> TYPE: PRT
<213> ORGANISM: Homo sapiens

<400> SEQUENCE: 1138

Val Pro Asp Ser Ser Gly Pro Glu Arg Ile Leu
1               5                   10

<210> SEQ ID NO 1139
<211> LENGTH: 9
<212> TYPE: PRT
<213> ORGANISM: Homo sapiens

<400> SEQUENCE: 1139

Gly Leu Ala Pro Ser Ile Arg Thr Lys
1               5

<210> SEQ ID NO 1140
<211> LENGTH: 9
<212> TYPE: PRT
<213> ORGANISM: Homo sapiens

<400> SEQUENCE: 1140

Arg Leu Phe Glu His Pro Leu Tyr Arg
1               5

<210> SEQ ID NO 1141
<211> LENGTH: 9
<212> TYPE: PRT
<213> ORGANISM: Homo sapiens

<400> SEQUENCE: 1141

Thr Pro Ser Glu Pro His Pro Val Leu
1               5

<210> SEQ ID NO 1142
<211> LENGTH: 10
<212> TYPE: PRT
<213> ORGANISM: Homo sapiens

<400> SEQUENCE: 1142

Gln Ile Phe Val Lys Thr Leu Thr Gly Lys
```

```
                1               5                  10

<210> SEQ ID NO 1143
<211> LENGTH: 9
<212> TYPE: PRT
<213> ORGANISM: Homo sapiens

<400> SEQUENCE: 1143

Ser Leu Met His Ser Phe Ile Leu Lys
1               5

<210> SEQ ID NO 1144
<211> LENGTH: 9
<212> TYPE: PRT
<213> ORGANISM: Homo sapiens

<400> SEQUENCE: 1144

Tyr Pro His Leu His Asn Ala Glu Leu
1               5

<210> SEQ ID NO 1145
<211> LENGTH: 9
<212> TYPE: PRT
<213> ORGANISM: Homo sapiens

<400> SEQUENCE: 1145

Arg Leu Phe Val Gly Ser Ile Pro Lys
1               5

<210> SEQ ID NO 1146
<211> LENGTH: 10
<212> TYPE: PRT
<213> ORGANISM: Homo sapiens

<400> SEQUENCE: 1146

Arg Val Phe Pro Asp Lys Gly Tyr Ser Phe
1               5                  10

<210> SEQ ID NO 1147
<211> LENGTH: 9
<212> TYPE: PRT
<213> ORGANISM: Homo sapiens

<400> SEQUENCE: 1147

Ser Leu Tyr Lys Lys Leu Glu Ile Lys
1               5

<210> SEQ ID NO 1148
<211> LENGTH: 10
<212> TYPE: PRT
<213> ORGANISM: Homo sapiens

<400> SEQUENCE: 1148

His Pro Val Ser Asp His Glu Ala Thr Leu
1               5                  10

<210> SEQ ID NO 1149
<211> LENGTH: 9
<212> TYPE: PRT
<213> ORGANISM: Homo sapiens

<400> SEQUENCE: 1149

Leu Pro Thr Arg Val Asp Phe Ser Leu
1               5
```

```
<210> SEQ ID NO 1150
<211> LENGTH: 11
<212> TYPE: PRT
<213> ORGANISM: Homo sapiens

<400> SEQUENCE: 1150

Lys Ser Phe Gly Ser Ala Gln Glu Phe Ala Trp
1               5                   10

<210> SEQ ID NO 1151
<211> LENGTH: 10
<212> TYPE: PRT
<213> ORGANISM: Homo sapiens

<400> SEQUENCE: 1151

Ser Pro Ser Thr Ser Arg Thr Pro Leu Leu
1               5                   10

<210> SEQ ID NO 1152
<211> LENGTH: 9
<212> TYPE: PRT
<213> ORGANISM: Homo sapiens

<400> SEQUENCE: 1152

Ser Thr Phe Asp Ser Pro Ala His Trp
1               5

<210> SEQ ID NO 1153
<211> LENGTH: 9
<212> TYPE: PRT
<213> ORGANISM: Homo sapiens

<400> SEQUENCE: 1153

Ala Pro Glu Glu His Pro Val Leu Leu
1               5

<210> SEQ ID NO 1154
<211> LENGTH: 9
<212> TYPE: PRT
<213> ORGANISM: Homo sapiens

<400> SEQUENCE: 1154

Arg Gln Ile Thr Gln Val Tyr Gly Phe
1               5

<210> SEQ ID NO 1155
<211> LENGTH: 9
<212> TYPE: PRT
<213> ORGANISM: Homo sapiens

<400> SEQUENCE: 1155

Lys Val Ser Asp Tyr Ile Leu Gln His
1               5

<210> SEQ ID NO 1156
<211> LENGTH: 9
<212> TYPE: PRT
<213> ORGANISM: Homo sapiens

<400> SEQUENCE: 1156

Lys Leu Leu Pro Ser Val Val Leu Lys
1               5

<210> SEQ ID NO 1157
```

```
<211> LENGTH: 9
<212> TYPE: PRT
<213> ORGANISM: Homo sapiens

<400> SEQUENCE: 1157

Gly Val Leu Lys Lys Val Ile Arg His
1               5

<210> SEQ ID NO 1158
<211> LENGTH: 10
<212> TYPE: PRT
<213> ORGANISM: Homo sapiens

<400> SEQUENCE: 1158

Lys Leu Phe Asp His Ala Val Ser Lys Phe
1               5                   10

<210> SEQ ID NO 1159
<211> LENGTH: 10
<212> TYPE: PRT
<213> ORGANISM: Homo sapiens

<400> SEQUENCE: 1159

Ile Thr Val Leu Thr Lys Pro Leu Pro Val
1               5                   10

<210> SEQ ID NO 1160
<211> LENGTH: 9
<212> TYPE: PRT
<213> ORGANISM: Homo sapiens

<400> SEQUENCE: 1160

His Pro Val His Pro Asp Ile Lys Leu
1               5

<210> SEQ ID NO 1161
<211> LENGTH: 10
<212> TYPE: PRT
<213> ORGANISM: Homo sapiens

<400> SEQUENCE: 1161

Ile Pro Arg Ala Ala Leu Leu Pro Leu Leu
1               5                   10

<210> SEQ ID NO 1162
<211> LENGTH: 9
<212> TYPE: PRT
<213> ORGANISM: Homo sapiens

<400> SEQUENCE: 1162

Ala Thr Asn Arg Ile Thr Val Thr Trp
1               5

<210> SEQ ID NO 1163
<211> LENGTH: 9
<212> TYPE: PRT
<213> ORGANISM: Homo sapiens

<400> SEQUENCE: 1163

Lys Ile Ala Asp Arg Phe Leu Leu Tyr
1               5

<210> SEQ ID NO 1164
<211> LENGTH: 10
<212> TYPE: PRT
```

<213> ORGANISM: Homo sapiens

<400> SEQUENCE: 1164

Asp His Asp Pro Val Asp Lys Ile Val Leu
1               5                   10

<210> SEQ ID NO 1165
<211> LENGTH: 9
<212> TYPE: PRT
<213> ORGANISM: Homo sapiens

<400> SEQUENCE: 1165

Asp His His Gln Glu Val Ile Gly Phe
1               5

<210> SEQ ID NO 1166
<211> LENGTH: 9
<212> TYPE: PRT
<213> ORGANISM: Homo sapiens

<400> SEQUENCE: 1166

Ile His Asp Leu Asp Asn Ile Ser Phe
1               5

<210> SEQ ID NO 1167
<211> LENGTH: 9
<212> TYPE: PRT
<213> ORGANISM: Homo sapiens

<400> SEQUENCE: 1167

Asp His Ile Asn Asp Ile Ile Lys Ile
1               5

<210> SEQ ID NO 1168
<211> LENGTH: 9
<212> TYPE: PRT
<213> ORGANISM: Homo sapiens

<400> SEQUENCE: 1168

Asp His Met Arg Phe Ile Ser Glu Leu
1               5

<210> SEQ ID NO 1169
<211> LENGTH: 9
<212> TYPE: PRT
<213> ORGANISM: Homo sapiens

<400> SEQUENCE: 1169

Thr His Ser Leu Pro Val Val Val Ile
1               5

<210> SEQ ID NO 1170
<211> LENGTH: 11
<212> TYPE: PRT
<213> ORGANISM: Homo sapiens

<400> SEQUENCE: 1170

Met Pro Val Gly Pro Asp Ala Ile Leu Arg Tyr
1               5                   10

<210> SEQ ID NO 1171
<211> LENGTH: 9
<212> TYPE: PRT
<213> ORGANISM: Homo sapiens

```
<400> SEQUENCE: 1171

Arg Leu Asp Asp Ala Ile His Val Leu
1               5

<210> SEQ ID NO 1172
<211> LENGTH: 9
<212> TYPE: PRT
<213> ORGANISM: Homo sapiens

<400> SEQUENCE: 1172

Gln His Glu Gly Thr Val Asn Ile Phe
1               5

<210> SEQ ID NO 1173
<211> LENGTH: 9
<212> TYPE: PRT
<213> ORGANISM: Homo sapiens

<400> SEQUENCE: 1173

Glu Thr Val Asn Ile Trp Thr His Phe
1               5

<210> SEQ ID NO 1174
<211> LENGTH: 9
<212> TYPE: PRT
<213> ORGANISM: Homo sapiens

<400> SEQUENCE: 1174

Val His Ile Leu Asp Thr Glu Thr Phe
1               5

<210> SEQ ID NO 1175
<211> LENGTH: 10
<212> TYPE: PRT
<213> ORGANISM: Homo sapiens

<400> SEQUENCE: 1175

Gln Thr Pro Asp Phe Thr Pro Thr Lys Tyr
1               5                   10

<210> SEQ ID NO 1176
<211> LENGTH: 9
<212> TYPE: PRT
<213> ORGANISM: Homo sapiens

<400> SEQUENCE: 1176

Arg His Val Glu Val Phe Glu Leu Leu
1               5

<210> SEQ ID NO 1177
<211> LENGTH: 9
<212> TYPE: PRT
<213> ORGANISM: Homo sapiens

<400> SEQUENCE: 1177

Asp Leu Ile Glu His Phe Ser Gln Phe
1               5

<210> SEQ ID NO 1178
<211> LENGTH: 9
<212> TYPE: PRT
<213> ORGANISM: Homo sapiens

<400> SEQUENCE: 1178
```

Glu Thr Val Trp Arg Leu Glu Glu Phe
1               5

<210> SEQ ID NO 1179
<211> LENGTH: 9
<212> TYPE: PRT
<213> ORGANISM: Homo sapiens

<400> SEQUENCE: 1179

Asp Val Leu Glu Ser Val Asn Leu Leu
1               5

<210> SEQ ID NO 1180
<211> LENGTH: 9
<212> TYPE: PRT
<213> ORGANISM: Homo sapiens

<400> SEQUENCE: 1180

Ile His Asp Asp Phe Val Thr Thr Phe
1               5

<210> SEQ ID NO 1181
<211> LENGTH: 9
<212> TYPE: PRT
<213> ORGANISM: Homo sapiens

<400> SEQUENCE: 1181

Ile His Leu Ile Asp Pro Asn Thr Leu
1               5

<210> SEQ ID NO 1182
<211> LENGTH: 9
<212> TYPE: PRT
<213> ORGANISM: Homo sapiens

<400> SEQUENCE: 1182

Ile His Val Ile Gly Gly Asn Asp Val
1               5

<210> SEQ ID NO 1183
<211> LENGTH: 9
<212> TYPE: PRT
<213> ORGANISM: Homo sapiens

<400> SEQUENCE: 1183

Lys Ala Phe Gln Lys Ile Val Val Leu
1               5

<210> SEQ ID NO 1184
<211> LENGTH: 9
<212> TYPE: PRT
<213> ORGANISM: Homo sapiens

<400> SEQUENCE: 1184

Gly His Tyr Glu Val Ala Glu Leu Leu
1               5

<210> SEQ ID NO 1185
<211> LENGTH: 9
<212> TYPE: PRT
<213> ORGANISM: Homo sapiens

<400> SEQUENCE: 1185

Ala Pro Ala Arg Leu Phe Ala Leu Leu
1               5

```
<210> SEQ ID NO 1186
<211> LENGTH: 9
<212> TYPE: PRT
<213> ORGANISM: Homo sapiens

<400> SEQUENCE: 1186

Ser Glu Phe Thr Gly Val Trp Lys Tyr
1               5

<210> SEQ ID NO 1187
<211> LENGTH: 8
<212> TYPE: PRT
<213> ORGANISM: Homo sapiens

<400> SEQUENCE: 1187

Tyr Asp Ser Ile Ile Tyr Arg Met
1               5

<210> SEQ ID NO 1188
<211> LENGTH: 9
<212> TYPE: PRT
<213> ORGANISM: Homo sapiens

<400> SEQUENCE: 1188

Asn Tyr Ile Asp Lys Val Arg Phe Leu
1               5

<210> SEQ ID NO 1189
<211> LENGTH: 10
<212> TYPE: PRT
<213> ORGANISM: Homo sapiens

<400> SEQUENCE: 1189

Pro Thr Gln Glu Leu Gly Leu Pro Ala Tyr
1               5                   10

<210> SEQ ID NO 1190
<211> LENGTH: 14
<212> TYPE: PRT
<213> ORGANISM: Homo sapiens

<400> SEQUENCE: 1190

Arg Arg Phe Asn Leu Gln Lys Asn Phe Val Gly Lys Val Ala
1               5                   10

<210> SEQ ID NO 1191
<211> LENGTH: 15
<212> TYPE: PRT
<213> ORGANISM: Homo sapiens

<400> SEQUENCE: 1191

Val Pro Gly Thr Tyr Lys Ile Thr Ala Ser Ala Arg Gly Tyr Asn
1               5                   10                  15

<210> SEQ ID NO 1192
<211> LENGTH: 9
<212> TYPE: PRT
<213> ORGANISM: Homo sapiens

<400> SEQUENCE: 1192

Phe Leu Asp Gly Asn Glu Met Thr Leu
1               5
```

```
<210> SEQ ID NO 1193
<211> LENGTH: 9
<212> TYPE: PRT
<213> ORGANISM: Homo sapiens

<400> SEQUENCE: 1193

Thr Glu Lys Val Leu Ala Ala Val Tyr
1               5

<210> SEQ ID NO 1194
<211> LENGTH: 9
<212> TYPE: PRT
<213> ORGANISM: Homo sapiens

<400> SEQUENCE: 1194

Val Glu Ser Pro Leu Ser Val Ser Phe
1               5

<210> SEQ ID NO 1195
<211> LENGTH: 10
<212> TYPE: PRT
<213> ORGANISM: Homo sapiens

<400> SEQUENCE: 1195

Ser Glu Ala Gly Ser His Thr Leu Gln Trp
1               5                   10

<210> SEQ ID NO 1196
<211> LENGTH: 9
<212> TYPE: PRT
<213> ORGANISM: Homo sapiens

<400> SEQUENCE: 1196

Ala Leu Ala Ala Val Val Thr Glu Val
1               5

<210> SEQ ID NO 1197
<211> LENGTH: 9
<212> TYPE: PRT
<213> ORGANISM: Homo sapiens

<400> SEQUENCE: 1197

Thr Leu Ile Glu Asp Ile Leu Gly Val
1               5

<210> SEQ ID NO 1198
<211> LENGTH: 9
<212> TYPE: PRT
<213> ORGANISM: Homo sapiens

<400> SEQUENCE: 1198

Ala Leu Phe Gly Ala Leu Phe Leu Ala
1               5

<210> SEQ ID NO 1199
<211> LENGTH: 9
<212> TYPE: PRT
<213> ORGANISM: Homo sapiens

<400> SEQUENCE: 1199

Val Leu Ala Thr Leu Val Leu Leu Leu
1               5

<210> SEQ ID NO 1200
<211> LENGTH: 9
```

```
<212> TYPE: PRT
<213> ORGANISM: Homo sapiens

<400> SEQUENCE: 1200

Thr Leu Asp Asp Leu Ile Ala Ala Val
1               5

<210> SEQ ID NO 1201
<211> LENGTH: 9
<212> TYPE: PRT
<213> ORGANISM: Homo sapiens

<400> SEQUENCE: 1201

Tyr Leu Asp Asn Gly Val Val Phe Val
1               5

<210> SEQ ID NO 1202
<211> LENGTH: 10
<212> TYPE: PRT
<213> ORGANISM: Homo sapiens

<400> SEQUENCE: 1202

Ser Leu Ile Asn Val Gly Leu Ile Ser Val
1               5                   10

<210> SEQ ID NO 1203
<211> LENGTH: 9
<212> TYPE: PRT
<213> ORGANISM: Homo sapiens

<400> SEQUENCE: 1203

Thr Tyr Gly Glu Ile Phe Glu Lys Glu
1               5

<210> SEQ ID NO 1204
<211> LENGTH: 9
<212> TYPE: PRT
<213> ORGANISM: Homo sapiens

<400> SEQUENCE: 1204

Tyr Tyr Met Ile Gly Glu Gln Lys Phe
1               5

<210> SEQ ID NO 1205
<211> LENGTH: 17
<212> TYPE: PRT
<213> ORGANISM: Homo sapiens

<400> SEQUENCE: 1205

Ser Ser Val Pro Gly Val Arg Leu Leu Gln Asp Ser Val Asp Phe Ser
1               5                   10                  15

Leu

<210> SEQ ID NO 1206
<211> LENGTH: 10
<212> TYPE: PRT
<213> ORGANISM: Homo sapiens

<400> SEQUENCE: 1206

Leu Leu Ala Ala Arg Ala Ile Val Ala Ile
1               5                   10
```